(12) United States Patent
Aliagas-Martin et al.

(10) Patent No.: US 8,637,537 B2
(45) Date of Patent: Jan. 28, 2014

(54) SERINE/THREONINE KINASE INHIBITORS

(75) Inventors: Ignacio Aliagas-Martin, San Francisco, CA (US); James Crawford, San Francisco, CA (US); Wendy Lee, San Ramon, CA (US); Simon Mathieu, San Francisco, CA (US); Joachim Rudolph, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/593,776

(22) Filed: Aug. 24, 2012

(65) Prior Publication Data

US 2013/0225620 A1    Aug. 29, 2013

Related U.S. Application Data

(60) Provisional application No. 61/527,453, filed on Aug. 25, 2011.

(51) Int. Cl.
*A01N 43/54* (2006.01)
*A61K 31/505* (2006.01)

(52) U.S. Cl.
USPC .......................................... 514/275; 544/295

(58) Field of Classification Search
USPC .......................................... 544/295; 514/275
See application file for complete search history.

(56) References Cited

U.S. PATENT DOCUMENTS

| | | | |
|---|---|---|---|
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,660,731 B2 | 12/2003 | Bebbington et al. | |
| 6,664,247 B2 | 12/2003 | Bebbington et al. | |
| 6,696,452 B2 | 2/2004 | Davies et al. | |
| 6,727,251 B2 | 4/2004 | Bebbington et al. | |
| 6,989,385 B2 | 1/2006 | Bebbington et al. | |
| 7,008,948 B2 | 3/2006 | Bebbington et al. | |
| 7,087,603 B2 | 8/2006 | Bebbington et al. | |
| 7,098,330 B2 | 8/2006 | Bebbington et al. | |
| 7,115,739 B2 | 10/2006 | Bebbington et al. | |
| 7,390,815 B2 | 6/2008 | Davies et al. | |
| 7,427,681 B2 | 9/2008 | Bebbington et al. | |
| 7,473,691 B2 | 1/2009 | Davies et al. | |
| 7,531,536 B2 | 5/2009 | Bebbington et al. | |
| 7,625,913 B2 | 12/2009 | Bebbington et al. | |
| 7,691,853 B2 | 4/2010 | Bebbington et al. | |
| 7,754,714 B2 | 7/2010 | Li et al. | |
| 7,858,633 B2 | 12/2010 | Li et al. | |
| 7,868,013 B2 | 1/2011 | Li et al. | |
| 7,884,111 B2 | 2/2011 | Argade et al. | |
| 2003/0004161 A1 | 1/2003 | Bebbington et al. | |
| 2003/0004164 A1 | 1/2003 | Bebbington et al. | |
| 2003/0022885 A1 | 1/2003 | Bebbington et al. | |
| 2003/0036543 A1 | 2/2003 | Bebbington et al. | |
| 2003/0055068 A1 | 3/2003 | Bebbington et al. | |
| 2003/0064981 A1 | 4/2003 | Knegtel et al. | |
| 2003/0064982 A1 | 4/2003 | Davies et al. | |
| 2003/0073687 A1 | 4/2003 | Bebbington et al. | |
| 2003/0078166 A1 | 4/2003 | Davies et al. | |
| 2003/0078275 A1 | 4/2003 | Bebbington et al. | |
| 2003/0083327 A1 | 5/2003 | Davies et al. | |
| 2003/0105090 A1 | 6/2003 | Bebbington et al. | |
| 2004/0097501 A1 | 5/2004 | Bebbington et al. | |

(Continued)

FOREIGN PATENT DOCUMENTS

| | | | |
|---|---|---|---|
| WO | 02/22601 A1 | 3/2002 | |
| WO | 02/22602 A2 | 3/2002 | |

(Continued)

OTHER PUBLICATIONS

International Search Report and Written Opinion for International Patent Application No. PCT/EP2012/066468.

*Primary Examiner* — James O Wilson
*Assistant Examiner* — Alexander R Pagano
(74) *Attorney, Agent, or Firm* — Brian L. Buckwalter

(57) ABSTRACT

Compounds having the formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$ and n are as defined herein are inhibitors of PAK1. Also disclosed are compositions and methods for treating cancer and hyperproliferative disorders.

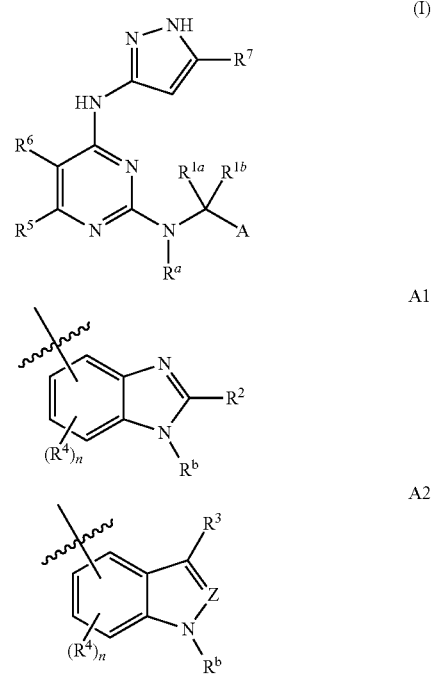

23 Claims, No Drawings

(56) References Cited

U.S. PATENT DOCUMENTS

| | | |
|---|---|---|
| 2004/0116454 A1 | 6/2004 | Davies et al. |
| 2004/0132781 A1 | 7/2004 | Bebbington et al. |
| 2004/0157893 A1 | 8/2004 | Bebbington et al. |
| 2004/0167141 a1 | 8/2004 | Bebbington et al. |
| 2004/0214814 A1 | 10/2004 | Bebbington et al. |
| 2005/0038023 A1 | 2/2005 | Bebbington et al. |
| 2005/0113398 A1 | 5/2005 | Argade et al. |
| 2006/0162249 A1 | 7/2006 | Zimmermann et al. |
| 2006/0258658 A1 | 11/2006 | Bebbington et al. |
| 2007/0270444 A1 | 11/2007 | Bebbington et al. |
| 2008/0009484 A1 | 1/2008 | Argade et al. |
| 2008/0287444 A1 | 11/2008 | Bebbington et al. |
| 2009/0197862 A1 * | 8/2009 | Steinig et al. ............ 514/210.18 |
| 2009/0312543 A1 | 12/2009 | Bebbington et al. |
| 2010/0256170 A1 | 10/2010 | Bebbington et al. |
| 2013/0178486 A1 * | 7/2013 | Aliagas-Martin et al. . 514/265.1 |

FOREIGN PATENT DOCUMENTS

| | | |
|---|---|---|
| WO | 02/22602 A3 | 3/2002 |
| WO | 02/22603 A1 | 3/2002 |
| WO | 02/22604 A1 | 3/2002 |
| WO | 02/22605 A1 | 3/2002 |
| WO | 02/22606 A1 | 3/2002 |
| WO | 02/22607 A1 | 3/2002 |
| WO | 02/22608 A1 | 3/2002 |
| WO | 02/50065 A2 | 6/2002 |
| WO | 02/50065 A3 | 6/2002 |
| WO | WO 0250065 A2 * | 6/2002 |
| WO | 02/057259 A2 | 7/2002 |
| WO | 02/057259 A3 | 7/2002 |
| WO | 02/059111 A2 | 8/2002 |
| WO | 02/059111 A3 | 8/2002 |
| WO | 02/059112 A2 | 8/2002 |
| WO | 02/059112 A3 | 8/2002 |
| WO | 02/062789 a1 | 8/2002 |
| WO | 02/066461 A1 | 8/2002 |
| WO | 02/068415 A1 | 9/2002 |
| WO | 2005/013996 A2 | 2/2005 |
| WO | 2005/013996 A3 | 2/2005 |
| WO | 2005/049033 A1 | 6/2005 |
| WO | 2006/074057 A2 | 7/2006 |
| WO | 2006/074057 A3 | 7/2006 |
| WO | 2006/115452 A1 | 11/2006 |
| WO | 2006/123113 A2 | 11/2006 |
| WO | 2006/123113 A3 | 11/2006 |
| WO | 2007/049041 A1 | 5/2007 |
| WO | 2007/056221 A2 | 5/2007 |
| WO | 2007/056221 A3 | 5/2007 |
| WO | 2007/059299 A1 | 5/2007 |
| WO | 2008/005538 A2 | 1/2008 |
| WO | 2008/005538 A3 | 1/2008 |
| WO | 2008/137619 A2 | 11/2008 |
| WO | 2008/137619 A3 | 11/2008 |
| WO | 2008/147626 A2 | 12/2008 |
| WO | 2008/147626 A3 | 12/2008 |
| WO | 2011/060295 A1 | 5/2011 |
| WO | 2011/060295 A8 | 5/2011 |

* cited by examiner

SERINE/THREONINE KINASE INHIBITORS

CROSS REFERENCE TO PRIOR APPLICATIONS

This application claims the benefit of priority to U.S. Ser. No. 61/527,453 filed Aug. 25, 2011 the contents of which is incorporated by reference in its entirety.

FIELD OF THE INVENTION

The present invention relates to compounds which inhibit serine/threonine kinases and which are useful for treating hyperproliferative and neoplastic diseases by inhibiting signal transduction pathways which commonly are overactive or overexpressed in cancerous tissue. The present compounds are inhibitors of PAK1. The present invention further relates to methods for treating cancer or hyperproliferative diseases with compounds within the scope of the present invention.

BACKGROUND OF THE INVENTION

Protein kinases are a family of enzymes that catalyze phosphorylation of the hydroxyl groups of specific tyrosine, serine, or threonine residues in proteins. Typically, such phosphorylation can dramatically change the function of the protein and thus protein kinases can be pivotal in the regulation of a wide variety of cellular process, including metabolism, cell proliferation, cell differentiation, and cell survival. The mechanism of these cellular processes provides a basis for targeting protein kinases to treat disease conditions resulting from or involving disorder of these cellular processes. Examples of such diseases include, but are not limited to, cancer and diabetes.

Protein kinases can be broken into two types, protein tyrosine kinases (PTKs) and serine-threonine kinases (STKs). Both PTKs and STKs can be receptor protein kinases or non-receptor protein kinases. PAK is a family of non-receptor STKs. The p21-activated protein kinase (PAK) family of serine/threonine protein kinases plays important roles in cytoskeletal organization, cellular morphogenesis, cellular processes and cell survival (Daniels et al., *Trends Biochem. Sci.* 1999 24: 350-355; Sells et al., *Trends Cell. Biol.* 1997 7:162-167). The PAK family consists of six members subdivided into two groups: PAK 1-3 (group I) and PAK 4-6 (group II) which are distinguished based upon sequence homologies and the presence of an autoinhibitory region in group I PAKs. p21-Activated kinases (PAKs) serve as important mediators of Rac and Cdc42 GTPase function as well as pathways required for Ras-driven tumorigenesis. (Manser et al., *Nature* 1994 367:40-46; B. Dummler et al., *Cancer Metathesis Rev.* 2009 28:51-63; R. Kumar et al., *Nature Rev. Cancer* 2006 6:459-473).

Changes in the levels and activities of PAKs and PAK1 in particular, are frequently associated with human malignancies including, but not limited to bladder carcinoma, breast carcinoma, colorectal carcinoma, gastric carcinoma, glioblastoma, hepatocellular carcinoma, ovarian carcinoma and renal cell carcinoma, primary breast adenocarcinoma, squamous non-small cell lung cancer or a squamous head and necks cancer. (J. V. Kichina et al., *Expert. Opin. Ther. Targets* 2010 14(7):703) PAK1 genomic amplification at 11q13 was prevalent in luminal breast cancer, and PAK1 protein expression was associated with lymph node metastasis. Squamous nonsmall cell lung carcinomas (NSCLCs), and head and neck squamous carcinomas have aberrant cytoplasmic expression of PAK1. (C. C. Ong et al., *Proc. Nat. Acad. Sci.*, USA 2011 108(17):7177)

SUMMARY OF THE INVENTION

There is a continuing need for new and novel therapeutic agents which can be used for cancer and hyperproliferative conditions. The PAK family are important signaling molecules frequently over-expressed and/or overactive in many cancerous tissues. Design and development of new pharmaceutical compounds that inhibit or modulate their activirt is essential. In one aspect of the present invention there is provided a compound according to formula I.

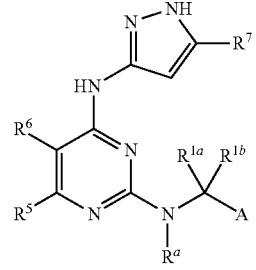

(I)

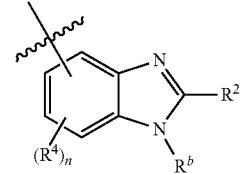

A1

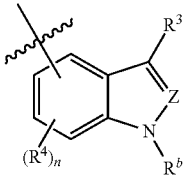

A2

A is A1 or A2. Z is N or $CR^2$. $R^{1a}$ and $R^{1b}$ are (i) each independently hydrogen, $C_{1-6}$ alkyl or $C_{1-6}$ haloalkyl or (ii) $R^{1a}$ and $R^{1b}$ together are $(CH_2)_{2-5}$. $R^2$ is hydrogen, $C_{1-6}$ alkyl, $C_{1-6}$ haloalkyl, $C_{1-6}$ alkoxy, $C_{3-6}$ cycloalkyl or $C_{3-7}$ cycloalkyl-$C_{1-6}$ alkyl. $R^b$ is hydrogen, $C_{1-6}$ alkyl or $C_{3-6}$ cycloalkyl. $R^a$ is hydrogen, $C_{1-6}$ alkyl, $C_{1-6}$ haloalkyl, $C_{1-6}$ hydroxyalkyl, $C_{3-7}$ cycloalkyl-$C_{1-6}$ alkyl or $C_{1-3}$ alkoxy-$C_{1-6}$ alkyl. $R^3$ is hydrogen, $C_{1-6}$ alkyl, $C_{1-6}$ haloalkyl, $C_{1-6}$ alkoxy, $C_{3-7}$ cycloalkyl-$C_{1-6}$ alkyl, $C_{1-3}$ alkoxy-$C_{1-6}$ alkyl, halogen, $C_{1-6}$ acyl or $C_{1-3}$ haloalkanoyl. $R^4$ is independently in each occurrence hydroxy, thiol, cyano, $C_{1-6}$ alkyl, $C_{1-6}$ alkoxy, $C_{3-7}$ cycloalkyl-$C_{1-6}$ alkyl, $C_{1-3}$ alkoxy-$C_{1-6}$ alkyl, $C_{1-6}$ haloalkyl, $C_{1-6}$ haloalkoxy, halogen, $C_{1-6}$ alkoxycarbonyl, carboxyl, $C_{1-6}$ alkylthio, $C_{1-6}$ hydroxyalkyl, nitro, amino, $C_{1-3}$ alkylamino, $C_{1-3}$ dialkylamino, amino-$C_{1-3}$ alkyl, $C_{1-3}$ alkylamino-$C_{1-3}$ alkyl, $C_{1-3}$ dialkylamino $C_{1-3}$ alkyl, $C_{1-6}$ alkylsulfonyl, arylsulfonyl, $C_{1-6}$ alkylaminosulfonyl, arylaminosulfonyl, $C_{1-6}$ alkylsulfonylamido, arylsulfonylamido, carbamoyl, $C_{1-3}$ alkylcarbamoyl and $C_{1-3}$ dialkylcarbamoyl, arylcarbamoyl, $C_{1-6}$ alkylcarbonylamino, arylcarbonylamino. n is zero, one, two or three. $R^5$ is hydrogen, $C_{1-6}$ alkyl, $C_{1-6}$ haloalkyl, $C_{1-6}$ hydroxyalkyl, $C_{1-3}$ alkoxy-$C_{1-6}$ alkyl, cyano, $C_{1-6}$ haloalkoxy or $OR^9$. $R^6$ is hydrogen, halogen, $C_{1-6}$ alkyl, $C_{1-6}$ haloalkyl, cyano, $C_{1-6}$ hydroxyalkyl or $C_{1-3}$ alkoxy-$C_{1-6}$ alkyl. $R^7$ is selected from the group consisting of (i) $C_{1-10}$ alkyl, (ii) $C_{1-10}$ haloalkyl, (iii) optionally substituted $C_{3-7}$ cycloalkyl (iv) $C_{3-7}$ cycloalkyl-$C_{1-6}$ alkyl, (v)

[C(R$^{10}$)$_2$]$_{0-6}$OR (vi) C$_{3-7}$ heterocyclyl and (vii) C$_{3-7}$ heterocyclyl-C$_{1-6}$ alkyl. R$^9$ is independently in each occurrence C$_{1-10}$ alkyl, C$_{1-6}$ haloalkyl, C$_{3-7}$ cycloalkyl, C$_{3-7}$ cycloalkyl-C$_{1-6}$ alkyl, phenyl-C$_{1-6}$ alkyl or phenyl. R$^{10}$ is independently in each occurrence hydrogen or C$_{1-6}$ alkyl. In each occurrence cycloalkyl is independently optionally substituted with C$_{1-6}$ alkyl, halogen or optionally substituted phenyl. In each occurrence phenyl is independently optionally substituted with C$_{1-6}$ alkyl, halogen or C$_{1-6}$ alkoxy. In each occurrence heterocyclyl is independently substituted with halogen or C$_{1-6}$ alkyl. The present invention further comprises a pharmaceutically acceptable salt of said compounds.

The present invention further relates to stereoisomers, tautomers or pharmaceutically acceptable salts of compounds of formula I as described above.

Another aspect of the present invention relates to a method for treating a hyperproliferative disorder by administering a therapeutically effective quantity of a compound according to formula I to a patient in need thereof. The compound can be administered alone or co-administered with at least one other anti-hyperproliferative or chemotherapeutic compound.

Another aspect of the present invention relates to a method for inhibiting PAK activity in a cell comprising treating a cell with a compound according to formula I in an amount effective to attenuate or eliminate PAK activity.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R$^1$, R$^{4a}$, Ar, X$^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:
MeC(=O)OR$^4$ wherein R$^4$=

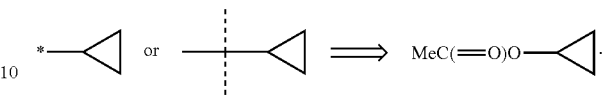

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—⇌—C(—OH)=CH—), amide/imidic acid (—C(=O)—NH—⇌—C(—OH)=N—) and amidine (—C(=NR)—NH—⇌—C(—NHR)=N—) tautomers. The latter two are particularly common in heteroaryl and heterocyclic rings and the present invention encompasses all tautomeric forms of the compounds.

The compounds of formula I may contain an acidic or basic center and suitable salts are formed from acids or bases may form non-toxic salts which have similar antiviral activity. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

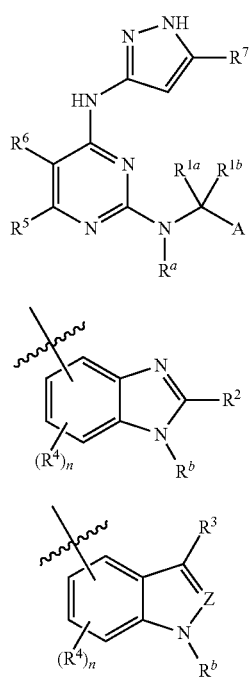

(I)

A1

A2

In one embodiment of the present invention there is provided a compound according to formula I wherein A is A-1 or A-2; Z is N or $CR^2$; $R^{1a}$ and $R^{1b}$ are (i) each independently hydrogen, $C_{1-6}$ alkyl, $C_{1-6}$ haloalkyl, $C_{1-6}$ hydroxyalkyl or $C_{1-3}$ alkoxy-$C_{1-6}$ alkyl, or, (ii) $R^{1a}$ and $R^{1b}$ together are $(CH_2)_{2-5}$; $R^2$ is hydrogen, $C_{1-6}$ alkyl, $C_{1-6}$ alkoxy or $C_{3-6}$ cycloalkyl; $R^b$ is hydrogen, $C_{1-6}$ alkyl or $C_{3-6}$ cycloalkyl; $R^a$ is hydrogen, $C_{1-6}$ alkyl, $C_{1-6}$ haloalkyl, $C_{1-6}$ hydroxyalkyl or $C_{1-3}$ alkoxy-$C_{1-6}$ alkyl; $R^3$ is hydrogen, $C_{1-6}$ alkyl, $C_{1-6}$ haloalkyl, $C_{1-6}$ alkoxy, halogen, $C_{1-6}$ acyl or $C_{1-3}$ haloalkanoyl; $R^4$ is independently in each occurrence hydroxy, thiol, cyano, $C_{1-6}$ alkyl, $C_{1-6}$ alkoxy, $C_{1-6}$ haloalkyl, $C_{1-6}$ haloalkoxy, halogen, $C_{1-6}$ alkoxycarbonyl, carboxyl, $C_{1-6}$ alkylthio, $C_{1-6}$ hydroxyalkyl, nitro, amino, $C_{1-3}$ alkylamino, $C_{1-3}$ dialkylamino, amino-$C_{1-3}$ alkyl, $C_{1-3}$ alkylamino-$C_{1-3}$ alkyl, $C_{1-3}$ dialkylamino $C_{1-3}$ alkyl, $C_{1-6}$ alkylsulfonyl, arylsulfonyl, $C_{1-6}$ alkylaminosulfonyl, arylaminosulfonyl, $C_{1-6}$ alkylsulfonylamido, arylsulfonylamido, carbamoyl, $C_{1-3}$ alkylcarbamoyl and $C_{1-3}$ dialkylcarbamoyl, arylcarbamoyl, $C_{1-6}$ alkylcarbonylamino, arylcarbonylamino; n is zero, one, two or three; $R^5$ is hydrogen, $C_{1-6}$ alkyl, $C_{1-6}$ haloalkyl, $C_{1-6}$ hydroxyalkyl, $C_{1-3}$ alkoxy-$C_{1-6}$ alkyl, cyano or $OR^9$; $R^6$ is hydrogen, halogen, $C_{1-6}$ alkyl, $C_{1-6}$ haloalkyl, cyano, $C_{1-6}$ hydroxyalkyl or $C_{1-3}$ alkoxy-$C_{1-6}$ alkyl; $R^7$ is selected from the group consisting of (i) $C_{1-10}$ alkyl, (ii) $C_{1-10}$ haloalkyl, (iii) optionally substituted $C_{3-7}$ cycloalkyl (iv) $C_{3-7}$ cycloalkyl-$C_{1-6}$ alkyl, (v) $R^9O[C(R^{10})_2]_{0-6}$, (vi) $C_{3-7}$ heterocyclyl and (vii) $C_{3-7}$ heterocyclyl-$C_{1-6}$ alkyl; $R^9$ is independently in each occurrence $C_{1-10}$ alkyl, $C_{1-6}$ haloalkyl, $C_{3-7}$ cycloalkyl, $C_{3-7}$ cycloalkyl-$C_{1-6}$ alkyl, phenyl-$C_{1-6}$ alkyl or phenyl; $R^{10}$ is independently in each occurrence hydrogen or $C_{1-6}$ alkyl; said cycloalkyl in each occurrence is independently optionally substituted with $C_{1-6}$ alkyl, halogen or optionally substituted phenyl; said phenyl in each occurrence is independently optionally substituted with $C_{1-6}$ alkyl, halogen or $C_{1-6}$ alkoxy; said heterocyclyl is independently substituted with halogen or $C_{1-6}$ alkyl; or, a pharmaceutically acceptable salt thereof.

In one embodiment of the present invention there is provided a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above. The phrase "as defined herein above" when referring to a variable incorporates by reference the broadest definition for each group as provided in the Summary of the Invention or the broadest claim. In all other embodiments provided below substituents which can be present in each embodiment and which are not explicitly defined retain the broadest definition permitted in the Summary of the Invention.

In another embodiment of the present invention there is provided a compound according to formula I wherein A is optionally substituted A2, Z is $CR^2$ and $R^2$ and $R^b$ are hydrogen.

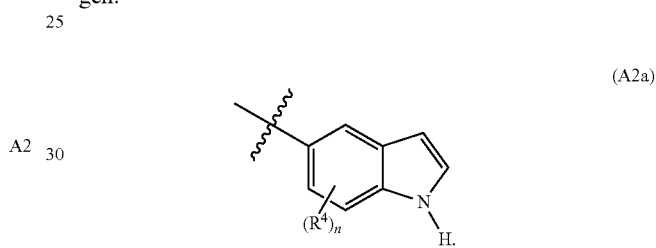

(A2a)

In another embodiment of the present invention there is provided a compound according to formula I wherein A is optionally substituted indol-5-yl (A2a).

In another embodiment of the present invention there is provided a compound according to formula I where A is optionally substituted A2a; $R^{1a}$ is hydrogen or $C_{1-6}$ alkyl; $R^a$ is hydrogen, $C_{1-6}$ alkyl or $R^cR^dN[C(R^{10})_2]_{2-6}$; $R^{1b}$ is hydrogen; $R^5$ is hydrogen, $C_{1-6}$ alkyl or $C_{1-6}$ haloalkyl; $R^6$ is hydrogen or halogen; and, $R^7$ is $C_{1-6}$ haloalkyl, optionally substituted $C_{4-7}$ cycloalkyl or $C_{3-7}$ heterocyclyl.

In another embodiment of the present invention there is provided a compound according to formula I where A is optionally substituted A2a; $R^{1a}$ is hydrogen or $C_{1-6}$ alkyl, $R^a$ is hydrogen, $C_{1-6}$ alkyl or $R^cR^dN[C(R^{10})_2]_{2-6}$; $R^{1b}$ is hydrogen; $R^5$ is $C_{1-6}$ alkyl or $C_{1-6}$ haloalkyl; $R^6$ is hydrogen or halogen; and $R^7$ is optionally substituted $C_{4-7}$ cycloalkyl or $C_{3-7}$ heterocyclyl.

In another embodiment of the present invention there is provided a compound according to formula I where A is optionally substituted A2a; $R^{1a}$ is hydrogen or $C_{1-6}$ alkyl; $R^a$ is $C_{1-6}$ hydroxyalkyl or $C_{1-3}$ alkoxy-$C_{1-6}$ alkyl; $R^{1b}$ is hydrogen; $R^5$ is hydrogen, $C_{1-6}$ alkyl or $C_{1-6}$ haloalkyl; $R^6$ is hydrogen or halogen; and $R^7$ is $C_{1-6}$ haloalkyl, optionally substituted $C_{4-7}$ cycloalkyl or $C_{3-7}$ heterocyclyl. In a subembodiment $R^7$ is optionally substituted mono- or difluorocyclopropyl.

In another embodiment of the present invention there is provided a compound according to formula I where A is optionally substituted A2a; $R^{1a}$ is hydrogen or $C_{1-6}$ alkyl; $R^a$ is hydrogen, $C_{1-6}$ alkyl or $R^cR^dN[C(R^{10})_2]_{2-6}$; $R^{1b}$ is hydrogen; $R^5$ is hydrogen, $C_{1-6}$ alkyl or $C_{1-6}$ haloalkyl; $R^6$ is hydrogen or halogen; and $R^7$ is optionally substituted $C_{3-7}$ cycloalkyl, $C_{1-6}$ haloalkyl, oxirane, oxetan-2-yl, oxetan-3-yl, tetrahydrofuran-2-yl, tetrahydrofuran-3-yl or tetrahydropyranyl.

In another embodiment of the present invention there is provided a compound according to formula I where A is optionally substituted A2a, $R^{1a}$ is hydrogen or $C_{1-6}$ alkyl; $R^a$ is hydrogen, $C_{1-6}$ alkyl or $R^cR^dN[C(R^{10})_2]_{2-6}$; $R^{1b}$ is hydrogen; $R^5$ is hydrogen, $C_{1-6}$ alkyl or $C_{1-6}$ haloalkyl; $R^6$ is hydrogen or halogen; and $R^7$ is mono- or difluorocyclopropyl.

In another embodiment of the present invention there is provided a compound according to formula I where A is optionally substituted A2a; $R^{1a}$ is hydrogen or $C_{1-6}$ alkyl; $R^2$ is hydrogen, $C_{1-6}$ alkyl or $R^cR^dN[C(R^{10})_2]_{2-6}$; $R^{1b}$ is hydrogen; $R^5$ is $C_{1-6}$ alkyl or $C_{1-6}$ haloalkyl; $R^6$ is hydrogen or halogen; and $R^7$ is optionally substituted mono- or difluorocyclopropyl.

(A2c)

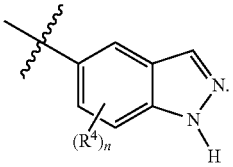

In another embodiment of the present invention there is provided a compound according to formula I where A is optionally substituted indazol-5-yl (A2c); $R^{1a}$ is hydrogen or $C_{1-6}$ alkyl; $R^a$ is hydrogen, $C_{1-6}$ alkyl or $R^cR^dN[C(R^{10})_2]_{2-6}$; $R^{1b}$ is hydrogen; $R^5$ is hydrogen, $C_{1-6}$ alkyl or $C_{1-6}$ haloalkyl; $R^6$ is hydrogen or halogen; and $R^7$ is optionally substituted $C_{3-7}$ cycloalkyl, $C_{1-6}$ haloalkyl, oxirane, oxetan-2-yl, oxetan-3-yl, tetrahydrofuran-2-yl, tetrahydrofuran-3-yl or tetrahydropyranyl.

In another embodiment of the present invention there is provided a compound according to formula I where A is optionally substituted indazol-5-yl (A2c); $R^{1a}$ is hydrogen or $C_{1-6}$ alkyl; $R^a$ is hydrogen, $C_{1-6}$ alkyl or $R^cR^dN[C(R^{10})_2]_{2-6}$; $R^{1b}$ is hydrogen; $R^5$ is hydrogen, $C_{1-6}$ alkyl or $C_{1-6}$ haloalkyl; $R^6$ is hydrogen or halogen; and, $R^7$ mono- or difluorocyclopropyl.

In another embodiment of the present invention there is provided a compound according to formula I where A is optionally substituted A2a; $R^{1a}$ is $C_{1-6}$ alkyl; $R^{1b}$ is hydrogen and the carbon bearing $R^{1a}$ and $R^{1b}$ is in the S configuration; $R^a$ is hydrogen, $C_{1-6}$ alkyl or $R^cR^dN[C(R^{10})_2]_{2-6}$; $R^5$ is $C_{1-6}$ alkyl or $C_{1-6}$ haloalkyl; $R^6$ is hydrogen or halogen; and, $R^7$ is $C_{1-6}$ haloalkyl, optionally substituted $C_{4-7}$ cycloalkyl or $C_{3-7}$ heterocyclyl. In a sub-embodiment $R^7$ optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl. In another subembodiment $R^7$ mono- or difluorocyclopropyl.

(A2b)

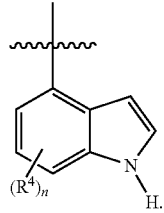

In another embodiment of the present invention there is provided a compound according to formula I wherein A is optionally substituted indol-4-yl (A2b).

In another embodiment of the present invention there is provided a compound according to formula I where A is optionally substituted A2b, $R^{1a}$ is hydrogen or $C_{1-6}$ alkyl; $R^a$ is hydrogen, $C_{1-6}$ alkyl or $R^cR^dN[C(R^{10})_2]_{2-6}$; $R^{1b}$ is hydrogen; $R^5$ is hydrogen, $C_{1-6}$ alkyl or $C_{1-6}$ haloalkyl; $R^6$ is hydrogen or halogen; and, $R^7$ is optionally substituted $C_{3-7}$ cycloalkyl, $C_{3-7}$ heterocyclyl or $C_{1-6}$ haloalkyl.

In another embodiment of the present invention there is provided a compound according to formula I where A is optionally substituted A2b, $R^{1a}$ is hydrogen or $C_{1-6}$ alkyl, $R^a$ is independently hydrogen, $C_{1-6}$ alkyl or $R^cR^dN[C(R^{10})_2]_{2-6}$; $R^{1b}$ is hydrogen; $R^5$ is hydrogen, $C_{1-6}$ alkyl or $C_{1-6}$ haloalkyl; $R^6$ is hydrogen or halogen; and, $R^7$ is mono- or difluorocycloalkyl.

In another embodiment of the present invention there is provided a compound according to formula I where A is optionally substituted A2b, $R^{1a}$ is hydrogen or $C_{1-6}$ alkyl; $R^a$ is independently hydrogen, $C_{1-6}$ alkyl or $R^cR^dN[C(R^{10})_2]_{2-6}$; $R^{1b}$ is hydrogen; $R^5$ is $C_{1-6}$ alkyl or $C_{1-6}$ haloalkyl; $R^6$ is hydrogen or halogen; and, $R^7$ is optionally substituted $C_{4-7}$ cycloalkyl or $C_{3-7}$ heterocyclyl.

In another embodiment of the present invention there is provided a compound according to formula I where A is optionally substituted A2b, $R^{1a}$ is hydrogen or $C_{1-6}$ alkyl; $R^a$ is $C_{1-6}$ hydroxyalkyl or $C_{1-3}$ alkoxy-$C_{1-6}$ alkyl; $R^{1b}$ is hydrogen; $R^5$ is hydrogen, $C_{1-6}$ alkyl or $C_{1-6}$ haloalkyl; $R^6$ is hydrogen or halogen; and, $R^7$ is optionally substituted $C_{3-7}$ cycloalkyl, $C_{3-7}$ heterocyclyl or $C_{1-6}$ haloalkyl. In a subembodiment $R^7$ is mono- or difluorocyclopropyl.

In another embodiment of the present invention there is provided a compound according to formula I where A is optionally substituted A2b, $R^{1a}$ is hydrogen or C1-6 alkyl; $R^a$ is hydrogen, $C_{1-6}$ alkyl or $R^cR^dN[C(R^{10})_2]_{2-6}$; $R^{1b}$ is hydrogen $R^5$ is hydrogen, $C_{1-6}$ alkyl or $C_{1-6}$ haloalkyl; $R^6$ is hydrogen or halogen; and, $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl.

In another embodiment of the present invention there is provided a compound according to formula I where A is optionally substituted A2b, $R^{1a}$ is $C_{1-6}$ alkyl; $R^{1b}$ is hydrogen and the carbon bearing $R^{1a}$ and $R^{1b}$ is in the S configuration; $R^a$ is hydrogen, $C_{1-6}$ alkyl or $R^cR^dN[C(R^{10})_2]_{2-6}$; $R^5$ is hydrogen, $C_{1-6}$ alkyl or $C_{1-6}$ haloalkyl; $R^6$ is hydrogen or halogen; and, $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl.

In another embodiment of the present invention there is provided a compound according to formula I wherein A is A-1 and $R^2$ are hydrogen or $C_{1-6}$ alkyl.

In another embodiment of the present invention there is provided a compound according to formula I wherein A is optionally substituted benzimidazol-5-yl (A1a) and $R^2$ is hydrogen or $C_{1-6}$ alkyl.

In another embodiment of the present invention there is provided a compound according to formula I where A is optionally substituted A1a; $R^{1a}$ is hydrogen or $C_{1-6}$ alkyl; $R^a$ is hydrogen, $C_{1-6}$ alkyl or $R^cR^dN[C(R^{10})_2]_{2-6}$; $R^{1b}$ is hydrogen; $R^2$ is hydrogen or $C_{1-6}$ alkyl; $R^5$ is hydrogen, $C_{1-6}$ alkyl or $C_{1-6}$ haloalkyl; $R^6$ is hydrogen or halogen; and $R^7$ is $C_{1-6}$ haloalkyl, optionally fluorinated $C_{4-7}$ cycloalkyl or $C_{3-7}$ heterocyclyl.

In another embodiment of the present invention there is provided a compound according to formula I where A is optionally substituted A1a; $R^{1a}$ is hydrogen or $C_{1-6}$ alkyl; $R^a$ is $C_{1-6}$ hydroxyalkyl or $C_{1-3}$ alkoxy-$C_{1-6}$ alkyl; $R^{1b}$ is hydrogen; $R^2$ is hydrogen or $C_{1-6}$ alkyl; $R^5$ is hydrogen $C_{1-6}$ alkyl or $C_{1-6}$ haloalkyl; $R^6$ is hydrogen or halogen; and $R^7$ is $C_{1-6}$ haloalkyl, optionally fluorinated $C_{4-7}$ cycloalkyl or $C_{3-7}$ heterocyclyl. In a subembodiment $R^7$ is mono- or difluorocyclopropyl.

In another embodiment of the present invention there is provided a compound according to formula I where A is optionally substituted A1a; $R^{1a}$ is hydrogen or $C_{1-6}$ alkyl; $R^a$ is hydrogen, $C_{1-6}$ alkyl or $R^cR^dN[C(R^{10})_2]_{2-6}$; $R^{1b}$ is hydrogen; $R^2$ is hydrogen or $C_{1-6}$ alkyl; $R^5$ is hydrogen, $C_{1-6}$ alkyl or $C_{1-6}$ haloalkyl; $R^6$ is hydrogen or halogen and $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl. In a subembodiment $R^7$ is mono- or difluorocyclopropyl.

In another embodiment of the present invention there is provided a compound according to formula I where A is optionally substituted A1a, $R^{1a}$ is hydrogen or $C_{1-6}$ alkyl; $R^a$ is $C_{1-6}$ hydroxyalkyl or $C_{1-3}$ alkoxy-$C_{1-6}$ alkyl; $R^{1b}$ is hydrogen; $R^5$ is hydrogen $C_{1-6}$ alkyl or $C_{1-6}$ haloalkyl; $R^6$ is hydrogen or halogen and $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl. In a sub-embodiment $R^7$ is mono- or difluoro-cycloalkyl.

In another embodiment of the present invention there is provided a compound according to formula I where A is optionally substituted A1a, $R^{1a}$ is $C_{1-6}$ alkyl; $R^{1b}$ is hydrogen and the carbon bearing $R^{1a}$ and $R^{1b}$ is in the S configuration; $R^a$ is hydrogen, $C_{1-6}$ alkyl or $R^cR^dN[C(R^{10})_2]_{2-6}$; $R^2$ is hydrogen or $C_{1-6}$ alkyl; $R^5$ is hydrogen $C_{1-6}$ alkyl or $C_{1-6}$ haloalkyl; $R^6$ is hydrogen or halogen and $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl. In a sub-embodiment $R^7$ is mono- or difluoro-cycloalkyl.

In another embodiment of the present invention there is provided a compound according to formula I wherein A is optionally substituted A1b.

In another embodiment of the present invention there is provided a compound according to formula I wherein A is optionally substituted A1b; $R^{1a}$ and $R^2$ are hydrogen or $C_{1-6}$ alkyl; $R^{1b}$ is hydrogen; $R^a$ is hydrogen, $C_{1-6}$ alkyl or $R^cR^dN[C(R^{10})_2]_{2-6}$; $R^5$ is hydrogen $C_{1-6}$ alkyl or $C_{1-6}$ haloalkyl; $R^6$ is hydrogen or halogen and $R^7$ is optionally substituted $C_{3-7}$ cycloalkyl, $C_{3-7}$ heterocyclyl or $C_{1-6}$ haloalkyl. In a sub-embodiment $R^7$ is mono- or difluorocycloalkyl.

In another embodiment of the present invention there is provided a compound according to formula I wherein A is optionally substituted A1b; $R^{1a}$ and $R^2$ are hydrogen or $C_{1-6}$ alkyl; $R^{1b}$ is hydrogen; $R^a$ is hydrogen, $C_{1-6}$ alkyl or $R^cR^dN[C(R^{10})_2]_{2-6}$; $R^{1b}$ is hydrogen; $R^5$ is hydrogen, $C_{1-6}$ alkyl or $C_{1-6}$ haloalkyl; $R^6$ is hydrogen or halogen and $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl. In a sub-embodiment $R^7$ is mono- or difluorocycloalkyl.

In another embodiment of the present invention there is provided a compound according to formula I wherein A is optionally substituted A1b; $R^{1a}$ and $R^2$ are hydrogen or $C_{1-6}$ alkyl; $R^a$ is $C_{1-6}$ hydroxyalkyl or $C_{1-3}$ alkoxy-$C_{1-6}$ alkyl; $R^{1b}$ is hydrogen; $R^5$ is hydrogen $C_{1-6}$ alkyl or $C_{1-6}$ haloalkyl; $R^6$ is hydrogen or halogen and $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl.

In another embodiment of the present invention there is provided a compound according to formula I wherein A is optionally substituted A1b; $R^{1a}$ is $C_{1-6}$ alkyl; $R^{1b}$ is hydrogen and the carbon bearing $R^{1a}$ and $R^{1b}$ is in the S configuration; $R^a$ is hydrogen, $C_{1-6}$ alkyl or $R^cR^dN[C(R^{10})_2]_{2-6}$; $R^{1b}$ is hydrogen; $R^2$ are hydrogen or $C_{1-6}$ alkyl; $R^5$ is hydrogen $C_{1-6}$ alkyl or $C_{1-6}$ haloalkyl; $R^6$ is hydrogen or halogen and $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl. In a sub-embodiment $R^7$ is mono- or difluorocycloalkyl.

In another embodiment of the present invention there is provided a compound according to formula I wherein A is optionally substituted A2; Z is N, $R^b$ is hydrogen and $R^3$ is hydrogen, $C_{1-6}$ alkyl or $C_{1-6}$ alkoxy.

In another embodiment of the present invention there is provided a compound according to formula I wherein A is optionally substituted A2; Z is N, $R^b$ is hydrogen and $R^3$ is hydrogen, $C_{1-6}$ alkyl or $C_{1-6}$ alkoxy; $R^{1a}$ is hydrogen or $C_{1-6}$ alkyl; $R^a$ is hydrogen, $C_{1-6}$ alkyl or $R^cR^dN[C(R^{10})_2]_{2-6}$; $R^{1b}$ is hydrogen; $R^5$ is hydrogen $C_{1-6}$ alkyl or $C_{1-6}$ haloalkyl; $R^6$ is hydrogen or halogen and $R^7$ is optionally substituted $C_{3-7}$ cycloalkyl, $C_{3-7}$ heterocyclyl or $C_{1-6}$ haloalkyl.

In another embodiment of the present invention there is provided a compound according to formula I wherein A is optionally substituted A-2, Z is N, $R^b$ is hydrogen and $R^3$ is hydrogen, $C_{1-6}$ alkyl or $C_{1-6}$ alkoxy; $R^{1a}$ is hydrogen or $C_{1-6}$ alkyl; $R^a$ is hydrogen, $C_{1-6}$ alkyl or $R^cR^dN[C(R^{10})_2]_{2-6}$; leis hydrogen; $R^5$ is hydrogen $C_{1-6}$ alkyl or $C_{1-6}$ haloalkyl; $R^6$ is hydrogen or halogen and $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl. In a sub-embodiment $R^7$ is mono- or difluoro-cycloalkyl.

In an embodiment of the present invention there is provided a compound according to formula I which compound is any one or more compounds selected from the group consisting of compounds I-1 to I-117 of TABLE I or compounds II-1 to II-113 of TABLE II.

In another embodiment of the present invention there is provided a method for inhibiting PAK1 activity in a cell comprising contacting the cell with a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above.

In another embodiment of the present invention there is provided a method for inhibiting PAK activity in a cell comprising treating the cell with a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above.

In another embodiment of the present invention there is provided a method for inhibiting PAK activity in a patient in need thereof comprising administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above.

In another embodiment of the present invention there is provided a method of treating or ameliorating the severity of cancer or a hyperproliferative disorder in a patient in need thereof comprising administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above.

In another embodiment of the present invention there is provided a method of treating or ameliorating the severity of cancer or a hyperproliferative disorder in a patient in need thereof herein said cancer or hyperproliferative disorder is selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, heptoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma comprising administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above.

In another embodiment of the present invention there is provided a method of treating or ameliorating the severity of cancer or a hyperproliferative disorder in a patient in need thereof wherein said cancer or hyperproliferative disorder is selected from the group consisting of lung cancer, breast cancer, ovarian cancer, bladder cancer and head and neck cancer comprising administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above.

In another embodiment of the present invention there is provided a method of treating or ameliorating the severity of cancer or a hyperproliferative disorder in a patient in need thereof wherein said cancer or hyperproliferative disorder is selected from the group consisting primary breast adenocarcinoma, squamous non-small cell lung cancer or a squamous head and neck cancer comprising administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above.

In another embodiment of the present invention there is provided a method of treating or ameliorating the severity of cancer or a hyperproliferative disorder in a patient in need thereof comprising administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n and wherein said cancer or hyperproliferative disorder is primary breast adenocarcinoma.

In another embodiment of the present invention there is provided a method of treating or ameliorating the severity of cancer or a hyperproliferative disorder in a patient in need thereof comprising administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n and wherein said cancer or hyperproliferative disorder is squamous non-small cell lung cancer.

In another embodiment of the present invention there is provided a method of treating or ameliorating the severity of cancer or a hyperproliferative disorder in a patient in need thereof comprising administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n and wherein said cancer or hyperproliferative disorder is squamous head and neck cancer.

In another embodiment of the present invention there is provided a method of treating or ameliorating the severity of cancer or a hyperproliferative disorder in a patient in need thereof comprising co-administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above with at least one other chemotherapeutic agent used to treat or ameliorate cancer or a hyperproliferative disorder.

In another embodiment of the present invention there is provided a method of treating or ameliorating the severity of cancer or a hyperproliferative disorder in a patient in need thereof comprising co-administering a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n as defined herein above and a chemotherapeutic agent is selected from the group consisting of inhibitor of apoptosis proteins (IAP), an EGFR inhibitor or antagonist, an inhibitor of Ras/Raf/Mek/Erk signaling cascade, an inhibitor of Akt kinase and a Src kinase inhibitor.

In another embodiment of the present invention there is provided a compound according to formula I wherein A, Z, $R^{1a}$, $R^{1b}$, $R^2$, $R^3$, $R^4$, $R^5$, $R^6$, $R^7$, $R^9$, $R^{10}$, $R^a$, $R^b$, $R^c$, $R^d$ and n are as defined herein above and at least one pharmaceutically acceptable carrier, excipient or diluent.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as Fieser and Fieser's *Reagents for Organic Synthesis*; Wiley & Sons: New York, Volumes 1-21; R. C. LaRock, Comprehensive Organic Transformations, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted by at least one substituent selected from the other specifically-named group. Thus, for example, "phenylalkyl" refers to an alkyl group having one to two phenyl substituents, and thus includes benzyl (phenylmethyl) and phenylethyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to a moiety that is either an aryl or a heteroaryl group.

The term "alkyl" as used herein without further limitation, alone or in combination with other groups, denotes an unbranched or branched chain, saturated, monovalent hydrocarbon residue containing 1 to 10 carbon atoms, for example, methyl, ethyl, propyl, isopropyl, n-butyl, iso-butyl, sec-butyl, or tert-butyl. The term "lower alkyl" denotes a straight or branched chain hydrocarbon residue containing 1 to 6 carbon atoms. "$C_{1-6}$ alkyl" as used herein refers to an alkyl composed of 1 to 6 carbons.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having one (e.g., a spirocycle) two or more carbon atoms in common. For example, "$C_{3-7}$ cycloalkyl" as used herein refers to a cycloalkyl composed of 3 to 7 carbons in the carbocyclic ring.

Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "alkoxy" as used herein means an —O-alkyl group, wherein alkyl is as defined above such as methoxy, ethoxy, n-propyloxy, iso-propyloxy, n-butyloxy, iso-butyloxy, tert-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "acyl", "alkanoyl" or "alkylcarbonyl" denotes a group of the formula —C(O)—R in which R is hydrogen or alkyl as defined above. The term $C_{1-6}$ acyl [or "alkanoyl"] refers to a group —C(=O)R contain 1 to 6 carbon atoms. The $C_1$ acyl or "alkanoyl" is the formyl group wherein R=H and a $C_6$ acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The terms "alkoxycarbonyl" and "aryloxycarbonyl" as used herein denotes a group of formula C(=O)OR wherein R is alkyl or aryl respectively and alkyl and aryl are as defined herein.

The term "haloalkoxy" as used herein refers to a group —OR where R is haloalkyl as defined herein. Examples of haloalkoxyl include monofluoro-, difluoro- or trifluoro-methoxy-, ethoxy- or propoxy-, 3,3,3-trifluoropropoxy-, 2-fluoroethoxy-, 2,2,2-trifluoroethoxy-, fluoromethoxy-, or trifluoromethoxy-. The term "haloalkylthio" as used herein refers to a group —SR where R is haloalkyl as defined herein.

The term "haloalkanoyl" refers to an alkanoyl group wherein at least one of the hydrogen atoms of the alkyl group has been replaced by same or different halogen atoms, The term "halo", "halogen", and "halide" are used interchangeably herein and denote fluoro, chloro, bromo, or iodo.

The terms "amino", "alkylamino" and "dialkylamino" as used herein refers to —NH$_2$, —NHR and —NR$_2$ respectively and R is alkyl as defined above. The two alkyl groups attached to a nitrogen in a dialkyl moiety can be the same or different.

The terms "aminoalkyl", "alkylaminoalkyl" and "dialkylaminoalkyl" as used herein refer to NH$_2$(alkylene)$_n$-RHN(alkylene)$_n$-, and R$_2$N(alkylene)$_n$- respectively wherein R is alkyl, and both alkylene and alkyl are as defined herein and n is the number of carbon atoms in the alkylene chain. "$C_{1-10}$ alkylamino" as used herein refers to an aminoalkyl wherein alkyl is $C_{1-10}$. "$C_{1-10}$ alkyl-amino-$C_{2-6}$ alkyl" as used herein refers to a $C_{1-10}$ alkylamino(alkylene)$_{2-6}$ wherein alkyl is $C_{1-10}$ and the alkylene is (CH$_2$)$_{2-6}$. When the alkylene group contains three or more carbon atoms, the alkylene can be linear, e.g. —(CH$_2$)$_4$— or branched, e.g., —(CMe$_2$CH$_2$)—. The term "phenylamino" as used herein refers to —NHPh wherein Ph represents an optionally substituted phenyl group.

The term "alkylene" as used herein denotes a divalent saturated linear hydrocarbon radical of 1 to 10 carbon atoms (e.g., (CH$_2$)$_n$) or a branched saturated divalent hydrocarbon radical of 2 to 10 carbon atoms (e.g., —CHMe- or —CH$_2$CH(i-Pr)CH$_2$—), unless otherwise indicated. "$C_{0-4}$ alkylene" refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkylsulfanyl" or "alkylthio" denotes the group —S—R', wherein R' is an alkyl group as defined herein. Examples of alkylthio groups include methylthio and butylthio.

The terms "alkylsulfonyl" and "arylsulfonyl" as used herein denotes a group of formula The terms "alkylsulfonyl" and "arylsulfonyl" as used herein denotes a group of formula —S(=O)$_2$R wherein R is alkyl or aryl respectively and alkyl and aryl are as defined herein. The term $C_{1-3}$ alkylsulfonylamido as used herein refers to a group RSO$_2$NH— wherein R is a $C_{1-3}$ alkyl group as defined herein.

The term "aminosulfonyl" as used herein refers to the radical —S(O)$_2$NH$_2$. The terms "alkylaminosulfonyl" and "dialkylaminosulfonyl" as used herein refers to the radical —S(O)$_2$NR'R", wherein R' and R" are hydrogen and lower alkyl and R' and R" are independently lower alkyl respectively. Examples of alkylaminosulfonyl include, but are not limited to methylaminosulfonyl, iso-propylaminosulfonyl. Examples of dialkylaminosulfonyl include, but are not limited to dimethylaminosulfonyl, iso-propyl-methylaminosulfonyl.

The term "alkylsulfonamido" refers to the radical —NH—S(O)$_2$-alkyl. The term alkyl can be replaced by other chemically relevant radicals such as aryl or heteroaryl to indicate, e.g. phenylsulfonamido —NH—S(O)$_2$-Ph. "N-alkylalkylsulfonamido" refers to the radical —NR—S(O)$_2$-alkyl where R is a lower alkyl group.

The term "carbamoyl" as used herein means the radical —CONH$_2$. The prefix "N-alkylcarbamoyl" and "N,N-dialkylcarbamoyl" means a the radical CONHR' or CONR'R" respectively wherein the R' and R" groups are independently alkyl as defined herein. The prefix N-arylcarbamoyl" denotes the radical CONHR' wherein R' is an aryl radical as defined herein.

The terms "alkylcarbonylamino" and "arylcarbonylamino" as used herein denotes a group of formula —NC(=O)R wherein R is alkyl or aryl respectively and alkyl and aryl are as defined herein.

The term "heterocyclyl" or "heterocycle" as used herein denotes a monovalent saturated cyclic radical, consisting of one or more rings, preferably one to two rings, of three to eight atoms per ring, incorporating one or more ring heteroatoms (chosen from N, O or S(=O)$_{0-2}$) with the remaining ring atoms being carbon, with the understanding that the attachment point of the heteroaryl radical will be on a carbon atom. The heterocyclyl moiety can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamido, arylsulfonylamido, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The terms "treat" and "treatment" refer to therapeutic treatment wherein the object is to slow down (lessen) an undesired physiological change or disorder, such as the spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®., Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Commonly used abbreviations include: acetyl (Ac), aqueous (aq.), atmospheres (Atm), tert-butoxycarbonyl (Boc), di-tert-butyl pyrocarbonate or boc anhydride (BOC2O), benzyl (Bn), benzotriazol-1-yloxy-tris-(dimethylamino)phosphonium hexafluorophosphate (BOP), butyl (Bu), benzoyl (Bz), Chemical Abstracts Registration Number (CASRN), benzyloxycarbonyl (CBZ or Z), carbonyl diimidazole (CDI), dibenzylideneacetone (DBA), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et2O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), MeSO2-(mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), petroleum ether (pet ether, i.e. hydrocarbons)) phenyl (Ph), propyl (Pr), iso-propyl (i-Pr), pounds per square inch (psi), bromo-tris-pyrrolidinophosphonium hexafluorophosphate (PyBrOP), pyridine (pyr), room temperature (rt or RT), satd. (saturated), tert-butyldimethylsilyl or t-BuMe$_2$Si (TBDMS), triethylamine (TEA or Et3N), triflate or CF3SO2-(Tf), trifluoroacetic acid (TFA), O-benzotriazol-1-yl-N,N,N', N'-tetramethyluronium tetrafluoroborate (TBTU), thin layer chromatography (TLC), tetrahydrofuran (THF), tetramethylethylenediamine (TMEDA), trimethylsilyl or Me3Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert- or -t) and neo- have their customary meaning when used with an alkyl moiety. (J. Rigaudy and D. P. Klesney, Nomenclature in Organic Chemistry, IUPAC 1979 Pergamon Press, Oxford.)

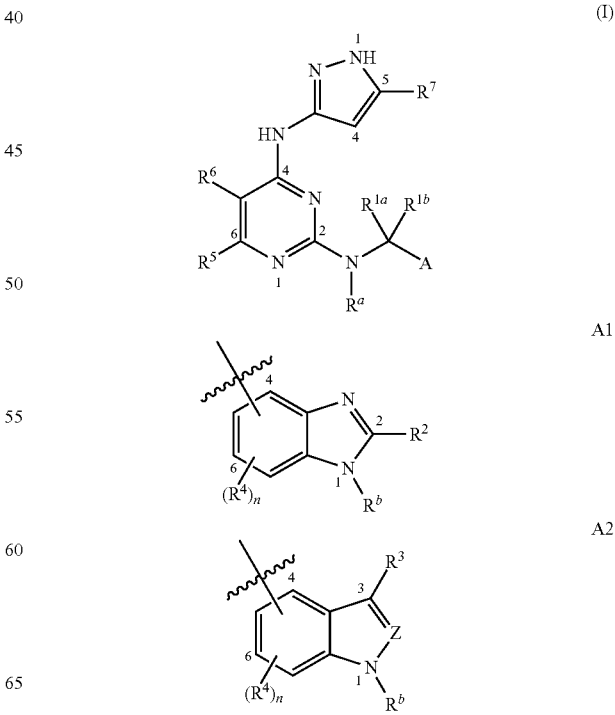

TABLE I

| Cpd. No. | Structure | $K_i^5$ | MS[2] | $^1$H NMR | Name |
|---|---|---|---|---|---|
| I-1 | 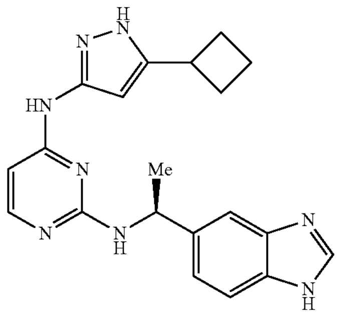 [SMILES: C[C@H](Nc1nccc(Nc2cc(C3CCC3)[nH]n2)n1)c1ccc2[nH]cnc2c1] | A | 375.2 | (DMSO-d$_6$) δ 12.29 (s, 1H), 11.86 (s, 1H), 9.22 (s, 1H), 8.12 (s, 1H), 7.76 (d, J = 5.0 Hz, 1H), 7.60-7.45 (m, 1H), 7.40 (t, J = 14.9 Hz, 1H), 7.24 (dd, J = 19.5, 8.4 Hz, 1H), 7.11 (s, 1H), 6.27 (s, 1H), 6.11 (s, 1H), 5.23 (s, 1H), 3.61-3.37 (m, 1H), 2.36-2.19 (m, 2H), 2.19-2.03 (m, 2H), 1.97 (dd, J = 18.4, 9.0 Hz, 1H), 1.84 (t, J = 26.9 Hz, 1H), 1.48 (d, J = 7.0 Hz, 3H). | N$^2$-[(S)-1-(1H-Benzoimidazol-5-yl)-ethyl]-N$^4$-(5-cyclopentyl-1H-pyrazol-3-yl)-pyrimidine-2,4-diamine |
| I-2 | 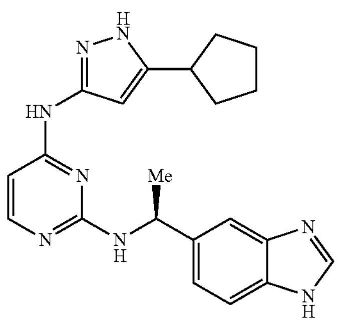 [SMILES: C[C@H](Nc1nccc(Nc2cc(C3CCCC3)[nH]n2)n1)c1ccc2[nH]cnc2c1] | A | 389.2 | (DMSO-d$_6$) δ 12.29 (s, 1H), 11.82 (s, 1H), 9.21 (s, 1H), 8.12 (s, 1H), 7.76 (d, J = 4.9 Hz, 1H), 7.64 (s, 1H), 7.53 (d, J = 8.2 Hz, 1H), 7.49 (s, 1H), 7.39 (t, J = 13.9 Hz, 1H), 7.26 (d, J = 8.2 Hz, 1H), 7.21 (d, J = 8.3 Hz, 1H), 7.07 (s, 1H), 6.30 (s, 1H), 6.13 (s, 1H), 5.23 (s, 1H), 2.98 (d, J = 7.7 Hz, 1H), 1.94 (d, J = 27.8 Hz, 2H), 1.72 (s, 2H), 1.61 (s, 4H), 1.48 (d, J = 7.0 Hz, 3H). | N$^2$-[(S)-1-(1H-Benzoimidazol-5-yl)-ethyl]-N$^4$-(5-cyclopentyl-1H-pyrazol-3-yl)-pyrimidine-2,4-diamine |
| I-3 | 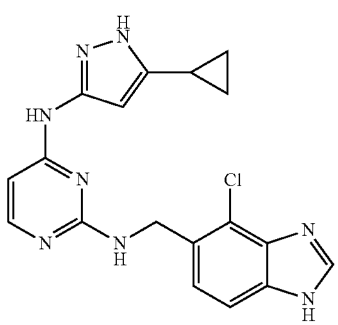 [SMILES: Clc1c(CNc2nccc(Nc3cc(C4CC4)[nH]n3)n2)ccc2[nH]cnc12] | A | 381.1 | (DMSO-d$_6$) δ 13.01-12.31 (m, 1H), 11.80 (s, 1H), 9.28 (s, 1H), 8.24 (s, 1H), 7.80 (s, 1H), 7.54-7.39 (m, 1H), 7.32-7.06 (m, 2H), 6.35-5.29 (m, 2H), 4.67 (d, J = 6.1 Hz, 2H), 1.89-1.55 (m, 1H), 0.99-0.21 (m, 4H) | N$^2$-(4-Chloro-1H-benzoimidazol-5-ylmethyl)-N$^4$-(5-cyclopropyl-1H-pyrazol-3-yl)-pyrimidine-2,4-diamine |
| I-4 | 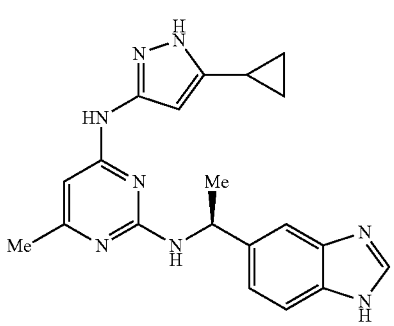 [SMILES: Cc1cc(Nc2cc(C3CC3)[nH]n2)nc(N[C@@H](C)c2ccc3[nH]cnc3c2)n1] | B | 375.2 | (DMSO-d$_6$) δ 12.30 (s, 1H), 11.80 (s, 1H), 9.11 (s, 1H), 7.52 (m, 2H), 7.17 (m, 2H), 6.59 (s, 1H), 6.11 (m, 2H), 5.23 (s, 1H), 2.06 (s, 3H), 1.83 (s, 1H), 1.47 (d, J = 6.9 Hz, 3H), 0.85 (m, 2H), 0.66 (s, 2H) | N$^2$-[(S)-1-(1H-Benzoimidazol-5-yl)-ethyl]-N$^4$-(5-cyclopropyl-1H-pyrazol-3-yl)-6-methyl-pyrimidine-2,4-diamine |

TABLE I-continued

| Cpd. No. | Structure | $K_i^5$ | $MS^2$ | $^1$H NMR | Name |
|---|---|---|---|---|---|
| I-5 | 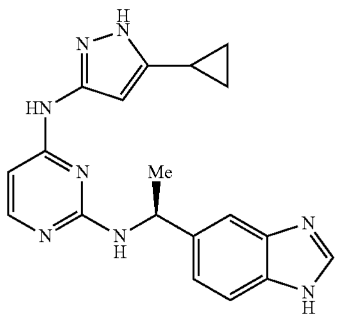 [SMILES: C[C@H](Nc1nccc(Nc2cc(C3CC3)[nH]n2)n1)c1ccc2[nH]cnc2c1] | A | 361.3 | (DMSO-d$_6$) δ 12.28 (s, 1H), 11.81 (s, 1H), 9.94 - 9.07 (m, 1H), 8.12 (s, 1H), 7.86-6.89 (m, 5H), 6.38-5.08 (m, 3H), 1.84 (s, 1H), 1.48 (d, J = 7.0 Hz, 3H), 0.84 (dd, J = 67.7, 32.0 Hz, 4H) | N$^2$-[(S)-1-(1H-Benzoimidazol-5-yl)-ethyl]-N$^4$-(5-cyclopropyl-1H-pyrazol-3-yl)-pyrimidine-2,4-diamine |
| I-6 | 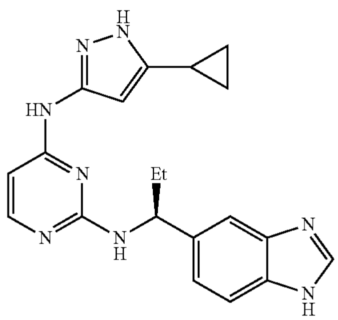 [SMILES: CC[C@H](Nc1nccc(Nc2cc(C3CC3)[nH]n2)n1)c1ccc2[nH]cnc2c1] | A | 375.2 | (DMSO-d$_6$): δ 12.30 (s, 1H), 11.84 (s, 1H), 10.00-8.99 (m, 1H), 8.13 (s, 1H), 7.82-7.66 (m, 1H), 7.68-6.81 (m, 4H), 6.08 (s, 2H), 5.03-4.87 (m, 1H), 1.98-1.65 (m, 3H), 1.03-0.50 (m, 7H) | N$^2$-[1-(1H-Benzoimidazol-5-yl)-propyl]-N$^4$-(5-cyclopropyl-1H-pyrazol-3-yl)-pyrimidine-2,4-diamine |
| I-7 | 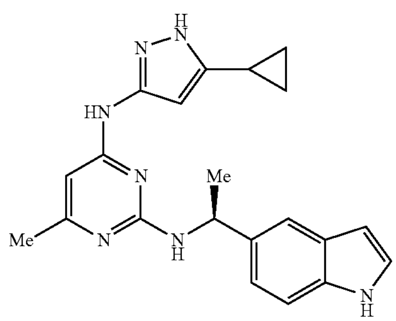 [SMILES: Cc1cc(Nc2cc(C3CC3)[nH]n2)nc(N[C@@H](C)c2ccc3[nH]ccc3c2)n1] | A | 374.2 | (DMSO-d$_6$): δ 11.79 (br s, 1H), 10.93 (s, 1H), 9.08 (br s, 1H), 7.52 (s, 1H), 7.35-7.23 (m, 2H), 7.14 (d, J = 8.4 Hz, 1H), 6.96 (br s, 1H), 6.34 (s, 1H), 6.16 (br s, 1H), 5.95 (br s, 1H), 5.19 (s, 1H), 2.06 (s, 3H), 1.89-1.78 (m, 1H), 1.45 (d, J = 6.9 Hz, 3H), 0.91 (s, 2H), 0.67 (s, 2H) | N$^4$-(5-Cyclopropyl-1H-pyrazol-3-yl)-N$^2$-[(S)-1-(1H-indol-5-yl)-ethyl]-6-methyl-pyrimidine-2,4-diamine |
| I-8 | 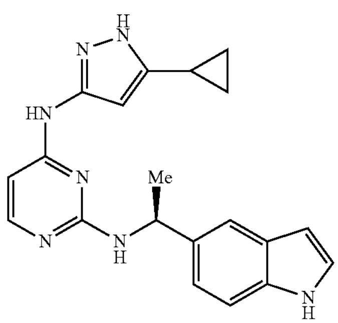 [SMILES: C[C@H](Nc1nccc(Nc2cc(C3CC3)[nH]n2)n1)c1ccc2[nH]ccc2c1] | A | 360.1 | (DMSO-d$_6$): δ 11.82 (br s, 1H), 10.92 (s, 1H), 9.16 (br s, 1H), 7.75 (s, 1H), 7.52 (s, 1H), 7.35-7.24 (m, 2H), 7.14 (d, J = 8.3 Hz, 1H), 6.93 (s, 1H), 6.34 (s, 1H), 6.32-5.80 (br m, 2H), 5.18 (s, 1H), 1.91-1.77 (m, 1H), 1.46 (d, J = 6.9 Hz, 3H), 1.00-0.80 (m, 2H), 0.68 (s, 2H) | N$^4$-(5-Cyclopropyl-2H-pyrazol-3-yl)-N$^2$-[(S)-1-(1H-indol-5-yl)-ethyl]-pyrimidine-2,4-diamine |
| I-9 | 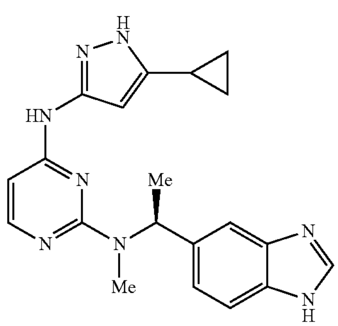 [SMILES: C[C@@H](c1ccc2[nH]cnc2c1)N(C)c1nccc(Nc2cc(C3CC3)[nH]n2)n1] | A | 375.3 | (CD$_3$OD) δ 8.04 (s, 1H), 7.81 (d, J = 6 Hz, 1H), 7.50 (s, 1H), 7.47 (d, J = 8.5 Hz, 1H), 7.16 (d, J = 8.5 Hz, 1H), 6.23 (brs, 1H), 6.08 (m, 1H), 2.70 (s, 3H), 1.68-1.72 (m, 1H), 1.56 (d, J = 6, 3H), 1.11 (t, J = 7 Hz, 1H), 0.78 (m, 2H), 0.49 (m, 2H) | N$^2$-[(S)-1-(1H-Benzoimidazol-5-yl)-ethyl]-N$^4$-(5-cyclopropyl-1H-pyrazol-3-yl)-N-methyl-pyrimidine-2,4-diamine |

TABLE I-continued

| Cpd. No. | Structure | $K_i{}^5$ | MS[2] | $^1$H NMR | Name |
|---|---|---|---|---|---|
| I-10 | 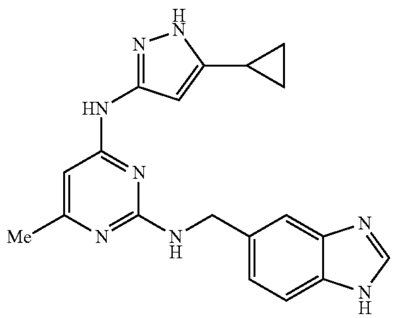 [SMILES: Cc1cc(Nc2cc(C3CC3)[nH]n2)nc(NCc2ccc3[nH]cnc3c2)n1] | A | 361.2 | (DMSO-d$_6$): δ 12.28 (s, 1H), 11.80 (s, 1H), 9.13 (s, 1H), 8.12 (s, 1H), 7.55 (d, J = 8.6 Hz, 1H), 7.43 (d, J = 7.5 Hz, 1H), 7.27 to 6.94 (m, 2H), 6.07 (br s, 2H), 4.64-4.55 (m, 2H), 2.08 (s, 3H), 1.77 (d, J = 4.8 Hz, 1H), 0.83 (d, J = 6.2 Hz, 2H), 0.57 (s, 2H) | N[2]-(1H-Benzoimidazol-5-ylmethyl)-N[4]-(5-cyclopropyl-1H-pyrazol-3-yl)-6-methyl-pyrimidine-2,4-diamine |
| I-11 | 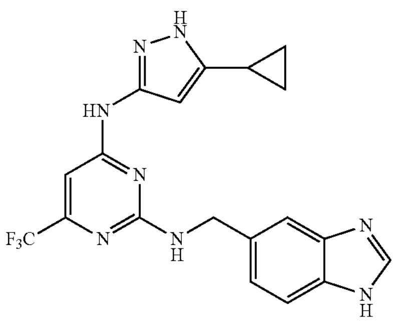 [SMILES: FC(F)(F)c1cc(Nc2cc(C3CC3)[nH]n2)nc(NCc2ccc3[nH]cnc3c2)n1] | A | 415.2 | (DMSO-d$_6$): δ 12.30 (d, J = 15.1 Hz, 1H), 12.00 (s, 1H), 9.89 (br s, 1H), 8.13 (s, 1H), 7.93 (br s, 1H), 7.57 (d, J = 8.3 Hz, 1H), 7.45 (d, J = 7.4 Hz, 1H), 7.19 (dd, J = 20.7, 7.9 Hz, 1H), 6.51 (br s, 1H), 6.04 (br s, 1H), 4.62 (s, 2H), 1.80 (s, 1H), 0.86 (s, 2H), 0.68 (br s, 1H), 0.51 (br s, 1H) | N[2]-(1H-Benzoimidazol-5-ylmethyl)-N[4]-(5-cyclopropyl-1H-pyrazol-3-yl)-6-trifluoromethyl-pyrimidine-2,4-diamine |
| I-12 | 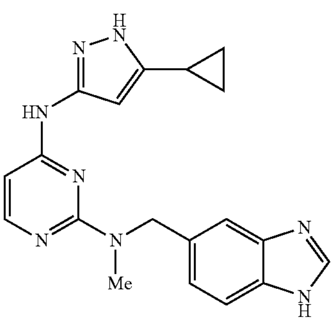 [SMILES: CN(Cc1ccc2[nH]cnc2c1)c1nccc(Nc2cc(C3CC3)[nH]n2)n1] | A | 361.3 | (DMSO-d$_6$) δ 12.51 (s, 1H), 11.92 (s, 1H), 9.41 (s, 1H), 8.16 (s, 1H), 7.91-7.90 (m, 1H), 7.57-7.11 (m, 3H), 6.27-6.08 (m, 2H), 4.94 (d, 2H), 3.05 (s, 3H), 1.77-1.74 (m, 1H), 0.80-0.48 (m, 4H) | N[2]-(1H-Benzoimidazol-5-ylmethyl)-N[4]-(5-cyclopropyl-1H-pyrazol-3-yl)-N[2]-methyl-pyrimidine-2,4-diamine |
| I-13 | 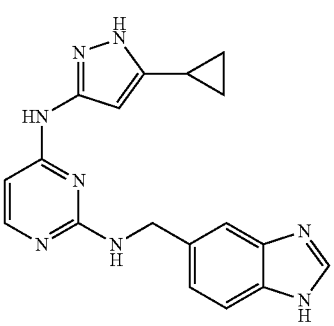 [SMILES: c1cc(Nc2cc(C3CC3)[nH]n2)nc(NCc2ccc3[nH]cnc3c2)n1] | A | 347.2 | (DMSO-d$_6$): δ 12.46 (br, 1H), 11.94 (br, 1H), 9.39 (br, 1H), 8.41 (s, 1H), 7.81 (s, 1H), 7.17-7.52 (m, 5H), 6.09-6.24 (brs, 1H), 4.60 (d, 2H), 1.80 (s, 1H), 0.84-0.85 (m, 2H), 0.47-0.59 (m, 2H) | N[2]-(1H-Benzoimidazol-5-ylmethyl)-N[4]-(5-cyclopropyl-1H-pyrazol-3-yl)-pyrimidine-2,4-diamine |

TABLE I-continued

| Cpd. No. | Structure | $K_i^5$ | $MS^2$ | $^1$H NMR | Name |
|---|---|---|---|---|---|
| I-14 | 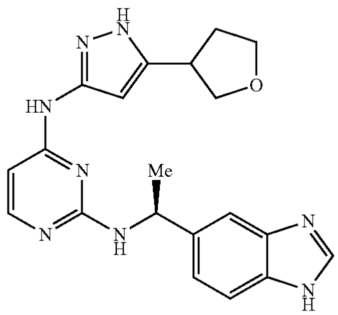 [SMILES: C[C@H](Nc1nccc(Nc2cc(C3CCOC3)[nH]n2)n1)c1ccc2[nH]cnc2c1] | A | 391.2 | (DMSO-d$_6$): δ 12.30 (s, 1H), 11.97 (s, 1H), 9.27 (s, 1H), 8.13 (s, 1H), 7.77 (s, 1H), 7.65 (s, 1H), 7.49 (t, J = 20.9 Hz, 2H), 7.23 (s, 1H), 7.10 (s, 1H), 6.37 (s, 1H), 6.03 (d, J = 78.4 Hz, 1H), 5.21 (s, 1H), 3.86 (dd, J = 55.4, 28.2 Hz, 3H), 3.60 (s, 2H), 2.24 (s, 1H), 1.97 (s, 1H), 1.48 (d, J = 6.9 Hz, 3H) | N$^2$-[1-(1H-Benzoimidazol-5-yl)-ethyl]-N$^4$-[5-(tetrahydrofuran-3-yl)-1H-pyrazol-3-yl]-pyrimidine-2,4-diamine |
| I-15 | 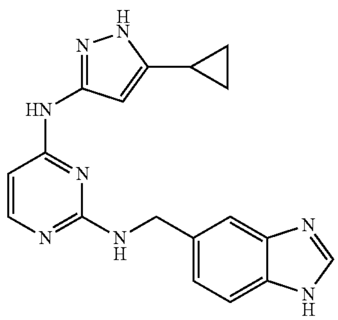 [SMILES: c1cc(Nc2cc(C3CC3)[nH]n2)nc(NCc2ccc3[nH]cnc3c2)n1] | A | 346.2 | (CD$_3$OD) δ 7.77 (s, 1H), 7.49 (s 1H), 7.30 (d, 1H), 7.15 (d, 1H), 7.08 (d, 1H), 6.34 (d, 1H), 6.15 (br, 2H) 4.65 (s, 2H), 1.81-1.87 (m, 1H), 0.89-0.93 (m, 2H), 0.64 (m, 2H) | N$^4$-(5-Cyclopropyl-1H-pyrazol-3-yl)-N$^2$-(1H-indol-5-ylmethyl)-pyrimidine-2,4-diamine |
| I-16 | 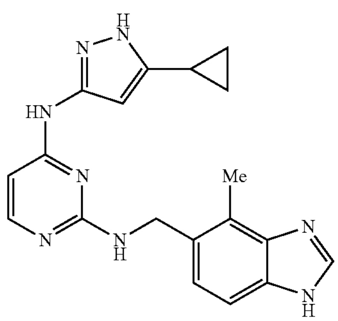 | B | 361.3 | (CD$_3$OD): δ 8.04 (s, 1H), 7.81 (d, J = 5.9 Hz, 1H), 7.55 (s, 1H), 7.44 (s, 1H), 6.12 (s, 1H), 5.81 (s, 1H), 4.63 (s, 2H), 2.47 (s, 3H), 1.86-1.63 (m, 1H), 0.95-0.78 (m, 2H), 0.72-0.40 (m, 2H) | N$^4$-(5-Cyclopropyl-1H-pyrazol-3-yl)-N$^2$-(4-methyl-1H-benzoimidazol-5-ylmethyl)-pyrimidine-2,4-diamine |
| I-17 | 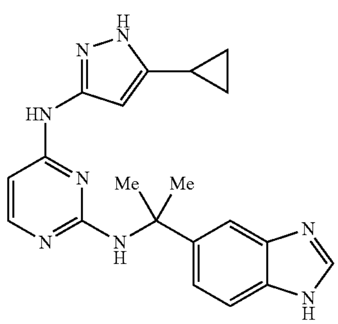 [SMILES: CC(C)(Nc1nccc(Nc2cc(C3CC3)[nH]n2)n1)c1ccc2[nH]cnc2c1] | B | 375.3 | (CD$_3$OD): δ 9.06 (s, 1H), 8.83 (s, 1H), 8.36 (d, J = 5.5, 1H), 7.71 (d, J = 8.5, 1H), 7.56 (dd, J$_1$ = 1.5, J$_2$ = 8.5, 1H), 7.04 (brs, 1H), 6.05 (brs, 1H), 1.99-1.94 (m, 1H), 1.62 (s, 6H), 1.05-1.01 (m, 2H), 0.80-0.77 (m, 2H) | N$^2$-(1-(1H-Benzoimidazol-5-yl)-1-methyl-ethyl]-N$^4$-(5-cyclopropyl-1H-pyrazol-3-yl)-pyrimidine-2,4-diamine |
| I-18 | 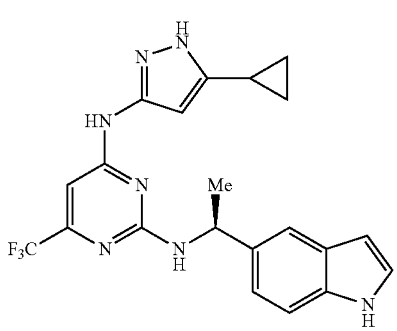 [SMILES: C[C@H](Nc1nc(Nc2cc(C3CC3)[nH]n2)cc(C(F)(F)F)n1)c1ccc2[nH]ccc2c1] | B | 428.2 | (DMSO-d$_6$): δ 11.99 (br s, 1H), 10.94 (s, 1H), 9.83 (br s, 1H), 7.84 (br s, 1H), 7.53 (s, 1H), 7.40-7.21 (m, 2H), 7.15 (d, J = 8.4 Hz, 1H), 6.60-6.15 (m, 2H), 5,19 (s, 1H), 1.88 (s, 1H), 1.48 (d, J = 5.5 Hz, 3H), 0.96 (s, 2H), 0.70 (s, 2H); 1 H not seen | N$^4$-(5- Cyclopropyl-1H-pyrazol-3-yl)-N$^2$-[(S)-1-(1H-indol-5-yl)-ethyl]-6-trifluoromethyl-pyrimidine-2,4-diamine |

TABLE I-continued

| Cpd. No. | Structure | $K_i^5$ | $MS^2$ | $^1H$ NMR | Name |
|---|---|---|---|---|---|
| I-19 | 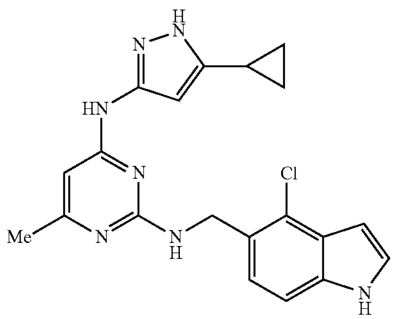 [SMILES: Cc1cc(Nc2cc(C3CC3)[nH]n2)nc(NCc2ccc3[nH]ccc3c2Cl)n1] | B | 394.1 | (DMSO-d$_6$): δ 11.76 (s, ]H), 11.30 (s, 1H), 9.15 (s, 1H), 7.40 (s, 1H), 7.30 (d, J = 8.2 Hz, 1H), 7.13 (s, 1H), 6.99 (s, 1H), 6.45 (s, 1H), 6.06 (br s, 2H), 4.65 (d, J = 6.1 Hz, 2H), 2.09 (s, 3H), 1.70 (s, 1H), 0.78 (s, 2H), 0.51 (s, 2H) | N$^2$-(4-Chloro-1H-indol-5-ylmethyl)-N$^4$-(5-cyclopropyl-1H-pyrazol-3-yl)-6-methyl-pyrimidine-2,4-diamine |
| I-20 | 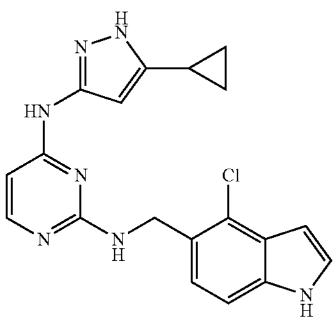 [SMILES: Clc1c(CNc2nccc(Nc3cc(C4CC4)[nH]n3)n2)ccc2[nH]ccc12] | B | 380.0 | (DMSO-d$_6$) δ 11.79 (s, 1H), 11.28 (s, 1H), 9.24 (s, 1H), 7.82 (m, 1H), 7.40 (s, 1H), 7.30 (d, J = 8.3 Hz, 1H), 7.22-6.83 (m, 2H), 6.45 (s, 1H), 6.08-5.42 (m, 2H), 4.65 (d, J = 6.1 Hz, 2H), 1.73 (s, 1H), 0.81 (s, 2H), 0.54 (s, 2H); MS (ESI) m/z = 380.0 [M + 1]$^+$. | N$^2$-(4-Chloro-1H-indol-5-ylmethyl)-N$^4$-(5-cyclopropyl-1H-pyrazol-3-yl)-pyrimidine-2,4-diamine |
| I-21 | 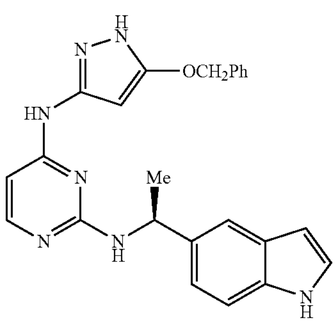 | B | 427.2 | (DMSO-d$_6$): δ 12.31 (s, 1H), 12.05 (s, 1H), 9.95 (s, 1H), 8.19-8.11 (m, 1H), 7.82 (s, 1H), 7.77 - 7.14 (m, 10H), 5.90 (d, J = 5.6 Hz, 1H), 5.27-5.09 (m, 3H), 1.48 (d, J = 6.9 Hz, 3H) | N$^2$-[(S)-1-(1H-Benzoimidazol-5-yl)-ethyl]-N$^4$-(5-benzyloxy-1H-pyrazol-3-yl)-pyrimidine-2,4-diamine |
| I-22 | 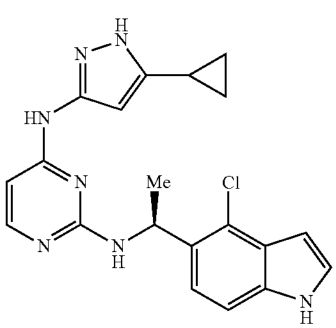 [SMILES: C[C@H](Nc1nccc(Nc2cc(C3CC3)[nH]n2)n1)c1ccc2[nH]ccc2c1Cl] | B | 445.2 | (CDCl$_3$) δ 8.01 (d, J = 8.5 Hz, 1H), 7.82-7.77 (m, 1H), 7.69 (d, J = 7.2 Hz, 2H), 7.60-7.56 (m, 1H), 7.48 (d, J = 8.2 Hz, 1H), 7.43 (d, J = 8.9 Hz, 2H), 7.37 (d, J = 7.0 Hz, 1H), 7.33 (t, J = 7.3 Hz, 2H), 7.25-7.20 (m, 2H), 6.66 (d, J = 3.7 Hz, 1H), 4.75 (s, 2H), 1.66 (s, 9H) | N$^2$-[(S)-1-(4-Chloro-1H-indol-5-yl)-ethyl]-N$^4$-(5-cyclopropyl-1H-pyrazol-3-yl)-pyrimidine-2,4-diamine |

TABLE I-continued

| Cpd. No. | Structure | $K_i{}^5$ | $MS^2$ | $^1H$ NMR | Name |
|---|---|---|---|---|---|
| I-23[3] | 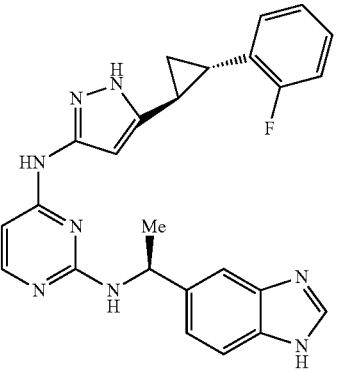 [SMILES: C[C@H](Nc1nccc(Nc2cc([C@H]3C[C@@H]3c3ccccc3F)[nH]n2)n1)c1ccc2[nH]cnc2c1] | B | 455.2 | (DMSO-d$_6$) δ 12.21 (s, 1H), 9.27 (s, 1H), 8.18 (s, 1H), 8.12 (s, 1H), 7.78 (d, J = 5.7 Hz, 1H), 7.56 (s, 1H) 7.46 (s, 1H), 7.23 (d, J = 4.2 Hz, 2H), 7.17 (d, J = 10.3 Hz, 3H), 6.05 (s, 2H), 5.34-5.08 (m, 1H), 2.35 (d, J = 19.4 Hz, 1H), 2.18 (dd, J = 13.4, 5.9 Hz, 1H), 1.48 (d, J = 6.9 Hz, 4H). | $N^2$-[(S)-1-(1H-Benzoimidazol-5-yl)-ethyl]-$N^4$-{5-[(1R, 2R)-2-(2-fluorophenyl)-cyclopropyl]-1H-pyrazol-3-yl}-pyrimidine-2,4-diamine |
| I-24[3] | 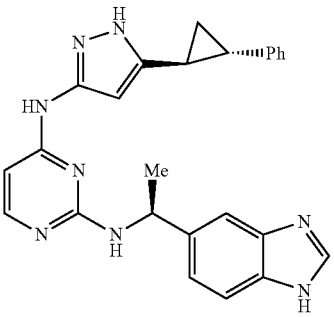 [SMILES: C[C@H](Nc1nccc(Nc2cc([C@H]3C[C@@H]3c3ccccc3)[nH]n2)n1)c1ccc2[nH]cnc2c1] | B | 437.2 | (DMSO-d$_6$): δ 12.45 (s, 1H), 11.13 (s, 1H), 9.03 (s, 1H), 7.86 (s, 1H), 7.71 (s, 1H), 7.62 (s, 1H), 7.45 (s, 1H), 7.32 (t, J = 7.4 Hz, 2H), 7.20 (dd, J = 11.7, 7.2 Hz, 3H), 6.31 (s, 1H), 6.18 (s, 1H), 5.35 (s, 1H), 2.16 (d, J = 8.8 Hz, 1H), 2.13-2.05 (m, (d, J = 6.8 Hz, 3H), 1.50 (s, 1H), 1.41 (s, 1H) | $N^2$-[(S)-1-(1H-Benzoimidazol-5-yl)-ethyl]-$N^4$-[5-((1R, 2R)-2-phenyl-cyclopropyl)-1H-pyrazol-3-yl]-pyrimidine-2,4-diamine |
| I-25 | 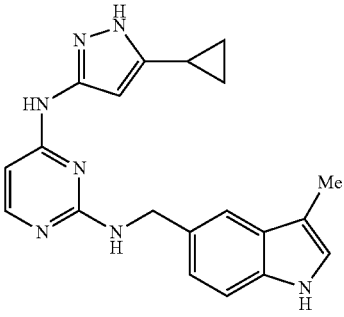 [SMILES: Cc1c[nH]c2ccc(CNc3nccc(Nc4cc(C5CC5)[nH]n4)n3)cc12] | B | 360.2 | (DMSO-d$_6$): δ 11.85 (s, 1H), 10.59 (s, 1H), 9.23 (s, 1H), 7.96-7.72 (m, 1H), 7.42 (s, 1H), 7.23 (d, J = 8.3 Hz, 1H), 7.13-6.97 (m, 3H), 6.45-5.85 (m, 2H), 4.56 (d, J = 6.1 Hz, 2H), 2.20 (s, 3H), 1.80 (d, J = 4.6 Hz, 1H), 0.94-0.75 (m, 2H), 0.61 (s, 2H) | $N^4$-(5-Cyclopropyl-1H-pyrazol-3-yl)-$N^2$-(3-methyl-1H-indol-5-ylmethyl)-pyrimidine-2,4-diamine |
| I-26 | 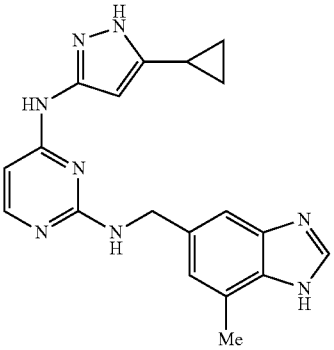 [SMILES: Cc1cc(CNc2nccc(Nc3cc(C4CC4)[nH]n3)n2)cc2nc[nH]c12] | B | 361.2 | (DMSO-d$_6$): δ 12.34 (s, 1H), 11.88 (s, 1H), 9.32 (s, 1H), 8.10 (s, 1H), 7.80 (s, 1H), 7.37-6.97 (m, 3H), 6.14-6.02 (m, 2H), 4.55 (d, 2H), 2.49 (s, 3H), 1.80-1.77 (m, 1H), 0.95-0.77 (m, 2H), 0.61-0.52 (m, 2H) | $N^4$-(5-Cyclopropyl-1H-pyrazol-3-yl)-$N^2$-(7-methyl-1H-benzoimidazol-5-ylmethyl)-pyrimidine-2,4-diamine |

TABLE I-continued

| Cpd. No. | Structure | $K_i{}^5$ | $MS^2$ | $^1H$ NMR | Name |
|---|---|---|---|---|---|
| I-27[3] | 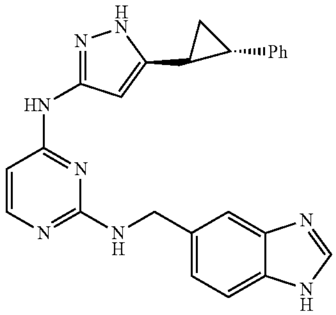 | B | 423.2 | (DMSO-d$_6$) δ 12.27 (s, 1H), 11.95 (s, 1H), 9.31 (s, 1H), 8.13 (s, 1H), 7.89-7.77 (m, 1H), 7.64-7.36 (m, 2H), 7.32-7.02 (m, 7H), 6.17 (s, 2H), 4.60 (s, 2H), 2.21-1.96 (m, 2H), 1.48-1.18 (m, 2H). | N$^2$-(1H-Benzoimidazol-5-ylmethyl)-N$^4$-[5-(2-phenyl-cyclopropyl)-1H-pyrazol-3-yl]-pyrimidine-2,4-diamine |
| I-28 | 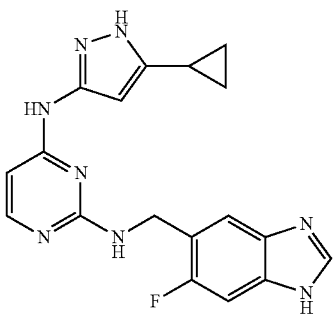 [SMILES: Fc1cc2[nH]cnc2cc1CNc1nccc(Nc2cc(C3CC3)[nH]n2)n1] | B | 365.3 | (CD$_3$OD) δ 8.05 (s, 1H), 7.71-7.70 (m, 1H), 7.50-7.49 (m, 1H), 7.27-7.25 (m, 1H), 6.14-6.10 (m, 1H), 5.88-5.84 (m, 1H), 4.68 (d, 2H), 1.70-1.73 (m, 1H), 0.82-0.80 (m, 2H), 0.47-0.42 (m, 2H) | N$^4$-(5-Cyclopropyl-1H-pyrazol-3-yl)-N$^2$-(6-fluoro-1H-benzoimidazol-5-ylmethyl)-pyrimidine-2,4-diamine |
| I-29 | 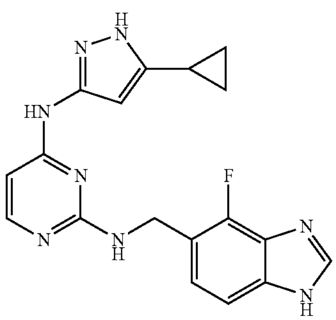 [SMILES: Fc1c(CNc2nccc(Nc3cc(C4CC4)[nH]n3)n2)ccc2[nH]cnc12] | C | 365.1 | (DMSO-d$_6$): δ 12.73-12.20 (m, 1H), 11.88 (s, 1H), 9.36 (s, 1H), 7.94-7.74 (m, 1H), 7.44-7.15 (m, 2H), 7.15-7.01 (m, 1H), 7.01-6.82 (m, 1H), 6.49-5.77 (m, 2H), 4.67 (d, J = 5.6 Hz, 2H), 1.88-1.69 (m, 1H), 0.93-0.50 (m, 4H) | N$^4$-(5-Cyclopropyl-1H-pyrazol-3-yl)-N$^2$-(4-fluoro-1H-benzoimidazol-5-ylmethyl)-pyrimidine-2,4-diamine |
| I-30 | 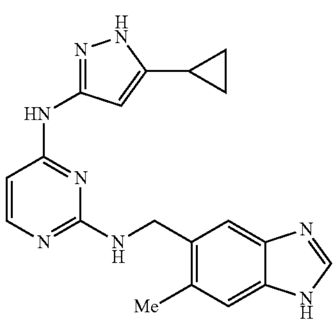 [SMILES: Cc1cc2[nH]cnc2cc1CNc1nccc(Nc2cc(C3CC3)[nH]n2)n1] | C | 361.2 | (CD$_3$OD): δ 8.11 (s, 1H), 7.86 (d, J = 5.3 Hz, 1H), 7.42 (d, J = 8.0 Hz, 1H), 7.30 (d, J = 8.3 Hz, 1H), 6.29-5.75 (m, 2H), 4.70 (s, 2H), 2.63 (s, 3H), 1.87-1.75 (m, 1H), 0.92-0.82 (m, 2H), 0.67-0.54 (m, 2H) | N$^4$-(5-Cyclopropyl-1H-pyrazol-3-yl)-N$^2$-(6-methyl-1H-benzoimidazol-5-ylmethyl)-pyrimidine-2,4-diamine |
| I-31 | 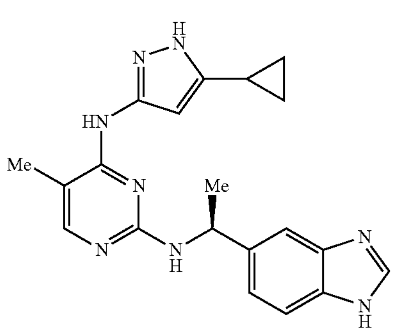 [SMILES: Cc1cnc(N[C@@H](C)c2ccc3[nH]cnc3c2)nc1Nc1cc(C2CC2)[nH]n1] | C | 374.2 | (DMSO-d$_6$ + TFA vapor): δ 11.05 (s, 1H), 10.02 (s, 1H), 8.52 (br s, 1H), 7.68 (s, 1H), 7.49 (s, 1H), 7.41-7.25 (m, 2H), 7.09 (d, J = 8.3 Hz, 1H), 6.38 (s, 1H), 6.24 (br s, 1H), 5.12 (br s, 1H), 2.06 (s, 3H), 1.97-1.88 (m, 1H), 1.55 (d, J = 6.8 Hz, 1H not seen; | N$^4$-(5-Cyclopropyl-1H-pyrazol-3-yl)-N$^2$-[(S)-1-(1H-indol-5-yl)-ethyl]-5-methyl-pyrimidine-2,4-diamine |

TABLE I-continued

| Cpd. No. | Structure | $K_i^5$ | $MS^2$ | $^1H$ NMR | Name |
|---|---|---|---|---|---|
| I-32 | 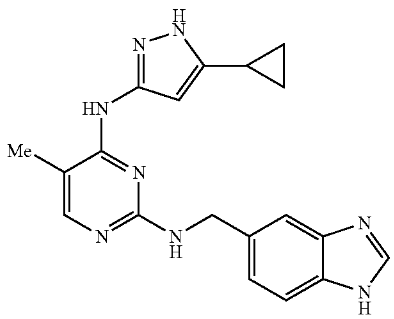 [SMILES: Cc1cnc(NCc2ccc3[nH]cnc3c2)nc1Nc1cc(C2CC2)[nH]n1] | C | 361.2 | (DMSO-$d_6$) δ 12.27 (br s, 1H), 8.54 (br s, 1H), 8.13 (s, 1H), 7.69 (s, 1H), 7.49 (br s, 2H), 7.16 (d, J = 7.8 Hz, 2H), 6.04 (br s, 1H), 4.57 (d, J = 6.1 Hz, 2H), 1.98 (s, 3H), 1.78 (s, 1H), 0.88-0.76 (m, 2H), 0.57 (s, 2H), 1 H not detected | $N^2$-(1H-Benzoimidazol-5-ylmethyl)-$N^4$-(5-cyclopropyl-1H-pyrazol-3-yl)-5-methyl-pyrimidine-2,4-diamine |
| I-33 | 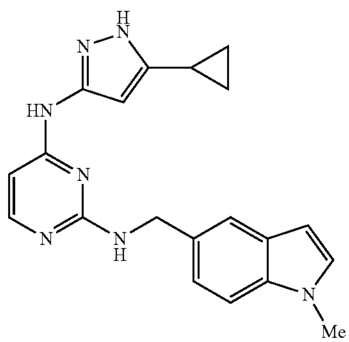 [SMILES: Cn1ccc2cc(CNc3nccc(Nc4cc(C5CC5)[nH]n4)n3)ccc21] | C | 360.2 | | $N^4$-(5-Cyclopropyl-1H-pyrazol-3-yl)-$N^2$-(1-methyl-1H-indol-5-ylmethyl)-pyrimidine-2,4-diamine |
| I-34 | 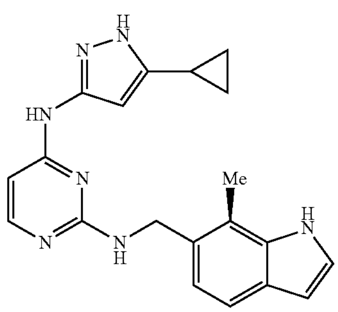 | C | 360.3 | (DMSO-$d_6$): δ 11.81 (s, 1H), 10.92 (s, 1H), 9.16 (s, 1H), 7.84-7.70 (m, 1H), 7.44 (d, J = 8.0 Hz, 1H), 7.37 (s, 1H), 7.25 (s, 1H), 7.08-6.90 (m, 2H), 6.34 (s, 1H), 6.28-5.31 (m, 2H), 5.20 (d, J = 7.5 Hz, 1H), 1.84 (s, 1H), 1.47 (d, J = 7.0 Hz, 3H), 0.92 (d, J = 8.2 Hz, 2H), 0.67 (s, 2H) | $N^4$-(5-Cyclopropyl-1H-pyrazol-3-yl)-$N^2$-[(S)-1-(1H-indol-6-yl)-ethyl]-pyrimidine-2,4-diamine |
| I-35 | 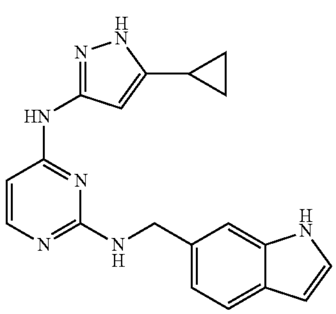 [SMILES: c1cc(Nc2cc(C3CC3)[nH]n2)nc(NCc2ccc3cc[nH]c3c2)n1] | D | 346.3 | (DMSO-$d_6$) δ 12.05 (s, 1H), 11.07 (s, 1H), 7.83 (d, 1H), 7.48-7.27 (m, 3H), 6.99 (d, 1H), 6.37-6.01 (m, 3H), 4.63 (d, 2H), 1.81-1.76 (m, 1H), 0.64-0.51 (m, 4H); | $N^4$-(5-Cyclopropyl-1H-pyrazol-3-yl)-$N^2$-(1H-indol-6-ylmethyl)-pyrimidine-2,4-diamine |

TABLE I-continued

| Cpd. No. | Structure | $K_i{}^5$ | $MS^2$ | $^1H$ NMR | Name |
|---|---|---|---|---|---|
| I-36 | 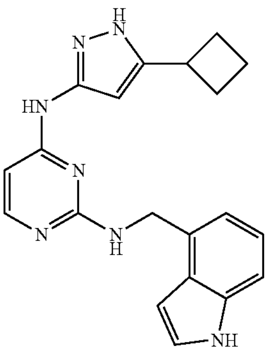 [SMILES: c1cc(CNc2nccc(Nc3cc(C4CCC4)[nH]n3)n2)c2cc[nH]c2c1] | A | 360.2 | (DMSO-d$_6$) δ 11.81 (s, 1H), 11.06 (s, 1H), 9.26 (s, 1H), 7.85 (t, J = 31.2 Hz, 1H), 7.38-7.27 (m, 1H), 7.25 (d, J = 7.8 Hz, 1H), 7.12-6.96 (m, 2H), 6.92 (s, 1H), 6.52 (d, J = 31.5 Hz, 1H), 6.23 (d, J = 27.1 Hz, 1H), 4.77 (d, J = 5.8 Hz, 2H), 2.11 (d, J = 27.8 Hz, 3H), 1.88 (s, 2H) 1.74 (d, J = 10.9 Hz, 1H). | N$^4$-(5-Cyclobutyl-1H-pyrazol-3-yl)-N$^2$-(1H-indol-4-ylmethyp-pyrimidine-2,4-diamine |
| I-37 | 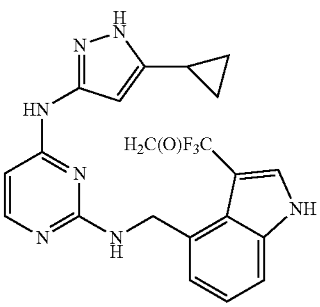 | A | 442.1 | (DMSO + TFA traces)): δ 12.91 (br s, 1H), 12.05 (br s, 1H), 11.12 (s, 1H), 8.61-8.56 (m, 1H), 8.42-8.35 (m, 1H), 7.91-7.79 (m, 1H), 7.53 (d, J +32 7.8 Hz, 1H), 7.34-7.26 (m, 1H), 7.27-7.14 (m, 1H), 6.31 (d, J = 7.0 Hz, 1H), 6.01 (s, 1H), 5.26-5.18 (m, 2H), 5.19-5.05 (m, 1H), 1.64-1.49 (m, 1H), 0.74-0.66 (m, 2H), 0.24-0.17 (m, 2H) | 1-(4-{[4-(5-Cyclopropyl-1H-pyrazol-3-ylamino)-pyrimidin-2-ylamino]-methyl}-1H-indol-3-yl)-2,2,2-trifluoro-ethanone |
| I-38 | 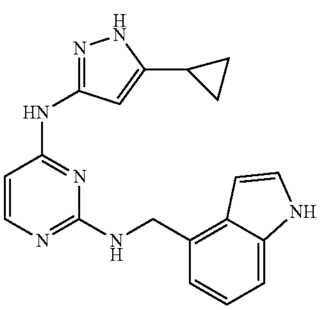 [SMILES: c1cc(CNc2nccc(Nc3cc(C4CC4)[nH]n3)n2)c2cc[nH]c2c1] | B | 346.2 | (DMSO-d$_6$): δ 11.84 (s, 1H), 11.09 (s, 1H), 9.26 (s, 1H), 7.90-7.78 (m, 1H), 7.31-7.25 (m, 2H), 7.05-6.91 (m, 3H), 6.54 (d, 1H), 6.19-5.96 (m , 2H), 4.75 (d, 2H), 1.77-1.70 (m, 1H), 0.59-0.46 (m, 4H) | N$^4$-(5-Cyclopropyl-1H-pyrazol-3-yl)-N$^2$-(1H-indol-4-ylmethyl)-pyrimidine-2,4 -diamine |
| I-39 | 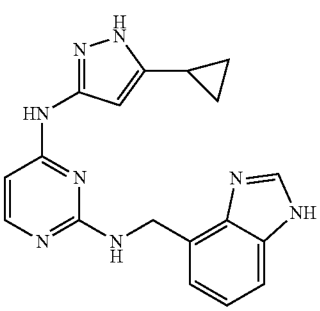 [SMILES: c1cc(CNc2nccc(Nc3cc(C4CC4)[nH]n3)n2)c2nc[nH]c2c1] | B | 347.3 | (CD$_3$OD): δ 8.17(s, 1H ), 7.83 (s 1H), 7.53 (s, 1H) 7.23 (m, 2H), 6.14 (s, 1H), 5.92 (br, 1H), 4.92 (s, 2H), 1.70 (m, 1H), 0.83 (m, 2H), 0.46 (m, 2H) | N$^2$-(1H-Benzoimidazol-4-ylmethyl)-N$^4$-(5-cyclopropyl-1H-pyrazol-3-yl)-pyrimidine-2,4-diamine |
| I-40 | 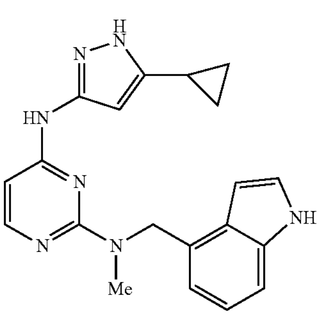 [SMILES: CN(Cc1cccc2[nH]ccc12)c1nccc(Nc2cc(C3CC3)[nH]n2)n1] | B | 360.3 | (CD$_3$OD): δ 7.91 (d, J = 5Hz, 1H ), 7.32 (d, J +32 7.5Hz, 1H), 7.22 (d, J = 3 Hz, 1H), 7.06 (t, J +32 8 Hz, 1H), 6.83 (d, J = 6 Hz, 1H), 6.49 (d, J +32 2.5Hz, 1H), 6.17 (brs, 1H), 6.02 (brs, 1H), 5.16 (s, 2H), 3.09 (s, 3H), 1.66 (brs, 1H), 0.76 (m, 2H), 0.36 (brs, 2H) | N$^4$-(5-Cyclopropyl-1H-pyrazol-3-yl)-N$^2$-(1H-indol-4-ylmethyl)- N$^2$-methyl-pyrimidine-2,4-diamine |

TABLE I-continued

| Cpd. No. | Structure | $K_i{}^5$ | $MS^2$ | $^1H$ NMR | Name |
|---|---|---|---|---|---|
| I-41 | 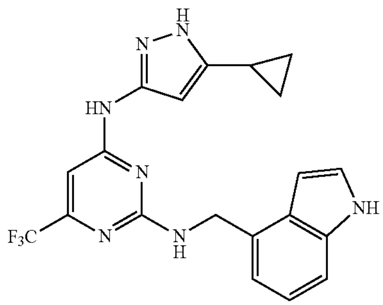 [SMILES: FC(F)(F)c1cc(Nc2cc(C3CC3)[nH]n2)nc(NCc2cccc3[nH]ccc23)n1] | C | 414.2 | (DMSO-$d_6$) δ 11.96 (br s, 1H), 11.07 (s, 1H), 9.86 (br s, 1H), 7.75 (br s, 1H), 7.38-7.20 (m, 2H), 7.06-6.86 (m, 2H), 6.58 (s, 1H), 6.24 (br s, 1H), 6.02 (br s, 1H), 4.78 (d, J = 5.6 Hz, 2H), 1.90 - 1.50 (m, 1H), 1.0-0.20 (m, 4H) | $N^4$-(5-Cyclopropyl-1H-pyrazol-3-yl)-$N^2$-(1H-indol-4-ylmethyl)-6-trifluoromethyl-pyrimidine-2,4-diamine |
| I-42 | 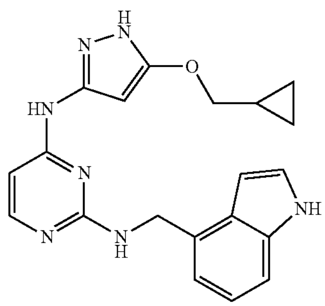 [SMILES: c1cc(CNc2nccc(Nc3cc(OCC4CC4)[nH]n3)n2)c2cc[nH]c2c1] | C | 376.2 | (DMSO-$d_6$) δ 11.93 (s, 1H), 11.09 (s, 1H), 9.84 (d, J = 64.8 Hz, 1H), 7.91 (s, 1H), 7.60 (s, 1H), 7.37-7.17 (m, 2H), 7.03 (dd, J = 9.3, 5.8 Hz, 1H), 6.97 (d, J = 7.0 Hz, 1H), 6.63-6.40 (m, 1H), 5.96 (s, 1H), 5.15 (s, 1H), 4.74 (d, J = 5.7 Hz, 2H), 3.83 (s, 2H), 1.18 (s, 1H), 0.51 (q, J +32 5.6 Hz, 2H), 0.27 (d, J = 3.8 Hz, 2H). | $N^4$-(5-Cyclopropylmethoxy-1H-pyrazol-3-yl)-$N^2$-(1H-indol-4-ylmethyl)-pyrimidine-2,4-diamine |
| I-43 | 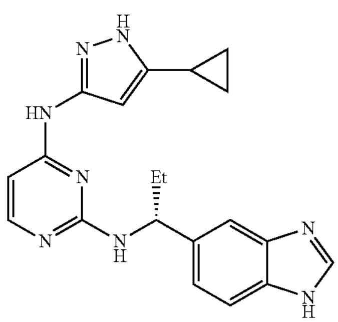 [SMILES: CC[C@@H](Nc1nccc(Nc2cc(C3CC3)[nH]n2)n1)c1ccc2[nH]cnc2c1] | C | 375.2 | (DMSO-$d_6$): δ 12.30 (s, 1H), 11.84 (s, 1H), 9.99 - 9.02 (m, 1H), 8.13 (s, 1H), 7.74 (s, 1), 7.67 - 6.81 (m, 4H), 6.49-5.30 (m, 2H), 5.06-4.88 (m, 1H), 1.95-1.68 (m, 3H), 1.04-0.53 (m, 7H) | $N^2$-[1-(1H-Benzoimidazol-5-yl)-propyl]-$N^4$-(5-cyclopropyl-1H-pyrazol-3-yl)-pyrimidine-2,4-diamine |
| I-44 | 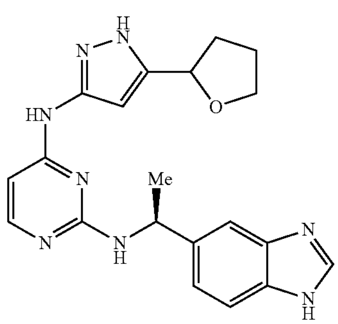 [SMILES: C[C@H](Nc1nccc(Nc2cc(C3CCCO3)[nH]n2)n1)c1ccc2[nH]cnc2c1] | B | 391.2 | (DMSO-$d_6$) δ 12.58 (s, 2H), 11.16 (s, 1H), 9.12 (s, 2H), 7.87 (s, 1H), 7.75 (s, 2H), 7.53 (s, 1H), 6.30 (s, 2H), 5.33 (s, 1H), 4.87 (dd, J = 17.9, 11.1 Hz, 1H), 2.33-2.05 (m, 1H), 1.96 (dt, J = 17.0, 10.0 Hz, 3H), 1.76 (s, 1H), 1.60 (d, J = 6.8 Hz, 3H). | $N^2$-[1-(1H-Benzoimidazol-5-yl)-ethyl]-$N^4$-[5-(tetrahydro-furan-2-yl)-1H-pyrazol-3-yl]-pyrimidine-2,4-diamine |
| I-45 | 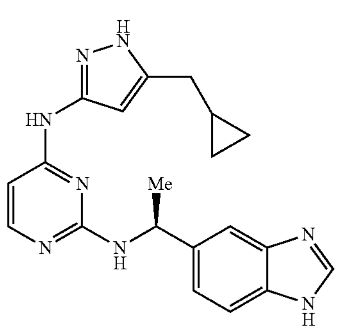 [SMILES: C[C@H](Nc1nccc(Nc2cc(CC3CC3)[nH]n2)n1)c1ccc2[nH]cnc2c1] | A | 375.2 | (DMSO-$d_6$) δ 12.29 (s, 1H), 11.81 (s, 1H), 9.23 (s, 1H), 8.12 (s, 1H), 7.76 (d, J = 5.5 Hz, 1H), 7.65 (s, 1H), 7.59-7.45 (m, 1H), 7.41 (d, J = 8.1 Hz, 1H), 7.24 (dd, J = 19.3, 8.1 Hz, 1H), 7.08 (s, 1H), 6.27 (s, 1H), 6.12 (s, 1H), 5.22 (s, 1H), 2.96 (dt, J = 13.1, 6.6 Hz, 1H), 1.48 (d, J = 7.0 Hz, 3H), 0.94 (t, J = 6.3 Hz, 2H), 0.46 (d, J = 7.2 Hz, 2H), 0.18 (s, 2H). | $N^2$-[(S)-1-(1H-Benzoimidazol-5-yl)-ethyl]-$N^4$-(5-cyclo-propylmethyl-1H-pyrazol-3-yl)-pyrimidine-2,4-diamine |

TABLE I-continued

| Cpd. No. | Structure | $K_i^5$ | $MS^2$ | $^1H$ NMR | Name |
|---|---|---|---|---|---|
| I-46 | 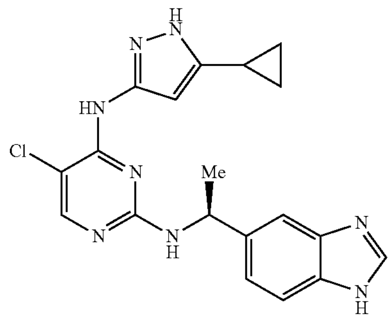 [SMILES: C[C@H](Nc1ncc(Cl)c(Nc2cc(C3CC3)[nH]n2)n1)c1ccc2[nH]cnc2c1] | B | 395.1 | (DMSO-d$_6$): δ 12.30 (s, 1H), 12.05 (s, 1H), 9.82-9.28 (m, 1H), 8.14 (s, 1H), 7.90 (s, 1H), 7.61 (s, 1H), 7.55 (d, J = 7.8 Hz, 1H), 7.47 (s, 1H), 7.19 (s, 1H), 7.06 (s, 1H), 6.18-5.94 (m, 1H), 5.13 (s, 1H), 1.88 (d, J = 19.2 Hz, 1H), 1.48 (d, J = 6.9 Hz, 3H), 1.05-0.77 (m, 3H), 0.68 (s, 2H) | $N^2$-[(S)-1-(1H Benzoimidazol-5-yl)-ethyl]-5-chloro-$N^4$-(5-cyclopropyl-1H-pyrazol-3-yl)-pyrimidine-2,4-diamine |
| I-47 | 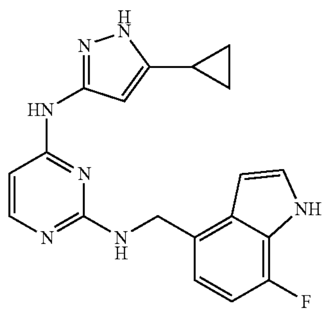 [SMILES: Fc1ccc(CNc2nccc(Nc3cc(C4CC4)[nH]n3)n2)c2cc[nH]c12] | C | 364.1 | (DMSO-d$_6$ + D$_2$O): δ 7.84 (s, 1H), 7.39 (s, 1H), 6.86-6.84 (m, 2H), 6.66 (s, 1H), 6.20-6.12 (m, 2H), 4.72 (d, 2H), 1.71-1.68 (m, 1H), 0.88-0.27 (m, 4H) | $N^4$-(5-Cyclopropyl-1H-pyrazol-3-yl)-$N^2$-(7-fluoro-1H-indol-4-ylmethyl)-pyrimidine-2,4-diamine |
| I-48 | 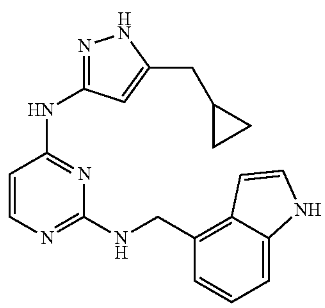 [SMILES: c1cc(CNc2nccc(Nc3cc(CC4CC4)[nH]n3)n2)c2cc[nH]c2c1] | B | 380.1 | (DMSO-d$_6$) δ 11.77 (s, 1H), 11.05 (s, 1H), 9.25 (s, 1H), 7.80 (d, J = 5.1 Hz, 1H), 7.30 (s, 1H), 7.25 (d, J = 7.8 Hz, 1H), 6.98 (dd, J = 15.7, 8.0 Hz, 2H), 6.92 (d, J = 7.1 Hz, 1H), 6.68-6.44 (m, 1H), 6.24 (d, J = 23.5 Hz, 2H), 4.76 (d, J = 6.0 Hz, 2H), 2.31 (d, J = 14.5 Hz, 2H), 1.02-0.65 (m, 1H), 0.36 (s, 2H), 0.11 (d, J = 31.0 Hz, 2H). | $N^4$-(5-Cyclopropylmethyl-1H-pyrazol-3-yl)-$N^2$-(1H-indol-4-ylmethyl)-pyrimidine-2,4-diamine |
| I-49 | 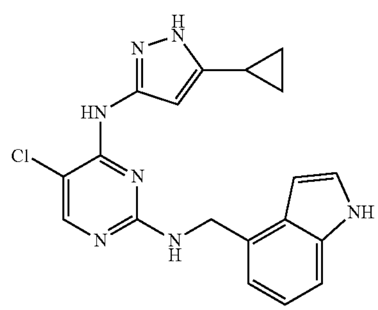 [SMILES: Clc1cnc(NCc2cccc3[nH]ccc23)nc1Nc1cc(C2CC2)[nH]n1] | C | | (DMSO-d$_6$) δ 11.16 (s, 1H), 9.96 (s, 1H), 8.39 (s, 1H), 8.16 (s, 1H), 7.47-7.27 (m, 2H), 7.03 (t, J = 7.6 Hz, 1H), 6.88 (s, 1H), 6.53 (s, 1H), 6.26 (s, 1H), 5.97 (s, 1H), 4.77 (s, 2H), 1.72 (d, J = 78.5 Hz, 1H), 0.81 (s, 1H), 0.75 (s, 2H), 0.35 (s, 1H). | 5-Chloro-$N^4$-(5-cyclopropyl-1H-pyrazol-3-yl)-$N^2$-(1H-indol-4-ylmethyl)-pyrimidine-2,4-diamine |
| I-50 | 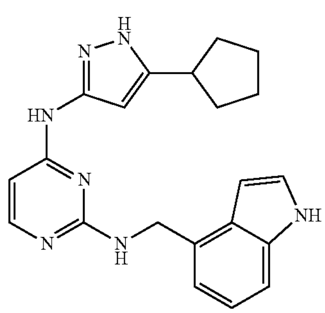 [SMILES: c1cc(CNc2nccc(Nc3cc(C4CCCC4)[nH]n3)n2)c2cc[nH]c2c1] | B | 374.2 | (DMSO-d$_6$) δ 11.06 (s, 1H), 9.34 (s, 1H), 8.16 (s, 1H), 7.81 (d, J = 5.7 Hz, 1H), 7.39-7.19 (m, 2H), 7.11 (s, 1H), 7.03-6.83 (m, 2H), 6.55 (s, 1H), 6.15 (s, 2H), 4.77 (d, J = 6.1 Hz, 2H), 1.83 (s, 2H), 1.45 (d, J = 65.6 Hz, 7H). | $N^4$-(5-Cyclopentyl-1H-pyrazol-3-yl)-$N^2$-(1H-indol-4-ylmethyl)-pyrimidine diamine |

TABLE I-continued

| Cpd. No. | Structure | $K_i^5$ | $MS^2$ | $^1$H NMR | Name |
|---|---|---|---|---|---|
| I-51 | 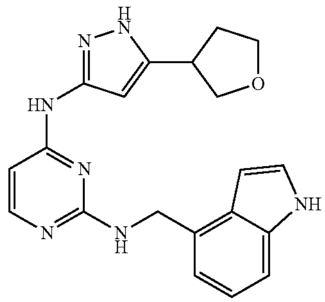 [SMILES: c1cc(CNc2nccc(Nc3cc(C4CCOC4)[nH]n3)n2)c2cc[nH]c2c1] | B | 376.2 | (DMSO-d$_6$) δ 12.51 (s, 1H), 11.20 (d, J = 22.1 Hz, 2H), 8.71 (s, 1H), 8.13 (s, 1H), 7.85 (d, J = 7.3 Hz, 1H), 7.37 (d, J = 8.7 Hz, 1H), 7.35 (d, J +32 7.8 Hz, 1H), 7.05 (s, 1H), 6.92 (s, 1H), 6.56 (s, 1H), 6.33 (d, J = 6.9 Hz, 1H), 6.24 (s, 1H), 4.89 (s, 2H), 3.11 (s, 1H), 1.96 (s, 1H), 1.55 (s, 1H). | N$^2$-(1H-Indol-4-ylmethyl)-N$^4$-[5-(tetrahydrofuran-3-yl)-1H-pyrazol-3-yl]-pyrimidine-2,4-diamine |
| I-52 | 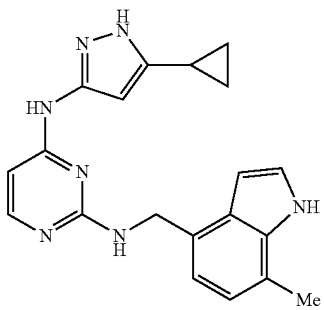 [SMILES: Cc1ccc(CNc2nccc(Nc3cc(C4CC4)[nH]n3)n2)c2cc[nH]c12] | B | 360.2 | (DMSO-d$_6$ + D$_2$O) δ 7.79 (s, 1H), 7.30 (s, 1H), 6.83-6.81 (m, 2H), 6.57 (s, 1H), 6.21-5.95 (m, 2H), 4.72 (s, 2H), 2.44 (s, 3H), 1.79-1.67 (m, 1H), 0.82-0.38 (m, 4H) | N$^4$-(5-Cyclopropyl-1H-pyrazol-3-yl)-N$^2$-(7-methyl-1H-indol-4-ylmethyl)-pyrimidine-2,4-diamine |
| I-53 | 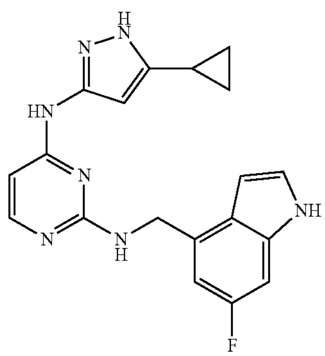 [SMILES: Fc1cc(CNc2nccc(Nc3cc(C4CC4)[nH]n3)n2)c2cc[nH]c2c1] | A | 364.2 | (CD$_3$OD) δ 7.72 (s, 1H), 7.13 (d, 1H, J = 3.5 Hz), 6.87 (d, 1H, J = 10 Hz), 6.68 (d, 1H, J = 10 Hz), 6.45 (d, 1H, J = 3.5 Hz), 6.06-5.81(m, 2H), 4.74 (d, 2H), 1.59-1.57 (m, 1H), 0.71-0.27 (m, 4H); MS (ESI) m/z = 364.2 [M + 1]$^+$. | N$^4$-(5-Cyclopropyl-1Hpyrazol-3-yl)-N$^2$-(6-fluoro-1H-indol-4-ylmethyl)-pyrimidine-2,4-diamine |
| I-54 | 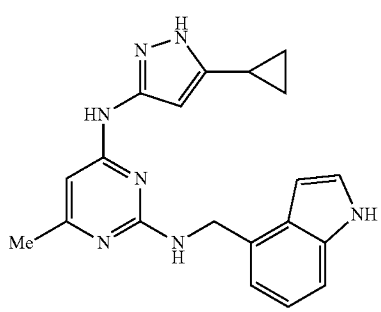 [SMILES: Cc1cc(Nc2cc(C3CC3)[nH]n2)nc(NCc2cccc3[nH]ccc23)n1] | B | 360.2 | (DMSO-d$_6$): δ 11.06 (s, 1H), 9.25 (br s, 1H), 8.16 (s, 1H Formic acid), 7.31 (t, J = 2.7 Hz, 1H), 7.26 (d, J = 8.0 Hz, 1H), 7.08 (s, 1H), 6.99 (d, J = 7.8 Hz, 1H), 6.93 (d, J = 7.1 Hz, 1H), 6.56 (s, 1H), 6.02 (br s, 1H), 5.94 (br s, 1H), 4.76 (d, J = 6.1 Hz, 2H), 2.09 (s, 3H), 1.72 (s, 1H), 0.79 (d, J +32 6.4 Hz, 2H), 0.51 (s, 2H) | N$^4$-(5-Cyclopropyl-1H-pyrazol-3-yl)-N$^2$-(1H-indol-4-ylmethyl)-6-methyl-pyrimidine-2,4-diamine |
| I-55 | 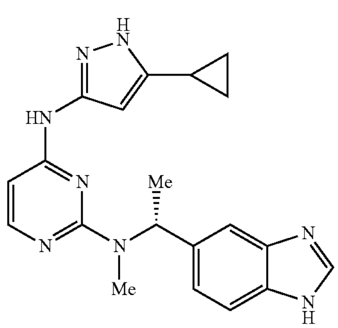 [SMILES: C[C@H](c1ccc2[nH]cnc2c1)N(C)c1nccc(Nc2cc(C3CC3)[nH]n2)n1] | B | 375.3 | (CD$_3$OD) δ 8.04 (s, 1H), 7.81 (d, J = 4.5 Hz, 1H), 7.48 (m, 2H), 7.16 (d, J = 9 Hz, 1H), 6.23 (brs, 1H), 6.09 (brs, 1H), 2.70 (s, 3H), 1.68-1.72 (m, 1H), 1.57 (d, J = 6, 3H), 1.14 (m, 1H), 0.79 (m, 2H), 0.47 (m, 2H) | N$^2$-[(R)-1-(1H-Benzoimidazol-5-yl)-ethyl]-N$^4$-(5-cyclopropyl-1H-pyrazol-3-yl)-N-methyl-pyrimidine-2,4-diamine |

TABLE I-continued

| Cpd. No. | Structure | $K_i{}^5$ | $MS^2$ | $^1H$ NMR | Name |
|---|---|---|---|---|---|
| I-56 | 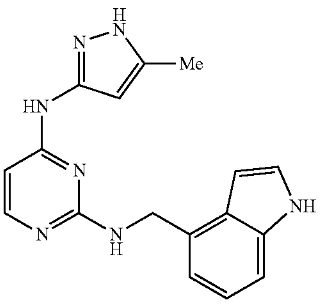 [SMILES: Cc1cc(Nc2ccnc(NCc3cccc4[nH]ccc34)n2)n[nH]1] | D | 320.2 | (DMSO-d$_6$) δ 11.59 (d, J = 118.3 Hz, 1H), 11.05 (s, 1H), 9.21 (s, 1H), 7.79 (d, J = 5.3 Hz, 1H), 7.31 (s, 1H), 7.25 (d, J = 8.0 Hz, 1H), 6.99 (t, J +32 7.4 Hz, 2H), 6.92 (d, J = 6.9 Hz, 1H), 6.56 (s, 1H), 6.21 (s, 1H), 5.97 (s, 1H), 4.75 (d, J = 6.1 Hz, 2H), 2.06 (d, J = 5.2 Hz, 3H). | N$^2$-(1H-Indol-4-ylm-ethyl)-N$^4$-(5-methyl-1H-pyra-zol-3-yl)-pyrimidine-2,4-di-amine |
| I-57[3] | 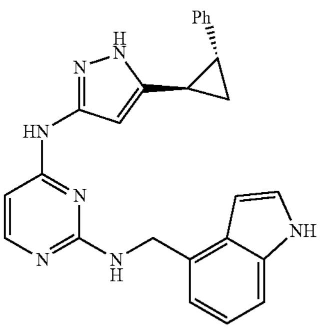 [SMILES: c1ccc([C@@H]2C[C@H]2c2cc(Nc3ccnc(NCc4cccc5[nH]ccc45)n3)n[nH]2)cc1] | C | 422.2 | (DMSO-d$_6$) δ 10.98 (s, 1H), 10.84 (s, 1H), 8.46 (s, 1H), 7.85 (d, J = 7.2 Hz, 1H), 7.38 (d, J = 8.0 Hz, 1H), 7.30 (dd, J = 5.2, 2.2 Hz, 2H), 7.26 (s, 1H), 7.18 (dd, J = 8.5, 6.1 Hz, 1H), 7.12 (d, J = 7.5 Hz, 2H), 7.07 (d, J = 7.8 Hz, 1H), 6.99 (d, J = 7.1 Hz, 1H), 6.57 (s, 1H), 6.50 (s, 1H), 6.28 (s, 1H), 4.92 (d, J = 4.2 Hz, 2H), 2.09 (dd, J = 13.9, 7.8 Hz, 2H), 1.35 (dt, J = 8.9, 5.5 Hz, 1H), 1.26 | N$^2$-(1H-Indol-4-ylm-ethyl)-N$^4$-[5-((1R,2R)-2-phenyl-cyclopropyl)-1H-pyrazol-3-yl]-pyrimidine-2,4 diamine |
| I-58 | 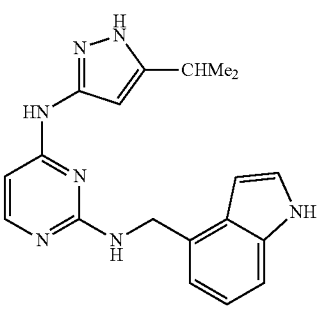 | B | 348.2 | (DMSO-d$_6$) δ 11.76 (s, 1H), 11.06 (s, 1H), 9.31 (s, 1H), 7.81 (d, J = 5.6 Hz, 1H), 7.30 (t, J = 2.7 Hz, 1H), 7.25 (d, J = 8.0 Hz, 1H), 7.17-7.03 (m, 1H), 7.03-6.95 (m, 1H), 6.93 (d, J = 7.1 Hz, 1H), 6.54 (d, J = 10.9 Hz, 1H), 6.17 (s, 2H), 4.77 (d, J = 6.1 Hz, 2H), 2.84-2.68 (m, 1H), 1.32 - 0.91 (m, 6H). | N$^2$-(1H-Indol-4-ylm-ethyl)-N$^4$-(5-isopropyl-1H-pyra-zol-3-yl)-pyrimidine-2,4-diamine |
| I-59 | 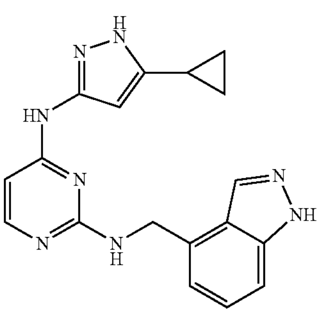 [SMILES: c1cc(CNc2nccc(Nc3cc(C4CC4)[nH]n3)n2)c2cn[nH]c2c1] | A | 347.3 | (DMSO-d$_6$) δ 13.13 (s, 1H), 11.89 (s, 1H), 9.32 (s, 1H), 8.20 (s, 1H), 7.81 (s, 1H), 7.40-7.38 (m, 1H), 7.27-7.25 (m, 2H), 7.01-7.00 (m, 1H), 6.18-6.12 (m, 2H), 4.81 (d, 2H), 1.78-1.75 (m, 1H), 0.80-0.62 (m, 4H) | N$^4$-(5-Cyclopropyl-1H-pyrazol-3-yl)-N$^2$-(1H-indazol 4-ylmethyl)-pyrimi-dine-2,4-diamine |
| I-60 | 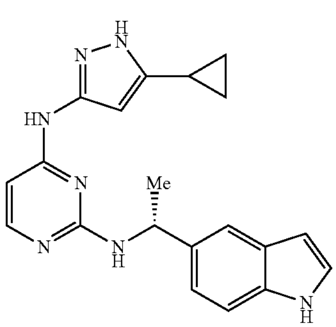 [SMILES: C[C@@H](Nc1nccc(Nc2cc(C3CC3)[nH]n2)n1)c1ccc2[nH]ccc2c1] | D | 360.3 | (DMSO-d$_6$): δ 11.82 (br s, 1H), 10.92 (s, 1H), 9.19 (br s, 1H), 7.76 (d, J = 4.6 Hz, 1H), 7.52 (s, 1H), 7.30 (d, J = 8.3 Hz, 1H), 7.27 (t, J = 2.6 Hz, 1H), 7.14 (d, J = 8.4 Hz, 1H), 6.94 (br s, 1H), 6.34 (s, 1H), 6.30-5.80 (br s, 2H), 5.25-5.11 (m, 1H), 1.84 (s, 1H), 1.47 (d, J = 6.9 Hz, 3H), 0.91 (s, 2H), 0.68 (s, 2H) | N$^4$-(5-Cyclopropyl-2H-pyrazol-3-yl)-N$^2$-[(R)-1-(1H-indol-5-yl)-ethyl]-pyrimidine-2,4-diamine |

TABLE I-continued

| Cpd. No. | Structure | $K_i$[5] | MS[2] | $^1$H NMR | Name |
|---|---|---|---|---|---|
| I-61 | 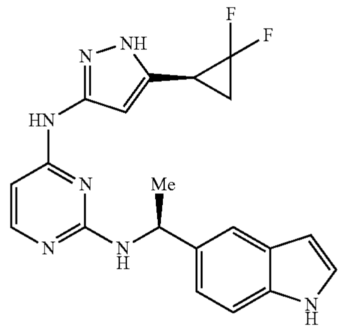 [SMILES: C[C@H](Nc1nccc(Nc2cc([C@@H]3CC3(F)F)[nH]n2)n1)c1ccc2[nH]ccc2c1] | B | 397.1 | (DMSO-$d_6$) δ 12.29 (s, 1H), 12.22-12.06 (m, 1H), 10.12-9.86 (m, 1H), 8.13 (s, 1H), 7.89 - 7.33 (m, 4H), 7.32-6.96 (m, 2H), 6.19-5.81 (m, 1H), 5.75-5.56 (m, 1H), 5.19 (s, 1H), 3.03 - 2.74 (m, 1H), 2.19-1.68 (m, 2H), 1.48 (d, J = 6.9 Hz, 3H) | $N^2$-[1-(1H-Benzoimidazol-5-yl)-ethyl]-$N^4$-[5-(2,2-difluoro-cyclopropyl)-1H-pyrazol-3-yl]-pyrimidine-2,4-diamine |
| I-62 | 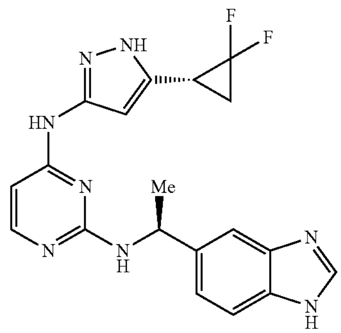 [SMILES: C[C@H](Nc1nccc(Nc2cc([C@H]3CC3(F)F)[nH]n2)n1)c1ccc2[nH]cnc2c1] | A | 397.1 | (DMSO-$d_6$) δ 13.07-11.78 (m, 1H), 10.23-9.17 (m, 1H), 8.13 (s, 1H), 7.80 (d, J = 5.7 Hz, 1H), 7.68-7.39 (m, 2H), 7.23 (d, J = 8.2 Hz, 1H), 6.00 (s, 1H), 5.28-5.11 (m, 1H), 3.00-2.79 (m, 1H), 2.10-1.92 (m, 1H), 1.92-1.78 (m, 1H), 1.48 (d, J = 6.9 Hz, 3H) | |
| I-63 | 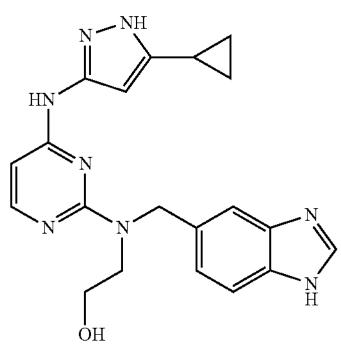 [SMILES: OCCN(Cc1ccc2[nH]cnc2c1)c1nccc(Nc2cc(C3CC3)[nH]n2)n1] | B | 391.0 | (DMSO-$d_6$) δ 11.81 (br s, 1H), 9.35 (br s, 1H), 8.12 (s, 1H), 7.89 (d, J = 5.7 Hz, 1H), 7.50 (d, J = 8.2 Hz, 1H), 7.42 (s, 1H), 7.12 (d, J = 8.3 Hz, 1H), 6.30-6.15 (m, 1H), 6.15-5.97 (m, 1H), 4.91 (s, 2H), 3.56 (q, J = 6.9 Hz, 2H), 1.84-1.66 (m, 1H), 1.08 (t, J = 6.9 Hz, 2H), 0.90-0.70 (m, 2H), 0.65-0.25 (m, 2H). | 2-{(1H-Benzoimidazol-5-ylmethyl)-[4-(5-cyclo-propyl-1H-pyrazol-3-ylamino)-pyrimidin-2-yl]-amino}-ethanol |
| I-64 | 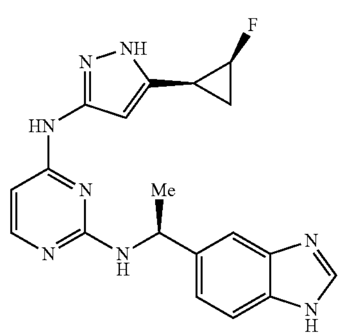 [SMILES: C[C@H](Nc1nccc(Nc2cc([C@@H]3C[C@@H]3F)[nH]n2)n1)c1ccc2[nH]cnc2c1] | B | 378.2 | (DMSO-$d_6$)† δ 11.98 (s, 1H), 10.92 (s, 1H), 9.21 (br s, 1H), 7.89-7.72 (m, 1H), 7.53 (s, 1H), 7.35-7.22 (m, 2H), 7.14 (d, J = 8.3 Hz, 1H), 7.07 - 6.81 (m, 1H), 6.34 (s, 1H), 6.26-5.83 (m, 1H), 5.35-5.07 (m, 1H), 5.10-4.67 (m, 1H), 2.10 - 1.97 (m, 1H), 1.47 (d, J = 6.9 Hz, 3H), 1.40 - 1.10 (m, 2H) | $N^4$-[5-(2-Fluoro-cyclopropyl)-1H-pyrazol-3-yl]-$N^2$-[1-(1H-indol-5-yl)-ethyl]-pyrimidine-2,4-diamine |

TABLE I-continued

| Cpd. No. | Structure | $K_i^5$ | $MS^2$ | $^1$H NMR | Name |
|---|---|---|---|---|---|
| I-65 | 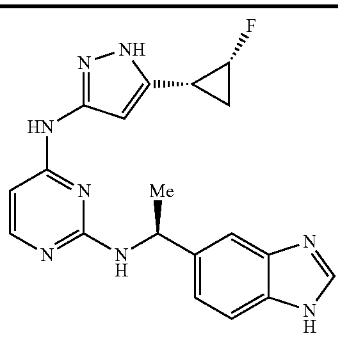 | A | 378.2 | (DMSO-d$_6$)† δ 11.98 (s, 1H), 10.92 (s, 1H), 9.21 (s, 1H), 7.86-7.70 (m, 1H), 7.52 (s, 1H), 7.35-7.25 (m, 2H), 7.14 (d, J = 8.2 Hz, 1H), 7.05-6.80 (m, 1H), 6.50-6.30 (m, 1H), 6.21-5.80 (m, 1H), 5.18 (s, 1H), 5.07-4.71 (m, 1H), 2.12-1.98 (m, 1H), 1.46 (d, J = 6.7 Hz, 3H), 1.42-1.02 (m, 2H) | N$^4$-[5-(2-Fluoro-cyclopropyl)-1H-pyrazol-3-yl]-N$^2$-[1-(1H-indol-5-yl)-ethyl]-pyrimidine-2,4-diamine |
| I-66[4] | 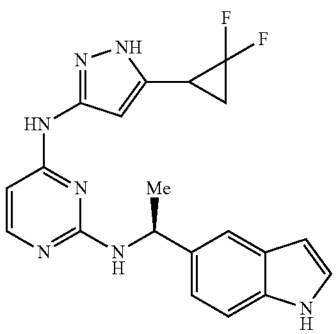 [SMILES: C[C@H](Nc1nccc(Nc2cc(C3CC3(F)F)[nH]n2)n1)c1ccc2[nH]ccc2c1] | B | 396.2 | | N$^4$-[5-(2,2-Difluoro-cyclopropyl)-1H-pyrazol-3-yl]-N$^2$[1-(1H-indol-5-yl)-ethyl]-pyrimidine-2,4-diamine |
| I-67 | 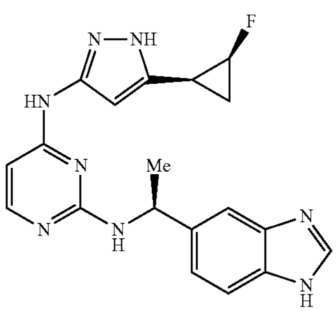 [SMILES: C[C@H](Nc1nccc(Nc2cc([C@@H]3C[C@@H]3F)[nH]n2)n1)c1ccc2[nH]cnc2c1] | A | 379.2 | | N$^2$-[1-(1H-Benzoimidazol-5-yl)-ethyl]-N$^4$-[5-(2-fluoro-cyclopropyl)-1H-pyrazol-3-yl]-pyrimidine-2,4-diamine |
| I-68 | 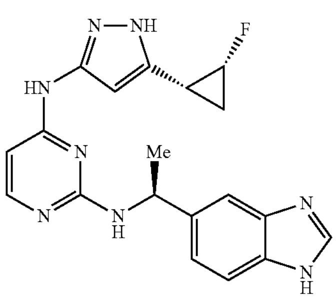 [SMILES: C[C@H](Nc1nccc(Nc2cc([C@H]3C[C@H]3F)[nH]n2)n1)c1ccc2[nH]cnc2c1] | A | 379.2 | | N$^2$-[1-(1H-Benzoimidazol-5-yl)-ethyl]-N$^4$-[5-(2-fluoro-cyclopropyl)-1H-pyrazol-3-yl]-pyrimidine-2,4-diamine |
| I-69 | 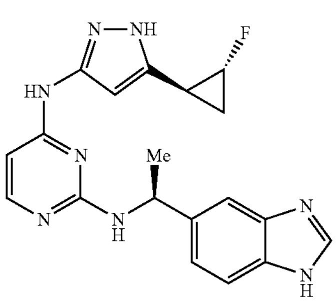 [SMILES: C[C@H](Nc1nccc(Nc2cc([C@@H]3C[C@H]3F)[nH]n2)n1)c1ccc2[nH]cnc2c1] | A | 379.1 | | N$^2$-[1-(1H-Benzoimidazol-5-yl)-ethyl]-N$^4$-[5-(2-fluoro-cyclopropyl)-1H-pyrazol-3-yl]-pyrimidine-2,4-diamine |

TABLE I-continued

| Cpd. No. | Structure | $K_i^5$ | MS² | ¹H NMR | Name |
|---|---|---|---|---|---|
| I-70 | 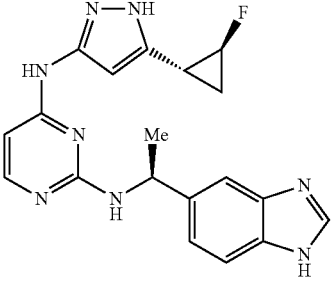 [SMILES: C[C@H](Nc1nccc(Nc2cc([C@H]3C[C@@H]3F)[nH]n2)n1)c1ccc2[nH]cnc2c1] | A | 379.1 | | N²-[1-(1H-Benzoimidazol-5-yl)-ethyl]-N⁴-[5-(2-fluoro-cyclopropyl)-1H-pyrazol-3-yl]-pyrimidine-2,4-diamine |
| I-71 | 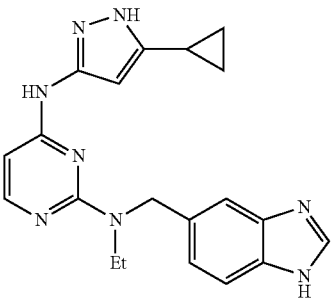 [SMILES: CCN(Cc1ccc2[nH]cnc2c1)c1nccc(Nc2cc(C3CC3)[nH]n2)n1] | A | 375.2 | (DMSO-d₆) δ 11.81 (br s, 1H), 9.35 (br s, 1H), 8.12 (s, 1H), 7.89 (d, J = 5.7 Hz, 1H), 7.50 (d, J = 8.2 Hz, 1H), 7.42 (s, 1H), 7.12 (d, J = 8.3 Hz, 1H), 6.30-6.15 (m, 1H), 6.15-5.97 (m, 1H), 4.91 (s, 2H), 3.56 (q, J = 6.9 Hz, 3H), 1.84-1.66 (m, 1H), 1.08 (t, J = 6.9 Hz, 2H), 0.90-0.70 (m, 2H), 0.65-0.25 (m, 2H) | N²-(1H-Benzoimidazol-5-ylmethyl)-N⁴-(5-cyclopropyl-1H-pyrazol-3-yl)-N²-ethyl-pyrimidine-2,4-diamine |
| I-72 | 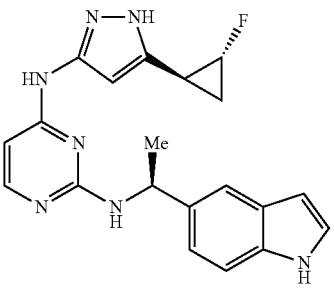 [SMILES: C[C@H](Nc1nccc(Nc2cc([C@@H]3C[C@H]3F)[nH]n2)n1)c1ccc2[nH]ccc2c1] | A | 378.2 | (DMSO-d₆) δ 12.09-11.78 (br s, 1H), 10.93 (s, 1H), 9.46-9.11 (br s, 1H), 7.79 (s, 1H), 7.52 (s, 1H), 7.36-7.23 (m, 2H), 7.13 (d, J = 8.3 Hz, 1H), 7.08-6.80 (m, 1H), 6.35 (s, 1H), 6.23-5.81 (m, 1H), 5.24-5.08 (m, 1H), 4.92-4.68 (m, 1H), 2.43-2.26 (m, 1H), 1.60-1.38 (m, 4H), 1.19-1.00 (m, 1H) | N⁴-[5-(2-Fluoro-cyclopropyl)-1H-pyrazol-3-yl]-N²-[1-(1H-indol-5-yl)-ethyl]-pyrimidine-2,4-diamine |
| I-73 | 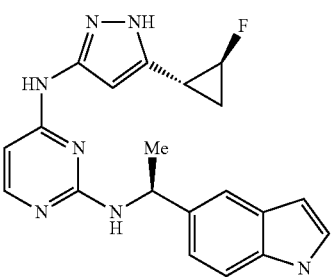 | A | 378.2 | (DMSO-d₆) δ 12.12-11.77 (br s, 1H), 10.93 (s, 1H), 9.41-9.11 (br s, 1H), 7.78 (s, 1H), 7.52 (s, 1H), 7.35-7.23 (m, 2H), 7.13 (d, J = 8.3 Hz, 1H), 7.10-6.83 (m, 1H), 6.35 (s, 1H), 6.23-5.83 (m, 1H), 5.16 (s, 1H), 5.00-4.62 (m, 1H), 2.44-2.26 (m, 1H), 1.64-1.34 (m, 4H), 1.18-1.00 (m, 1H) | N⁴-[5-(2-Fluoro-cyclopropyl)-1H-pyrazol-3-yl]-N²-[1-(1H-indol-5-yl)-ethyl]-pyrimidine-2,4-diamine |
| I-74 | 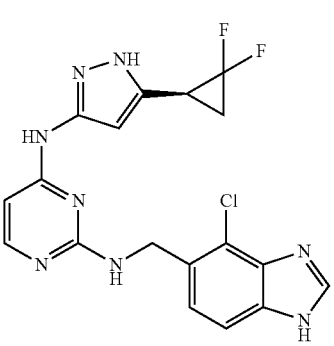 [SMILES: FC1(F)C[C@H]1c1cc(Nc2ccnc(NCc3ccc4[nH]cnc4c3Cl)n2)n[nH]1] | A | 417.1 | (DMSO-d₆)† δ 13.04-11.88 (m, 2H), 10.16-9.32 (m, 1H), 8.25 (s, 1H), 7.86 (d, J = 5.5 Hz, 1H), 7.60-7.20 (m, 3H), 6.47-5.79 (m, 2H), 4.68 (d, J = 6.0 Hz, 2H), 2.89-2.70 (m, 1H), 2.00-1.60 | N²-(4-Chloro-1H-benzoimidazol-5-ylmethyl)-N⁴-[5-(2-fluoro-cyclopropyl)-1H-pyrazol-3-yl]-pyrimidine-2,4-diamine |

TABLE I-continued

| Cpd. No. | Structure | $K_i^5$ | $MS^2$ | $^1H$ NMR | Name |
|---|---|---|---|---|---|
| I-75 | 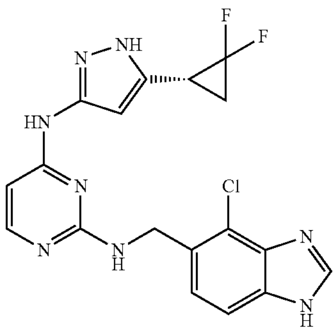 [SMILES: FC1(F)C[C@@H]1c1cc(Nc2ccnc(NCc3ccc4[nH]cnc4c3Cl)n2)n[nH]1] | A | 417.1 | (DMSO-d$_6$)† δ 13.04-11.88 (m, 2H), 10.16-9.32 (m, 1H), 8.25 (s, 1H), 7.86 (d, J = 5.5 Hz, 1H), 7.60-7.20 (m, 3H), 6.47-5.79 (m, 2H), 4.68 (d, J = 6.0 Hz, 2H), 2.89-2.70 (m, 1H), 2.00-1.60 (m, 2H) | N$^2$-(4-Chloro-1H-benzoimidazol-5-ylmethyl)-N$^4$-[5-(2-fluoro-cyclopropyl)-1H-pyrazol-3-yl]-pyrimidine-2,4-diamine |
| I-76 | 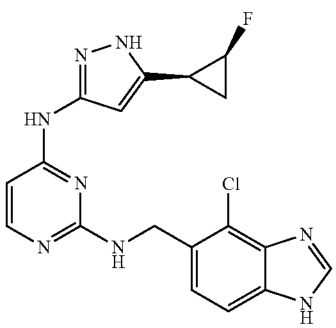 [SMILES: F[C@H]1C[C@H]1c1cc(Nc2ccnc(NCc3ccc4[nH]cnc4c3Cl)n2)n[nH]1] | A | 399.1 | (DMSO-d$_6$)† δ 12.64 (br s, 1H), 11.96 (br s, 1H), 9.33 (br s, 1H), 8.25 (s, 1H), 7.82 (s, 1H), 7.62-7.37 (m, 1H), 7.35-7.04 (m, 2H), 6.41-5.90 (m, 2H), 4.96-4.71 (m, 1H), 4.68 (d, J = 6.0 Hz, 2H), 2.04-1.82 (m, 1H), 1.30-0.82 (m, 2H) | N$^2$-(4-Chloro-1H-benzoimidazol-5-ylmethyl)-N$^4$-[5-(2-fluoro-cyclopropyl)-1H-pyrazol-3-yl]-pyrimidine-2,4-diamine |
| I-77 | 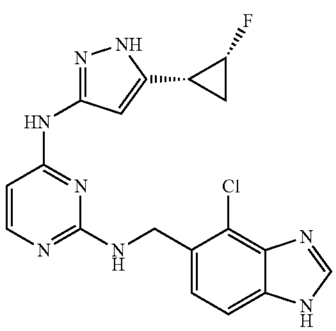 [SMILES: F[C@@H]1C[C@@H]1c1cc(Nc2ccnc(NCc3ccc4[nH]cnc4c3Cl)n2)n[nH]1] | A | 399 | (DMSO-d$_6$)† δ 12.64 (br s, 1H), 11.96 (br s, 1H), 9.33 (br s, 1H), 8.25 (s, 1H), 7.82 (s, 1H), 7.62-7.37 (m, 1H), 7.35-7.04 (m, 2H), 6.41-5.90 (m, 2H), 4.96-4.71 (m, 1H), 4.68 (d, J = 6.0 Hz, 2H), 2.04-1.82 (m, 1H), 1.30-0.82 (m, 2H) | N$^2$-(4-Chloro-1H-benzoimidazol-5-ylmethyl)-N$^4$-[5-(2-fluoro-cyclopropyl)-1H-pyrazol-3-yl]-pyrimidine-2,4-diamine |
| I-78 | 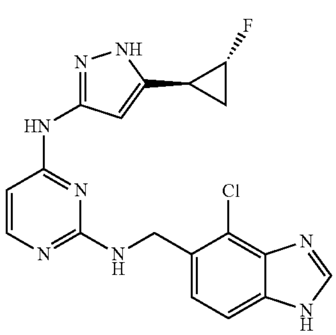 [SMILES: F[C@@H]1C[C@H]1c1cc(Nc2ccnc(NCc3ccc4[nH]cnc4c3Cl)n2)n[nH]1] | A | 399.1 | (DMSO-d$_6$)† δ 12.65 (s, 1H), 11.95 (br s, 1H), 9.34 (s, 1H), 8.26 (s, 1H), 7.90-7.76 (m, 1H), 7.63-7.39 (m, 1H), 7.38-7.04 (m, 2H), 6.27-5.80 (m, 2H), 4.90-4.42 (m, 3H), 2.40-2.02 (m, 1H), 1.54-0.63 (m, 3H) | N$^2$-(4-Chloro-1H-benzoimidazol-5-ylmethyl)-N$^4$-[5-(2-fluoro- |

TABLE I-continued

| Cpd. No. | Structure | $K_i^5$ | $MS^2$ | $^1H$ NMR | Name |
|---|---|---|---|---|---|
| I-79 | 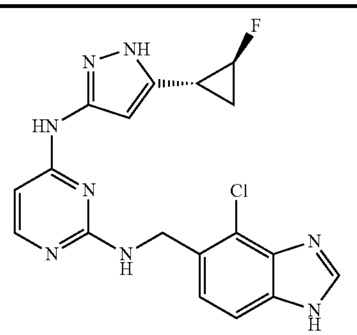 | A | 399.1 | (DMSO-$d_6$)† δ 12.65 (s, 1H), 11.95 (br s, 1H), 9.34 (br s, 1H), 8.26 (s, 1H), 7.90-7.76 (m, 1H), 7.63-7.39 (m, 1H), 7.38-7.04 (m, 2H), 6.27-5.80 (m, 2H), 4.90-4.42 (m, 3H), 2.40-2.02 (m, 1H), 1.54-0.63 (m, 3H) | $N^2$-(4-Chloro-1H-benzoimidazol-5-ylmethyl)-$N^4$-[5-(2-fluoro-cyclopropyl)-1H-pyrazol-3-yl]-pyrimidine-2,4-diamine |
| I-80[3] | 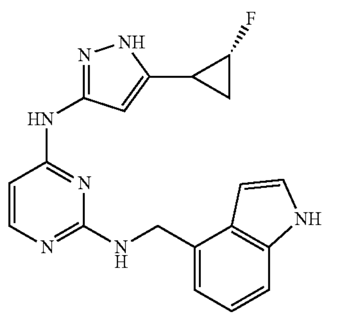 [SMILES: F[C@@H]1CC1c1cc(Nc2ccnc(NCc3cccc4[nH]ccc34)n2)n[nH]1] | A | 364.2 | (DMSO-$d_6$)† δ 12.85-11.69 (m, 1H), 11.09 (s, 1H), 10.06-9.14 (m, 1H), 7.84 (s, 1H), 7.34-7.21 (m, 2H), 7.22-6.87 (m, 2H), 6.55 (s, 1H), 6.26-5.50 (m, 2H), 4.95-4.50 (m, 1H), 4.75 (d, J = 6.0 Hz, 2H), 2.42-2.11 (m, 1H), 1.50-1.28 (m, 1H), 1.20-0.77 (m, 1H) | $N^4$-[5-(2-Fluoro-cyclopropyl)-1H-pyrazol-3-yl]-$N^2$-(1H-indol-4-ylmethyl)-pyrimidine-2,4-diamine |
| I-81[3] | 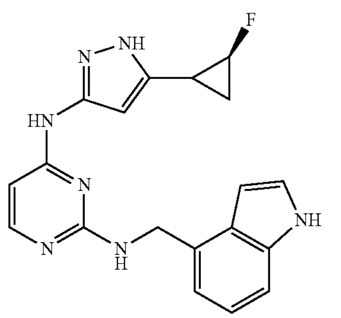 [SMILES: F[C@H]1CC1c1cc(Nc2ccnc(NCc3cccc4[nH]ccc34)n2)n[nH]1] | B | 364.2 | (DMSO-$d_6$)† δ 12.09-11.82 (br s, 1H), 11.05 (s, 1H), 9.39-9.16 (br s, 1H), 7.97-7.74 (m, 1H), 7.38-7.21 (m, 2H), 7.08-6.90 (m, 2H), 6.56 (s, 1H), 6.47-5.88 (m, 2H), 4.97-4.86 (m, 1H), 4.75 (d, J = 5.9 Hz, 2H), 2.05-1.86 (m, 1H), 1.42-1.04 (m, 2H) | $N^4$-[5-(2-Fluoro-cyclopropyl)-1H-pyrazol-3-yl]-$N^2$-(1H-indol-4-ylmethyl)-pyrimidine-2,4-diamine |
| I-82 | 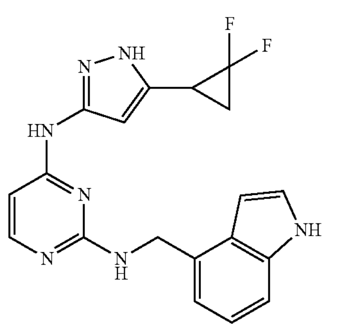 [SMILES: FC1(F)CC1c1cc(Nc2ccnc(NCc3cccc4[nH]ccc34)n2)n[nH]1] | A | 382.2 | (DMSO-$d_6$) δ 12.95-11.90 (m, 1H), 11.08 (s, 1H), 10.20-9.23 (m, 1H), 7.87 (s, 1H), 7.37-7.21 (m, 2H), 7.21-6.85 (m, 3H), 6.54 (s, 1H), 6.41-5.90 (m, 2H), 4.75 (d, J = 5.9 Hz, 2H), 2.93-2.71 (m, 1H), 2.00-1.65 (m, 2H) | $N^4$-[5-(2,2-Difluoro-cyclopropyl)-1H-pyrazol-3-yl]-$N^2$-(1H-indol-4-ylmethyl)-pyrimidine-2,4-diamine |
| I-83 | 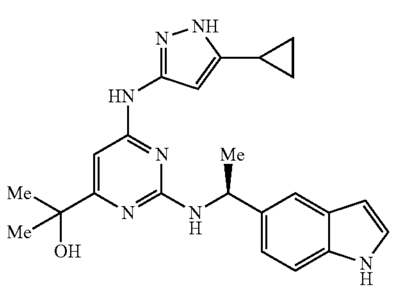 [SMILES: C[C@H](Nc1nc(Nc2cc(C3CC3)[nH]n2)cc(C(C)(C)O)n1)c1ccc2[nH]ccc2c1] | A | 418.3 | (DMSO-$d_6$) δ 10.91 (s, 1H), 9.34 (br s, 1H), 8.16 (s, 1H), 7.54 (s, 1H), 7.33-7.24 (m, 2H), 7.16 (d, J = 8.4 Hz, 1H), 7.11-6.89 (m, 1H), 6.36-6.24 (m, 2H), 6.18-5.80 (m, 1H), 5.21-5.10 (m, 1H), 5.05 ? | 2-{6-(5-Cyclopropyl-1H-pyrazol-3-ylamino)-2-[(S)-1-(1H-indol-5-yl)-ethylamino]-pyrimidin-4-yl}-propan-2-ol |

TABLE I-continued

| Cpd. No. | Structure | $K_i^5$ | $MS^2$ | $^1H$ NMR | Name |
|---|---|---|---|---|---|
| I-84 | 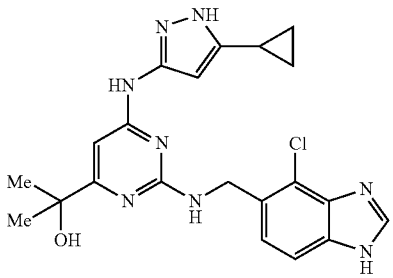 [SMILES: CC(C)(O)c1cc(Nc2cc(C3CC3)[nH]n2)nc(NCc2ccc3[nH]cnc3c2Cl)n1] | A | 439.1 | (DMSO-d$_6$) δ 12.97-12.47 (m, 1H), 11.73 (br s, 1H), 9.17 (br s, 1H), 8.23 (s, 1H), 7.77-7.38 (m, 2H), 7.37-7.16 (m, 1H), 7.14-6.89 (m, 1H), 6.54-6.22 (m, 1H), 4.90 (s, 1H), 4.67 (d, J = 5.9 Hz, 2H) 1.87-1.55 (m, 1H), 1.31 (s, 6H), 0.87-0.68 (m, 2H), 0.71-0.27 (m, 2H) | 2-[2-[(4-Chloro-1H-benzoimidazol-5-ylmethyl)-amino]-6-(5-cyclopropyl-1H-pyrazol-3-ylamino)-pyrimidin-4-yl]-propan-2-ol |
| I-85 | 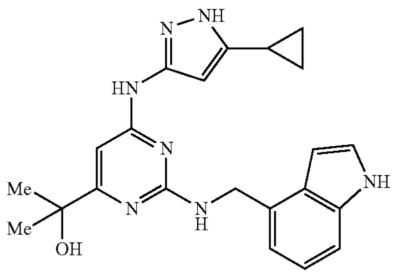 [SMILES: CC(C)(O)c1cc(Nc2cc(C3CC3)[nH]n2)nc(NCc2cccc3[nH]ccc23)n1] | B | 404.2 | (DMSO-d$_6$) δ 11.79 (br s, 1H), 11.03 (s, 1H), 9.13 (br s, 1H), 7.32-7.22 (m, 2H), 7.05-6.85 (m, 3H), 6.59 (s, 1H), 6.53-6.32 (m, 1H), 6.36-5.95 (m, 1H), 4.91 (s, 1H), 4.75 (d, J = 6.1 Hz, 2H), 1.85-1.60 (m, 1H), 0.86-0.74 (m, 2H), 0.70-0.35 (m, 2H) | 2-{6-(5-Cyclopropyl-1H-pyrazol-3-ylamino)-2-[(1H-indol-4-ylmethyl)-amino]-pyrimidin-4-yl}-propan-2-ol |
| I-86 | 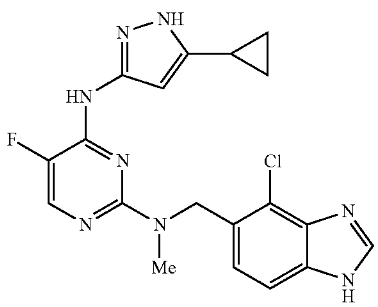 [SMILES: CN(Cc1ccc2[nH]cnc2c1Cl)c1ncc(F)c(Nc2cc(C3CC3)[nH]n2)n1] | A | 413.1 | (DMSO-d$_6$) δ 12.69 (br s, 1H), 11.95 (br s, 1H), 9.41 (br s, 1H), 8.26 (s, 1H), 8.00-7.90 (m, 1H), 7.57-7.35 (m, 1H), 6.95 (d, J = 8.3 Hz, 1H), 6.17-5.85 (m, 1H), 4.96 (s, 2H), 3.11 (s, 3H), 1.74-1.57 (m, 1H), 0.83-0.64 (m, 2H), 0.47-0.25 (m, 2H) | $N^2$-(4-Chloro-1H-benzoimidazol-5-ylmethyl)-$N^4$-(5-cyclopropyl-1H-pyrazol-3-yl)-5-fluoro-$N^2$-methyl-pyrimidine-2,4-diamine |
| I-87 | 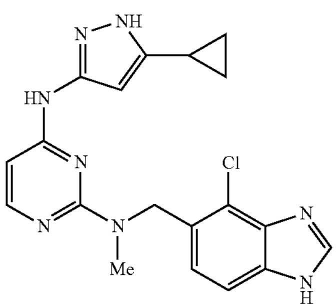 [SMILES: CN(Cc1ccc2[nH]cnc2c1Cl)c1nccc(Nc2cc(C3CC3)[nH]n2)n1] | A | 395.1 | (DMSO-d$_6$) δ 12.67 (br s, 1H), 11.83 (br s, 1H), 9.36 (br s, 1H), 8.26 (s, 1H), 7.90 (d, J = 5.7 Hz, 1H), 7.62-7.37 (m, 1H), 6.97 (d, J = 8.3 Hz, 1H), 6.38-6.10 (m, 1H), 6.10-5.77 (m, 1H), 5.02 (s, 2H), 3.11 (s, 3H), 1.85-1.57 (m, 1H), 0.85-0.65 (m, 2H), 0.65-0.28 (m, 2H) | $N^2$-(4-Chloro-1H-benzoimidazol-5-ylmethyl)-$N^4$-(5-cyclopropyl-1H-pyrazol-3-yl)-$N^2$-methyl-pyrimidine-2,4-diamine |
| I-88 | 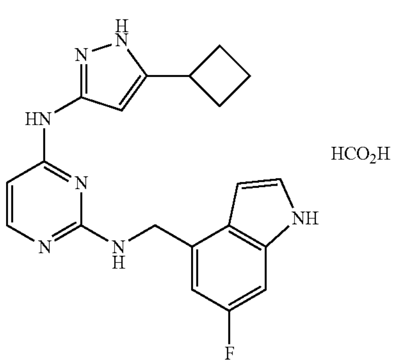 [SMILES: Fc1cc(CNc2nccc(Nc3cc(C4CCC4)[nH]n3)n2)c2cc[nH]c2c1 ; "HCO2H"] | A | 378.1 | (CD$_3$OD) δ 8.33 (s, 1H), 7.69-7.68 (m, 1H), 7.17 (s, 1H), 6.93-6.91 (m, 1H), 6.70-6.68 (m, 1H), 6.47 (s, 1H), 6.29-6.24 (m, 1), 6.04 (s, 1H), 4.84 (d, 2H), 3.07-3.06 (m, 1H), 2.11-1.19 (m, 6H) | $N^4$-(5-Cyclobutyl-1H-pyrazol-3-yl)-$N^2$-(6-fluoro-1H-indol-4-ylmethyl)-pyrimidine-2,4-diamine |

TABLE I-continued

| Cpd. No. | Structure | $K_i^5$ | MS² | ¹H NMR | Name |
|---|---|---|---|---|---|
| I-89 | 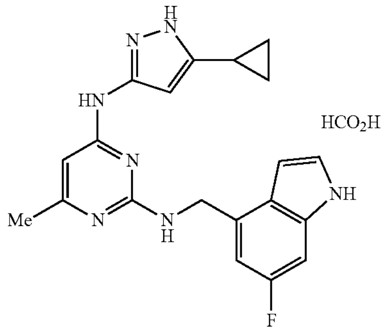 [SMILES: Cc1cc(Nc2cc(C3CC3)[nH]n2)nc(NCc2cc(F)cc3[nH]ccc23)n1 ; "HCO2H"] | C | 378.1 | (CD₃OD) δ 8.36 (s, 1H), 7.25 (s, 1H), 6.94-6.92 (m, 1H), 6.69-6.67 (m, 1H), 6.40 (s, 1H), 6.13-6.11 (m, 1H), 5.79 (s, 1H), 4.83 (d, 2H), 2.19 (s, 3H), 1.56-1.52 (m, 1H), 0.86-0.29 (m, 4H) | N⁴-(5-Cyclopropyl-1H-pyrazol-3-yl)-N²-(6-fluoro-1H-indol-4-ylmethyl)-6-methyl-pyrimidine-2,4-diamine |
| I-90 | 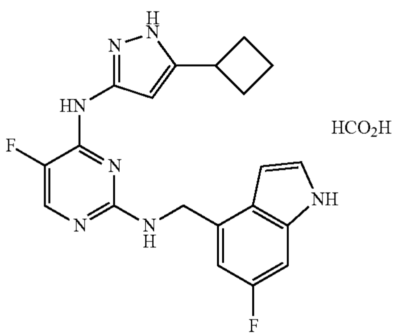 [SMILES: Fc1cc(CNc2ncc(F)c(Nc3cc(C4CCC4)[nH]n3)n2)c2cc[nH]c2c1 ; "HCO2H"] | C | 396.2 | (CD₃OD) δ 8.29 (s, 1H), 7.23 (s, 1H), 7.14 (s, 1H), 6.89-6.87 (m, 1H), 6.68-6.66 (m, 1H), 6.45 (s, 1H), 6.06 (s, 1H), 4.99 (d, 2H), 3.13-3.12 (m, 1H), 2.08-2.04 (m, 2H), 1.84-1.19 (m, 4H) | N⁴-(5-Cyclobutyl-1H-pyrazol-3-yl)-5-fluoro-N²-(6-fluoro-1H-indol-4-ylmethyl)-pyrimidine-2,4-diamine |
| I-91 | 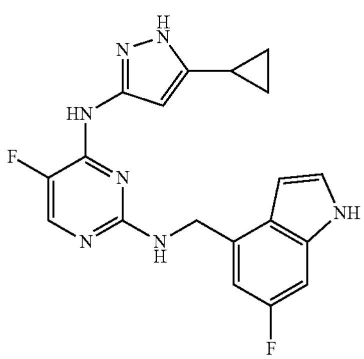 [SMILES: Fc1cc(CNc2ncc(F)c(Nc3cc(C4CC4)[nH]n3)n2)c2cc[nH]c2c1] | C | 382.2 | (CD₃OD) δ 8.25 (s, 2H), 7.72 (s, 1H), 7.13 (s, 1H), 6.89-6.87 (m, 1H), 6.67-6.65 (m, 1H), 6.45 (s, 1H), 5.84 (s, 1H), 4.70 (d, 2H), 1.56-1.52 (m, 1H), 0.70-0.26 (m, 4H) | N⁴-(5-Cyclopropyl-1H-pyrazol-3-yl)-5-fluoro-N²-(6-fluoro-1H-indol-4-ylmethyl)-pyrimidine-2,4-diamine |
| I-92 | 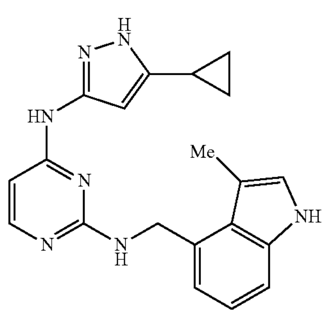 [SMILES: Cc1c[nH]c2cccc(CNc3nccc(Nc4cc(C5CC5)[nH]n4)n3)c12] | A | 360.2 | (CD₃OD) δ 7.73 (s, 1H), 7.15-7.14 (m, 1H), 6.92-6.82 (m, 3H), 6.08-5.91 (m, 2H), 4.89 (d, 2H), 2.38 (s, 3H), 1.61-1.59 (m, 1H), 0.51-0.35 (m, 4H) | N⁴-(5-Cyclopropyl-1H-pyrazol-3-yl)-N-(3-methyl-1H-indol-4-ylmethyl)-pyrimidine-2,4-diamine |

TABLE I-continued

| Cpd. No. | Structure | $K_i{}^5$ | $MS^2$ | $^1$H NMR | Name |
|---|---|---|---|---|---|
| I-93 | 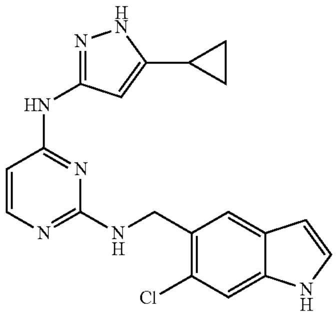 [SMILES: Clc1cc2[nH]ccc2cc1CNc1nccc(Nc2cc(C3CC3)[nH]n2)n1] | B | 380.2 | (CD$_3$OD) δ 7.71 (s, 1H), 7.46 (s, 1H), 7.34 (s, 1H), 7.10 (d, 1H, J = 3.0 Hz), 6.28 (d, 1H, J = 2.0 Hz), 6.05 (s, 1H), 5.92 (s, 1H), 4.60 (s, 2H), 1.71(m, 1H), 0.78 (m, 2H), 0.50 (m, 2H) | N$^2$-(6-Chloro-1H-indol-5-ylmethyl)-N$^4$-(5-cyclopropyl-1H-pyrazol-3-yl)-pyrimidine-2,4-diamine |
| I-94 | 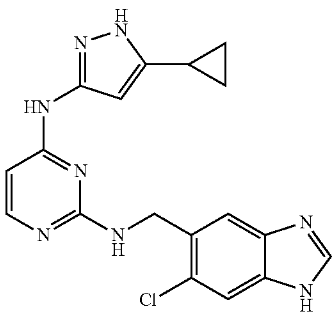 [SMILES: Clc1cc2[nH]cnc2cc1CNc1nccc(Nc2cc(C3CC3)[nH]n2)n1] | B | 381.2 | (DMSO-d$_6$) δ 11.84 (s, 1H), 9.35 (s, 1H), 8.21 (s, 1H), 7.81-7.21 (m, 4H), 6.30-5.44 (m, 2H), 4.61 (d, J = 6.0, 2H), 1.80-1.65 (m, 1H), 0.84 (brs, 2H), 0.73-0.32 (m, 2H) | N$^2$-(6-Chloro-3H-benzoimidazol-5-ylmethyl)-N$^4$-(5-cyclopropyl-1H-pyrazol-3-yl)-pyrimidine-2,4-diamine |
| I-95 | 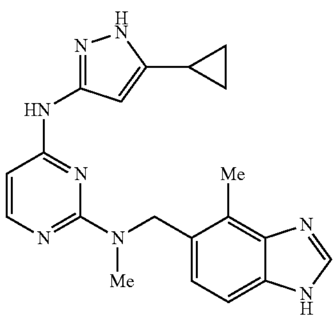 [SMILES: Cc1c(CN(C)c2nccc(Nc3cc(C4CC4)[nH]n3)n2)ccc2[nH]cnc12] | A | 375.3 | (CD$_3$OD) δ 8.16 (s, 1H), 7.91-7.90 (m, 1H), 7.38 (s, 1H), 6.91 (d, 1H), 6.18 (br, 1H), 5.99-5.89 (m, 1H), 4.92 (s, 2H), 4.07 (s, 3H) 3.04 (s, 3H), 1.71-1.69 (m, 1H), 0.82-0.79 (m, 2H), 0.47-0.33 (m, 2H) | N$^4$-(5-Cyclopropyl-1H-pyrazol-3-yl)-N$^2$-methyl-N$^2$-(4-methyl-1H-benzoimidazol-5-ylmethyl)-pyrimidine-2,4-diamine |
| I-96 | 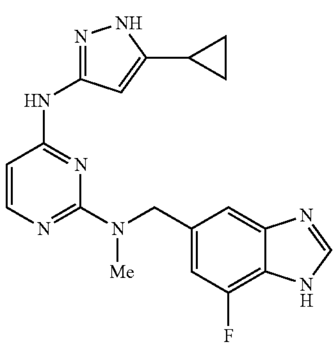 [SMILES: CN(Cc1cc(F)c2[nH]cnc2c1)c1nccc(Nc2cc(C3CC3)[nH]n2)n1] | B | 365.2 | (CD$_3$OD) δ 8.15 (s, 1H), 7.82 (s, 1H), 7.40 (s, 1H), 7.03 (d, 1H), 6.19 (s, 1H), 6.05-6.04 (m, 1H), 4.71 (s, 2H), 1.80 (m, 1H), 0.90-0.89 (m, 2H), 0.64-0.54 (m, 2H) | N$^4$-(5-Cyclopropyl-1H-pyrazol-3-yl)-N$^2$-(7-fluoro-1H-benzoimidazol-5-ylmethyl)-pyrimidine-2,4-diamine |
| I-97 | 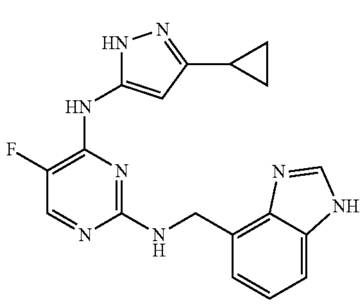 [SMILES: Fc1cnc(NCc2cccc3[nH]cnc23)nc1Nc1cc(C2CC2)n[nH]1] | A | 365.2 | (CD$_3$OD) δ 8.18 (s, 1H), 7.81 (s, 1H), 7.53 (s, 1H), 7.24-7.21 (m, 2H), 6.03-5.96 (s, 1H), 4.90 (s, 2H), 1.69 (m, 1H), 0.83 (m, 2H), 0.55-0.32 (m, 2H) | N$^2$-(3H-Benzoimidazol-4-ylmethyl)-N$^4$-(5-cyclopropyl-2H-pyrazol-3-yl)-5-fluoro-pyrimidine-2,4-diamine |

TABLE I-continued

| Cpd. No. | Structure | $K_i^5$ | $MS^2$ $^1H$ NMR | Name |
|---|---|---|---|---|
| I-98 | 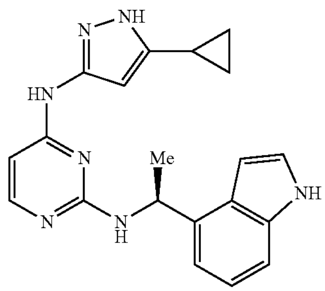 [SMILES: C[C@H](Nc1nccc(Nc2cc(C3CC3)[nH]n2)n1)c1cccc2[nH]ccc12] | A | 360.2 (DMSO-$d_6$) δ 11.05 (s, 1H), 9.43 (s, 1H), 8.18 (HCO$_2$H), 7.75 (d, J = 5.7 Hz, 1H), 7.35-7.18 (m, 3H), 7.04-6.96 (m, 2H), 6.60 (s, 1H), 6.17-5.86 (m, 2H), 5.51 (dq, J = 7.0 Hz, 1H), 1.79 (s, 1H), 1.53 (d, J = 7.0 Hz, 3H), 0.92-0.53 (m, 4H) | N$^4$-(5-Cyclopropyl-1H-pyrazol-3-yl)-N$^2$-[1-(1H-indol-4-yl)-ethyl]-pyrimidine-2,4-diamine |
| I-99 | 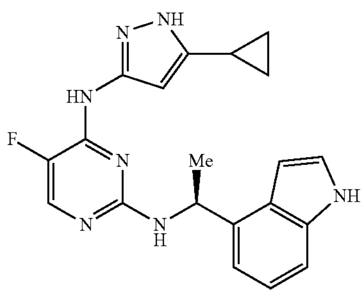 [SMILES: C[C@H](Nc1ncc(F)c(Nc2cc(C3CC3)[nH]n2)n1)c1cccc2[nH]ccc12] | B | 378.2 (DMSO-$d_6$)$^1$ δ 1.36-10.91 (m, 2H), 8.71 (s, 1H), 8.13 (s, 1H), 7.41-7.35 (m, 1H), 7.33 (br d, J = 8.0 Hz, 1H), 7.07 (br dd, J = 8.0, 7.1 Hz, 1H), 6.98 (br d, J = 7.1 Hz, 1H), 6.59-6.49 (m, 1H), 6.15 (s, 1H), 5.43 (s, 1H), 1.77 (s, 1H), 1.62 (d, J = 6.9 Hz, 3H), 1.00-0.50 (m, 4H). | N$^4$-(5-Cyclopropyl-1H-pyrazol-3-yl)-5-fluoro-N$^2$-[1-(1H-indol-4-yl)-ethyl]-pyrimidine-2,4-diamine |
| I-100 | 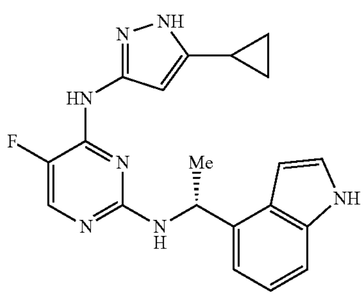 [SMILES: C[C@@H](Nc1ncc(F)c(Nc2cc(C3CC3)[nH]n2)n1)c1cccc2[nH]ccc12] | D | 378.1 (DMSO-$d_6$) δ 11.30-10.99 (m, 2H), 8.69 (br s, 1H), 8.12 (br s, 1H), 7.39-7.35 (m, 1H), 7.33 (d, J = 8.0 Hz, 1H), 7.07 (br dd, J = 8.0, 7.1 Hz, 1H), 6.98 (br d, J = 7.1 Hz, 1H), 6.63-6.44 (m, 1H), 6.15 (s, 1H), 5.43 (s, 1H), 1.77 (s, 1H), 1.62 (d, J = 6.9 Hz, 3H), 1.03-0.45 (m, 4H) | N$^4$-(5-Cyclopropyl-1H-pyrazol-3-yl)-5-fluoro-N$^2$-[1-(1H-indol-4-yl)-ethyl] pyrimidine-2,4-diamine |
| I-101 | 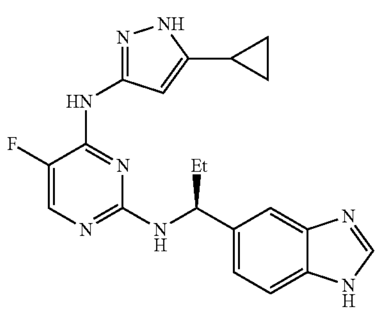 [SMILES: CC[C@H](Nc1ncc(F)c(Nc2cc(C3CC3)[nH]n2)n1)c1ccc2[nH]cnc2c1] | B | 393.2 (DMSO-$d_6$) δ 12.87-11.62 (m, 2H), 10.46-8.83 (m, 1H), 8.12 (s, 1H), 7.94-7.01 (m, 5H), 6.69 - 5.58 (m, 1H), 5.03-4.60 (m, 1H), 1.94-1.58 (m, 3H), 1.15-0.49 (m, 7H) | N$^4$-(5-Cyclopropyl-1H-pyrazol-3-yl)-5-fluoro-N$^2$-[1-(1H-indol-4-yl)-ethyl]-pyrimidine-2,4-diamine |
| I-102 | 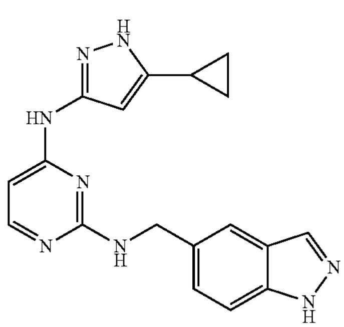 [SMILES: c1cc(Nc2cc(C3CC3)[nH]n2)nc(NCc2ccc3[nH]ncc3c2)n1] | C | 347.2 (DMSO-$d_6$) δ 12.92 (s, 1H), 11.84 (s, 1H), 9.22 (s, 1H), 8.06-7.57 (m, 3H), 7.46 (d, J = 8.4 Hz, 1H), 7.35 (d, J = 8.6 Hz, 1H), 7.14 (s, 1H), 6.08 (d, J = 90.5 Hz, 2H), 4.58 (d, J = 6.2 Hz, 2H), 1.84-1.72 (m, 1H), 0.93-0.45 (m, 4H) | N$^4$-(5-Cyclopropyl-1H-pyrazol-3-yl)-N$^2$-(1H-indazol-5-ylmethyl)-pyrimidine-2,4-diamine |

TABLE I-continued

| Cpd. No. | Structure | $K_i^5$ | MS[2] | $^1$H NMR | Name |
|---|---|---|---|---|---|
| I-103 | 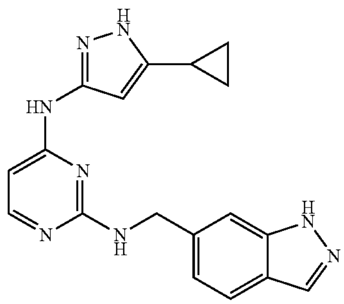 [SMILES: c1cc(Nc2cc(C3CC3)[nH]n2)nc(NCc2ccc3cn[nH]c3c2)n1] | D | 347.2 | (DMSO-d$_6$) δ 12.86 (s, 1H), 9.35 (s, 1H), 8.18 (s, 1H), 7.98 (s, 1H), 7.81 (d, J = 5.7 Hz, 1H), 7.67 (d, J = 8.3 Hz, 1H), 7.41 (s, 1H), 7.30 (s, 1H), 7.09 (d, J = 8.3 Hz, 1H), 6.24-5.88 (m, 2H), 4.62 (d, J = 6.3 Hz, 2H), 1.76 (s, 1H), 0.84 (d, J +32 7.1 Hz, 2H), 0.56 (s, 2H). | N$^2$-(4-Chloro-1H-benzoimidazol-5-ylmethyl)-N$^4$-[5-(3,3-difluoro-cyclobutyl)-1H-pyrazol-3-yl]-pyrimidine 2,4-diamine |
| I-104 | 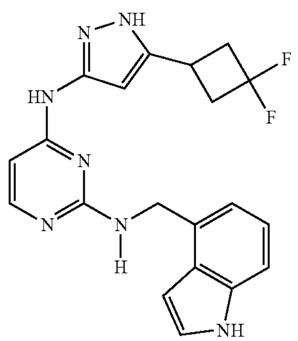 [SMILES: FC1(F)CC(c2cc(Nc3ccnc(NCc4cccc5[nH]ccc45)n3)n[nH]2)C1] | B | 396.1 | (DMSO-d$_6$) δ 12.01 (s, 1H), 11.07 (s, 1H), 9.31 (s, 1H), 7.87 (d, J = 40.3 Hz, 1H), 7.60 (s, 1H), 7.29 (d, J = 15.5 Hz, 2H), 6.96 (d, J = 25.6 Hz, 2H), 6.55 (s, 1H), 6.20 (s, 1H), 5.98 (s, 1H), 4.76 (d, J = 5.3 Hz, 2H), 3.25-3.08 (m, 1H), 2.89 (s, 2H), 2.67 (s, 2H) | N$^4$-(5-Cyclopropyl-1H-pyrazol-3-yl)-N$^2$-(1H-indazol-6-ylmethyl)-pyrimidine-2,4-diamine |
| I-105 | 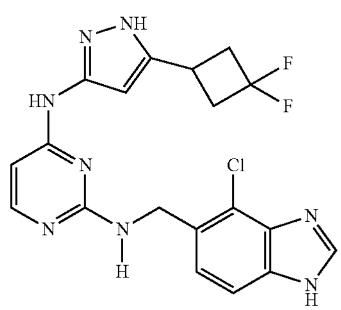 [SMILES: FC1(F)CC(c2cc(Nc3ccnc(NCc4ccc5[nH]cnc5c4Cl)n3)n[nH]2)C1] | A | 431.1 | (DMSO-d$_6$) δ 12.64 (s, 1H), 12.06 (s, 1H), 9.47 (s, 1H), 8.26 (s, 1H), 7.83 (s, 1H), 7.56 (s, 1H), 7.43 (s, 1H), 7.24 (s, 2H), 6.21 (s, 1H), 4.68 (d, J = 6.0 Hz, 2H), 2.89 (s, 2H), 2.67 (s, 2H) | N$^4$-[5-(3,3-Difluoro-cyclobutyl)-1H-pyrazol-3-yl]-N$^2$-(1H-indol-4-ylmethyl)-pyrimidine-2,4-diamine |
| I-106 | 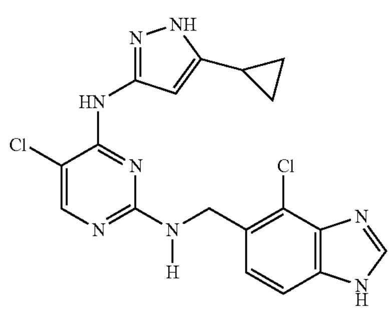 [SMILES: Clc1cnc(NCc2ccc3[nH]cnc3c2Cl)nc1Nc1cc(C2CC2)[nH]n1] | A | 415.1 | (DMSO-d$_6$) δ 12.66 (s, 1H), 12.02 (s, 1H), 8.47 (d, J = 73.8 Hz, 1H), 8.25 (s, 1H), 7.96 (s, 1H), 7.56 (s, 1H), 7.47 (s, 1H), 7.34-7.05 (m, 1H), 5.79 (s, 1H), 4.65 (d, J = 5.8 Hz, 2H), 1.68 (d, J +32 56.5 Hz, 1H), 0.80 (s, 3H), 0.32 (s, 1H) | 5-Chloro-N$^2$-(4-chloro-1H-benzoimidazol-5-ylmethyl)-N$^4$-(5-cyclopropyl-1H-pyrazol-3-yl)-pyrimidine-2,4-diamine |
| I-107 | 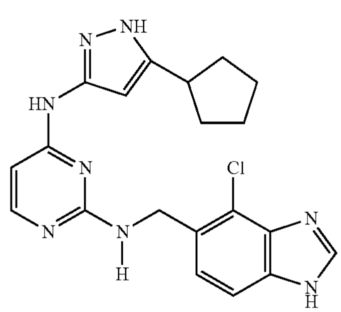 [SMILES: Clc1c(CNc2nccc(Nc3cc(C4CCCC4)[nH]n3)n2)ccc2[nH]cnc12] | A | 409.2 | (DMSO-d$_6$) δ 12.62 (s, 1H), 11.80 (s, 1H), 9.40 (s, 1H), 8.25 (s, 1H), 7.81 (d, J = 5.2 Hz, 1H), 7.42 (d, J = 8.3 Hz, 1H), 7.21 (s, 2H), 6.18 (s, 1H), 6.10-5.78 (m, 1H), 4.68 (d, J = 6.1 Hz, 2H), 3.08-2.59 (m, 1H), 1.83 (d, J = 61.8 Hz, 2H), 1.51 (s, 5H), 1.24 (s, 2H) | N$^2$-(4-Chloro-1H-benzoimidazol-5-ylmethyl)-N$^4$-(5-cyclopentyl-1H-pyrazol-3-yl)-pyrimidine-2,4-diamine |

TABLE I-continued

| Cpd. No. | Structure | $K_i^5$ | $MS^2$ | $^1H$ NMR | Name |
|---|---|---|---|---|---|
| I-108 | 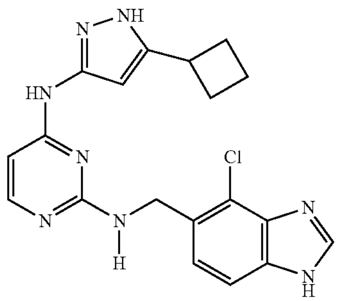 [SMILES: Clc1c(CNc2nccc(Nc3cc(C4CCC4)[nH]n3)n2)ccc2[nH]cnc12] | A | 395.1 | (DMSO-d$_6$) δ 12.62 (s, 1H), 11.81 (s, 1H), 9.21 (d, J = 105.0 Hz, 1H), 8.25 (s, 1H), 7.81 (d, J = 4.7 Hz, 1H), 7.42 (d, J = 8.2 Hz, 1H), 7.22 (s, 2H), 6.19 (s, 1H), 6.10-5.84 (m, 1H), 4.68 (d, J = 6.1 Hz, 2H), 3.17 (d, J = 5.2 Hz, 1H), 2.09 (s, 3H), 1.80 (dd, J = 61.0, 23.5 Hz, 3H). | N$^2$-(4-Chloro-1H-benzoimidazol-5-ylmethyl)-N$^4$-(5-cyclobutyl-1H-pyrazol-3-yl)-pyrimidine-2,4-diamine |
| I-109 | 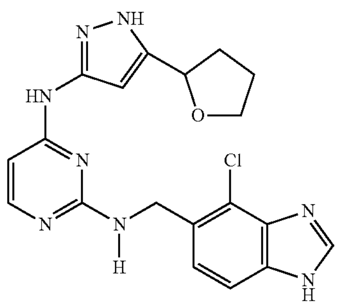 [SMILES: Clc1c(CNc2nccc(Nc3cc(C4CCCO4)[nH]n3)n2)ccc2[nH]cnc12] | A | 411.1 | (DMSO-d$_6$) δ 12.63 (s, 1H), 11.92 (d, J = 87.0 Hz, 1H), 9.28 (d, J = 76.3 Hz, 1H), 8.25 (s, 1H), 7.82 (s, 1H), 7.55 (d, J = 8.2 Hz, 1H), 7.42 (d, J = 7.8 Hz, 1H), 7.22 (s, 2H), 6.18 (s, 1H), 4.67 (d, J = 5.9 Hz, 2H), 3.67 (s, 2H), 3.17 (d, J = 5.2 Hz, 1H), 2.18-1.68 (m, 4H) | N$^2$-(4-Chloro-1H-benzoimidazol-5-ylmethyl)-N$^4$-[5-(tetrahydro-furan-2-yl)-1H-pyrazol-3-yl]-pyrimidine-2,4-diamine |
| I-110 | 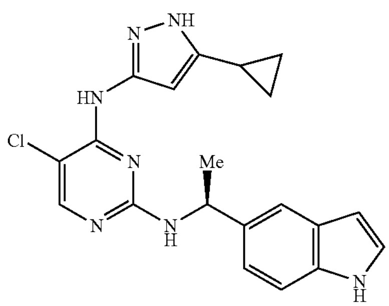 [SMILES: C[C@H](Nc1ncc(Cl)c(Nc2cc(C3CC3)[nH]n2)n1)c1ccc2[nH]ccc2c1] | C | 394.1 | (DMSO-d$_6$) δ 11.96 (d, J = 72.2 Hz, 1H), 10.94 (s, 1H), 8.22 (s, 1H), 7.89 (s, 1H), 7.49 (s, 1H), 7.34-7.22 (m, 2H), 7.11 (d, J = 8.4 Hz, 1H), 6.35 (s, 1H), 5.09 (s, 1H), 1.87 (s, 1H), 1.47 (d, J = 6.9 Hz, 3H), 0.95 (s, 2H), 0.69 (s, 2H) | |
| I-111 | 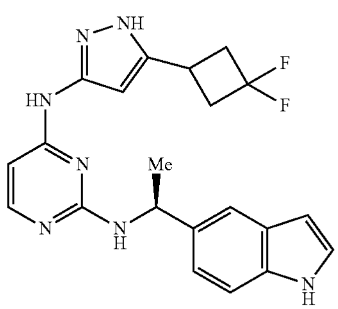 [SMILES: C[C@H](Nc1nccc(Nc2cc(C3CC(F)(F)C3)[nH]n2)n1)c1ccc2[nH]ccc2c1] | A | 410.2 | (DMSO-d$_6$) δ 11.96 (d, J = 66.9 Hz, 1H), 10.93 (s, 1H), 9.27 (s, 1H), 7.80 (d, J = 23.6 Hz, 1H), 7.52 (s, 1H), 7.28 (s, 2H), 7.13 (d, J = 7.8 Hz, 1H), 6.53 (d, J = 39.6 Hz, 1H), 6.34 (s, 1H), 6.11 (s, 1H), 5.91 (s, 1H), 5.64 (s, 1H), 5.19 (s, 1H), 2.97 (s, 2H), 2.71 (t, J = 14.1 Hz, 2H), 1.47 (d, J = 6.9 Hz, 3H). | N$^4$-[5-(3,3-Difluoro-cyclobutyl)-1H-pyrazol-3-yl]-N$^2$-[(S)-1-(1H-indol-5-yl)-ethyl]pyrimidine-2,4-diamine |
| I-112 | 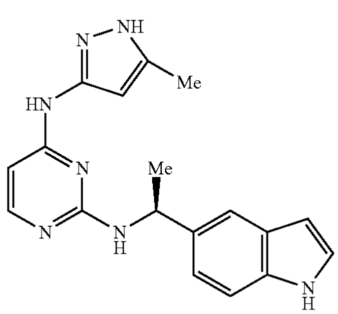 [SMILES: Cc1cc(Nc2ccnc(N[C@@H](C)c3ccc4[nH]ccc4c3)n2)n[nH]1] | C | 334.2 | (DMSO-d$_6$) δ 11.75 (s, 1H), 10.91 (s, 1H), 9.14 (s, 1H), 7.79 (d, J = 29.4 Hz, 1H), 7.52 (s, 1H), 7.36-7.23 (m, 2H), 7.14 (d, J = 8.4 Hz, 1H), 6.91 (s, 1H), 6.34 (s, 1H), 6.12 (s, 1H), 5.25-5.04 (m, 1H), 2.19 (s, 3H), 1.46 (d, J = 6.9 Hz, 3H). | N$^2$-[(S)-1-(1H-Indol-5-yl)-ethyl]-N$^4$-(5-methyl-1H-pyrazol-3-yl)-pyrimidine-2,4-diamine |

TABLE I-continued

| Cpd. No. | Structure | $K_i^5$ | $MS^2$ | $^1H$ NMR | Name |
|---|---|---|---|---|---|
| I-113 | 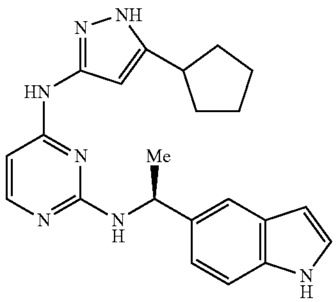 [SMILES: C[C@H](Nc1nccc(Nc2cc(C3CCCC3)[nH]n2)n1)c1ccc2[nH]ccc2c1] | A | 388.2 | (DMSO-d$_6$) δ 11.81 (s, 1H), 10.92 (s, 1H), 9.18 (s, 1H), 7.75 (s, 1H), 7.52 (s, 1H), 7.28 (dd, J = 8.4, 5.8 Hz, 2H), 7.14 (d, J = 8.4 Hz, 1H), 6.91 (s, 1H), 6.32 (s, 1H), 6.11 (s, 1H), 5.21 (s, 1H), 2.96 (dd, J = 27.9, 20.2 Hz, 1H), 1.99 (s, 2H), 1.74 (s, 2H), 1.62 (s, 4H), 1.47 (d, J = 6.9 Hz, 3H). | $N^4$-(5-Cyclopentyl-1H-pyrazol-3-yl)-$N^2$-[(S)-1-(1H-indol-5-yl)-ethyl]-pyrimidine-2,4-diamine |
| I-114 | 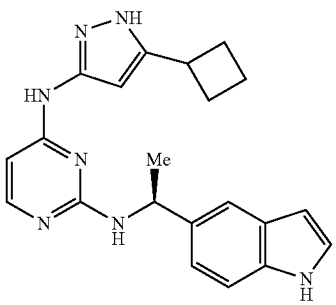 [SMILES: C[C@H](Nc1nccc(Nc2cc(C3CCC3)[nH]n2)n1)c1ccc2[nH]ccc2c1] | A | 374.2 | (DMSO-d$_6$) δ 11.82 (s, 1H), 10.92 (s, 1H), 9.25 (s, 1H), 7.76 (d, J = 5.6 Hz, 1H), 7.53 (s, 1H), 7.35-7.21 (m, 2H), 7.15 (d, J = 8.2 Hz, 1H), 7.01 (s, 1H), 6.33 (s, 1H), 6.08 (s, 1H), 5.28-5.08 (m, 1H), 3.44 (dt, J = 24.7, 8.0 Hz, 2H), 2.28 (d, J = 8.5 Hz, 2H), 2.14 (ddd, J = 14.3, 10.4, 6.1 Hz, 2H), 1.98 (dt, J = 18.1, 9.1 Hz, 1H), 1.88 (dd, J = 16.0, 6.9 Hz, 1H), 1.47 (d, J = 6.9 Hz, 3H). | $N^4$-(5-Cyclobutyl-1H-pyrazol-3-yl)-$N^2$-[(S)-1-(1H-indol-5-yl)-ethyl]-pyrimidine-2,4-diamine |
| I-115 | 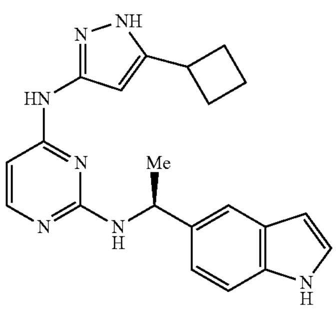 [SMILES: C[C@H](Nc1nccc(Nc2cc(C3CCC3)[nH]n2)n1)c1ccc2[nH]ccc2c1] | A | 390.2 | (DMSO-d$_6$) δ 11.95 (s, 1H), 10.92 (s, 1H), 9.24 (s, 1H), 7.77 (s, 1H), 7.52 (s, 1H), 7.36-7.21 (m, 2H), 7.14 (d, J = 8.3 Hz, 1H), 6.96 (s, 1H), 6.35 (s, 1H), 6.34 (s, 1H), 6.09 (s, 1H), 5.18 (s, 1H), 4.00 (t, J = 7.6 Hz, 1H), 3.88 (s, 1H), 3.79 (d, J = 7.1 Hz, 1H), 3.67-3.50 (m, 1H), 2.29 (d, J +32-31.8 Hz, 1H), 2.03 (d, J = 32.3 Hz, 1H), 1.47 (d, J = 6.9 Hz, 3H). | $N^2$-[1-(1H-Indol-5-yl)-ethyl]-$N^4$-[5-[5-furan-3-yl]-1H-pyrazol-3-yl]-pyrimidine-2,4-diamine |
| I-116 | 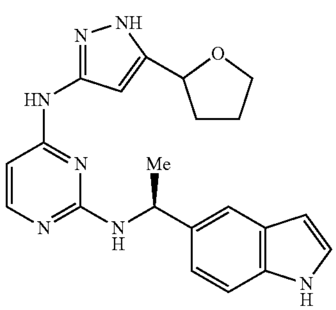 [SMILES: C[C@H](Nc1nccc(Nc2cc(C3CCCO3)[nH]n2)n1)c1ccc2[nH]ccc2c1] | C | 390.2 | (DMSO-d$_6$) δ 12.06 (s, 1H), 10.92 (s, 1H), 9.25 (s, 1H), 7.80 (d, J = 28.2 Hz, 1H), 7.52 (s, 1H), 7.29 (d, J = 12.0 Hz, 2H), 7.14 (d, J = 8.4 Hz, 1H), 6.94 (s, 1H), 6.52 (d, J = 39.9 Hz, 1H), 6.34 (s, 1H), 6.11 (s, 1H), 5.18 (s, 1H), 4.84 (s, 1H), | $N^2$-[1-(1H-Indol-5-yl)-ethyl]-$N^4$-[5-(tetrahydro-furan-2-yl)-1H-pyrazol-3-yl]-pyrimidine-2,4-diamine |
| I-117 | 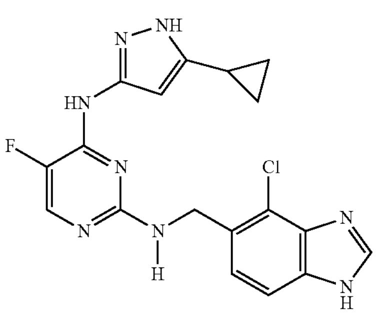 [SMILES: Fc1cnc(NCc2ccc3[nH]cnc3c2Cl)nc1Nc1cc(C2CC2)[nH]n1] | A | 399 | | $N^2$-(4-Chloro-1H-benzoimidazol-5-ylmethyl)-$N^4$-(5-cyclopropyl-1H-pyrazol-3-yl)-5-fluoro-pyrimidine-2,4-diamine |

TABLE I-continued

| Cpd. No. | Structure | $K_i^5$ | $MS^2$ | $^1$H NMR | Name |
|---|---|---|---|---|---|
| I-118[3] | 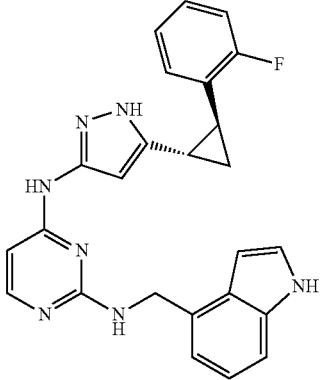 [SMILES: Fc1ccccc1[C@H]1C[C@@H]1c1cc(Nc2ccnc(NCc3cccc4[nH]ccc34)n2)n[nH]1] | C | 311.1 | (DMSO-d$_6$) δ 11.05 (s, 1H), 9.44 (s, 1H), 8.15 (s, 1H), 7.84 (d, J = 5.3 Hz, 1H), 7.23 (dd, J = 19.5, 6.7 Hz, 3H), 7.18-7.05 (m, 3H), 7.05-6.87 (m, 2H), 6.54 (s, 1H), 6.12 (s, 2H), 4.76 (d, J = 5.9 Hz, 2H), 1.40 (s, 2H) | N$^4$-{5-[(1S,2S)-2-(2-Fluoro-phenyl)-cyclopropyl]-1H-pyrazol-3-yl}-N$^2$-(1H-indol-4-ylmethyl)-pyrimidine-2,4-diamine |
| I-119 | 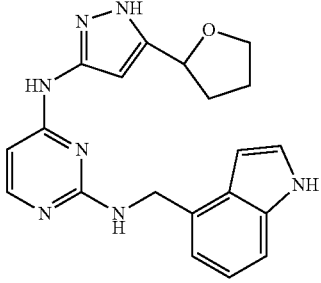 [SMILES: c1cc(CNc2nccc(Nc3cc(C4CCCO4)[nH]n3)n2)c2cc[nH]c2c1] | C | 376.2 | (DMSO-d$_6$) δ 11.07 (s, 1H), 9.47 (s, 1H), 8.15 (s, 1H), 7.84 (d, J = 5.4 Hz, 1H), 7.31 (t, J = 2.7 Hz, 1H), 7.27 (d, J = 8.0 Hz, 1H), 7.23-7.09 (m, 1H), 7.00 (t, J = 7.6 Hz, 1H), 6.93 (d, J = 7.1 Hz, 1H), 6.55 (s, 1H), 6.13 (s, 2H), 4.76 (d, J = 6.0 Hz, 2H), 4.72-4.52 (m, 1H), 3.77 (s, 1H), 3.69 (s, 2H), 2.07 (s, 1H), 1.84 (s, 3H). | N$^2$-(1H-Indol-4-yl-methyl)-N$^4$-[5-(tetrahydro-furan-2-yl)-1H-pyrazol-3-yl]-pyrimidine-2,4-diamine |
| I-120 | 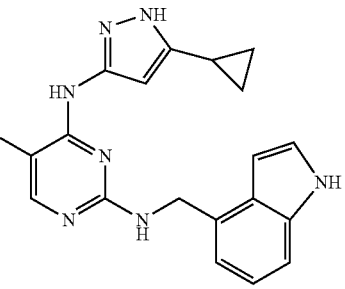 | B | 364.1 | (DMSO-d$_6$) δ 11.93 (s, 1H), 11.06 (s, 1H), 9.24 (s, 1H), 7.83 (s, 1H), 7.38-7.22 (m, 2H), 7.13 (t, J = 15.3 Hz, 1H), 6.99 (s, 1H), 6.88 (d, J = 20.4 Hz, 1H), 6.62-6.44 (m, 1H), 6.26 (s, 1H), 4.70 (d, J = 6.0 Hz, 2H), 1.75 (s, 1H), 0.79 (d, J = 5.7 Hz, 2H), 0.57 (s, 2H). | N$^4$-(5-Cyclopropyl-1H-pyrazol-3-yl)-5-fluoro-N$^2$-(1H-indol-4-ylmethyl)-pyrimidine-2,4-diamine |
| I-121 | 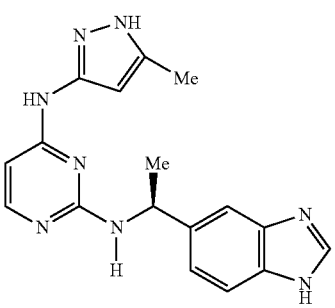 [SMILES: Cc1cc(Nc2ccnc(N[C@@H](C)c3ccc4[nH]cnc4c3)n2)n[nH]1] | C | 335.2 | (DMSO-d$_6$) δ 12.29 (s, 1H), 11.76 (s, 1H), 9.19 (s, 1H), 8.12 (s, 1H), 7.78 (t, J = 17.5 Hz, 1H), 7.68-7.51 (m, 1H), 7.51-7.38 (m, 1H), 7.24 (dd, J = 17.7, 8.3 Hz, 1H), 7.09 (s, 1H), 6.10 (s, 1H), 5.30-5.07 (m, 1H), 2.17 (s, 3H), 1.47 (d, J = 7.0 Hz, 3H) | N$^2$-[(S)-1-(1H-Benzoimidazol-5-yl)-ethyl]-N$^4$-(5-methyl-1H-pyrazol-3-yl)-pyrimidine-2,4-diamine |

TABLE I-continued

| Cpd. No. | Structure | $K_i{}^5$ | $MS^2$ | $^1H$ NMR | Name |
|---|---|---|---|---|---|
| I-122 | 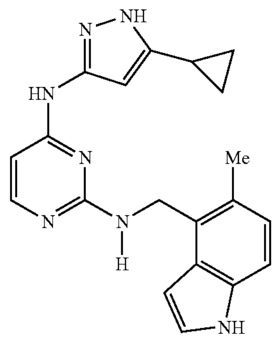 [SMILES: Cc1ccc2[nH]ccc2c1CNc1nccc(Nc2cc(C3CC3)[nH]n2)n1] | B | 360.3 | (CD$_3$OD) δ 7.92-7.85 (m, 1H), 7.26 (d, J = 8.5, 1H), 7.21 (d, J = 3.0, 1H), 7.00 (d, J = 8.0, 1H), 6.52 (d, J = 3.5, 1H), 6.23-5.45 (m, 2H), 4.82 (s, 2H), 2.47 (2, 3H), 1.87 (brs, 1H), 0.93 (brs, 2H), 0.69 (brs, 2H), | $N^4$-(5-Cyclopropyl-1H-pyrazol-3-yl)-$N^2$-(5-methyl-1H-indol-4-ylmethyl)-pyrimidine-2,4-di-amine |

[1]TFA vapor added to sharpen peaks masked 1 × NH peak
[2]m/z obtained from ESI mass spectrometer
[3]mixture of (2R,3R) and (2S,3S) isomers of cyclopropyl ring
[4]diastereomeric mixture
[5]Example 57 $K_i$: A ≤ 0.050 μM: 0.050 μM < B ≤ 0.250 μM: 0.250 μM < C ≤ 1.0 μM; D > 1.0 μM
[†]NMR consistent with a mixture of rotamers Compounds and Preparation Examples of representative compounds within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it. The following numbering system is used herein.

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, or, about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

SCHEME A

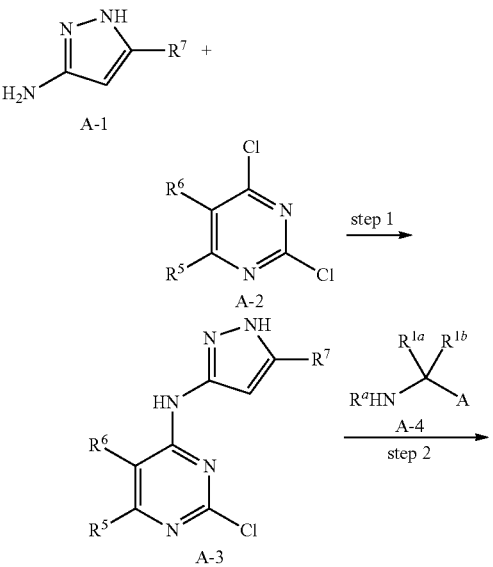

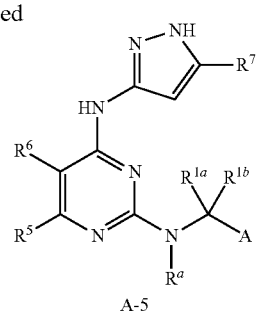

A-5

Compounds of the present invention can be assembled by a two step process comprising (a) condensation of a suitably substituted pyrazole A-1 and a suitably substituted 2,4-dichloropyrimidine A-2 which results in the displacement of the more reactive 4-chloro substituent affording the pyrimidine A-3 which is subsequently condensed with an appropriate amine A-4 to afford the diamino pyrimidines A-5 of the present invention.

Step 1 is carried out by contacting A-1 and A-2 in a organic solvent in the presence of a base at temperatures sufficient to initiate the reaction. Typical bases include tertiary amines such as DIPEA, TEA, DABCO and typical solvents include EtOH or DMSO. Temperatures between 50 and 100° C. and frequently between 50 and 70° C. are adequate to maintain an acceptable reaction rate. The introduction of the amine at C-4 deactivates the ring to a subsequent displacement, thus monosubstitution is easily achieved. Introduction of A-4, is therefore carried out under analogous conditions except higher-boiling solvents such as n-BuOH or isopropanol are used and the reaction is run at a higher temperature using an thermal or a microwave heat source. Steric hindrance about the amino group in A-4 can further inhibit the reaction which may require temperatures up to 140° C. and running the reaction solvent free to achieve acceptable reaction rates. One skilled in the art will appreciate that it may be necessary or advantageous to incorporate protecting groups into A-4 to mask potentially competing nucleophilic sites and in such cases there will be subsequent steps to remove the protecting group.

SCHEME B

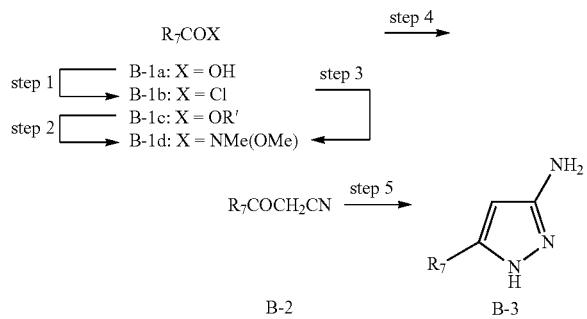

5-Substituted amino-pyrazoles B-3 were prepared by contacting hydrazine and a 3-cyclopropyl-3-oxopropanenitrile derivative B-2 in EtOH at reflux temperature. The cyanoketone compounds can be prepared by deprotonation of acetonitrile and condensation of the resulting conjugate base with an acyl equivalent which can be an acyl chloride B-1b, an ester B-1c or a methoxymethylamine B-1d. Deprotonation of the nitrile can be conveniently accomplished with a variety of strong bases including, for example, n-BuLi/THF/−65° C., LiHMDS/THF/−65° C., NaH/dioxane/RT, potassium amyloxide/THF/RT. Esters and methoxymethylamides are prepared using any of the well-established protocols.

Many requisite bicyclic heteroaryl aminomethyl compounds were either commercially available or were prepared through known routes. The examples that follow provide routes to specific fragments used to prepare compounds within the scope of the present invention.

4-Aminomethylindole, 5-aminomethylindole and 6-aminomethylindole are known compounds. It is sometimes convenient to protect the indole nitrogen and in those instances a tosyl group was first introduced. 1-Tosyl-1H-indole-6-carbonitrile (CASRN31274-87-1) was reduced with $H_2$ and RaNi in 7N ammonical methanol to afford the corresponding aminomethyl derivative. 1-Tosyl-1H-indole-4-carbaldehyde was converted to the oxime and reduced with Zn and $NH_4Cl$ in EtOH to afford (1-tosyl-1H-indol-6-yl)methanamine.

Substituted indoles can be prepared by a variety of routes and indole syntheses have been extensively reviewed (see, e.g., G. R. Humphrey and J. T. Kuethe Chem. Rev. 2006 2875-2911). Aminomethyl indoles with additional substitution were prepared by a variety of processes (SCHEME C) including addition of vinyl Grignard reagents to substituted nitrobenzenes (G. Bartoli et al., Tetrahedron Lett. 1989 30(16):1989; M. Schlosser et al., Eur. J. Org. Chem., 2006 2956), condensation of substituted o-nitro toluenes with DMF-dimethyl acetal followed by subsequent reduction and cyclization (M. M. Faul et al., Tetrahedron 2003 59:7215), cyclization of substituted o-ethynyl amines (G. Kalbalka et al., Tetrahedron 2001 8017-8028). A cyano substitutent was frequently introduced a palladium catalyzed displacement and subsequently reduced to the aminomethyl derivative by catalytic hydrogenolysis.

SCHEME C

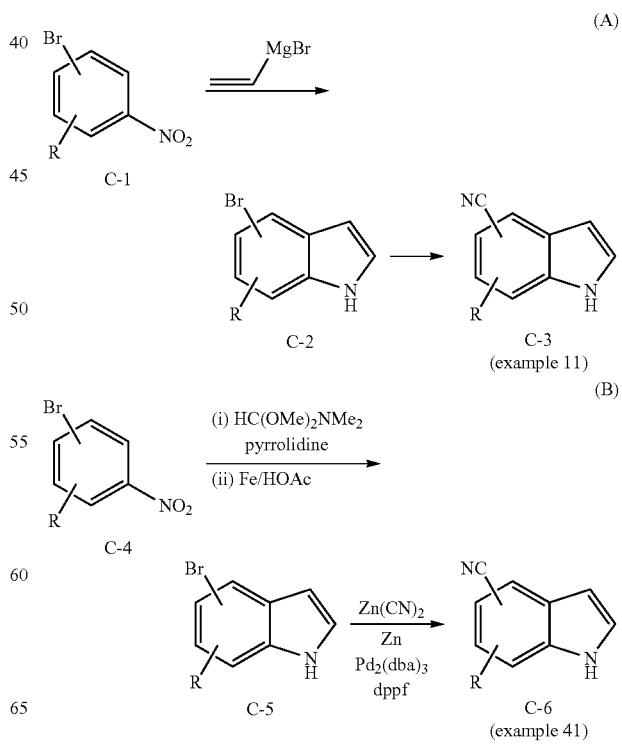

75
-continued (C)

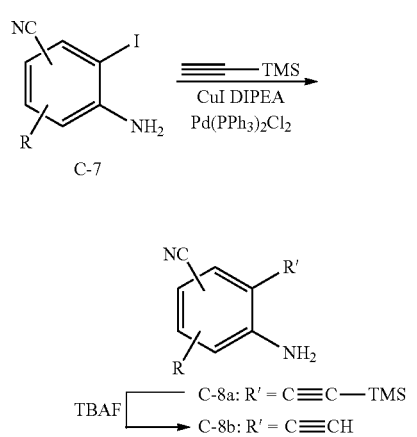

76
-continued

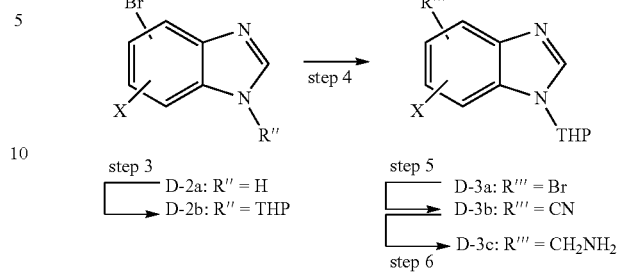

Further examples of compounds which inhibit PAK1 can be found in TABLE II. Compounds exemplified in TABLE II can be readily prepared by one skilled in the art using methodology disclosed herein and the appropriate starting materials.

C-9
(example 45)

Substituted benzimidazoles were typically prepared from ortho-diamines which in turn were prepared from ortho nitroanilines. Formic acid catalyzed cyclization afforded the benzimidazole (SCHEME D). Displacement of the bromide with cyanide and reduction of the nitrile was carried out as previously described.

SCHEME D

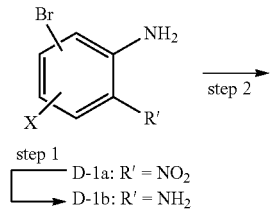

Biological Activity

Determination of the activity of PAK activity of a compound of formula I was accomplished using the PAK1 inhibition assay in Example 65. Efficacy of exemplary compounds in PAK1 assays are reported (Example 65). The range of PAK binding activities of Examples I-1 to I-122 was less than 1 nM (nanomolar) to about 10 µM (micromolar). A cell-based function assay (Example 66) was used to determine the effect of PAK inhibitors on down-stream signaling. Representative values for these assays can be found in TABLE III in example 65.

TABLE II

| Cpd. No. | Structure | $K_i^1$ | $MS^2$ | $^1$H NMR | Name |
|---|---|---|---|---|---|
| II-1 | (structure) | A | 377.1 | (400 MHz, DMSO-d$^6$) δ 12.71-11.58 (m, 2H), 9.42-9.06 (m, 1H), 8.17-8.04 (m, 1H), 7.87-7.72 (m, 1H), 7.39-5.78 (m, 5H), 4.67-4.46 (m, 2H), 4.32 and 3.95 (2 × s, 3H), 1.83-1.64 (m, 1H), 0.91-0.40 (m, 4H). Rotamers visible | N$^4$-(5-Cyclopropyl-1H-pyrazol-3-yl)-N$^2$-[(4-methoxy-1H-benzimidazol-5-yl)methyl]-pyrimidine-2,4-diamine |

TABLE II-continued

| Cpd. No. | Structure | $K_i^1$ | $MS^2$ | $^1$H NMR | Name |
|---|---|---|---|---|---|
| II-2 | 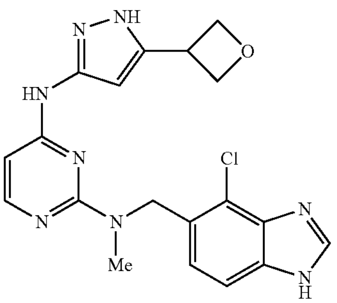 [SMILES: CN(Cc1ccc2[nH]cnc2c1Cl)c1nccc(Nc2cc(C3COC3)[nH]n2)n1] | A | 411.3 | (400 MHz, DMSO-d$^6$) δ 12.88 and 12.63 2 (2 × s, 1H), 12.08 (br s, 1H), 9.45 (s, 1H), 8.26 (s, 1H), 7.92 (d, J = 5.6 Hz, 1H), 7.62-7.36 (m, 1H), 6.99 (d, J = 8.1 Hz, 1H), 6.57-6.07 (m, 2H), 5.03 (s, 2H), 4.84-4.64 (m, 2H), 4.60-4.35 (m, 2H), 4.25-3.99 (m, 1H), 3.14 (s, 3H). | N$^2$-[(4-Chloro-1H-benzimidazol-5-yl)methyl]-N$^2$-methyl-N4-[5-(oxetan-3-yl)-1H-pyrazol-3-yl]pyrimidine-2,4-diamine |
| II-3 | 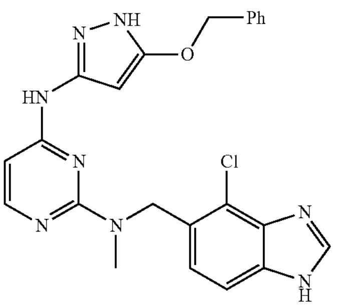 [SMILES: CN(Cc1ccc2[nH]cnc2c1Cl)c1nccc(Nc2cc(OCc3ccccc3)[nH]n2)n1] | A | 461.1 | (400 MHz, DMSO-d$^6$) δ 10.85 (s, 1H), 8.40 (s, 1H), 7.90 (d, J = 7.0 Hz, 1H), 7.57 (d, J = 8.4 Hz, 1H), 7.33-7.22 (m, 5H), 7.17 (d, J = 8.2 Hz, 1H), 6.47 (s, 1H), 5.76 (s, 1H), 5.07 (s, 2H), 4.92 (s, 3H), 3.12 (s, 3H). | N$^4$-(5-Benzyloxy-1H-pyrazol-3-yl)-N$^2$-[(4-chloro-1H-benzimidazol-5-yl)methyl]-N$^2$-methyl-pyrimidine-2,4-diamine |
| II-4 | 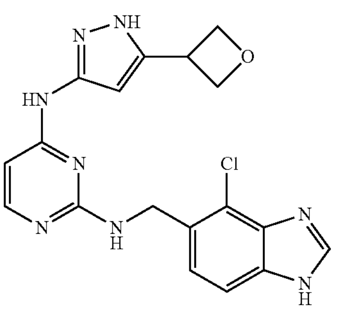 [SMILES: Clc1c(CNc2nccc(Nc3cc(C4COC4)[nH]n3)n2)ccc2[nH]cnc12] | A | 397.1 | (400 MHz, DMSO-d$^6$) δ 13.35-11.81 (m, 2H), 9.49 (br s, 1H), 8.25 (s, 1H), 8.16 (s, 1H), 7.85 (d, J = 5.7 Hz, 1H), 7.59-7.15 (m, 3H), 6.34-5.93 (m, 2H), 4.91-4.37 (m, 6H), 4.29-4.00 (m, 1H). | N$^2$-[(4-chloro-1H-benzimidazol-5-yl)methyl]-N$^4$-[5-(oxetan-3-yl)-1H-pyrazol-3-yl]pyrimidine-2,4-diamine, formic acid salt |
| II-5 | 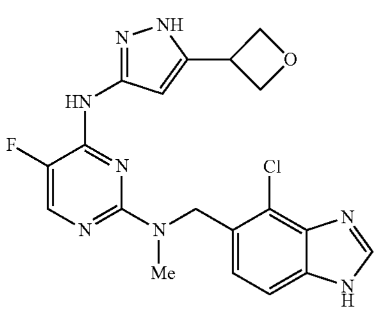 [SMILES: CN(Cc1ccc2[nH]cnc2c1Cl)c1ncc(F)c(Nc2cc(C3COC3)[nH]n2)n1] | A | 429.0 | (400 MHz, DMSO-d$^6$) δ 13.06-12.54 (m, 1H), 12.50-12.03 (m, 1H), 9.60 (s, 1H), 8.27 (s, 1H), 7.99 (d, J = 3.6 Hz, 1H), 7.59-7.34 (m, 1H), 6.95 (d, J = 8.2 Hz, 1H), 6.73-6.06 (m, 1H), 4.97 (s, 2H), 4.78-4.64 (m, 2H), 4.54-4.35 (m, 2H), 4.19-3.99 (m, 1H), 3.14 (s, 3H) | N$^2$-[(4-Chloro-1H-benzimidazol-5-yl)methyl]-5-fluoro-N$^2$-methyl-N$^4$-[5-(oxetan-3-yl)-1H-pyrazol-3-yl]pyrimidine-2,4-diamine |
| II-6 | 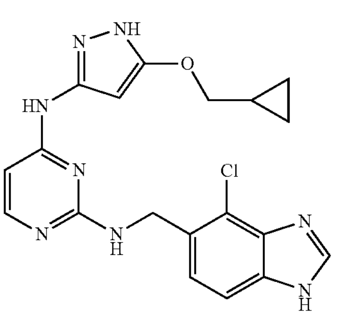 [SMILES: Clc1c(CNc2nccc(Nc3cc(OCC4CC4)[nH]n3)n2)ccc2[nH]cnc12] | A | 411.0 | (400 MHz, DMSO-d$^6$) δ 13.29-12.28 (m, 1H), 11.92 (br s, 1H), 9.94 (s, 1H), 8.25 (s, 1H), 7.90 (d, J = 5.5 Hz, 1H), 7.70-7.40 (m, 2H), 7.30 (d, J = 8.3 Hz, 1H), 5.99 (br s, 1H), 5.31-5.06 (m, 1H), 4.68 (d, J = 5.9 Hz, 2H), 3.96-3.68 (m, 2H), 1.32-1.07 (m, 1H), 0.60-0.38 (m, 2H), 0.38-0.15 (m, 2H) | N$^2$-(4-Chloro-1H-benzoimidazol-5-ylmethyl)-N4-(5-cyclopropylmethoxy-1H-pyrazol-3-yl)-pyrimidine-2,4-diamine |

TABLE II-continued

| Cpd. No. | Structure | $K_i^1$ | $MS^2$ | $^1H$ NMR | Name |
|---|---|---|---|---|---|
| II-7 | 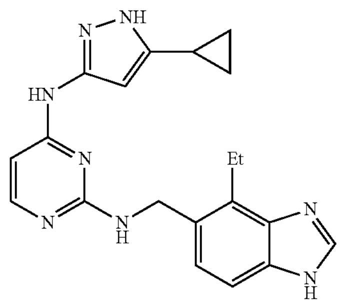 [SMILES: CCc1c(CNc2nccc(Nc3cc(C4CC4)[nH]n3)n2)ccc2[nH]cnc12] | A | 375.1 | (400 MHz, DMSO-d$^6$) δ 12.33 (br s, 1H), 11.08 (br s, 1H), 9.02-8.23 (m, 2H), 7.86 (s, 1H), 7.61-7.14 (m, 2H), 6.45-6.22 (m, 1H), 6.21-5.93 (m, 1H), 4.76 (s, 2H), 3.04 (s, 2H), 1.87-1.58 (m, 1H), 1.21 (t, J = 7.5 Hz, 3H), 0.92-0.27 (m, 4H). one proton not visible | N$^4$-(5-Cyclopropyl-1H-pyrazol-3-yl)-N$^2$-[(4-ethyl-1H-benzimidazol-5-yl)methyl]pyrimidine-2,4-diamine |
| II-8 | 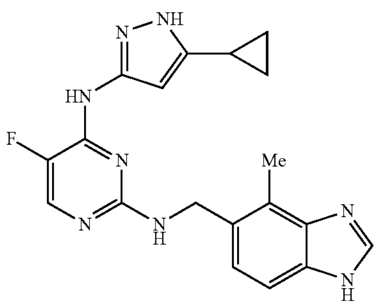 [SMILES: Cc1c(CNc2ncc(F)c(Nc3cc(C4CC4)[nH]n3)n2)ccc2[nH]cnc12] | B | 379.2 | (400 MHz, DMSO-d$^6$) δ 12.62-11.42 (m, 2H), 10.36-9.00 (m, 1H), 8.13 (d, J = 15.8 Hz, 1H), 7.89 (br s, 1H), 7.59-6.88 (m, 3H), 6.42-5.39 (m, 1H), 4.51 (d, J = 5.7 Hz, 2H), 1.91-1.59 (m, 1H), 0.96-0.37 (m, 4H). NMR in DMSO was complex due to the presence of rotamers. The methyl group was masked by solvent peaks. | N$^4$-(5-Cyclopropyl-1H-pyrazol-3-yl)-5-fluoro-N$^2$-[(4-methyl-1H-benzimidazol-5-yl)methyl]pyrimidine-2,4-diamine |
| II-9 | 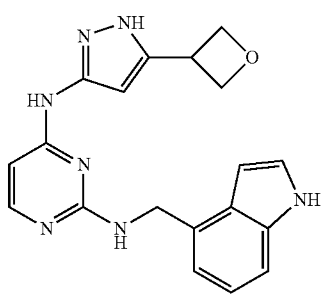 [SMILES: c1cc(CNc2nccc(Nc3cc(C4COC4)[nH]n3)n2)c2cc[nH]c2c1] | B | 362.1 | (400 MHz, DMSO-d$^6$) δ 12.90-11.84 (m, 1H), 11.05 (s, 1H), 10.09-9.13 (m, 1H), 7.92-7.77 (m, 1H), 7.35-7.20 (m, 2H), 7.15-6.87 (m, 2H), 6.55 (s, 1H), 6.50-5.55 (m, 2H), 4.87-4.70 (m, 4H), 4.68-4.42 (m, 2H), 4.25-3.99 (m, 1H), 3.24-3.16 (m, 1H). Rotamers visible | N$^2$-(1H-indol-4-ylmethyl)-N$^4$-[5-(oxetan-3-yl)-1H-pyrazol-3-yl]pyrimidine-2,4-diamine |
| II-10 | 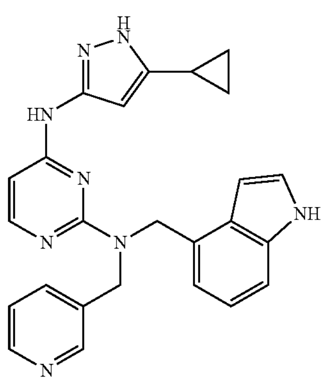 [SMILES: c1cncc(CN(Cc2cccc3[nH]ccc23)c2nccc(Nc3cc(C4CC4)[nH]n3)n2)c1] | B | 437.2 | (400 MHz, DMSO-d$^6$) δ 11.86 (s, 1H), 11.10 (s, 1H), 9.42 (s, 1H), 8.45-8.33 (m, 2H), 7.94 (d, J = 5.6 Hz, 1H), 7.61 (d, J = 7.9 Hz, 1H), 7.38-7.17 (m, 3H), 7.00 (dd, J = 8.0 Hz, 1H), 6.78 (d, J = 7.1 Hz, 1H), 6.44 (s, 1H), 6.29 (br s, 1H), 5.85 (s, 1H), 5.10 (s, 2H), 4.77 (s, 2H), 1.72-1.45 (m, 1H), 0.85-0.14 (m, 4H) | N$^4$-(5-Cyclopropyl-1H-pyrazol-3-yl)-N$^2$-(1H-indol-4-ylmethyl)-N$^2$-(3-pyridylmethyl)pyrimidine-2,4-diamine |

TABLE II-continued

| Cpd. No. | Structure | $K_i^1$ | $MS^2$ | $^1$H NMR | Name |
|---|---|---|---|---|---|
| II-11 | 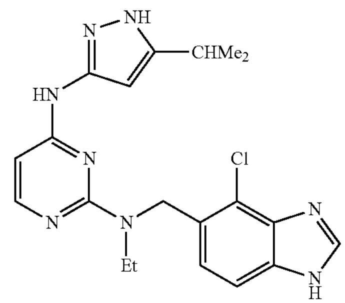 | A | 411.1 | (500 MHz, MeOD-d$_4$) δ 8.25 (s, 1H), 7.89-7.88 (d, 1H), 7.52-7.50 (d, 1H), 7.19-7.17 (d, 1H), 6.23 (brs, 1H), 6.03 (brs, 1H), 5.10 (s, 2H), 3.69-3.67 (br, 2H), 2.77 (brs, 1H), 1.26-1.24 (t, 3H), 1.04 (d, 6H) | $N^2$-((4-Chloro-1H-benzo[d]imidazol-5-yl)methyl)-$N^2$-ethyl-$N^4$-(5-isopropyl-1H-pyrazol-3-yl)pyrimidine-2,4-diamine |
| II-12 | 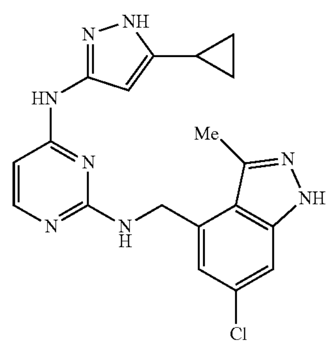 [SMILES: Cc1n[nH]c2cc(Cl)cc(CNc3nccc(Nc4cc(C5CC5)[nH]n4)n3)c12] | A | 395.0 | (500 MHz, DMSO-d$_6$) δ 12.75 (s, 1H), 11.83 (brs, 1H), 9.37 (brs, 1H), 7.81 (s, 1H), 7.35-7.28 (d, 2H), 6.86 (s, 1H), 6.57-5.44 (m, 2H), 4.94 (s, 2H), 2.63 (s, 3H), 1.51 (m, 1H), 0.95-0.60 (m, 4H); | $N^2$-((6-Chloro-3-methyl-1H-indazol-4-yl)methyl)-$N^4$-(5-cyclopropyl-1H-pyrazol-3-yl)pyrimidine-2,4-diamine |
| II-13 | 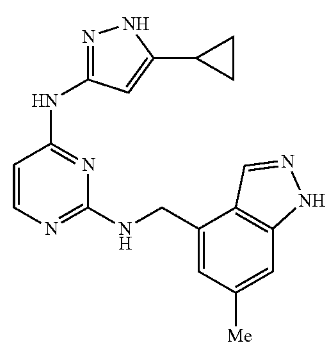 [SMILES: Cc1cc(CNc2nccc(Nc3cc(C4CC4)[nH]n3)n2)c2cn[nH]c2c1] | A | 361.3 | (500 MHz, MeOD-d$_4$) δ 8.11 (s, 1H), 7.84 (s, 1H), 7.25 (s, 1H), 6.98 (s, 1H), 6.16-5.95 (m, 2H), 4.91 (s, 2H), 2.45 (s, 3H), 1.73-1.65 (m, 1H), 0.84 (m, 2H), 0.51 (m, 2H) | $N^4$-(5-Cyclopropyl-1H-pyrazol-3-yl)-$N^2$-((6-methyl-1H-indazol-4-yl)methyl)pyrimidine-2,4-diamine |
| II-14 | 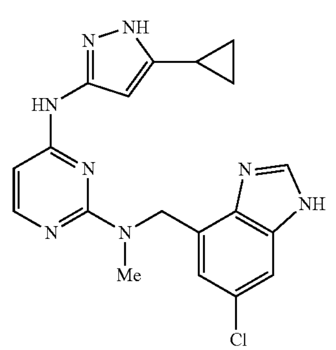 [SMILES: CN(Cc1cc(Cl)cc2[nH]cnc12)c1nccc(Nc2cc(C3CC3)[nH]n2)n1] | A | 395.3 | (500 MHz, MeOD-d$_4$) δ 8.23 (s, 1H), 7.95 (d, 1H), 7.55 (s, 1H), 7.06 (s, 1H), 6.20 (s, 1H), 5.89 (s, 1H), 5.16 (s, 2H), 3.19 (s, 3H), 1.69 (m, 1H), 0.79 (m, 2H), 0.36 (m, 2H) | $N^2$-((6-Chloro-1H-benzo[d]imidazol-4-yl)methyl)-$N^4$-(5-cyclopropyl-1H-pyrazol-3-yl)-$N^2$-methylpyrimidine-2,4-diamine |

TABLE II-continued

| Cpd. No. | Structure | $K_i^1$ | $MS^2$ | $^1H$ NMR | Name |
|---|---|---|---|---|---|
| II-15 | 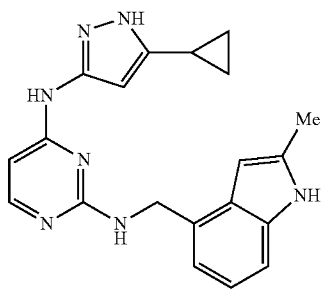 [SMILES: Cc1cc2c(CNc3nccc(Nc4cc(C5CC5)[nH]n4)n3)cccc2[nH]1] | A | 360.2 | (500 MHz, MeOD-$d_4$) δ 7.83 (s, 1H), 7.19 (d, 1H), 7.00-6.95 (m, 2H), 6.24 (s, 1H), 6.15-5.46 (m, 2H), 4.79 (s, 2H), 2.43 (s, 3H), 1.75 (m, 1H), 0.85 (m, 2H), 0.54 (m, 2H) | $N^4$-(5-Cyclopropyl-1H-pyrazol-3-yl)-$N^2$-((2-methyl-1H-indol-4-yl)methyl)pyrimidine-2,4-diamine |
| II-16 | 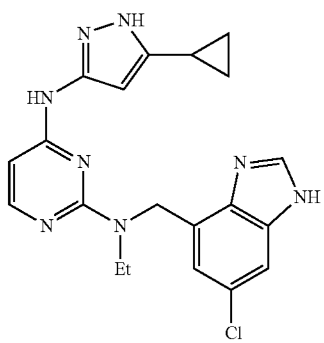 [SMILES: CCN(Cc1cc(Cl)cc2[nH]cnc12)c1nccc(Nc2cc(C3CC3)[nH]n2)n1] | A | 409.3 | (500 MHz, MeOD-$d_4$) δ 8.11 (s, 1H), 7.83 (d, 1H), 7.43 (s, 1H), 6.95 (s, 1H), 6.07 (s, 1H), 5.76 (m, 1H), 5.03 (s, 2H), 3.56 (q, 2H), 1.54 (m, 1H), 1.08 (t, 3H), 0.68 (m, 2H), 0.23 (m, 2H) | $N^2$-((6-Chloro-1H-benzo[d]imidazol-4-yl)methyl)-$N^4$-(5-cyclopropyl-1H-pyrazol-3-yl)-$N^2$-ethylpyrimidine-2,4-diamine |
| II-17 | 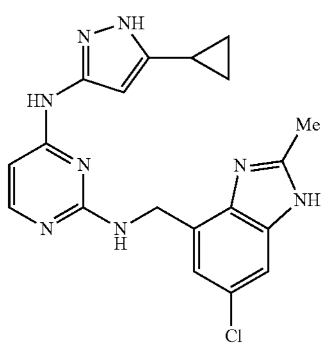 [SMILES: Cc1nc2c(CNc3nccc(Nc4cc(C5CC5)[nH]n4)n3)cc(Cl)cc2[nH]1] | A | 395.3 | (500 MHz, MeOD-$d_4$) δ 7.85-7.84 (d, 1H), 7.39 (s, 1H), 7.14 (s, 1H), 6.17-6.09 (br, 1H), 5.90-5.84 (br, 1H), 4.86-4.85 (s, 2H), 2.57 (s, 3H), 1.82-1.65 (m, 1H), 0.86-0.84 (m, 2H), 0.48-0.43 (m, 2H) | $N^2$-((6-Chloro-2-methyl-1H-benzo[d]imidazol-4-yl)methyl)-$N^4$-(5-cyclopropyl-1H-pyrazol-3-yl)pyrimidine-2,4-diamine |
| II-18 | 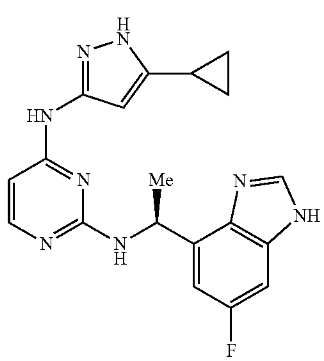 [SMILES: C[C@H](Nc1nccc(Nc2cc(C3CC3)[nH]n2)n1)c1cc(F)cc2[nH]cnc12] | A | 379.3 | (500 MHz, MeOD-$d_4$) δ 8.21 (s, 1H), 7.79 (d, 1H), 7.18 (d, 1H), 7.06 (d, 1H), 6.09 (br, 1H), 5.88 (br, 1H), 5.58 (br, 1H), 1.73 (m, 1H), 1.67 (d, 3H), 0.92 (m, 2H), 0.63 (m, 2H) | (S)-$N^4$-(5-cyclopropyl-1H-pyrazol-3-yl)-$N^2$-(1-(6-fluoro-1H-benzo[d]imidazol-4-yl)ethyl)pyrimidine-2,4-diamine |

TABLE II-continued

| Cpd. No. | Structure | $K_i^1$ | MS[2] | $^1$H NMR | Name |
|---|---|---|---|---|---|
| II-19 | 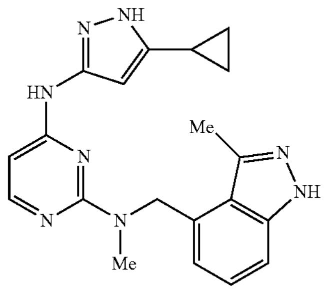 [SMILES: Cc1n[nH]c2cccc(CN(C)c3nccc(Nc4cc(C5CC5)[nH]n4)n3)c12] | A | 374 | (500 MHz, MeOD-d$_4$) δ 8.15 (s, 1H), 7.88 (d, 1H), 7.35 (d, 1H), 7.24 (d, 1H), 6.61 (d, 1H), 6.26 (s, 1H), 5.34 (s, 2H), 3.22 (s, 3H), 2.67 (s, 3H), 1.42 (m, 1H), 0.84 (m, 2H), 0.67 (m, 2H) | N$^4$-(5-Cyclopropyl-1H-pyrazol-3-yl)-N$^2$-methyl-N$^2$-((3-methyl-1H-indazol-4-yl)methyl)pyrimidine-2,4-diamine |
| II-20 | 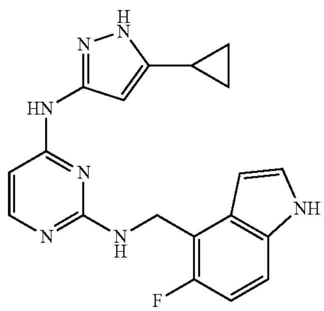 [SMILES: Fc1ccc2[nH]ccc2c1CNc1nccc(Nc2cc(C3CC3)[nH]n2)n1] | A | 364.1 | (500 MHz, MeOD-d$_4$) δ 7.93-7.80 (m, 1H), 7.32-7.29 (m, 2H), 6.92 (t, 1H), 6.58 (d, 1H), 6.23-5.46 (m, 2H), 4.89 (s, 2H), 1.87 (m, 1H), 0.92 (m, 2H), 0.70 (n, 2H) | N$^4$-(5-cyclopropyl-1H-pyrazol-3-yl)-N$^2$-((5-fluoro-1H-indol-4-yl)methyl)pyrimidine-2,4-diamine |
| II-21 | 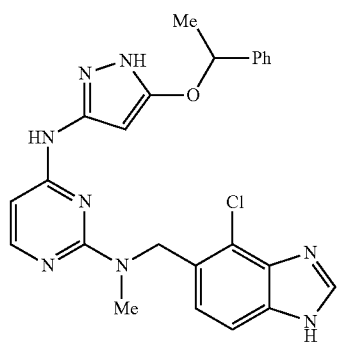 [SMILES: CC(Oc1cc(Nc2ccnc(N(C)Cc3ccc4[nH]cnc4c3Cl)n2)n[nH]1)c1ccccc1] | A | 475.1 | (500 MHz, DMSO-d$_6$) δ 12.82-12.74 (m, 1H), 11.74-11.15 (m, 1H), 9.56 (brs, 1H), 8.28 (brs, 1H), 7.91 (brs, 1H), 7.49 (brs, 1H), 7.25-7.21 (m, 5H), 6.97 (d, J = 8.5 Hz, 1H), 6.04 (br s, 1H), 5.55 (brs, 1H), 5.07-4.96 (m, 3H), 3.05 (s, 3H), 1.44 (s, 3H) | (R)-N$^2$-((4-Chloro-1H-benzo[d]imidazol-5-yl)methyl)-N$^2$-methyl-N$^4$-(5-(1-phenylethoxy)-1H-pyrazol-3-yl)pyrimidine-2,4-diamine |
| II-22 | 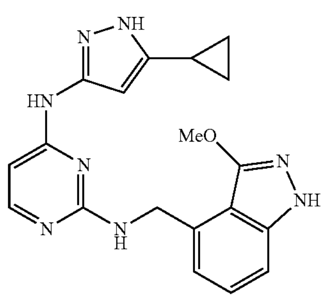 [SMILES: COc1n[nH]c2cccc(CNc3nccc(Nc4cc(C5CC5)[nH]n4)n3)c12] | A | 377 | (500 MHz, DMSO-d$_6$) δ 11.87 (s, 1H), 11.82 (m, 1H), 9.29 (s, 1H), 7.78 (s, 1H), 7.18 (m, 2H), 7.03 (s, 1H), 6.81 (s, 1H), 6.17 (m, 1H), 5.83 (m, 1H), 4.87 (d, 2H), 4.01 (s, 3H), 1.81 (m, 1H), 0.73 (m, 4H) | N$^4$-(5-Cyclopropyl-1H-pyrazol-3-yl)-N$^2$-((3-methoxy-1H-indazol-4-yl)methyl)pyrimidine-2,4-diamine |
| II-23 | 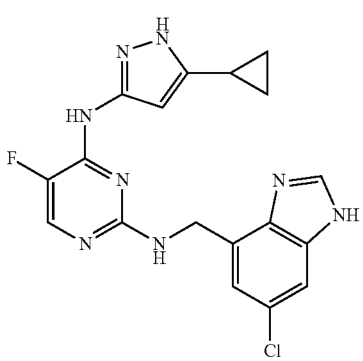 | A | 399.3 | (500 MHz, MeOD-d$_4$) δ 7.98 (s, 1H), 7.85 (s, 1H), 7.27 (s, 1H), 6.95 (s, 1H), 5.76-5.65 (br, 1H), 4.83-4.49 (d, 2H), 1.70-1.34 (m, 1H), 0.77-0.69 (m, 2H), 0.48-0.37 (m, 2H) | N$^2$-((6-Chloro-1H-benzo[d]imidazol-4-yl)methyl)-N$^4$-(5-cyclopropyl-1H-pyrazol-3-yl)-5-fluoropyrimidine-2,4-diamine |

TABLE II-continued

| Cpd. No. | Structure | $K_i^1$ | MS[2] | $^1$H NMR | Name |
|---|---|---|---|---|---|
| II-24 | 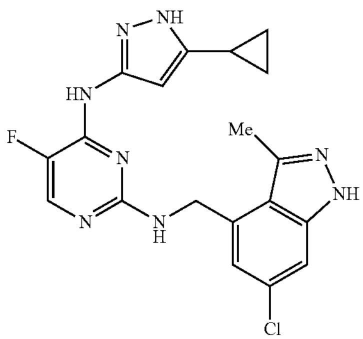 [SMILES: Cc1n[nH]c2cc(Cl)cc(CNc3ncc(F)c(Nc4cc(C5CC5)[nH]n4)n3)c12] | A | 413.0 | (500 MHz, DMSO-$d_6$) δ 12.76 (s, 1H), 11.94 (brs, 1H), 9.41 (brs, 1H), 7.88 (s, 1H), 7.46-7.07 (m, 2H), 6.86 (s, 1H), 4.88 (s, 2H), 2.69 (s, 3H), 1.23 (m, 1H), 0.89-0.41 (m, 4H) | $N^2$-((6-Chloro-3-methyl-1H-indazol-4-yl)methyl)-$N^4$-(5-cyclopropyl-1H-pyrazol-3-yl)-5-fluoropyrimidine-2,4-diamine |
| II-25 | 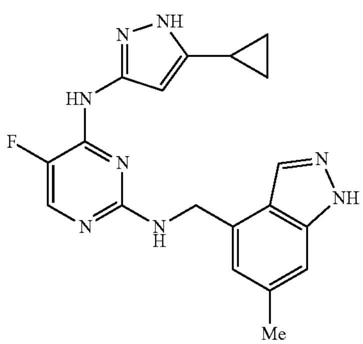 [SMILES: Cc1cc(CNc2ncc(F)c(Nc3cc(C4CC4)[nH]n3)n2)c2cn[nH]c2c1] | A | 379.1 | (500 MHz, DMSO-$d_6$) δ 12.86 (s, 1H), 11.97 (s, 1H), 9.31 (s, 1H), 8.09 (s, 1H), 7.85 (s, 1H), 7.33 (s, 1H), 7.15 (s, 1H), 6.83 (s, 1H), 4.72 (d, J = 6.Hz, 2H), 2.07 (s, 3H), 1.73 (m, 1H), 0.81 (m, 2H), 0.58 (m, 2H); | $N^4$-(5-Cyclopropyl-1H-pyrazol-3-yl)-5-fluoro-$N^2$-((6-methyl-1H-indazol-4-yl)methyl)-pyrimidine-2,4-diamine |
| II-26 | 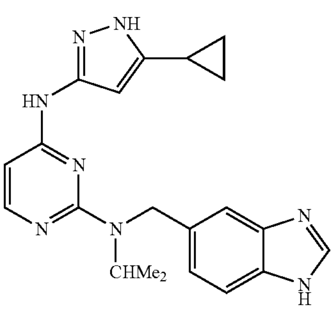 | A | 389.3 | (500 MHz, MeOD-$d_4$) δ 7.91 (s, 1H), 7.70 (s, 1H), 7.36-7.31 (d, 2H), 7.06-7.05 (s, 1H), 5.94 (br, 1H), 5.68-5.68 (br, 1H), 4.84-4.80 (m, 1H), 4.75 (s, 2H), 1.43-1.42 (m, 1H), 1.06-1.05 (d, 6H), 0.52 (m, 2H), 0.06-0.00 (m, 2H) | $N^2$-((1H-Benzo[d]imidazol-5-yl)methyl)-$N^4$-(5-cyclopropyl-1H-pyrazol-3-yl)-$N^2$-isopropylpyrimidine-2,4-diamine |
| II-27 | 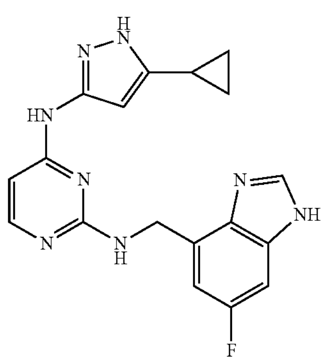 [SMILES: Fc1cc(CNc2nccc(Nc3cc(C4CC4)[nH]n3)n2)c2nc[nH]c2c1] | B | 365.2 | (500 MHz, MeOD-$d_4$) δ 8.21 (s, 1H), 7.84 (s, 1H), 7.20 (s, 1H), 7.01 (s, 1H), 6.19-5.91 (m, 2H), 4.91 (s, 2H), 1.74-1.71 (m, 1H), 0.84 (m, 2H), 0.50-0.40 (m, 2H) | $N^4$-(5-Cyclopropyl-1H-pyrazol-3-yl)-$N^2$-((6-fluoro-1H-benzo[d]imidazol-4-yl)methyl)-pyrimidine-2,4-diamine |

TABLE II-continued

| Cpd. No. | Structure | $K_i^1$ | MS[2] | $^1$H NMR | Name |
|---|---|---|---|---|---|
| II-28 | 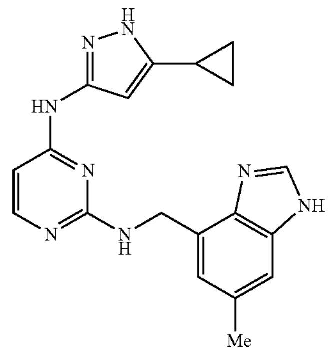 [SMILES: Cc1cc(CNc2nccc(Nc3cc(C4CC4)[nH]n3)n2)c2nc[nH]c2c1] | B | 361.1 | (500 MHz, MeOD-d$_4$) δ 8.10 (s, 1H), 7.83 (s, 1H), 7.32 (s, 1H), 7.09 (s, 1H), 5.97 (d, 2H), 4.90 (s, 2H), 2.43 (s, 3H), 1.74 (m, 1H), 0.84 (m, 2H), 0.45 (m, 2H) | $N^4$-(5-Cyclopropyl-1H-pyrazol-3-yl)-$N^2$-((6-methyl-1H-benzo[d]imidazol-4-yl)methyl)-pyrimidine-2,4-diamine |
| II-29 | 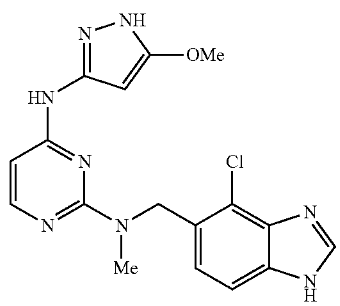 [SMILES: COc1cc(Nc2ccnc(N(C)Cc3ccc4[nH]cnc4c3Cl)n2)n[nH]1] | B | 385.1 | (500 MHz, MeOD-d$_4$) δ 8.28 (s, 1H), 7.96-7.95 (m, 1H), 7.45-7.44 (m, 1H), 7.00-6.99 (m, 1H), 6.07 (br s, 1H), 5.56 (br s, 1H), 5.04 (s, 2H), 3.62 (s, 3H), 3.11 (s, 3H | $N^2$-((4-Chloro-1H-benzo[d]imidazol-5-yl)methyl)-$N^4$-(5-methoxy-1H-pyrazol-3-yl)-$N^2$-methylpyrimidine-2,4-diamine |
| II-30 | 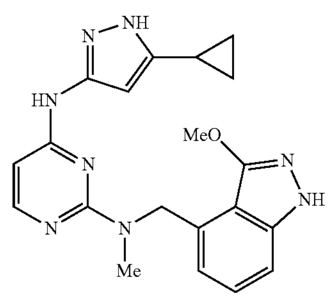 [SMILES: COc1n[nH]c2cccc(CN(C)c3nccc(Nc4cc(C5CC5)[nH]n4)n3)c12] | B | 391.0 | (500 MHz, MeOD-d$_4$) δ 7.66 (d, 1H), 7.01-6.01 (m, 2H), 6.44 (brs, 1H), 5.89 (s, 1H), 5.60 (brs, 1H), 5.05 (s, 2H), 3.85 (s, 3H), 2.97 (s, 3H), 1.35 (m, 1H), 1.06-1.01 (m, 2H), 0.49 (m, 2H) | $N^4$-(5-cyclopropyl-1H-pyrazol-3-yl)-$N^2$-((3-methoxy-1H-indazol-4-yl)methyl)-$N^2$-methylpyrimidine-2,4-diamine |
| II-31 | 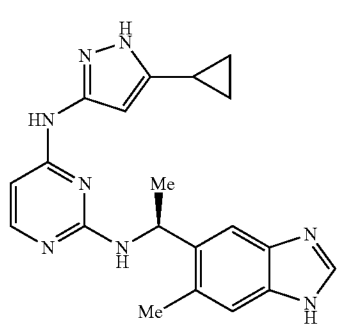 [SMILES: Cc1cc2[nH]cnc2cc1[C@H](C)Nc1nccc(Nc2cc(C3CC3)[nH]n2)n1] | B | 375.4 | (500 MHz, MeOD-d$_4$) δ 8.10 (s, 1H), 7.79 (d, 1H), 7.28 (s, 1H), 7.12 (s, 1H), 6.09 (brs, 1H), 5.78 (brs, 1H), 5.58 (d, 1H), 2.43 (s, 3H), 1.78 (m, 1H), 1.67 (d, 3H), 0.93 (m, 2H), 0.64 (m, 2H); | (S)-$N^4$-(5-Cyclopropyl-1H-pyrazol-3-yl)-$N^2$-(1-(6-methyl-1H-benzo[d]imidazol-5-yl)ethyl)pyrimidine-2,4-diamine |

TABLE II-continued

| Cpd. No. | Structure | $K_i$[1] | MS[2] | $^1$H NMR | Name |
|---|---|---|---|---|---|
| II-32 | 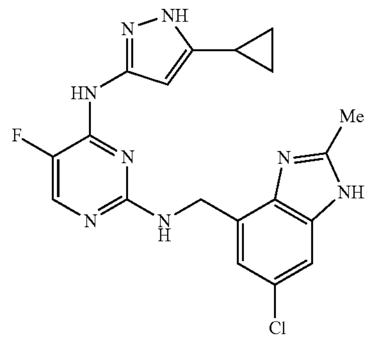 [SMILES: Cc1nc2c(CNc3ncc(F)c(Nc4cc(C5CC5)[nH]n4)n3)cc(Cl)cc2[nH]1] | B | 413.3 | (500 MHz, MeOD-d$_4$) δ 7.82 (s, 1H), 7.38 (s, 1H), 7.11 (s, 1H), 5.97-5.91 (br, 1H), 4.80-4.69 (d, 2H), 2.57 (s, 3H), 1.95-1.70 (m, 1H), 0.84-0.74 (m, 2H), 0.61-0.42 (m, 2H); | $N^2$-((6-Chloro-2-methyl-1H-benzo[d]imidazol-4-yl)methyl)-$N^4$-(5-cyclopropyl-1H-pyrazol-3-yl)-5-fluoropyrimidine-2,4-diamine |
| II-33 | 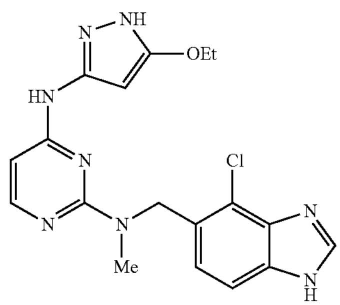 | B | 399.3 | NMR (500 MHz, MeOD-d$_4$) δ 8.24 (s, 1H), 7.99-7.96 (m, 1H), 7.51-7.49 (m, 1H), 7.15-7.14 (m, 1H), 6.09 (brs, 1H), 5.41 (brs, 1H), 5.13 (s, 2H), 3.97-3.93 (q, 2H), 3.19 (s, 3H), 1.31 (t, 3H) | $N^2$-((4-Chloro-1H-benzo[d]imidazol-5-yl)methyl)-$N^4$-(5-ethoxy-1H-pyrazol-3-yl)-$N^2$-methylpyrimidine-2,4-diamine |
| II-34 | 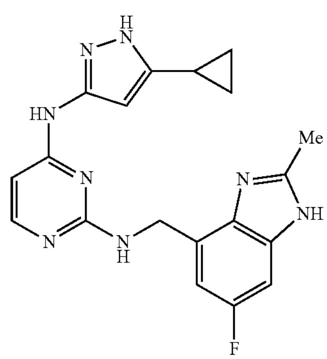 [SMILES: Cc1nc2c(CNc3nccc(Nc4cc(C5CC5)[nH]n4)n3)cc(F)cc2[nH]1] | B | 379.0 | (500 MHz, MeOD-d$_4$) δ 7.84 (d, 1H), 7.07 (d, 1H), 6.91 (d, 1H), 6.15 (s, 1H), 5.82 (s, 1H), 4.92 (s, 2H), 2.51 (s, 3H), 1.74 (m, 1H), 0.84 (m, 2H), 0.49 (m, 2H); | $N^4$-(5-Cyclopropyl-1H-pyrazol-3-yl)-$N^2$-((6-fluoro-2-methyl-1H-benzo[d]imidazol-4-yl)methyl)pyrimidine-2,4-diamine |
| II-35 | 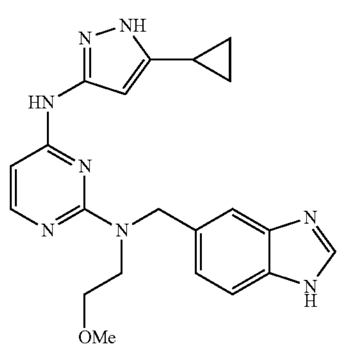 [SMILES: COCCN(Cc1ccc2[nH]cnc2c1)c1nccc(Nc2cc(C3CC3)[nH]n2)n1] | B | 405.3 | (500 MHz, MeOD-d$_4$) δ 8.13 (s, 1H), 7.9-7.89 (d, 1H), 7.60-7.58 (d, 1H), 7.51 (s, 1H), 7.24-7.23 (d, 1H), 6.18 (br, 1H), 6.10-6.06 (br, 1H), 5.07 (s, 2H), 3.78 (br, 2H), 3.62-3.59 (t, 2H), 3.28 (s, 3H), 1.83-1.72 (m, 1H), 0.91-0.77 (m, 2H), 0.64-0.37 (m, 2H); | $N^2$-((1H-benzo[d]imidazol-5-yl)methyl)-$N^4$-(5-cyclopropyl-1H-pyrazol-3-yl)-$N^2$-(2-methoxyethyl)pyrimidine-2,4-diamine |

TABLE II-continued

| Cpd. No. | Structure | $K_i^1$ | $MS^2$ | $^1$H NMR | Name |
|---|---|---|---|---|---|
| II-36 | 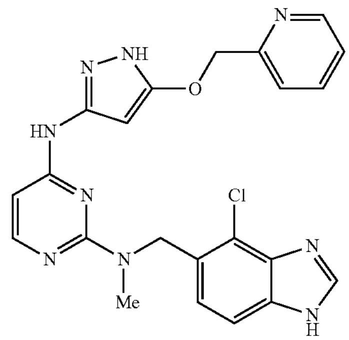 [SMILES: CN(Cc1ccc2[nH]cnc2c1Cl)c1nccc(Nc2cc(OCc3ccccn3)[nH]n2)n1] | B | 462.1 | NMR (500 MHz, DMSO-d$_6$) δ 12.77 (brs, 1H), 11.26 (brs, 1H), 9.93 (brs, 1H), 8.51 (s, 1H), 8.26 (s, 1H), 7.96-7.91 (m, 1H), 7.80-7.77 (m, 1H), 7.47-7.28 (m, 3H), 7.00-6.99 (m, 1H), 6.13-6.08 (m, 1H), 5.68-5.64 (m, 1H), 5.13 (s, 2H), 4.99 (s, 2H), 3.08 (s, 3H) | $N^2$-((4-Chloro-1H-benzo[d]imidazol-5-yl)methyl-$N^2$-methyl-$N^4$-(5-(pyridin-2-ylmethoxy)-1H-pyrazol-3-yl)pyrimidine-2,4-diamine |
| II-37 | 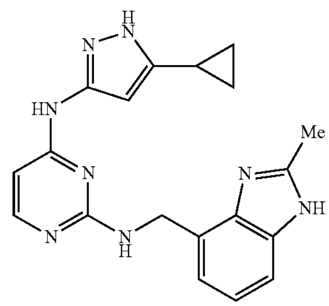 [SMILES: Cc1nc2c(CNc3nccc(Nc4cc(C5CC5)[nH]n4)n3)cccc2[nH]1] | | 361 | (500 MHz, MeOD-d$_4$) δ 7.63 (s, 1H), 7.54 (s, 1H), 7.40 (s, 1H), 7.10 (s, 1H), 6.10 (s, 1H), 5.18 (s, 1H), 4.35 (s, 2H), 2.51 (s, 3H), 2.22 (m, 1H), 0.99 (m, 2H), 0.75 (m, 2H) | $N^4$-(5-Cyclopropyl-1H-pyrazol-3-yl)-$N^2$-((2-methyl-1H-benzo[d]imidazol-4-yl)methyl)pyrimidin-2,4-diamine |
| II-38 | 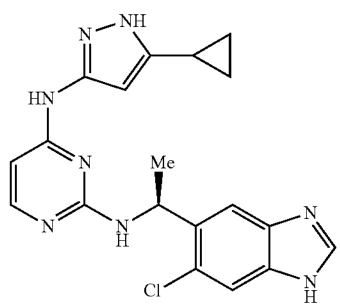 [SMILES: C[C@H](Nc1nccc(Nc2cc(C3CC3)[nH]n2)n1)c1cc2nc[nH]c2cc1Cl] | B | 395.2 | (500 MHz, MeOD-d$_4$) δ 8.05 (s, 1H), 7.67-7.57 (m, 3H), 5.97-5.96 (m, 1H), 5.41-5.38 (m, 1H), 4.50 (br s, 1H), 1.82-1.78 (m, 1H), 1.48 (d, 3H), 0.86-0.60 (m, 4H) | (S)-$N^2$-(1-(6-Chloro-1H-benzo[d]imidazol-5-yl)ethyl)-$N^4$-(5-cyclopropyl-1H-pyrazol-3-yl)pyrimidine-2,4-diamine |
| II-39 | 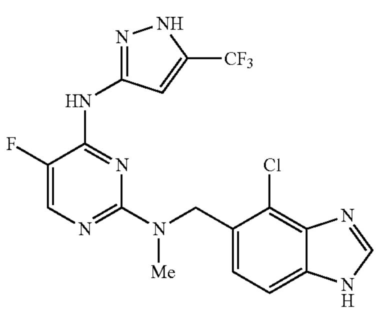 [SMILES: CN(Cc1ccc2[nH]cnc2c1Cl)c1ncc(F)c(Nc2cc(C(F)(F)F)[nH]n2)n1] | B | 441.1 | (500 MHz, MeOD-d$_4$) δ 8.23 (s, 1H), 8.01 (d, 1H), 7.49 (brs, 1H), 7.12 (d, 1H), 6.37 (brs, 1H), 5.08 (s, 2H), 3.22 (s, 3H) | $N^2$-((4-Chloro-1H-benzo[d]imidazol-5-yl)methyl)-5-fluoro-$N^4$-(5-(trifluoromethyl)-1H-pyrazol-3-yl)-N2-methylpyrimidine-2,4-diamine |
| II-40 | 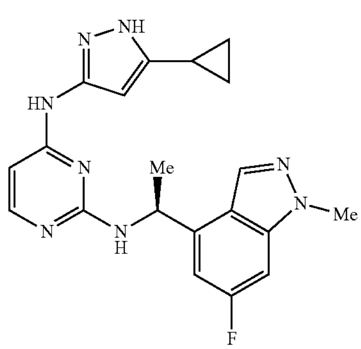 [SMILES: C[C@H](Nc1nccc(Nc2cc(C3CC3)[nH]n2)n1)c1cc(F)cc2c1cnn2C] | B | 393.3 | (500 MHz, DMSO-d$_6$) δ 11.80 (br s, 1H), 9.25 (br s, 1H), 8.29 (s, 1H), 7.76-7.69 (m, 1H), 7.34-7.32 (m, 1H), 6.95-6.93 (m, 1H), 6.14-6.08 (m, 1H), 5.47-5.44 (m, 1H), 3.97 (s, 3H), 1.81-1.79 (m, 1H), 1.54 (d, 3H), 1.81-1.79 (m, 1H), 0.96-0.78 (m, 2H), 0.78-0.57 (m, 2H); | (S)-$N^4$-(5-cyclopropyl-1H-pyrazol-3-yl)-$N^2$-(1-(6-fluoro-1-methyl-1H-indazol-4-yl)ethyl)pyrimidine-2,4-diamine |

TABLE II-continued

| Cpd. No. | Structure | $K_i^1$ | MS[2] | $^1$H NMR | Name |
|---|---|---|---|---|---|
| II-41 | 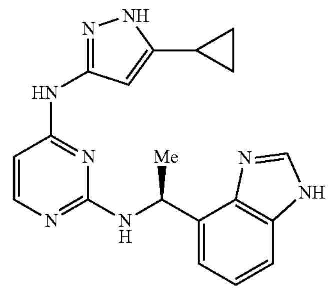 [SMILES: C[C@H](Nc1nccc(Nc2cc(C3CC3)[nH]n2)n1)c1cccc2[nH]cnc12] | B | 361.1 | (500 MHz, MeOD-$d_4$) δ 8.19 (s, 1H), 7.79-7.78 (d, 1H), 7.52-7.50 (brs, 1H), 7.29-7.22 (m, 2H), 6.16-6.09 (brs, 1H), 5.66-5.60 (brs, 1H), 3.07-3.05 (s, 1H), 1.69-1.68 (d, 3H), 1.36-1.30 (m, 1H), 0.93-0.92 (m, 2H), 0.63-0.62 (m, 2H) | (S)-$N^2$-(1-(1H-benzo[d]imidazol-4-yl)ethyl)-$N^4$-(5-cyclopropyl-1H-pyrazol-3-yl)pyrimidine-2,4-diamine |
| II-42 | 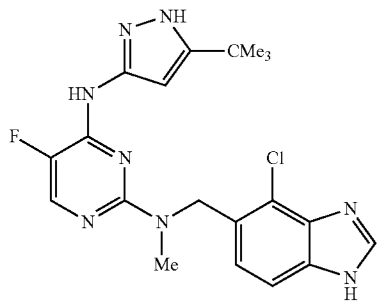 | B | 429 | (500 MHz, MeOD-$d_4$) δ 8.11 (s, 1H), 7.78 (d, 1H), 7.38 (s, 1H), 7.01 (d, 1H), 6.09 (m, 1H), 4.97 (s, 2H), 3.05 (s, 3H), 0.93 (s, 9H) | $N^4$-(5-tert-Butyl-1H-pyrazol-3-yl)-$N^2$-((4-chloro-1H-benzo[d]imidazol-5-yl)methyl)-5-fluoro-$N^2$-methylpyrimidine-2,4-diamine |
| II-43 | 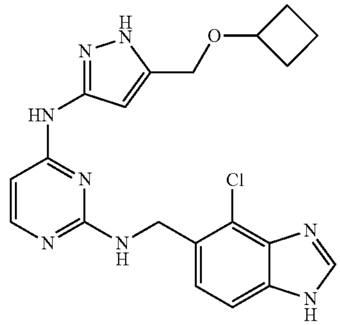 [SMILES: Clc1c(CNc2nccc(Nc3cc(COC4CCC4)[nH]n3)n2)ccc2[nH]cnc12] | B | 425.2 | (500 MHz, DMSO-$d_6$) δ 12.50 (brs, 1H), 12.15 (brs, 1H), 9.45 (brs, 1H), 8.30 (s, 1H), 7.70 (s, 1H), 7.48 (s, 1H), 7.32 (s, 2H), 6.30-5.90 (brs, 2H), 4.74 (s, 2H), 4.20-4.00 (brs, 2H), 4.00-3.60 (brs, 1H), 2.20-1.90 (brs, 2H), 1.90-1.60 (brs, 2H), 1.60-1.50 (brs, 1H), 1.50-1.40 (brs, 1H); | $N^2$-((4-Chloro-1H-benzo[d]imidazol-5-yl)methyl)-$N^4$-(5-(cyclobutoxymethyl)-1H-pyrazol-3-yl)pyrimidine-2,4-diamine |
| II-44 | 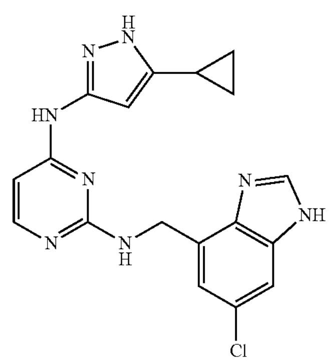 [SMILES: Clc1cc(CNc2nccc(Nc3cc(C4CC4)[nH]n3)n2)c2nc[nH]c2c1] | A | 381.3 | (500 MHz, MeOD-$d_4$) δ 8.24 (s, 1H), 7.85-7.83 (s, 1H), 7.54 (s, 1H), 7.22 (s, 1H), 6.22 (br, 1H), 5.86 (br, 1H), 4.93-4.89 (d, 2H), 1.73 (m, 1H), 0.85-0.80 (m, 2H), 0.47-0.40 (m, 2H) | $N^2$-((6-Chloro-1H-benzo[d]imidazol-4-yl)methyl)-$N^4$-(5-cyclopropyl-1H-pyrazol-3-yl)-pyrimidine-2,4-diamine |
| II-45 | 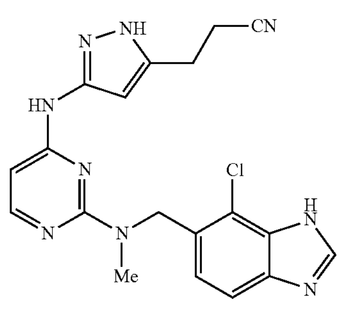 [SMILES: CN(Cc1ccc2nc[nH]c2c1Cl)c1nccc(Nc2cc(CCC#N)[nH]n2)n1] | B | 408.3 | NMR (500 MHz, MeOD-$d_4$) δ 8.24 (s, 1H), 7.93 (d, 1H), 7.50 (d, 1H), 7.11 (d, 1H), 6.16-6.06 (m, 2H), 5.09 (s, 2H), 3.22 (s, 3H), 2.77 (brs, 2H), 2.49 (brs, 2H) | 3-(3-(2-(((4-Chloro-3H-benzo[d]imidazol-5-yl)methyl)(methyl)amino)pyrimidin-4-ylamino)-1H-pyrazol-5-yl)propanenitrile |

TABLE II-continued

| Cpd. No. | Structure | $K_i^1$ | $MS^2$ | $^1$H NMR | Name |
|---|---|---|---|---|---|
| II-46 | 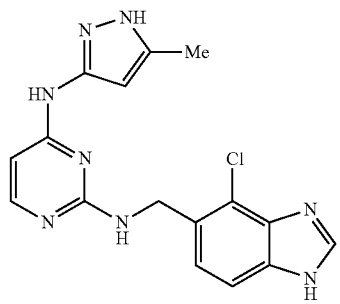 [SMILES: Cc1cc(Nc2ccnc(NCc3ccc4[nH]cnc4c3Cl)n2)n[nH]1] | B | 355.0 | (400 MHz, DMSO-$d_6$) δ 12.62 (s, 1H), 9.33 (s, 1H), 8.26-8.19 (m, 3H), 7.81 (d, J = 5.7 Hz, 1H), 7.49-7.42 (m, 1H), 7.28-7.18 (m, 2H), 6.30-5.73 (m, 1H), 4.66 (d, J = 6.1 Hz, 2H), 2.05 (s, 3H). | $N^2$-((4-Chloro-1H-benzo[d]imidazol-5-yl)methyl)-$N^4$-(5-methyl-1H-pyrazol-3-yl)pyrimidine-2,4-diamine |
| II-47 | 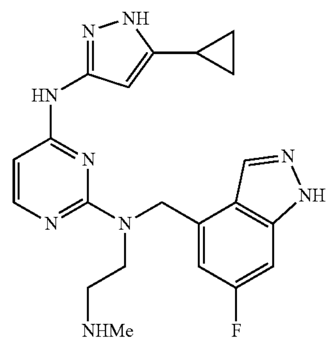 [SMILES: CNCCN(Cc1cc(F)cc2[nH]ncc12)c1nccc(Nc2cc(C3CC3)[nH]n2)n1] | A | 422.1 | (400 MHz, DMSO-$d_6$) δ 13.19 (br s, 1H), 11.86 (br s, 1H), 9.48 (br s, 1H), 8.10 (s, 1H), 7.96-7.83 (m, 1H), 7.19 (d, J = 9.1 Hz, 1H), 6.69 (d, J = 9.9 Hz, 1H), 6.38-6.04 (m, 2H), 5.18 (s, 2H), 3.73-3.58 (m, 2H), 2.83-2.69 (m, 2H), 2.30 (s, 3H), 1.95-1.48 (m, 1H), 1.00-0.05 (m, 4H) | $N^4$-(5-cyclopropyl-1H-pyrazol-3-yl)-$N^2$-((6-fluoro-1H-indazol-4-yl)methyl)-$N^2$-(2-(methylamino)ethyl)pyrimidine-2,4-diamine |
| II-48 | 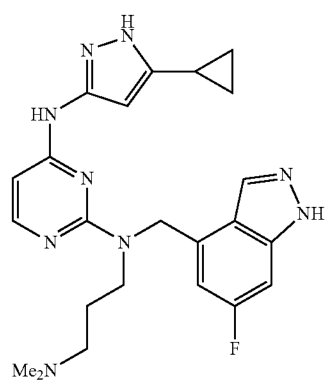 [SMILES: CN(C)CCCN(Cc1cc(F)cc2[nH]ncc12)c1nccc(Nc2cc(C3CC3)[nH]n2)n1] | A | 450.2 | (400 MHz, DMSO-$d_6$) δ 13.16 (br s, 1H), 9.47 (br s, 1H), 8.16-8.05 (m, 1H), 7.99-7.81 (m, 1H), 7.19 (d, J = 9.3 Hz, 1H), 6.77-6.64 (m, 1H), 6.36-6.11 (m, 1H), 5.96-5.59 (m, 1H), 5.16 (s, 2H), 3.62-3.49 (m, 2H), 2.31-2.22 (m, 2H), 2.10 (s, 6H), 1.78-1.65 (m, 2H), 1.02-0.04 (m, 4H) | $N^4$-(5-cyclopropyl-1H-pyrazol-3-yl)-$N^2$-(3-(dimethylamino)propyl)-$N^2$-((6-fluoro-1H-indazol-4-yl)methyl)pyrimidine-2,4-diamine |
| II-49 | 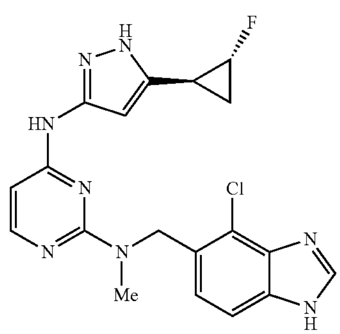 [SMILES: CN(Cc1ccc2[nH]cnc2c1Cl)c1nccc(Nc2cc([C@@H]3C[C@H]3F)[nH]n2)n1] | A | 413.0 | (400 MHz, DMSO-$d_6$) δ 12.66 (s, 1H), 11.97 (br s, 1H), 9.43 (br s, 1H), 8.27 (s, 1H), 7.91 (d, J = 5.5 Hz, 1H), 7.43 (d, J = 8.2 Hz, 1H), 6.97 (d, J = 7.7 Hz, 1H), 6.32-5.75 (m, 2H), 5.01 (s, 2H), 3.12 (s, 3H), 2.33-2.11 (m, 1H), 1.51-1.26 (m, 1H), 0.94-0.68 (m, 1H) | $N^2$-((4-chloro-1H-benzo[d]imidazol-5-yl)methyl)-$N^4$-(5-((1S,2R)-2-fluorocyclopropyl)-1H-pyrazol-3-yl)-$N^2$-methylpyrimidine-2,4-diamine |

TABLE II-continued

| Cpd. No. | Structure | $K_i^1$ | MS[2] | $^1$H NMR | Name |
|---|---|---|---|---|---|
| II-50 | 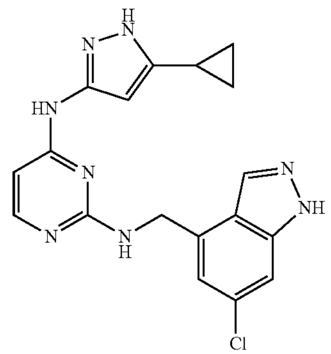 [SMILES: Clc1cc(CNc2nccc(Nc3cc(C4CC4)[nH]n3)n2)c2cn[nH]c2c1] | A | 381.0 | (400 MHz, DMSO-$d_6$) δ 13.14 (s, 1H), 11.81 (br s, 1H), 9.25 (br s, 1H), 8.24 (s, 1H), 7.93-7.73 (m, 1H), 7.45 (s, 1H), 7.37-7.18 (m, 1H), 6.99 (s, 1H), 6.32-5.86 (m, 2H), 4.81 (d, J = 6.2 Hz, 2H), 1.84-1.58 (m, 1H), 0.89-0.70 (m, 2H), 0.70-0.30 (m, 2H) | $N^2$-((6-chloro-1H-indazol-4-yl)methyl)-$N^4$-(5-cyclopropyl-1H-pyrazol-3-yl)pyrimidine-2,4-diamine |
| II-51 | 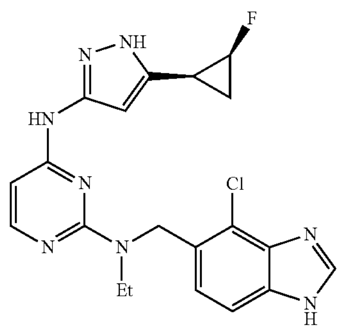 [SMILES: CCN(Cc1ccc2[nH]cnc2c1Cl)c1nccc(Nc2cc([C@@H]3C[C@@H]3F)[nH]n2)n1] | A | 427.1 | (400 MHz, DMSO-$d_6$) δ 12.66 (s, 1H), 12.01 (br s, 1H), 9.44 (br s, 1H), 8.28 (s, 1H), 7.95-7.80 (m, 1H), 7.47-7.33 (m, 1H), 7.09-6.95 (m, 1H), 6.31-5.84 (m, 2H), 4.97 (s, 2H), 4.92-4.61 (m, 1H), 3.59 (q, J = 6.6 Hz, 2H), 2.06-1.68 (m, 1H), 1.24-0.82 (m, 5H). | $N^2$-((4-chloro-1H-benzo[d]imidazol-5-yl)methyl)-$N^2$-ethyl-$N^4$-(5-((1S,2S)-2-fluorocyclopropyl)-1H-pyrazol-3-yl)pyrimidine-2,4-diamine |
| II-52 | 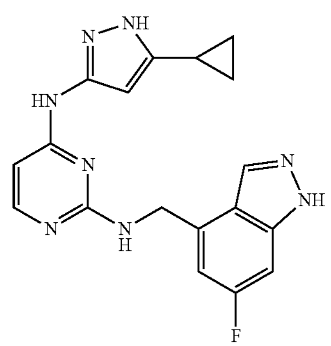 [SMILES: Fc1cc(CNc2nccc(Nc3cc(C4CC4)[nH]n3)n2)c2cn[nH]c2c1] | A | 365.1 | (400 MHz, DMSO-$d_6$) δ 13.08 (s, 1H), 11.82 (s, 1H), 9.27 (s, 1H), 8.22 (s, 1H), 7.81 (s, 1H), 7.28 (s, 1H), 7.14 (d, J = 9.4 Hz, 1H), 6.83 (d, J = 9.6 Hz, 1H), 6.31-5.86 (m, 2H), 4.81 (d, J = 6.1 Hz, 2H), 1.86-1.54 (m, 1H), 0.80-0.72 (m, 2H), 0.72-0.21 (m, 2H) | $N^4$-(5-cyclopropyl-1H-pyrazol-3-yl)-$N^2$-((6-fluoro-1H-indazol-4-yl)methyl)pyrimidine-2,4-diamine |
| II-53 | 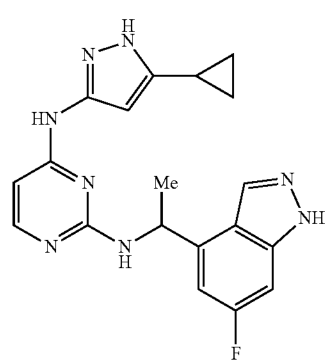 [SMILES: CC(Nc1nccc(Nc2cc(C3CC3)[nH]n2)n1)c1cc(F)cc2[nH]ncc12] | A | 379.1 | (400 MHz, DMSO-$d_6$) δ 13.06 (s, 1H), 11.79 (br s, 1H), 9.20 (br s, 1H), 8.30 (s, 1H), 7.82-7.66 (m, 1H), 7.36-7.18 (m, 1H), 7.11 (d, J = 9.2 Hz, 1H), 6.93 (d, J = 10.6 Hz, 1H), 6.25-5.87 (m, 2H), 5.55-5.36 (m, 1H), 1.88-1.64 (m, 1H), 1.55 (d, J = 7.0 Hz, 3H), 0.95-0.77 (m, 2H), 0.75-0.50 (m, 2H) | (S)-$N^4$-(5-cyclopropyl-1H-pyrazol-3-yl)-$N^2$-(1-(6-fluoro-1H-indazol-4-yl)ethyl)pyrimidine-2,4-diamine |

TABLE II-continued

| Cpd. No. | Structure | $K_i^1$ | MS[2] | $^1$H NMR | Name |
|---|---|---|---|---|---|
| II-54 | 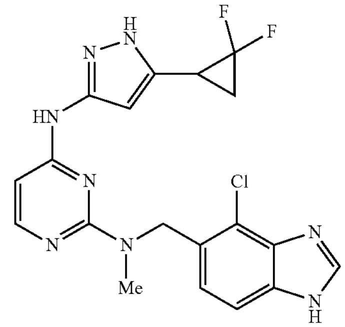 [SMILES: CN(Cc1ccc2[nH]cnc2c1Cl)c1nccc(Nc2cc(C3CC3(F)F)[nH]n2)n1] | A | 431.0 | (400 MHz, DMSO-$d_6$) δ 12.65 (s, 1H), 12.22 (br s, 1H), 9.50 (s, 1H), 8.26 (s, 1H), 7.92 (d, J = 5.6 Hz, 1H), 7.60-7.33 (m, 1H), 6.98 (d, J = 8.3 Hz, 1H), 6.36-5.96 (m, 2H), 5.12-4.94 (m, 2H), 3.11 (s, 3H), 2.90-2.68 (m, 1H), 2.04-1.78 (m, 1H), 1.78-1.36 (m, 1H) | (R)-$N^2$-((4-chloro-1H-benzo[d]imidazol-5-yl)methyl)-$N^4$-(5-(2,2-difluorocyclopropyl)-1H-pyrazol-3-yl)-$N^2$-methylpyrimidine-2,4-diamine |
| II-55 | 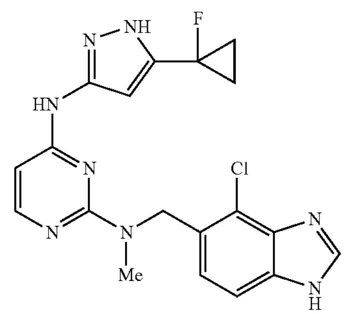 [SMILES: CN(Cc1ccc2[nH]cnc2c1Cl)c1nccc(Nc2cc(C3(F)CC3)[nH]n2)n1] | A | 413.1 | (400 MHz, DMSO-$d_6$) δ 12.72 (br s, 2H), 9.62 (br s, 1H), 8.28 (s, 1H), 8.20 (s, 1H), 8.00-7.86 (m, 1H), 7.46 (d, J = 8.3 Hz, 1H), 6.97 (d, J = 8.3 Hz, 1H), 6.51-6.03 (m, 2H), 5.01 (s, 2H), 3.12 (s, 3H), 1.43-1.18 (m, 2H), 1.08-0.57 (m, 2H). MS(ESI) m/z: 413.1 [M + 1]$^+$. | $N^2$-((4-chloro-1H-benzo[d]imidazol-5-yl)methyl)-$N^4$-(5-(1-fluorocyclorpropyl)-1H-pyrazol-3-yl)-$N^2$-methylpyrimidine-2,4-diamine |
| II-56 | 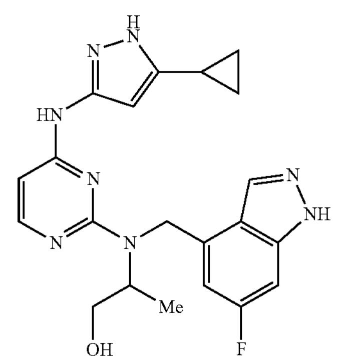 [SMILES: CC(CO)N(Cc1cc(F)cc2[nH]ncc12)c1nccc(Nc2cc(C3CC3)[nH]n2)n1] | A | 423.2 | (400 MHz, DMSO-$d_6$) δ 13.13 (s, 1H), 11.79 (br s, 2H), 9.42 (br s, 1H), 8.20-8.09 (m, 1H), 7.95-7.79 (m, 1H), 7.13 (d, J = 9.0 Hz, 1H), 6.67 (d, J = 10.4 Hz, 1H), 6.27-6.06 (m, 1H), 5.60-5.37 (m, 1H), 5.14 (d, J = 17.8 Hz, 1H), 5.02 (d, J = 17.7 Hz, 1H), 4.97-4.84 (m, 1H), 4.81-4.66 (m, 1H), 3.59-3.47 (m, 1H), 1.10 (d, J = 6.8 Hz, 3H), 1.00-0.30 (m, 4H) | 2-((4-((5-cyclopropyl-1H-pyrazol-3-yl)amino)pyrimidin-2-yl)((6-fluoro-1H-indazol-4-yl)methyl)amino)propan-1-ol |
| II-57 | 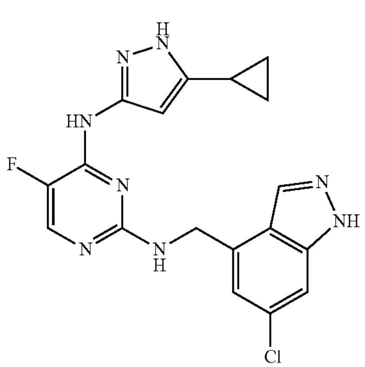 | A | 399.0 | (400 MHz, DMSO-$d_6$) δ 13.16 (br s, 1H), 11.94 (br s, 1H), 9.27 (br s, 1H), 8.23 (s, 1H), 7.88 (s, 1H), 7.54-7.32 (m, 2H), 6.98 (s, 1H), 6.21 (br s, 1H), 4.76 (d, J = 6.1 Hz, 2H), 1.83-1.58 (m, 1H), 0.88-0.67 (m, 2H), 0.67-0.33 (m, 2H) | $N^2$-((6-chloro-1H-indazol-4-yl)methyl)-$N^4$-(5-cyclopropyl-1H-pyrazol-3-yl)-5-fluoropyrimidine-2,4-diamine |

TABLE II-continued

| Cpd. No. | Structure | $K_i^1$ | $MS^2$ | $^1$H NMR | Name |
|---|---|---|---|---|---|
| II-58 | 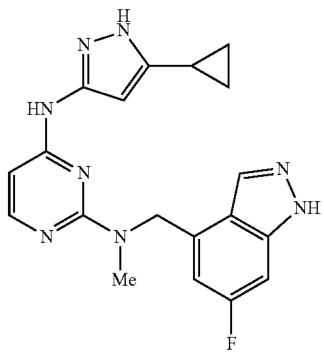 [SMILES: CN(Cc1cc(F)cc2[nH]ncc12)c1nccc(Nc2cc(C3CC3)[nH]n2)n1] | A | 379.1 | (400 MHz, DMSO-$d_6$) δ 13.12 (br s, 1H), 11.88 (br s, 1H), 9.38 (br s, 1H), 8.06 (s, 1H), 7.92 (d, J = 5.7 Hz, 1H), 7.18 (d, J = 9.4 Hz, 1H), 6.71 (d, J = 10.1 Hz, 1H), 6.27 (br s, 1H), 5.94 (br s, 1H), 5.15 (s, 2H), 3.10 (s, 3H), 1.76-1.53 (m, 1H), 0.87-0.64 (m, 2H), 0.54-0.23 (m, 2H) | $N^4$-(5-cyclopropyl-1H-pyrazol-3-yl)-$N^2$-((6-fluoro-1H-indazol-4-yl)methyl)-$N^2$-methylpyrimidine-2,4-diamine |
| II-59 | 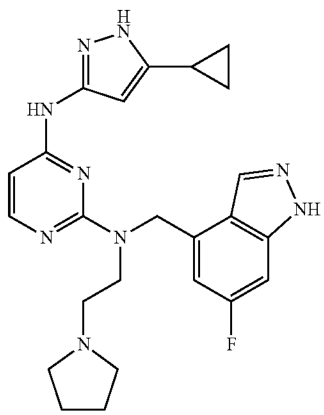 [SMILES: Fc1cc(CN(CCN2CCCC2)c2nccc(Nc3cc(C4CC4)[nH]n3)n2)c2cn[nH]c2c1] | A | 462.2 | | $N^4$-(5-cyclopropyl-1H-pyrazol-3-yl)-$N^2$-((6-fluoro-1H-indazol-4-yl)methyl)-$N^2$-(2-(pyrrolidin-1-yl)ethyl)pyrimidine-2,4-diamine |
| II-60 | 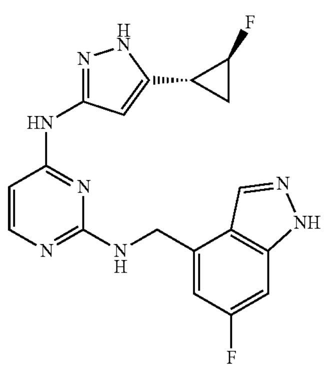 [SMILES: Fc1cc(CNc2nccc(Nc3cc([C@H]4C[C@@H]4F)[nH]n3)n2)c2cn[nH]c2c1] | A | 383.1 | | $N^2$-((6-fluoro-1H-indazol-4-yl)methyl)-$N^4$-(5-((1R,2S)-2-fluorocyclopropyl)-1H-pyrazol-3-yl)pyrimidine-2,4-diamine |
| II-61 | 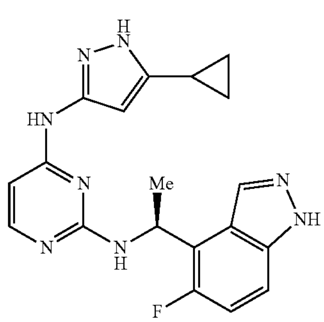 [SMILES: C[C@H](Nc1nccc(Nc2cc(C3CC3)[nH]n2)n1)c1c(F)ccc2[nH]ncc12] | A | 379.1 | (400 MHz, DMSO-$d_6$) δ 13.03 (s, 1H), 11.82 (br s, 1H), 9.25 (br s, 1H), 8.45 (s, 1H), 7.71 (s, 1H), 7.61-7.30 (m, 2H), 7.16 (t, J = 9.7 Hz, 1H), 6.42-5.82 (m, 2H), 5.66-5.47 (m, 1H), 1.91-1.79 (m, 1H), 1.56 (d, J = 7.1 Hz, 3H), 1.00-0.80 (m, 2H), 0.80-0.58 (m, 2H | (S)-$N^4$-(5-cyclopropyl-1H-pyrazol-3-yl)-$N^2$-(1-(5-fluoro-1H-indazol-4-yl)ethyl)pyrimidine-2,4-diamine |

TABLE II-continued

| Cpd. No. | Structure | $K_i^1$ | $MS^2$ | $^1$H NMR | Name |
|---|---|---|---|---|---|
| II-62 | 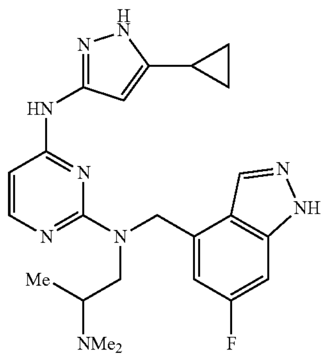 [SMILES: CC(CN(Cc1cc(F)cc2[nH]ncc12)c1nccc(Nc2cc(C3CC3)[nH]n2)n1)N(C)C] | A | 450.3 | (400 MHz, DMSO-d$_6$) δ 13.12 (s, 1H), 11.85 (br s, 1H), 9.37 (br s, 1H), 8.15-7.99 (m, 1H), 7.99-7.79 (m, 1H), 7.16 (d, J = 9.2 Hz, 1H), 6.70 (d, J = 10.2 Hz, 1H), 6.32-6.07 (m, 1H), 5.29 (d, J = 16.9 Hz, 1H), 5.10 (d, J = 16.8 Hz, 1H), 3.68-3.45 (m, 2H), 3.12-2.94 (m, 1H), 2.15 (s, 6H), 1.88-1.41 (m, 1H), 0.84 (d, J = 6.5 Hz, 3H), 0.81-0.07 (m, 4H). | (R)-N$^4$-(5-cyclopropyl-1H-pyrazol-3-yl)-N$^2$-(2-(dimethylamino)propyl)-N$^2$-((6-fluoro-1H-indazol-4-yl)methyl)pyrimidine-2,4-diamine |
| II-63 | 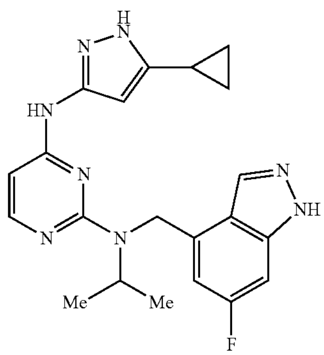 [SMILES: CC(C)N(Cc1cc(F)cc2[nH]ncc12)c1nccc(Nc2cc(C3CC3)[nH]n2)n1] | A | 407.2 | (400 MHz, DMSO-d$_6$) δ 13.10 (s, 1H), 11.78 (br s, 1H), 9.37 (br s, 1H), 8.21 (s, 1H), 7.96-7.83 (m, 1H), 7.12 (d, J = 9.1 Hz, 1H), 6.63 (d, J = 10.4 Hz, 1H), 6.34-6.07 (m, 1H), 5.17-5.06 (m, 1H), 5.03 (s, 2H), 1.11 (d, J = 6.7 Hz, 6H), 0.91--0.18 (m, 4H). | N$^4$-(5-cyclopropyl-1H-pyrazol-3-yl)-N$^2$-((6-fluoro-1H-indazol-4-yl)methyl)-N$^2$-isopropylpyrimidine-2,4-diamine |
| II-64 | 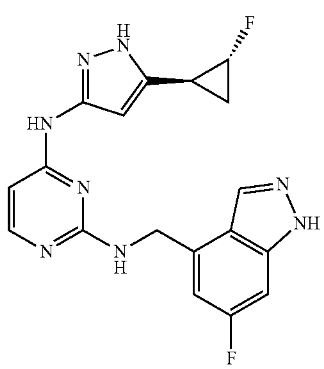 [SMILES: Fc1cc(CNc2nccc(Nc3cc([C@@H]4C[C@H]4F)[nH]n3)n2)c2cn[nH]c2c1] | A | 383.2 | | N$^2$-((6-fluoro-1H-indazol-4-yl)methyl)-N$^4$-(5-((1S,2R)-2-fluorocyclopropyl)-1H-pyrazol-3-yl)pyrimidine-2,4-diamine |
| II-65 | 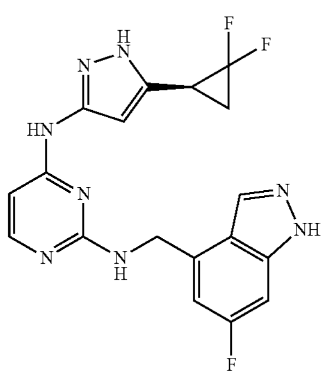 [SMILES: Fc1cc(CNc2nccc(Nc3cc([C@@H]4CC4(F)F)[nH]n3)n2)c2cn[nH]c2c1] | A | 401.0 | | (S)-N$^4$-(5-(2,2-difluorocyclopropyl)-1H-pyrazol-3-yl)-N$^2$-((6-fluoro-1H-indazol-4-yl)methyl)pyrimidine-2,4-diamine |

TABLE II-continued

| Cpd. No. | Structure | $K_i^1$ | MS[2] | $^1$H NMR | Name |
|---|---|---|---|---|---|
| II-66 | 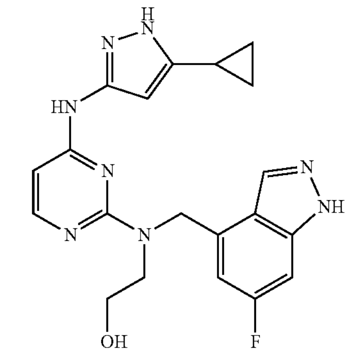 [SMILES: OCCN(Cc1cc(F)cc2[nH]ncc12)c1nccc(Nc2cc(C3CC3)[nH]n2)n1] | A | 409.1 | (400 MHz, DMSO-$d_6$) δ 13.16 (s, 1H), 11.92 (br s, 1H), 9.47 (br s, 1H), 8.14-8.01 (m, 1H), 7.97-7.80 (m, 1H), 7.19 (d, J = 9.4 Hz, 1H), 6.73-6.62 (m, 1H), 6.29-6.11 (m, 1H), 5.90-5.58 (m, 1H), 5.20 (s, 2H), 3.69-3.55 (m, 4H), 1.95-1.57 (m, 1H), 1.08-0.03 (m, 4H). | 2-((4-((5-cyclopropyl-1H-pyrazol-3-yl)amino)pyrimidin-2-yl)((6-fluoro-1H-indazol-4-yl)methyl)anino)ethanol |
| II-67 | 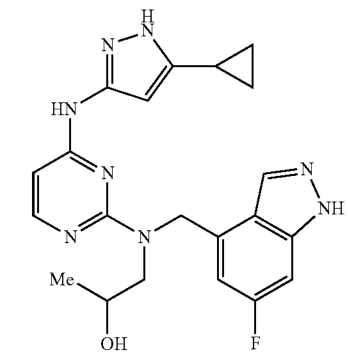 [SMILES: CC(O)CN(Cc1cc(F)cc2[nH]ncc12)c1nccc(Nc2cc(C3CC3)[nH]n2)n1] | A | 423.2 | | (R)-1-((4-((5-cyclopropyl-1H-pyrazol-3-yl)amino)pyrimidin-2-yl)((6-fluoro-1H-indazol-4-yl)methyl)amino)propan-2-ol |
| II-68 | 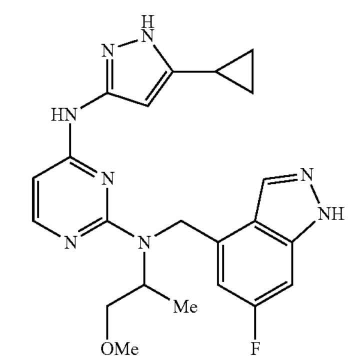 [SMILES: COCC(C)N(Cc1cc(F)cc2[nH]ncc12)c1nccc(Nc2cc(C3CC3)[nH]n2)n1] | | 437.2 | | (R)-N[4]-(5-cyclopropyl-1H-pyrazol-3-yl)-N[2]-((6-fluoro-1H-indazol-4-yl)methyl-N[2]-(1-methoxypropan-2-yl)pyrimidine-2,4-diamine |
| II-69 | 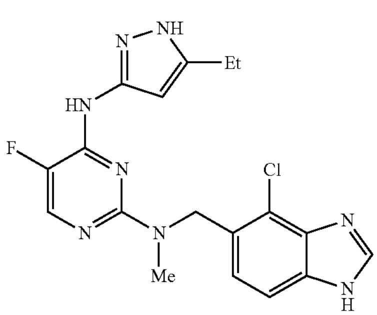 [SMILES: CCc1cc(Nc2nc(N(C)Cc3ccc4[nH]cnc4c3Cl)ncc2F)n[nH]1] | C | 401.1 | (400 MHz, DMSO-$d_6$) δ 12.64 (s, 1H), 11.90 (br s, 1H), 9.42 (s, 1H), 8.26 (s, 1H), 7.96 (d, J = 3.6 Hz, 1H), 7.42 (d, J = 8.3 Hz, 1H), 6.94 (d, J = 8.1 Hz, 1H), 6.15-5.88 (m, 1H), 4.96 (s, 2H), 3.14 (s, 3H), 2.43-2.22 (m, 2H), 1.03-0.71 (m, 3H). | N[2]-((4-chloro-1H-benzo[d]imidazol-5-yl)methyl)-N[4]-(5-ethyl-1H-pyrazol-3-yl)-5-fluoro-N[2]-methylpyrimidine-2,4-diamine |

TABLE II-continued

| Cpd. No. | Structure | $K_i{}^1$ | $MS^2$ | $^1$H NMR | Name |
|---|---|---|---|---|---|
| II-70 | 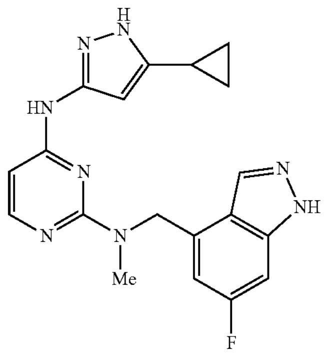 [SMILES: CN(Cc1cc(F)cc2[nH]ncc12)c1nccc(Nc2cc(C3CC3)[nH]n2)n1] | A | 393.1 | (400 MHz, DMSO-$d_6$) δ 13.12 (br s, 1H), 12.04 (br s, 1H), 9.40 (br s, 1H), 8.10 (s, 1H), 7.91 (d, J = 5.7 Hz, 1H), 7.18 (d, J = 9.1 Hz, 1H), 6.71 (d, J = 10.2 Hz, 1H), 6.29-6.14 (m, 1H), 6.13-5.72 (m, 2H), 5.13 (s, 2H), 3.60 (q, J = 6.9 Hz, 2H), 1.63 (s, 1H), 1.10 (t, J = 6.9 Hz, 3H), 0.91-0.60 (m, 2H), 0.60-0.19 (m, 2H). | $N^4$-(5-cyclopropyl-1H-pyrazol-3-yl)-$N^2$-ethyl-$N^2$-((6-fluoro-1H-indazol-4-yl)methyl)pyrimidine-2,4-diamine |
| II-71 | 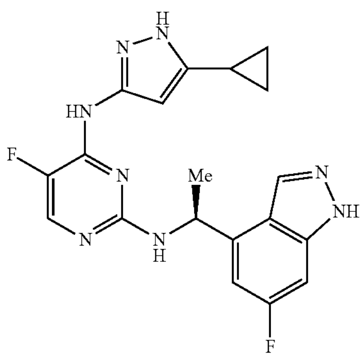 [SMILES: C[C@H](Nc1ncc(F)c(Nc2cc(C3CC3)[nH]n2)n1)c1cc(F)cc2[nH]ncc12] | A | 397.1 | (400 MHz, DMSO) δ 13.07 (s, 1H), 11.90 (br s, 1H), 9.22 (br s, 1H), 8.29 (s, 1H), 7.89-7.76 (m, 1H), 7.48-7.26 (m, 1H), 7.11 (d, J = 8.9 Hz, 1H), 6.90 (d, J = 9.7 Hz, 1H), 5.46-5.27 (m, 1H), 1.89-1.69 (m, 1H), 1.54 (d, J = 7.0 Hz, 3H), 0.96-0.77 (m, 2H), 0.77-0.49 (m, 2H) | (S)-$N^4$-(5-cyclopropyl-1H-pyrazol-3-yl)-5-fluoro-$N^2$-(1-(6-fluoro-1H-indazol-4-yl)ethyl)pyrimidine-2,4-diamine |
| II-72 | 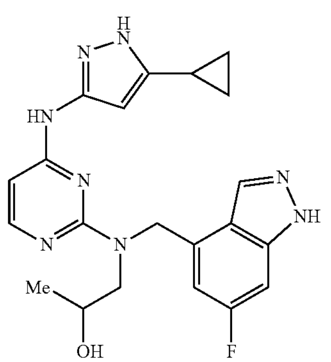 [SMILES: CC(O)CN(Cc1cc(F)cc2[nH]ncc12)c1nccc(Nc2cc(C3CC3)[nH]n2)n1] | A | 423.2 | | (S)-1-((4-((5-cyclopropyl-1H-pyrazol-3-yl)amino)pyrimidin-2-yl)((6-fluoro-1H-indazol-4-yl)methyl)amino)propan-2-ol |
| II-73 | 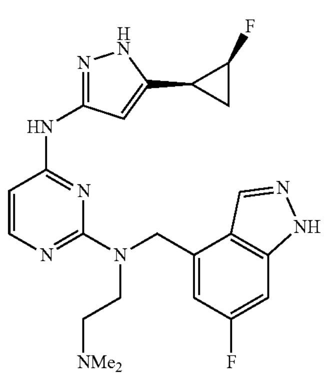 [SMILES: CN(C)CCN(Cc1cc(F)cc2[nH]ncc12)c1nccc(Nc2cc([C@@H]3C[C@@H]3F)[nH]n2)n1] | A | 454.2 | | $N^2$-(2-(dimethylamino)ethyl)-$N^2$-((6-fluoro-1H-indazol-4-yl)methyl)-$N^4$-(5-((1S,2S)-2-fluorocyclopropyl)-1H-pyrazol-3-yl)pyrimidine-2,4-diamine |

TABLE II-continued

| Cpd. No. | Structure | $K_i^1$ | $MS^2$ | $^1H$ NMR | Name |
|---|---|---|---|---|---|
| II-74 | 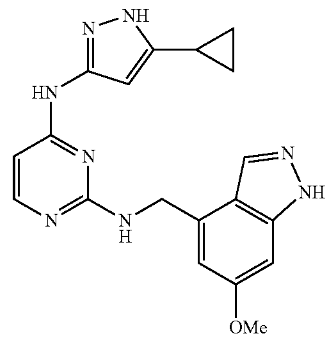 [SMILES: COc1cc(CNc2nccc(Nc3cc(C4CC4)[nH]n3)n2)c2cn[nH]c2c1] | A | 377.1 | (400 MHz, DMSO-d$_6$) δ 12.78 (s, 1H), 11.83 (br s, 1H), 9.28 (br s, 1H), 8.05 (s, 1H), 7.87-7.73 (m, 1H), 7.33-7.13 (m, 1H), 6.76 (s, 1H), 6.63 (s, 1H), 6.37-5.86 (m, 2H), 4.74 (d, J = 6.2 Hz, 2H), 3.76 (s, 3H), 1.87-1.53 (m, 1H), 0.95-0.66 (m, 2H), 0.66-0.26 (m, 2H) | $N^4$-(5-cyclopropyl-1H-pyrazol-3-yl)-$N^2$-((6-methoxy-1H-indazol-4-yl)methyl)pyrimidine-2,4-diamine |
| II-75 | 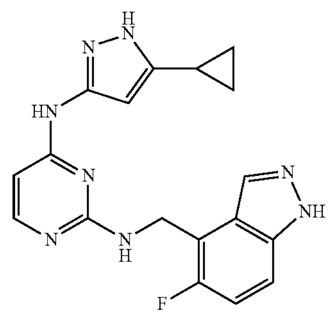 [SMILES: Fc1ccc2[nH]ncc2c1CNc1nccc(Nc2cc(C3CC3)[nH]n2)n1] | A | 365.1 | (400 MHz, DMSO-d$_6$) δ 13.07 (br s, 1H), 11.84 (br s, 1H), 9.26 (br s, 1H), 8.17 (s, 1H), 7.89-7.74 (m, 1H), 7.51-7.35 (m, 1H), 7.26-7.10 (m, 2H), 6.29-5.90 (m, 2H), 4.82 (d, J = 6.0 Hz, 2H), 1.85-1.73 (m, 1H), 0.91-0.77 (m, 2H), 0.65-0.51 (m, 2H) | $N^4$-(5-cyclopropyl-1H-pyrazol-3-yl)-$N^2$-((5-fluoro-1H-indazol-4-yl)methyl)pyrimidine-2,4-diamine |
| II-76 | 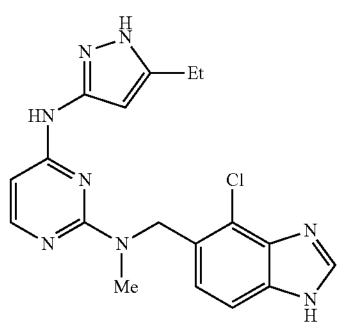 [SMILES: CCc1cc(Nc2ccnc(N(C)Cc3ccc4[nH]cnc4c3Cl)n2)n[nH]1] | A | 369.1 | (400 MHz, DMSO-d$_6$) δ 12.66 (br s, 1H), 11.77 (br s, 1H), 9.35 (s, 1H), 8.26 (s, 1H), 7.89 (d, J = 5.7 Hz, 1H), 7.59-7.35 (m, 1H), 6.97 (d, J = 8.3 Hz, 1H), 6.40-6.10 (m, 1H), 6.10-5.69 (m, 1H), 5.01 (s, 2H), 3.15 (s, 3H), 2.04 (s, 3H) | $N^2$-((4-chloro-1H-benzo[d]imidazol-5-yl)methyl)-$N^2$-methyl-$N^4$-(5-methyl-1H-pyrazol-3-yl)pyrimidine-2,4-diamine |
| II-77 | 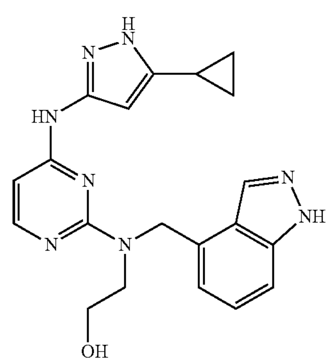 [SMILES: OCCN(Cc1cccc2[nH]ncc12)c1nccc(Nc2cc(C3CC3)[nH]n2)n1] | A | 391.1 | (400 MHz, DMSO-d$_6$) δ 13.05 (s, 1H), 11.85 (br s, 1H), 9.39 (br s, 1H), 8.03 (s, 1H), 7.89 (d, J = 5.6 Hz, 1H), 7.41 (d, J = 8.3 Hz, 1H), 7.35-7.17 (m, 1H), 6.86 (d, J = 6.9 Hz, 1H), 6.31-6.05 (m, 1H), 6.05-5.59 (m, 1H), 5.22 (s, 2H), 4.68 (br s, 1H), 3.58 (s, 4H), 1.92-1.35 (m, 1H), 1.03-0.02 (m, 4H) | 2-(((1H-indazol-4-yl)methyl)(4-((5-cyclopropyl-1H-pyrazol-3-yl)amino)pyrimidin-2-yl)amino)ethanol |

TABLE II-continued

| Cpd. No. | Structure | $K_i^1$ | $MS^2$ | $^1$H NMR | Name |
|---|---|---|---|---|---|
| II-78 | 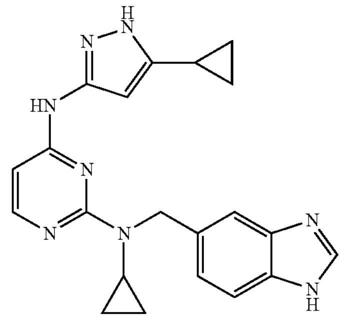 [SMILES: c1cc(Nc2cc(C3CC3)[nH]n2)nc(N(Cc2ccc3[nH]cnc3c2)C2CC2)n1] | A | 387.27 008 | (400 MHz, DMSO-d$_6$) δ 12.26 (br s, 1H), 9.46 (br s, 1H), 8.20 (s, 1H), 8.12 (s, 1H), 7.92 (d, J = 5.7 Hz, 1H), 7.57-7.43 (m, 1H), 7.43-7.29 (m, 1H), 7.08 (d, J = 8.3 Hz, 1H), 6.35-6.05 (m, 2H), 4.94 (s, 2H), 2.74-2.63 (m, 1H), 1.80-1.66 (m, 1H), 0.86-0.72 (m, 3H), 0.71-0.61 (m, 2H), 0.54-0.37 (m, 2H). | $N^2$-((1H-benzo[d]imidazol-5-yl)methyl)-$N^2$-cyclopropyl-$N^4$-(5-cyclopropyl-1H-pyrazol-3-yl)pyrimidine-2,4-diamine |
| II-79 | 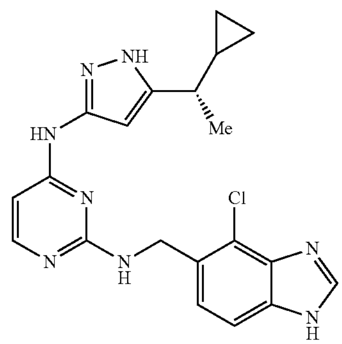 [SMILES: C[C@H](c1cc(Nc2ccnc(NCc3ccc4[nH]cnc4c3Cl)n2)n[nH]1)C1CC1] | A | 409.2 | | (S)-$N^2$-((4-chloro-1H-benzo[d]imidazol-5-yl)methyl)-$N^4$-(5-(1-cyclopropylethyl)-1H-pyrazol-3-yl)pyrimidine-2,4-diamine |
| II-80 | 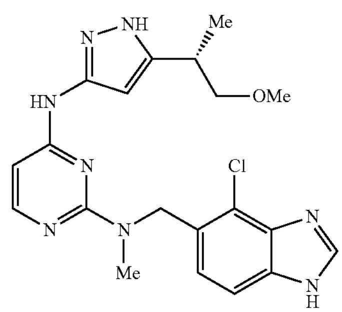 [SMILES: COC[C@@H](C)c1cc(Nc2ccnc(N(C)Cc3ccc4[nH]cnc4c3Cl)n2)n[nH]1] | A | 427.2 | (400 MHz, DMSO-d$_6$) δ 12.67 (s, 1H), 11.87 (br s, 1H), 9.46 (br s, 1H), 8.27 (s, 1H), 7.94-7.83 (m, 1H), 7.43 (d, J = 8.3 Hz, 1H), 7.04-6.89 (m, 1H), 6.38-5.88 (m, 2H), 5.03 (s, 2H), 3.26-2.98 (m, 8H), 2.98-2.70 (m, 1H), 1.17-0.78 (m, 3H). | (S)-$N^2$-((4-chloro-1H-benzo[d]imidazol-5-yl)methyl)-$N^4$-(5-(1-methoxypropan-2-yl)-1H-pyrazol-3-yl)-$N^2$-methylpyrimidine-2,4-diamine |
| II-81 | 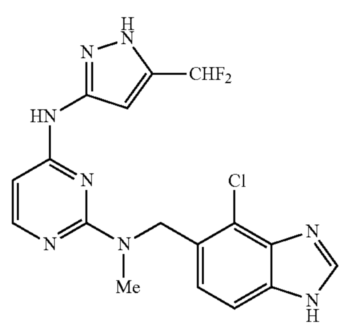 [SMILES: CN(Cc1ccc2[nH]cnc2c1Cl)c1nccc(Nc2cc(C(F)F)[nH]n2)n1] | A | 405.1 | | $N^2$-((4-chloro-1H-benzo[d]imidazol-5-yl)methyl)-$N^4$-(5-difluoromethyl)-1H-pyrazol-3-yl)-$N^2$-methylpyrimidine-2,4-diamine |

TABLE II-continued

| Cpd. No. | Structure | $K_i^1$ | MS[2] | $^1$H NMR | Name |
|---|---|---|---|---|---|
| II-82 | 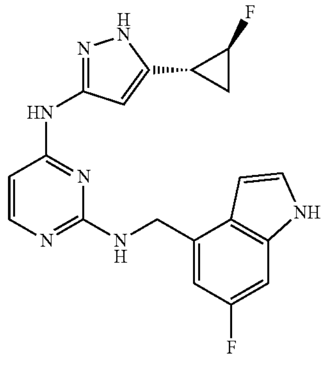 [SMILES: Fc1cc(CNc2nccc(Nc3cc([C@H]4C[C@@H]4F)[nH]n3)n2)c2cc[nH]c2c1] | A | 382.2 | (400 MHz, DMSO-d$_6$) δ 11.93 (br s, 1H), 11.16 (s, 1H), 9.33 (br s, 1H), 7.93-7.74 (m, 1H), 7.32 (s, 1H), 7.24-7.11 (m, 1H), 7.11-6.95 (m, 1H), 6.87-6.67 (m, 1H), 6.62-6.50 (m, 1H), 6.30-5.90 (m, 2H), 4.90-4.57 (m, 3H), 2.45-2.08 (m, 1H), 1.56-0.97 (m, 2H) | N$^2$-((6-fluoro-1H-indol-4-yl)methyl)-N$^4$-(5-((1R,2S)-2-fluorocyclopropyl)-1H-pyrazol-3-yl)pyrimidine-2,4-diamine |
| II-83 | 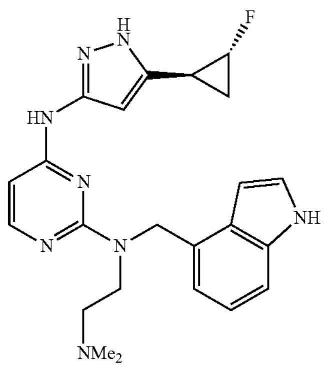 [SMILES: CN(C)CCN(Cc1cccc2[nH]ccc12)c1nccc(Nc2cc([C@@H]3C[C@H]3F)[nH]n2)n1] | A | 435.3 | | N$^2$-((1H-indol-4-yl)methyl)-N$^2$-(2-(dimethylamino)ethyl)-N$^4$-(5-((1S,2R)-2-fluorocyclopropyl)-1H-pyrazol-3-yl)pyrimidine-2,4-diamine |
| II-84 | 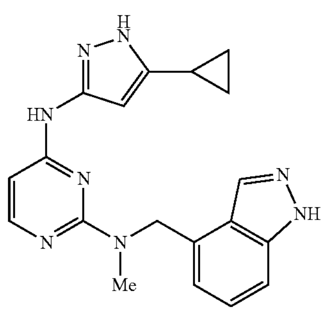 [SMILES: CN(Cc1cccc2[nH]ncc12)c1nccc(Nc2cc(C3CC3)[nH]n2)n1] | A | 361.1 | (400 MHz, DMSO-d$_6$) δ 13.03 (br s, 1H), 9.34 (br s, 1H), 8.03 (s, 1H), 7.92 (d, J = 5.7 Hz, 1H), 7.42 (d, J = 8.3 Hz, 1H), 7.30-7.20 (m, 1H), 6.88 (d, J = 6.9 Hz, 1H), 6.26 (br s, 1H), 5.97 (s, 1H), 5.16 (s, 2H), 3.06 (s, 3H), 1.77-1.59 (m, 1H), 0.82-0.67 (m, 2H), 0.49-0.29 (m, 2H) | N$^2$-((1H-indazol-4-yl)methyl)-N$^4$-(5-cyclopropyl-1H-pyrazol-3-yl)-N$^2$-methylpyrimidine-2,4-diamine |
| II-85 | 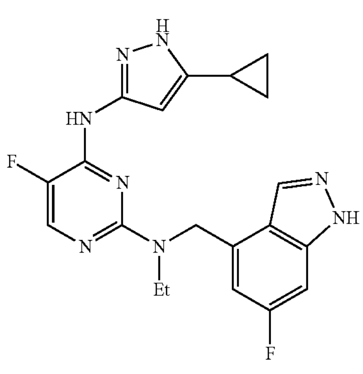 [SMILES: CCN(Cc1cc(F)cc2[nH]ncc12)c1ncc(F)c(Nc2cc(C3CC3)[nH]n2)n1] | A | 411.2 | (400 MHz, DMSO-d$_6$) δ 13.11 (br s, 1H), 11.96 (br s, 1H), 9.40 (br s, 1H), 8.09 (s, 1H), 7.96 (d, J = 3.4 Hz, 1H), 7.17 (d, J = 9.3 Hz, 1H), 6.70 (d, J = 10.2 Hz, 1H), 6.14-5.80 (m, 1H), 5.08 (s, 2H), 3.58 (q, J = 6.9 Hz, 2H), 1.74-1.47 (m, 1H), 1.17-1.03 (m, 3H), 0.85-0.49 (m, 2H), 0.44-0.10 (m, 2H) | N$^4$-(5-cyclopropyl-1H-pyrazol-3-yl)-N$^2$-ethyl-5-fluoro-N$^2$-((6-fluoro-1H-indazol-4-yl)methyl)pyrimidine-2,4-diamine |

TABLE II-continued

| Cpd. No. | Structure | $K_i^1$ | MS[2] | $^1$H NMR | Name |
|---|---|---|---|---|---|
| II-86 | 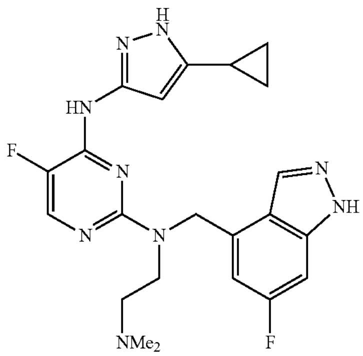 [SMILES: CN(C)CCN(Cc1cc(F)cc2[nH]ncc12)c1ncc(F)c(Nc2cc(C3CC3)[nH]n2)n1] | A | 454.2 | (400 MHz, DMSO-$d_6$) δ 13.13 (br s, 1H), 11.97 (br s, 1H), 9.41 (br s, 1H), 8.08 (s, 1H), 7.95 (s, 1H), 7.18 (d, J = 9.3 Hz, 1H), 6.72 (d, J = 10.1 Hz, 1H), 5.11 (s, 2H), 3.68-3.55 (m, 2H), 2.45-2.36 (m, 2H), 2.12 (s, 6H), 1.83-1.33 (m, 1H), 0.90-0.25 (m, 4H) | $N^4$-(5-cyclopropyl-1H-pyrazol-3-yl)-$N^2$-(2-(dimethylamino)ethyl)-5-fluoro-$N^2$-((6-fluoro-1H-indazol-4-yl)methyl)pyrimidine-2,4-diamine |
| II-87 | 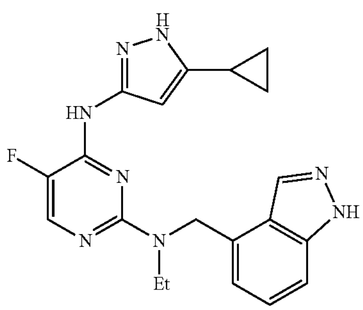 [SMILES: CCN(Cc1cccc2[nH]ncc12)c1ncc(F)c(Nc2cc(C3CC3)[nH]n2)n1] | A | 393.1 | (400 MHz, DMSO-$d_6$) δ 12.98 (br s, 1H), 11.99 (br s, 1H), 9.31 (br s, 1H), 8.03 (s, 1H), 7.96-7.91 (m, 1H), 7.47-7.36 (m, 1H), 7.32-7.19 (m, 1H), 6.90-6.81 (m, 1H), 6.09-5.79 (m, 1H), 5.03 (s, 2H), 3.58-3.47 (m, 2H), 1.66-1.46 (m, 1H), 1.06 (t, J = 7.0 Hz, 3H), 0.81-0.59 (m, 2H), 0.41-0.02 (m, 2H) | $N^2$-((1H-indazol-4-yl)methyl)-$N^4$-(5-cyclopropyl-1H-pyrazol-3-yl)-$N^2$-ethyl-5-fluoropyrimidine-2,4-diamine |
| II-88 | 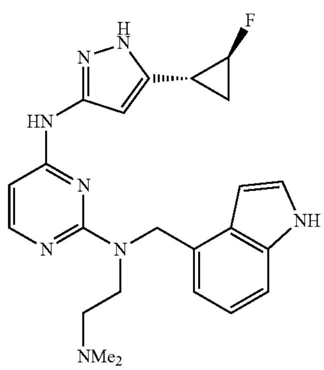 [SMILES: CN(C)CCN(Cc1cccc2[nH]ccc12)c1nccc(Nc2cc([C@H]3C[C@@H]3F)[nH]n2)n1] | A | 435.3 | | $N^2$-((1H-indol-4-yl)methyl)-$N^2$-(2-(dimethylamino)ethyl)-$N^4$-(5-((1R,2S)-2-fluorocyclopropyl)-1H-pyrazol-3-yl)pyrimidine-2,4-diamine |
| II-89 | 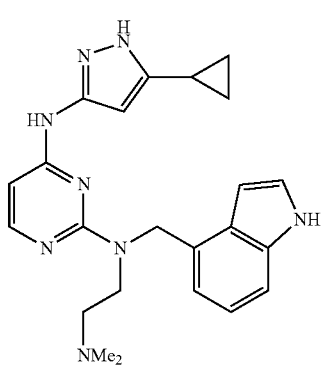 [SMILES: CN(C)CCN(Cc1cccc2[nH]ccc12)c1nccc(Nc2cc(C3CC3)[nH]n2)n1] | A | 417.3 | (400 MHz, DMSO-$d_6$) δ 11.80 (br s, 1H), 11.08 (s, 1H), 9.35 (s, 1H), 7.95-7.84 (m, 1H), 7.34-7.24 (m, 2H), 7.00 (t, J = 7.7 Hz, 1H), 2.50-2.40 (m, 2H), 6.79 (d, J = 7.1 Hz, 1H), 6.49-6.42 (m, 1H), 6.28-5.85 (m, 1H), 5.11 (s, 2H), 3.65-3.51 (m, 2H), 2.17 (s, 6H), 1.88-1.38 (m, 1H), 0.98-0.13 (m, 4H) | $N^2$-((1H-indol-4-yl)methyl)-$N^4$-(5-cyclopropyl-1H-pyrazol-3-yl)-$N^2$-(2-(dimethylamino)ethyl)-pyrimidine-2,4-diamine |

TABLE II-continued

| Cpd. No. | Structure | $K_i$[1] | MS[2] | $^1$H NMR | Name |
|---|---|---|---|---|---|
| II-90 | 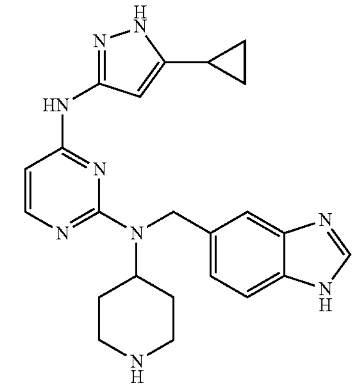 [SMILES: c1cc(Nc2cc(C3CC3)[nH]n2)nc(N(Cc2ccc3[nH]cnc3c2)C2CCNCC2)n1] | A | 430.2 | | $N^2$-((1H-benzo[d]imidazol-5-yl)methyl)-$N^4$-(5-cyclopropyl-1H-pyrazol-3-yl)-$N^2$-(piperidin-4-yl)pyrimidine-2,4-diamine |
| II-91 | 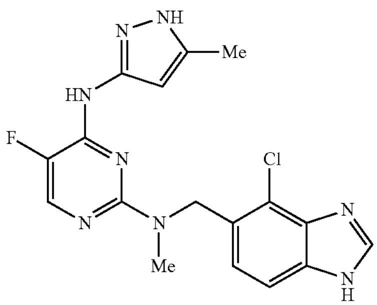 [SMILES: Cc1cc(Nc2nc(N(C)Cc3ccc4[nH]cnc4c3Cl)ncc2F)n[nH]1] | A | 387.1 | (400 MHz, DMSO-$d_6$) δ 12.64 (br s, 1H), 11.92 (br s, 1H), 9.41 (s, 1H), 8.26 (d, J = 3.4 Hz, 1H), 7.95 (d, J = 3.7 Hz, 1H), 7.61-7.32 (m, 1H), 6.94 (d, J = 8.3 Hz, 1H), 6.16-5.73 (m, 1H), 4.95 (s, 2H), 3.16 (s, 3H), 2.04 (s, 3H | $N^2$-((4-chloro-1H-benzo[d]imidazol-5-yl)methyl)-5-fluoro-$N^2$-methyl-$N^4$-(5-methyl-1H-pyrazol-3-yl)pyrimidine-2,4-diamine |
| II-92 | 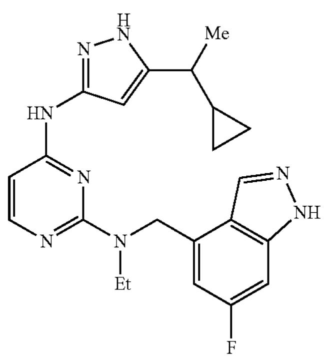 [SMILES: CCN(Cc1cc(F)cc2[nH]ncc12)c1nccc(Nc2cc(C(C)C3CC3)[nH]n2)n1] | A | 421.2 | | (R)-$N^4$-(5-(1-cyclopropylethyl)-1H-pyrazol-3-yl)-$N^2$-ethyl-$N^2$((6-fluoro-1H-indazol-4-yl)methyl)pyrimidine-2,4-diamine |
| II-93 | 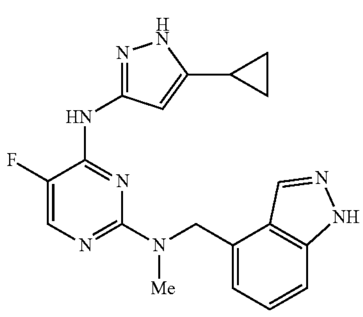 | A | 379.1 | (400 MHz, DMSO-$d_6$) δ 13.05 (br s, 1H), 11.95 (br s, 1H), 9.40 (br s, 1H), 8.02 (s, 1H), 7.97 (d, J = 3.7 Hz, 1H), 7.42 (d, J = 8.4 Hz, 1H), 7.33-7.23 (m, 1H), 6.85 (d, J = 7.0 Hz, 1H), 6.02 (br s, 1H), 5.12 (s, 2H), 3.06 (s, 3H), 1.69-1.52 (m, 1H), 0.77-0.62 (m, 2H), 0.39-0.19 (m, 2H) | $N^2$-((1H-indazol-4-yl)methyl)-$N^4$-(5-cyclopropyl-1H-pyrazol-3-yl)-5-fluoro-$N^2$-methylpyrimidine-2,4-diamine |

TABLE II-continued

| Cpd. No. | Structure | $K_i$[1] | MS[2] | $^1$H NMR | Name |
|---|---|---|---|---|---|
| II-94 | 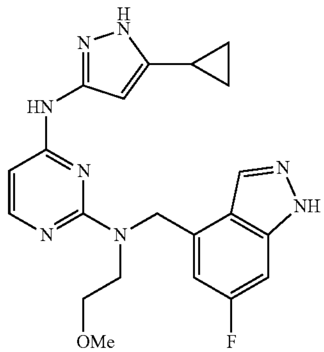 [SMILES: COCCN(Cc1cc(F)cc2[nH]ncc12)c1nccc(Nc2cc(C3CC3)[nH]n2)n1] | A | 423.2 | (400 MHz, DMSO-d$_6$) δ 13.15 (s, 1H), 12.11 (br s, 1H), 9.48 (br s, 1H), 8.12-8.00 (m, 1H), 7.96-7.79 (m, 1H), 7.18 (d, J = 9.2 Hz, 1H), 6.76-6.62 (m, 1H), 6.37-6.13 (m, 1H), 5.90-5.57 (m, 1H), 5.18 (s, 2H), 3.82-3.67 (m, 2H), 3.57-3.42 (m, 2H), 3.22 (s, 3H), 1.98-1.62 (m, 1H), 0.99-0.02 (m, 4H) | N$^4$-(5-cyclopropyl-1H-pyrazol-3-yl)-N$^2$-((6-fluoro-1H-indazol-4-yl)methyl)-N$^2$-(2-methoxyethyl)pyrimidine-2,4-diamine |
| II-95 | 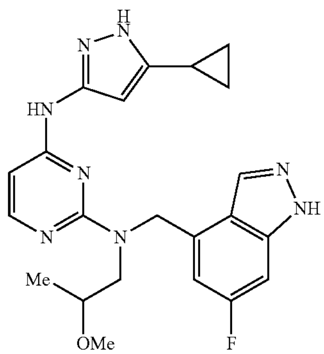 [SMILES: COC(C)CN(Cc1cc(F)cc2[nH]ncc12)c1nccc(Nc2cc(C3CC3)[nH]n2)n1] | A | 437.2 | (400 MHz, DMSO-d$_6$) δ 13.12 (s, 1H), 11.86 (br s, 1H), 9.42 (br s, 1H), 8.07 (s, 1H), 7.98-7.81 (m, 1H), 7.16 (d, J = 9.0 Hz, 1H), 6.63 (d, J = 9.7 Hz, 1H), 6.39-6.09 (m, 1H), 5.34 (d, J = 16.8 Hz, 1H), 5.10 (d, J = 16.8 Hz, 1H), 3.77-3.58 (m, 2H), 3.58-3.44 (m, 1H), 3.19 (s, 3H), 1.07 (d, J = 6.0 Hz, 3H), 1.00-0.07 (m, 4H). | (S)-N$^4$-(5-cyclopropyl-1H-pyrazol-3-yl)-N$^2$-((6-fluoro-1H-indazol-4-yl)methyl)-N$^2$-(2-methoxypropyl)pyrimidine-2,4-diamine |
| II-96 | 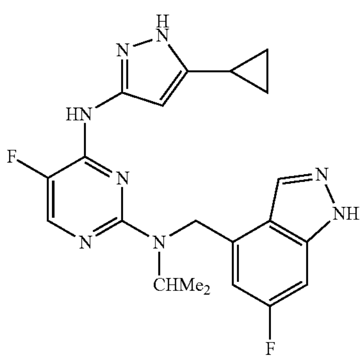 | A | 425.2 | | N$^4$-(5-cyclopropyl-1H-pyrazol-3-yl)-5-fluoro-N$^2$-((6-fluoro-1H-indazol-4-yl)methyl)-N$^2$-isopropylpyrimidine-2,4-diamine |
| II-97 | 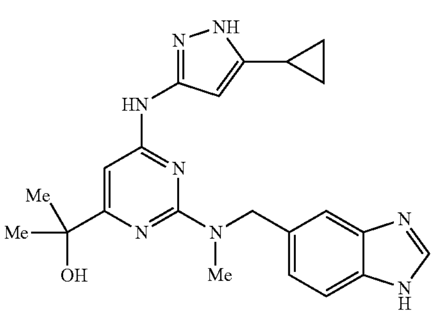 [SMILES: CN(Cc1ccc2[nH]cnc2c1)c1nc(Nc2cc(C3CC3)[nH]n2)cc(C(C)(C)O)n1] | A | 419.2 | (400 MHz, DMSO-d$_6$) δ 12.31 (br s, 1H), 11.83 (s, 1H), 9.25 (br s, 1H), 8.14 (s, 1H), 7.64-7.30 (m, 2H), 7.14 (d, J = 7.2 Hz, 1H), 6.61-6.38 (m, 1H), 6.18-5.98 (m, 1H), 4.93 (s, 3H), 3.06 (s, 3H), 1.83-1.69 (m, 1H), 1.35 (s, 6H), 0.89-0.67 (m, 2H), 0.66-0.33 (m, 2H) | 2-[2-[(1H-Benzoimidazol-5-ylmethyl)-methyl-amino]-6-(5-cyclopropyl-1H-pyrazol-3-ylamino)-pyrimidin-4-yl]-propan-2-ol |

TABLE II-continued

| Cpd. No. | Structure | $K_i^1$ | $MS^2$ | $^1H$ NMR | Name |
|---|---|---|---|---|---|
| II-98 | 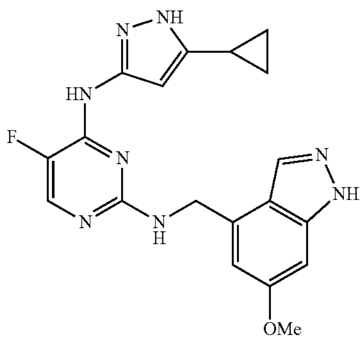 [SMILES: COc1cc(CNc2ncc(F)c(Nc3cc(C4CC4)[nH]n3)n2)c2cn[nH]c2c1] | A | 365.1 | (400 MHz, DMSO-$d_6$) δ 12.79 (br s, 1H), 9.50 (br s, 1H), 8.02 (s, 1H), 7.87 (d, J = 3.6 Hz, 1H), 7.53-7.35 (m, 1H), 6.76 (s, 1H), 6.62 (s, 1H), 6.23-5.88 (m, 1H), 4.70 (d, J = 6.2 Hz, 2H), 3.76 (s, 3H), 1.82-1.58 (m, 1H), 0.91-0.64 (m, 2H), 0.64-0.28 (m, 2H) | $N^4$-(5-cyclopropyl-1H-pyrazol-3-yl)-5-fluoro-$N^2$-((6-methoxy-1H-indazol-4-yl)methyl)pyrimidine-2,4-diamine |
| II-99 | 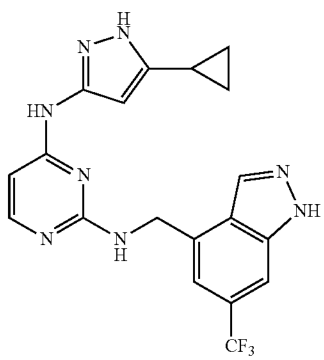 [SMILES: FC(F)(F)c1cc(CNc2nccc(Nc3cc(C4CC4)[nH]n3)n2)c2cn[nH]c2c1] | A | 415.1 | | $N^4$-(5-Cyclopropyl-1H-pyrazol-3-yl)-$N^2$-((6-(trifluoromethyl)-1H-indazol-4-yl)methyl)pyrimidine-2,4-diamine |
| II-100 | 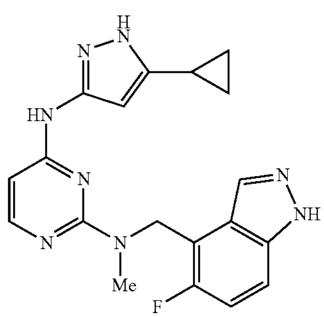 [SMILES: CN(Cc1c(F)ccc2[nH]ncc12)c1nccc(Nc2cc(C3CC3)[nH]n2)n1] | A | 379.2 | 1H NMR (400 MHz, DMSO-$d_6$) δ 13.13 (s, 1H), 11.91 (s, 1H), 9.41 (br s, 1H), 7.96 (d, J = 5.7 Hz, 1H), 7.84 (s, 1H), 7.52-7.41 (m, 1H), 7.32-7.20 (m, 1H), 6.47-6.20 (m, 1H), 6.19-5.94 (m, 1H), 5.20 (s, 2H), 2.99 (s, 3H), 1.85-1.68 (m, 1H), 0.92-0.75 (m, 2H), 0.60-0.37 (m, 2H) | $N^4$-(5-cyclopropyl-1H-pyrazol-3-yl)-$N^2$-((5-fluoro-1H-indazol-4-yl)methyl)-$N^2$-methylpyrimidine-2,4-diamine |
| II-101 | 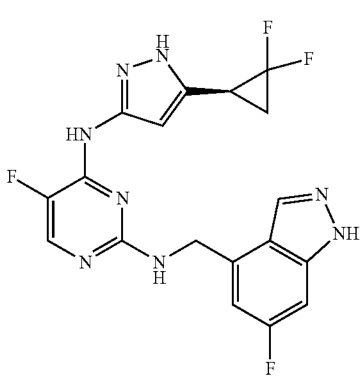 [SMILES: Fc1cc(CNc2ncc(F)c(Nc3cc([C@@H]4CC4(F)F)[nH]n3)n2)c2cn[nH]c2c1] | B | 419.1 | | (S)-$N^4$-(5-(2,2-difluorocyclopropyl)-1H-pyrazol-3-yl)-5-fluoro-$N^2$-((6-fluoro-1H-indazol-4-yl)methyl)pyrimidine-2,4-diamine |

TABLE II-continued

| Cpd. No. | Structure | $K_i^1$ | $MS^2$ | $^1H$ NMR | Name |
|---|---|---|---|---|---|
| II-102 | 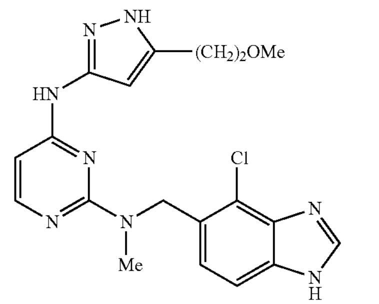 | B | 413.1 | (400 MHz, DMSO-$d_6$) δ 12.66 (br s, 1H), 11.85 (br s, 1H), 9.41 (s, 1H), 8.26 (s, 1H), 7.90 (d, J = 5.7 Hz, 1H), 7.58-7.38 (m, 1H), 6.97 (d, J = 8.3 Hz, 1H), 6.34-5.93 (m, 2H), 5.02 (s, 2H), 3.13 (s, 6H), 2.72-2.55 (m, 2H). | $N^2$-((4-chloro-1H-benzo[d]imidazol-5-yl)methyl)-$N^4$-(5-(2-methoxyethyl)-1H-pyrazol-3-yl)-$N^2$-methylpyrimidine-2,4-diamine |
| II-103 | 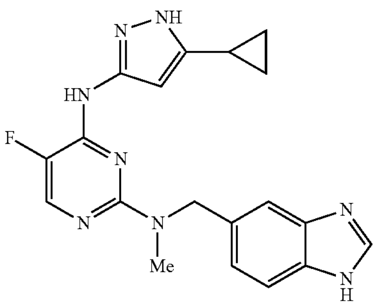 [SMILES: CN(Cc1ccc2[nH]cnc2c1)c1ncc(F)c(Nc2cc(C3CC3)[nH]n2)n1] | B | 379.2 | | $N^2$-((1H-benzo[d]imidazol-5-yl)methyl)-$N^4$-(5-cyclopropyl-1H-pyrazol-3-yl)-5-fluoro-$N^2$-methylpyrimidine-2,4-diamine |
| II-104 | 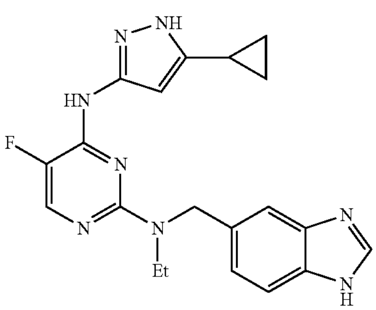 [SMILES: CCN(Cc1ccc2[nH]cnc2c1)c1ncc(F)c(Nc2cc(C3CC3)[nH]n2)n1] | B | 393.2 | | $N^2$-((1H-benzo[d]imidazol-5-yl)methyl)-$N^4$-(5-cyclopropyl-1H-pyrazol-3-yl)-$N^2$-ethyl-5-fluoropyrimidine-2,4-diamine |
| II-105 | 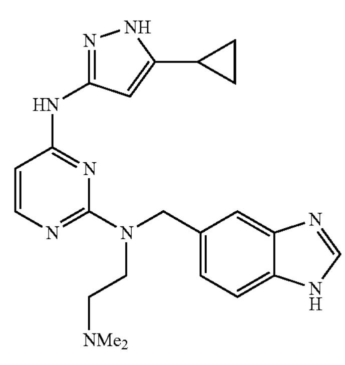 [SMILES: CN(C)CCN(Cc1ccc2[nH]cnc2c1)c1nccc(Nc2cc(C3CC3)[nH]n2)n1] | B | 418.2 | (400 MHz, DMSO-$d_6$) δ 9.37 (br s, 1H), 8.18 (s, 1H), 8.14 (s, 1H), 7.89 (d, J = 5.5 Hz, 1H), 7.51 (d, J = 8.1 Hz, 1H), 7.45-7.36 (m, 1H), 7.12 (d, J = 8.3 Hz, 1H), 6.30-5.89 (m, 2H), 4.95 (s, 2H), 3.65-3.58 (m, 2H), 2.48-2.41 (m, 2H), 2.18 (s, 6H), 1.84-1.62 (m, 1H), 0.91-0.19 (m, 4H) | $N^2$-((1H-benzo[d]imidazol-5-yl)methyl)-$N^4$-(5-cyclopropyl-1H-pyrazol-3-yl)-$N^2$-(2-(dimethylamino)ethyl)pyrimidine-2,4-diamine |

TABLE II-continued

| Cpd. No. | Structure | $K_i^1$ | MS[2] | $^1$H NMR | Name |
|---|---|---|---|---|---|
| II-106 | 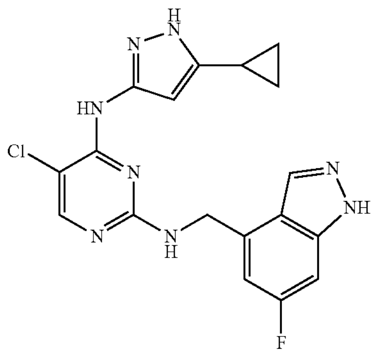 [SMILES: Fc1cc(CNc2ncc(Cl)c(Nc3cc(C4CC4)[nH]n3)n2)c2cn[nH]c2c1] | B | 399.1 | | 5-chloro-N[4]-(5-cyclopropyl-1H-pyrazol-3-yl)-N[2]-((6-fluoro-1H-indazol-4-yl)methyl)pyrimidine-2,4-diamine |
| II-107 | 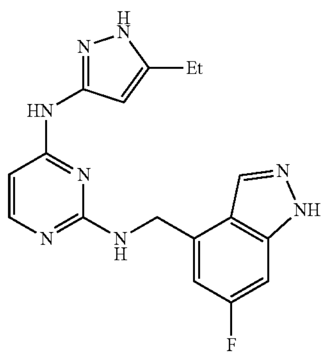 [SMILES: CCc1cc(Nc2ccnc(NCc3cc(F)cc4[nH]ncc34)n2)n[nH]1] | B | 353.1 | | N[4]-(5-ethyl-1H-pyrazol-3-yl)-N[2]-((6-fluoro-1H-indazol-4-yl)methyl)pyrimidine-2,4-diamine |
| II-108 | 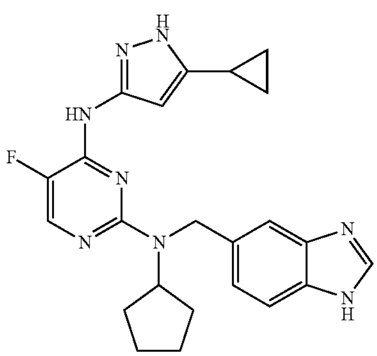 [SMILES: Fc1cnc(N(Cc2ccc3[nH]cnc3c2)C2CCCC2)nc1Nc1cc(C2CC2)[nH]n1] | B | 433.2 | (400 MHz, DMSO-$d_6$) δ 12.16 (s, 1H), 11.97 (br s, 1H), 9.35 (br s, 1H), 8.16-8.04 (m, 1H), 7.99-7.87 (m, 1H), 7.54 (d, J = 8.3 Hz, 1H), 7.44-7.38 (m, 1H), 7.31-7.23 (m, 1H), 7.13-7.00 (m, 1H), 6.13-5.76 (m, 1H), 5.06-4.91 (m, 1H), 4.83 (s, 2H), 1.80-1.38 (m, 8H), 0.82-0.59 (m, 2H), 0.40-0.09 (m, 2H). | N[2]-((1H-benzo[d]imidazol-5-yl)methyl)-N[2]-cyclopentyl-N[4]-(5-cyclopropyl-1H-pyrazol-3-yl)-5-fluoropyrimidine-2,4-diamine |
| II-109 | 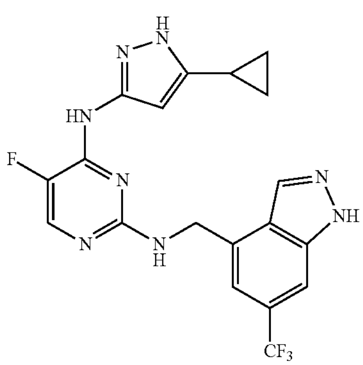 [SMILES: Fc1cnc(NCc2cc(C(F)(F)F)cc3[nH]ncc23)nc1Nc1cc(C2CC2)[nH]n1] | C | 433.0 | | N[4]-(5-cyclopropyl-1H-pyrazol-3-yl)-5-fluoro-N[2]-((6-(trifluoromethyl)-1H-indazol-4-yl)methyl)pyrimidine-2,4-diamine |

TABLE II-continued

| Cpd. No. | Structure | $K_i^1$ | $MS^2$ | $^1$H NMR | Name |
|---|---|---|---|---|---|
| II-110 | 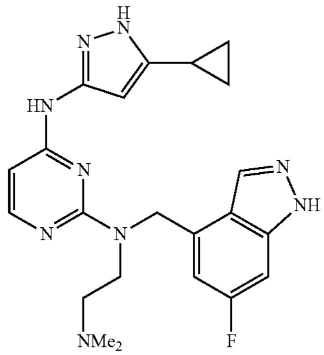 [SMILES: CN(C)CCN(Cc1cc(F)cc2[nH]ncc12)c1nccc(Nc2cc(C3CC3)[nH]n2)n1] | A | 436.2 | (400 MHz, DMSO-$d_6$) δ 13.14 (br s, 1H), 9.42 (br s, 1H), 8.08 (s, 1H), 7.93-7.79 (m, 1H), 7.18 (d, J = 9.0 Hz, 1H), 6.73 (d, J = 10.0 Hz, 1H), 6.33-5.94 (m, 2H), 5.16 (s, 2H), 3.76-3.62 (m, 2H), 2.46-2.35 (m, 2H), 2.14 (s, 6H), 1.91-1.40 (m, 1H), 1.03-0.40 (m, 4H). | $N^4$-(5-cyclopropyl-1H-pyrazol-3-yl)-$N^2$-(2-(dimethylamino)ethyl)-$N^2$-((6-fluoro-1H-indazol-4-yl)methyl)pyrimidine-2,4-diamine |
| II-111 | 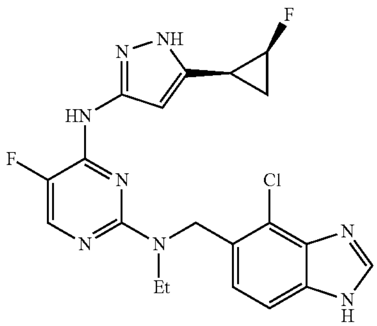 [SMILES: CCN(Cc1ccc2[nH]cnc2c1Cl)c1ncc(F)c(Nc2cc([C@@H]3C[C@@H]3F)[nH]n2)n1] | A | 445.1 | (400 MHz, DMSO-$d_6$) δ 12.64 (s, 1H), 12.13 (br s, 1H), 9.45 (br s, 1H), 8.25 (s, 1H), 8.02-7.85 (m, 1H), 7.41 (d, J = 8.3 Hz, 1H), 7.02 (d, J = 8.1 Hz, 1H), 6.41-5.92 (m, 1H), 4.94 (s, 2H), 4.90-4.59 (m, 1H), 3.65-3.50 (m, 2H), 1.99-1.75 (m, 1H), 1.11 (t, J = 6.9 Hz, 3H), 1.06-0.83 (m, 1H) | $N^2$-((4-chloro-1H-benzo[d]imidazol-5-yl)methyl)-$N^2$-ethyl-5-fluoro-$N^4$-(5-((1S,2S)-2-fluorocyclopropyl)-1H-pyrazol-3-yl)pyrimidine-2,4-diamine |
| II-112 | 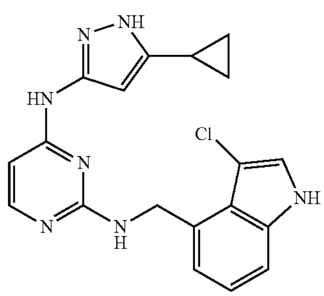 [SMILES: Clc1c[nH]c2cccc(CNc3nccc(Nc4cc(C5CC5)[nH]n4)n3)c12] | A | 380.0 | (400 MHz, DMSO-$d_6$) δ 11.35 (s, 1H), 9.34 (br s, 1H), 7.81 (d, J = 5.7 Hz, 1H), 7.46 (d, J = 2.6 Hz, 1H), 7.26 (d, J = 8.1 Hz, 1H), 7.04 (d, J = 7.9 Hz, 1H), 6.95 (d, J = 7.0 Hz, 1H), 6.14 (br s, 1H), 5.91 (br s, 1H), 5.07 (d, J = 5.6 Hz, 2H), 1.68 (br s, 1H), 0.95 to 0.10 (m, 4H) | $N^2$-((3-chloro-1H-indol-4-yl)methyl)-$N^4$-(5-cyclopropyl-1H-pyrazol-3-yl)pyrimidine-2,4-diamine |
| II-113 | 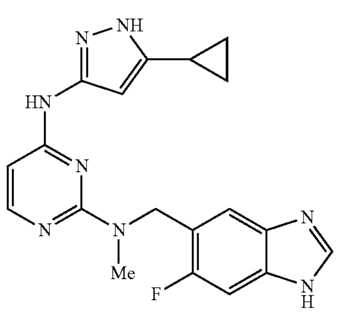 [SMILES: CN(Cc1cc2nc[nH]c2cc1F)c1nccc(Nc2cc(C3CC3)[nH]n2)n1] | A | 379.2 | (400 MHz, DMSO-$d_6$) δ 12.30 (br d, 1H), 11.89 (br s, 1H), 9.38 (s, 1H), 8.17 (s, 1H), 7.90 (d, J = 5.7 Hz, 1H), 7.33 (br d, 2H), 6.24 (br s, 1H), 5.98 (br s, 1H), 4.95 (s, 2H), 3.14 (s, 3H), 1.75 (br s, 1H), 0.83 (d, J = 7.1 Hz, 2H), 0.49 (br s, 2H) | $N^4$-(5-cyclopropyl-1H-pyrazol-3-yl)-$N^2$-((6-fluoro-1H-benzo[d]imidazol-5-yl)methyl)-$N^2$-methylpyrimidine-2,4-diamine |

$^1$Example 66 $K_i$: A ≤ 0.050 μM; 0.050 μM < B ≤ 0.250 μM; 0.250 μM < C ≤ 1.0 μM; D > 1.0 μM
$^2$m/z obtained from ESI mass spectrometer Dosage & Administration The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of formula I with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the particular disorder being treated, the severity of the disorder, the particular patient being treated, the clinical condition of the individual patient, the cause of the disorder, the site of delivery of the agent, the method of administration, the scheduling of administration, and other factors known to medical practitioners The term "treating" or "treatment" of a disease state includes (1) inhibiting the disease state, i.e., arresting the development of the disease state or its clinical symptoms, or (2) relieving the disease state, i.e., causing temporary or permanent regression of the disease state or its clinical symptoms.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.1 mg to about 1000 mg of a compound of formula I. A typical dose may be about 1 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of formula I, or a stereoisomer or pharmaceutically acceptable salt thereof. In a further embodiment includes a pharmaceutical composition comprising a compound of formula I, or a stereoisomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of formula I may be employed alone or in combination with other therapeutic agents for the treatment of a disease or disorder described herein, such as a hyperproliferative disorder (e.g., cancer). In certain embodiments, a compound of formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of formula I such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the newly identified agent and other chemotherapeutic agents or treatments.

Combination therapies according to the present invention thus comprise the administration of at least one compound of formula I, or a stereoisomer, geometric isomer, tautomer, metabolite, or pharmaceutically acceptable salt and the use of at least one other cancer treatment method. The amounts of the compound(s) of formula I and the other pharmaceutically active chemotherapeutic agent(s) and the relative timings of administration will be selected in order to achieve the desired combined therapeutic effect.

Articles of Manufacture

In another embodiment of the invention, an article of manufacture, or "kit", containing materials useful for the treatment of the diseases and disorders described above is provided. In one embodiment, the kit comprises a container comprising a compound of formula I, or a stereoisomer, tautomer, or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or a formulation thereof which is effective for treating the condition and may have a sterile access port (for example, the container may be an intravenous solution bag or a vial having a stopper pierceable by a hypodermic injection needle). At least one active agent in the composition is a compound of formula I. Alternatively, or additionally, the article of manufacture may further comprise a second container comprising a pharmaceutically diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of formula I, such as tablets or capsules. Such a kit can include a number of unit dosages. An example of such a kit is a "blister pack". Blister packs are well known in the packaging industry and are widely used for packaging pharmaceutical unit dosage forms.

According to one embodiment, a kit may comprise (a) a first container with a compound of formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Referential Example 1

Racemic trans-3-(2-phenylcyclopropyl)-1H-pyrazol-5-amine (41)

Step 1:

To a stirred mixture of lithium tert-butoxide (124.6 g, 1.56 mol, 1.10 equiv) in DCM (2000 mL) under $N_2$ at RT was added ethyl 2-(diethoxyphosphoryl)acetate (317 g, 1.41 mol, 1.00 equiv). Benzaldehyde (150 g, 1.41 mol, 1.0 equiv) was then added dropwise to the stirred reaction, and the resulting reaction mixture was stirred under $N_2$ at 25° C. overnight. The reaction mixture was diluted with DCM (2 L). The organic layer was washed with water (3×2 L) and brine (1×2 L), dried ($Na_2SO_4$), filtered, and evaporated in vacuo. The crude residue was purified by $SiO_2$ chromatograph eluting with EtOAc/petroleum ether (3.3 to 1% EtOAc) to afford 180 g (72%) of ethyl (2E)-3-phenylprop-2-enoate (31) as a light yellow oil.

Step 2:

To a stirred mixture of NaH (40.7 g) in DMSO (2.5 L) under $N_2$ was added portion wise trimethyl sulfoxonium iodide (396 g, 1.80 mol, 1.76 equiv). A solution of 31 (180 g, 1.02 mol, 1.00 equiv) in 1:1 DMSO/THF (2 L) was added, and the reaction mixture was stirred at 25° C. overnight. The reaction mixture was quenched with 1N HCl (1 L) and extracted with EtOAc (2×2 L). The combined organic layers were washed with water (2×2 L) and brine (1×2 L), dried ($Na_2SO_4$), filtered and concentrated in vacuo. The residue was purified by $SiO_2$ chromatography eluting with EtOAc/petroleum ether (5 to 12.5% EtOAc) to afford 153 g (79%) of trans-ethyl-2-phenylcyclopropane-1-carboxylate (33) as a light yellow oil.

Step 3:

To a stirred mixture of 33 (153 g, 804.25 mmol, 1.00 equiv) in EtOH (1 L) was added 1M aq. LiOH (1 L), and the resultant solution was stirred at reflux for 1 h. Volatile solvent was removed under reduced pressure and the residue diluted with EtOAc (1.5 L). The organic phase was washed with water (3×1 L) and brine (1×1 L), dried ($Na_2SO_4$), filtered and concentrated in vacuo to afford 117.5 g (90%) of trans-2-phenylcyclopropane-1-carboxylic acid (35) as a white solid.

Step 4:

To a stirred solution of 35 (117.5 g, 724.48 mmol, 1.00 equiv) in DMF (1.2 L) under $N_2$ was added methoxy(methyl)amine hydrochloride (82.3 g, 844.10 mmol, 1.17 equiv), HATU (329 g, 775.58 mmol, 1.07 equiv), and DIPEA (117.5 mL). The reaction mixture was stirred under N2 at 25° C. overnight and then diluted with water (700 mL). The organic phase was extracted with EtOAc (3×1 L), and the combined organic layers were washed with water (3×1 L) and brine (1×1 L), dried ($Na_2SO_4$), filtered and concentrated in vacuo. The residue purified by $SiO_2$ chromatography and eluted with EtOAc/petroleum ether (10 to 50% EtOAc) to afford 62.5 g (42%) of trans-N-methoxy-N-methyl-2-phenylcyclopropane-1-carboxamide (37) as a light yellow oil.

Step 5:

To a stirred solution of MeCN (208.3 mL) and THF (200 mL) at −60° C. under N2 was added dropwise 1M LHMDS in THF (1040 mL). The reaction mixture was stirred at −60° C. for 3 h, and 37 (62.5 g, 304.5 mmol, 1.00 equiv) was then added dropwise. The resulting solution was stirred at −60° C. for 10 min and then quenched with sat'd. aq. $NH_4Cl$ solution (400 mL). The reaction mixture was extracted with EtOAc (3×1 L), and the combined organic layers were dried ($Na_2SO_4$), filtered and concentrated in vacuo. The crude residue was purified by $SiO_2$ chromatography eluting with EtOAc/petroleum ether (10 to 25% EtOAc) to afford 28.5 g (51%) of trans-3-oxo-3-(2-phenylcyclopropyl)propanenitrile (39) as a light yellow oil.

Step 6:

To a stirred solution of 39 (28.5 g, 153.87 mmol, 1.00 equiv) in EtOH (300 mL) under N2 was added 85% hydrazine hydrate (5.7 g, 100 mmol, 0.65 equiv), and the reaction mixture was stirred at 80° C. for 6 h. The reaction was cooled to RT, and concentrated in vacuo. The crude residue was purified by $SiO_2$ chromatography eluting with DCM/MeOH gradient (1 to 5% MeOH) to afford 25.4 g (83%) of trans-3-(2-phenylcyclopropyl)-1H-pyrazol-5-amine (41) as a light yellow oil: 1H NMR (400 MHz, DMSO-d6): δ 7.30-7.10 (m, 5H), 5.15 (s, 1H), 4.90-4.20 (br s, 2H), 2.10-2.07 (m, 1H), 2.00-1.95 (m, 1H), 1.35-1.31 (m, 2H), 1H not seen; MS (ESI+) m/z=200 [M+1]+.

trans-3-[2-(2-Fluorophenyl)cyclopropyl]-1H-pyrazol-5-amine (43) was prepared analogously using 2-fluorobenzaldehyde in place of benzaldedyde as the starting material: 1H NMR (400 MHz, DMSO-d6) δ 7.24-7.06 (m, 4H), 5.17 (1H, s), 2.33-2.20 (m, 1H), 2.05-2.01 (m, 1H), 1.42-1.24 (m, 2H); MS (ESI+) m/z=218 [M+1]+.

Referential Example 2

5-(2,2-Difluorocyclopropyl)-1H-pyrazol-3-amine (45)

To a solution of MeCN (1.1 g, 16.8 mmol) in THF (60 mL) was added dropwise n-BuLi in THF (11.2 mL, 40.3 mmol) at −78° C., and the reaction mixture was stirred at −78° C. under $N_2$ for 30 min. Butyl 2,2-difluorocyclopropanecarboxylate (3.0 g, 16.8 mmol) was added at −78° C., and the reaction mixture was allowed to warm to RT over 3 h. The reaction mixture was quenched with water and adjusted to pH 7 with 1N HCl. The mixture was extracted with EtOAc, and the organic layer was washed with brine, dried ($Na_2SO_4$), filtered and concentrated in vacuo to afford crude 3-(2,2-difluorocyclopropyl)-3-oxopropanenitrile. A mixture of crude 3-(2,2-difluorocyclopropyl)-3-oxopropanenitrile and hydrazine (2.0 g, 50.4 mmol, 85% pure) in EtOH (30 mL) was stirred at reflux for 16 h. The reaction mixture was concentrated to dryness under reduced pressure. The crude residue was purified by chromatography eluting with an EtOAc/petroleum ether gradient (12.5 to 100% EtOAc) to afford 2.1 g (78.5%) of 45 as a yellow solid: 1H NMR (400 MHz, DMSO-d6): δ 11.40 (br s, 1H), 5.26 (s, 1H), 4.80 (br s, 2H), 2.78-2.66 (m, 1H), 2.04-1.75 (m, 1H), 1.73-1.21 (m, 1H); MS (ESI+) m/z=160.1 [M+1]+.

Racemic trans-5-(2-fluorocyclopropyl)-1H-pyrazol-3-amine (47) was prepared analogously except ethyl trans2-fluorocyclopropane-1-carboxylate was used in place of butyl 2,2-difluorocyclopropanecarboxylate as the starting material: 1H NMR (300 MHz, DMSO-d6) δ 5.09 (s, 1H), 4.60-4.85 (m, 1H), 4.50 (br, 2H), 3.40 (br s, 1H), 2.28-2.14 (m, 1H), 1.40-1.32 (m, 1H), 1.08-0.92 (m, 1H); MS (ESI+) m/z=142 [M+1]+.

Racemic cis-5-(2-fluorocyclopropyl)-1H-pyrazol-3-amine (49) was prepared analogously using the procedure as described for 5-(2,2-difluorocyclopropyl)-1H-pyrazol-3-amine, using ethyl cis-2-fluorocyclopropane-1-carboxylate in place of butyl 2,2-difluorocyclopropanecarboxylate as the starting material: 1H NMR (300 MHz, DMSO-d6) δ 5.16 (s, 1H), 4.67-4.95 (m, 1H), 4.50 (br, 2H), 3.40 (br s, 1H), 1.95-1.84 (m, 1H), 1.20-1.12 (m, 2H); MS (ESI+) m/z=142 [M+1]+.

Referential Example 3

5-(Cyclopropylmethoxy)-1H-pyrazol-3-amine (51)

A mixture of $Ph_3P$ (75.5 g, 0.29 mol) and DIAD (58.5 g, 0.29 mol) in DCM (1.8 L) was stirred at RT for 30 min. The mixture was cooled to 0° C. and 3-amino-5-hydroxy pyrazole (24.0 g, 0.24 mol) was added slowly over 10 min. After the addition was complete, the mixture was stirred at 0° C. for 10 min, and cyclopropylmethanol (19.0 g, 0.265 mol) was added dropwise within 10 min at the same temperature. The mixture was stirred under RT for 48 h. The undissolved solid was filtered off, and the filtrate was concentrated to about 1 L. Aqueous HCl (25 mL con HCl in 70 mL water) was added to the solution until the pH was between 1 and 2. The solution was stirred for another 10 min and then $H_2O$ (350 mL) was added. After vigorous stirring for 30 min, the upper aqueous phase was separated and 20 g solid NaOH was added slowly to the aqueous phase until pH was ca. 9 to 11. The reaction mixture was extracted with EtOAc (6×300 mL) and the combined organic layers were dried (Na₂SO₄), filtered and concentrated in vacuo. The crude product was purified by SiO₂ column chromatography eluting with an EtOAc/petroleum ether gradient (50 to 100% EtOAc) affording 4.8 g of an oily product. Trituration with DCM (200 mL) and petroleum ether (250-300 mL) afforded 3.2 g (9%) of 51 as white to pale yellow solid: 1H NMR (400 MHz, DMSO-d6) δ 10.31 (m, 1H), 4.89 (m, 2H), 4.67 (s, 1H), 3.75 (d, J=7.2 Hz, 2H), 1.24-1.11 (m, 1H), 0.52-0.50 (m, 2H), 0.30-0.15 (m, 2H); MS (ESI+) m/z=154.0 [M+1]+.

Referential Example 4

2-Chloro-N-(3-cyclopropyl-1H-pyrazol-5-yl)pyrimidin-4-amine (53)

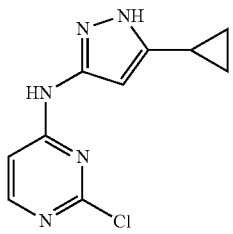

(53)

A dried 5-L, three-neck round bottom flask fitted with an overhead stirrer and reflux condenser was charged with a solution of 2,4-dichloropyrimidine (250 g, 1.678 mol) in anhydrous DMSO (2300 mL). 3-Cyclopropyl-1H-pyrazol-5-amine (227.4 g, 1.8458 mol) and DIPEA (438 mL, 2.517 mol) were added sequentially at RT. The resulting solution was stirred at 60° C. for 16 h, cooled to RT, and poured into ice water. The precipitated yellow solid was collected by vacuum filtration, and washed well with water, 1.5 N HCl (3×1 L), and finally rinsed of water (4×500 mL). The precipitate was dried by air suction overnight to give 320 g (81%) of 53 as yellow solid: 1H NMR (400 MHz, DMSO-d6) δ 12.19 (s, 1H), 10.29 (s, 1H), 8.15 (s, 1H), 7.0 (br s, 1H), 6.0 (br s, 1H), 1.85-1.92 (m, 1H), 0.91-0.95 (m, 2H), 0.7 (m, 2H); MS (ESI+) m/z=236 [M+1]+.

2-Chloro-N-(5-cyclopropyl-1H-pyrazol-3-yl)-5-fluoropyrimidin-4-amine (55) was prepared analogously except 2,4-dichloro-5-fluoro-pyrimidine was used in place of 2,4-dichloropyrimidine: 1H NMR (400 MHz, DMSO-d6, 125° C.) δ 12.28 (s, 1H), 10.38 (s, 1H), 8.24 (s, 1H), 6.27 (s, 1H), 1.94-1.89 (m, 1H), 0.95-0.93 (m, 2H), 0.71-0.69 (m, 2H); MS (ESI+) m/z=254.1 [M+1]+.

2,5-Dichloro-N-(5-cyclopropyl-1H-pyrazol-3-yl)pyrimidin-4-amine (57) was prepared was prepared analogously except 2,4,5-trichloropyrimidine was used in place of 2,4-dichloropyrimidine: 1H NMR (400 MHz, DMSO-d6) δ 12.32 (br s, 1H), 9.68 (br s, 1H), 5.17 (1H, s), 8.32 (s, 1H), 6.2 (s, 1H), 1.89-1.94 (m, 1H), 0.92-0.97 (m, 2H), 0.5-0.9 (m, 2H); MS (ESI+) m/z=272 [M+1]+.

2-Chloro-N-(5-isopropyl-1H-pyrazol-3-yl)pyrimidin-4-amine (59) was prepared analogously except 5-isopropyl-1H-pyrazol-3-amine was used in place of 3-cyclopropyl-1H-pyrazol-5-amine: 1H NMR (400 MHz, DMSO) δ 12.17 (s, 1H), 10.28 (s, 1H), 8.19-8.13 (m, 1H), 7.29 (br s, 1H), 6.12 (br s, 1H), 2.99-2.87 (m, 1H), 1.22 (d, J=6.9 Hz, 6H). LCMS m/z=238.1 [M+1]+.

2-Chloro-N-(5-(cyclopropylmethyl)-1H-pyrazol-3-yl)pyrimidin-4-amine was prepared (61) analogously except 5-(cyclopropylmethyl)-1H-pyrazol-3-amine (CASRN 852443-64-2) was used in place of 3-cyclopropyl-1H-pyrazol-5-amine: 1H NMR (400 MHz, DMSO) δ 12.16 (s, 1H), 10.29 (s, 1H), 8.19-8.12 (m, 1H), 7.22 (br s, 1H), 6.13 (br s, 1H), 1.05-0.91 (m, 1H), 0.54-0.42 (m, 2H), 0.19 (q, J=4.9 Hz, 2H). (CH2 hidden underneath DMSO signal). LCMS m/z=250.1 [M+1]+.

2-Chloro-N-(5-(3,3-difluorocyclobutyl)-1H-pyrazol-3-yl)pyrimidin-4-amine (63) was prepared analogously except 5-(3,3-difluorocyclobutyl)-1H-pyrazol-3-amine (45) was used in place of 3-cyclopropyl-1H-pyrazol-5-amine: 1H NMR (400 MHz, DMSO-d6) δ 12.43 (s, 1H), 10.40 (s, 1H), 8.19 (s, 1H), 7.20 (br s, 1H), 6.20 (br s, 1H), 3.43-3.35 (m, 1H), 3.20-2.85 (m, 2H), 2.75-2.72 (m, 2H); MS (ESI+) m/z=286 [M+1]+.

2-Chloro-N-(5-cyclobutyl-1H-pyrazol-3-yl)pyrimidin-4-amine (65) was prepared analogously except 3-cyclobutyl-1H-pyrazol-5-amine (CASRN 326827-21-8) was used in place of 3-cyclopropyl-1H-pyrazol-5-amine: 1H NMR (300 MHz, DMSO-d6) δ 12.19 (br s, 1H) 10.30 (s, 1H), 8.17 (s, 1H), 6.91-8.12 (br s, 1H), 6.09-6.39 (br s, 1H), 3.49-3.76 (m, 1H), 2.22-2.24 (m, 2H), 2.09-2.18 (m, 2H), 1.80-1.93 (2H, m); MS (ESI+) m/z=250 [M+1]+.

2-Chloro-N-(5-cyclopentyl-1H-pyrazol-3-yl)pyrimidin-4-amine (67) was prepared analogously except 3-cyclopentyl-1H-pyrazol-5-amine (CASRN 264209-16-7) was used in place of 3-cyclopropyl-1H-pyrazol-5-amine: 1H NMR (300 MHz, DMSO-d6) δ 12.19 (s, 1H), 10.30 (s, 1H), 8.15-8.16 (s, 1H), 7.00 (br s, 1H), 6.10 (br s, 1H), 3.01 (m, 1H), 1.95-2.01 (m, 2H), 1.59-1.71 (m, 6H); MS (ESI+) m/z=264 [M+1]+.

N-(5-Benzyloxy-1H-pyrazol-3-yl)-2-chloro-pyrimidin-4-amine (69) was prepared analogously except 5-benzyloxy-1H-pyrazol-3-amine was used in place of 3-cyclopropyl-1H-pyrazol-5-amine: MS (ESI+) m/z=302.1 [M+1]+.

trans-2-Chloro-N-[5-(2-fluorocyclopropyl)-1H-pyrazol-3-yl]pyrimidin-4-amine (71) was prepared analogously except trans-5-(2-fluorocyclo-propyl)-1H-pyrazol-3-amine was used in place of 3-cyclopropyl-1H-pyrazol-5-amine.

Racemic cis-2-chloro-N-[5-(2-fluorocyclopropyl)-1H-pyrazol-3-yl]pyrimidin-4-amine (73) was prepared analogously except cis-5-(2-fluorocyclo-propyl)-1H-pyrazol-3-amine was used in place of 3-cyclopropyl-1H-pyrazol-5-amine: 1H NMR (300 MHz, DMSO-d6) δ 12.35 (s, 1H), 10.32 (s, 1H), 8.16 (d, J=7.2 Hz, 1H), 7.23 (br, 1H), 6.10 (br, 1H), 4.80-5.06 (m, 1H), 2.13-2.07 (m, 1H), 1.37-1.22 (m, 2H); MS (ESI+) m/z=254 [M+1]+.

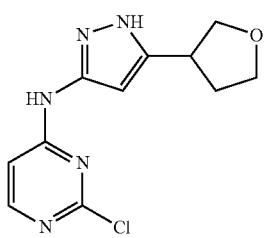

(75)

2-Chloro-N-(5-(tetrahydrofuran-3-yl)-1H-pyrazol-3-yl)pyrimidin-4-amine (75) was prepared analogously except 5-(tetrahydro-furan-3-yl)-1H-pyrazol-3-amine (CASRN 1186609-16-4) was used in place of 5-cyclopropyl-1H-pyrazol-3-amine: 1H NMR (400 MHz, CDCl3) δ 8.33 (s, 1H), 8.17 (d, J=6.0 Hz, 1H), 7.00 (br s, 1H), 6.19 (br s, 1H), 4.10-3.94 (m, 2H), 3.95-3.88 (m, 2H), 3.57-3.51 (m, 1H), 2.46-238 (m, 1H), 2.35-2.01 (m, 1H), 1H not detected; MS (ESI+) m/z=266 [M+1]+.

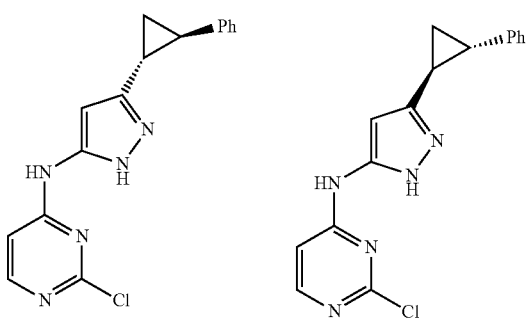

(77)

Racemic trans-2-chloro-N-[3-(2-phenylcyclopropyl)-1H-pyrazol-5-yl]pyrimidin-4-amine (77) was prepared analogously except trans-3-(2-phenyl-cyclopropyl)-1H-pyrazol-5-amine was used in place of 3-cyclopropyl-1H-pyrazol-5-amine as the starting material. 1H NMR (400 MHz, DMSO-d$_6$) δ 12.29 (s, 1H), 10.33 (s, 1H), 8.17 (s, 1H), 7.17-7.48 (m, 7H), 2.18-2.25 (m, 2H), 1.44-1.48 (m, 2H); MS (ESI+) m/z=312 [M+1]+.

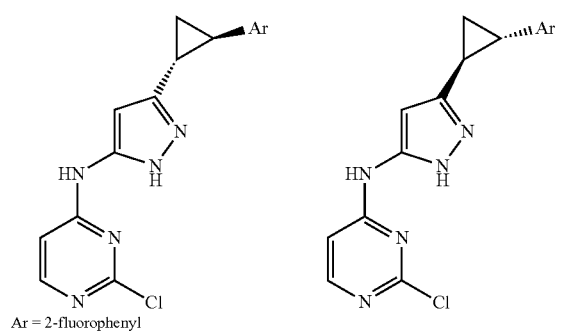

(79)

Ar = 2-fluorophenyl

Racemic trans-2-chloro-N-[3-[2-(2-fluorophenyl)cyclopropyl]-1H-pyrazol-5-yl]pyrimidin-4-amine (79) was prepared analogously except trans-3-[2-(2-fluoro-phenyl)cyclopropyl]-1H-pyrazol-5-amine was used in place of 3-cyclopropyl-1H-pyrazol-5-amine as the starting material: 1H NMR (400 MHz, DMSO-d$_6$) δ 12.31 (s, 1H), 10.34 (s, 1H), 8.37 (s, 1H), 7.36-7.14 (m, 5H), 6.10 (br s, 1H), 2.37-2.24 (d, 2H), 1.56-1.49 (m, 2H); MS (ESI+) m/z=330 [M+1]+.

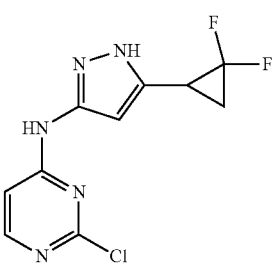

(81)

2-Chloro-N-(5-(2,2-difluorocyclopropyl)-1H-pyrazol-3-yl)pyrimidin-4-amine (81) was prepared analogously except 5-(2,2-difluoro-cyclopropyl)-1H-pyrazol-3-amine (CASRN 1186609-07-3) was used in place of 3-cyclopropyl-1H-pyrazol-5-amine: 1H NMR (400 MHz, DMSO-d$_6$): δ 12.53 (s, 1H), 10.39 (s, 1H), 8.18 (d, J=5.2 Hz, 1H), 7.19 (br s, 1H), 6.21 (br s, 1H), 3.05-2.94 (m, 1H), 2.12-1.88 (m, 2H).

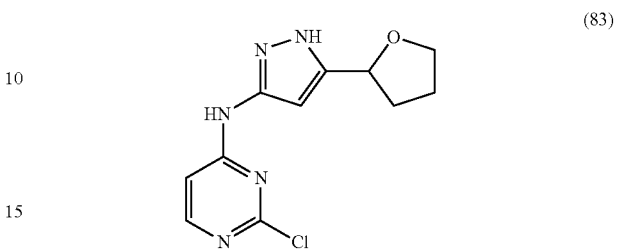

(83)

2-Chloro-N-(5-(tetrahydrofuran-2-yl)-1H-pyrazol-3-yl)pyrimidin-4-amine (83) was prepared analogously except of 5-(tetrahydrofuran-2-yl)-1H-pyrazol-3-amine (CASRN 1028843-21-1) was used in place of was used in place of 3-cyclopropyl-1H-pyrazol-5-amine: 1H NMR (400 MHz, DMSO-d$_6$) δ 12.44 (s, 1H), 10.38 (s, 1H), 8.18 (s, 1H), 8.00-6.00 (br s, 2H), 4.88 (t, J=6.8 Hz, 1H), 3.92-3.86 (m, 1H), 3.79-3.72 (m, 1H), 2.26-2.16 (m, 1H), 1.99-1.83 (m, 3H); MS (ESI+) m/z=266 [M+1]+.

Referential Example 5

2-Chloro-N-(5-cyclopropyl-1H-pyrazol-3-yl)-6-methylpyrimidin-4-amine (189)

A mixture of 5-cyclopropyl-1H-pyrazol-3-amine (1.98 g, 16.07 mmol), 2,4-dichloro-6-methyl-pyrimidine (2.62 g, 16.07 mmol), DIPEA (5.7 mL, 32.15 mmol) and anhydrous EtOH (50 mL) was stirred at 70° C. under N$_2$ for 3 d. The reaction mixture was cooled and poured into water (ca. 700 mL). The reaction was stirred at RT overnight until solid precipitated out. The solid was filtered, washed with additional water and pumped dry under high-vacuum to afford 2.37 g (59%) of 189 as a solid: 1H NMR (400 MHz, DMSO-d6) δ 12.12 (s, 1H), 10.08 (s, 1H), 7.04 (br s, 1H), 5.93 (br s, 1H), 2.27 (s, 3H), 1.93 to 1.84 (m, 1H), 0.96-0.88 (m, 2H), 0.70-0.64 (m, 2H).

2-Chloro-N-(5-cyclopropyl-1H-pyrazol-3-yl)-5-methylpyrimidin-4-amine (184) was prepared analogously except 2,4-dichloro-5-methyl-pyrimidine was used in place 2,4-dichloro-6-methyl-pyrimidine: 1H NMR (400 MHz, DMSO-d$_6$) δ 12.17 (s, 1H), 9.23 (s, 1H), 7.97 (s, 1H), 6.28 (s, 1H), 2.12 (s, 3H), 1.97-1.85 (m, 1H), 0.93 (d, J=7.4 Hz, 2H), 0.69 (d, J=4.6 Hz, 2H); MS (ESI) m/z=250.2 [M+1]$^+$.

2-Chloro-N-(5-cyclopropyl-1H-pyrazol-3-yl)-6-(trifluoromethyl)pyrimidin-4-amine (186) was prepared analogously except 2,4-dichloro-6-(trifluoromethyl)pyrimidine was used in place of 2,4-dichloro-6-methyl-pyrimidine: 1H NMR (400 MHz, DMSO-d6): δ 12.35 (br d, J=30.2 Hz, 1H), 10.97 (s, 1H), 8.14 (s, 0.50H, rotamer), 7.13 (s, 0.50H, rotamer), 6.38 (s, 0.50H, rotamer), 5.73 (s, 0.50H, rotamer), 1.91 (s, 1H), 0.98-0.90 (m, 2H), 0.70 (q, J=5.5 Hz, 2H); MS (ESI) m/z=304.2/306.2 [M+1]+.

Referential Example 6

5-(3,3-Difluorocyclobutyl)-1H-pyrazol-3-amine (85)

Step 1:
To a solution of 3-oxocyclobutanecarboxylic acid (20.0 g, 175.3 mmol) in DCM (500 mL) was added satd. aq. NaHCO$_3$ (293 mL), tetrabutyl ammonium bromide (75.3 g, 227.9 mmol) and 4-methoxybenzyl chloride (33.0 g, 210.4 mmol) and the mixture was stirred at RT overnight. After the reaction was completed, the mixture was diluted with water and twice extracted with DCM (250 mL). The organic layer was washed with water, dried (Na$_2$SO$_4$), filtered and concentrated in vacuo. The crude product was purified by SiO$_2$ chromatography eluting with petroleum ether/EtOAc (8:1) to afford 15.2 g (37%) of 4-methoxybenzyl 3-oxocyclobutanecarboxylate as an off-white solid.

Step 2:

To a solution of 4-methoxybenzyl 3-oxocyclobutanecarboxylate (15.2 g, 64.9 mmol) in DCM (300 mL) was added DAST (20.9 g, 130 mmol) and the mixture was stirred at RT overnight. After the reaction was complete, 5% aqueous NaHCO3 was added, and the mixture was twice extracted with DCM (300 mL). The combined organic layer was washed with water (200 mL), dried (Na$_2$SO$_4$), filtered and concentrated in vacuo. The crude product, was purified by SiO$_2$ chromatography eluting with petroleum ether/EtOAc (10:1) to afford 14.0 g (84%) of 4-methoxybenzyl 3,3-difluorocyclobutanecarboxylate.

Step 3:

To a solution of NaH (2.85 g, 71.1 mmol) in dioxane (200 mL) was added MeCN (2.92 g. 71.1 mmol). The mixture was stirred for 20 min, then the solution of 4-methoxybenzyl 3,3-difluorocyclobutanecarboxylate (14.0 g, 54.7 mmol) in dioxane (100 mL) was added dropwise. After the mixture was heated at reflux for 4 h, the reaction mixture was poured into water (400 mL) and extracted with EtOAc (200 mL). The pH of the aqueous layer adjusted to 7 with 3N HCl and extracted with EtOAc. The organic layer was washed with brine (200 mL), dried (Na$_2$SO$_4$), filtered and concentrated to afford 13.5 g crude 3-(3,3-difluorocyclobutyl)-3-oxopropanenitrile which was used in the next step without purification.

Step 4:

To a solution of 3-(3,3-difluorocyclobutyl)-3-oxopropanenitrile (12.5 g, 78.6 mmol) in EtOH (250 mL) was added hydrazine hydrate (5.9 g, 117.9 mmol) and the resulting mixture was stirred at 75° C. overnight. After concentrating the reaction mixture in vacuo, the residue was redissolved in EtOAc (500 mL) and washed with satd. aq. NaHCO3. The aqueous layer was extracted with EtOAc and the combined extracts washed with brine (100 mL), dried (Na$_2$SO$_4$), filtered and concentrated in vacuo. The crude product was purified by SiO$_2$ chromatography eluting with DCM/MeOH (10:1) to afford 3.46 g (39%) of 85 as a light yellow solid: 1H NMR (400 MHz, DMSO-d6) δ 11.20 (br s, 1H), 5.23 (s, 1H), 4.65 (br s, 2H), 3.16-3.13 (m, 1H), 2.88-2.84 (m, 2H), 2.64-2.57 (m, 2H); MS (ESI+) m/z=174 [M+1]+.

Referential Example 7

3-(3-Amino-1H-pyrazol-5-yl)propanenitrile (87)

Step 1:

To a solution of (4-methoxyphenyl)methanol (76.3 g, 552.4 mmol) in anhydrous toluene (1 L) at 0° C. was added portionwise NaH (27.6 g, 630.5 mmol) over a period of 30 min, followed by ethyl 3-bromopropanoate (100 g, 552.4 mmol). The mixture was stirred at RT for 3 h and then quenched with 20% aqueous NH$_4$Cl (500 mL). The organic layer was separated, and the aqueous layer was extracted with EtOAc (2×500 mL). The combined organic layers were washed with brine, dried (Na$_2$SO$_4$) and then concentrated in vacuo to give ethyl 3-((4-methoxybenzyl)oxy)propanoate (112 g, 85%) as colorless oil.

Step 2:

To a solution of MeCN (31.8 mL, 611.0 mmol) in anhydrous THF (500 mL) at −78° C. was slowly added n-BuLi (2.5 M, 244.4 mL, 611.0 mmol) The mixture was stirred at the same temperature for 1 h and to it was added a solution of at −78° C. was slowly. The mixture was stirred added n-BuLi (2.5 M, 244.4 mL, 611.0 mmol). The mixture was stirred ethyl 3-((4-methoxybenzyl)oxy)propanoate (112 g, 470.0 mmol) in THF (200 mL). The resulting mixture was stirred at −40° C. for 2 h and then quenched with 1 N aqueous HCl (300 mL). The organic layer was separated, and the aqueous layer was extracted with EtOAc (3×300 mL). The combined organic layers were washed with brine, dried (Na$_2$SO$_4$) and then concentrated in vacuo to give 5-((4-methoxybenzyl)oxy)-3-oxo-pentanenitrile (78 g, 79%) as yellow oil.

Step 3:

A mixture of 5-((4-methoxybenzyl)oxy)-3-oxo-pentanenitrile (78 g, 334.4 mmol) and hydrazine hydrate (50 g, 1 mol) in EtOH (500 mL) was heated under reflux for 16 h. After cooling to RT, the solvent was removed in vacuo and the residue was partitioned between DCM (400 mL) and water (400 mL). The organic layer was separated and washed with brine, dried (Na$_2$SO$_4$), and then concentrated in vacuo. The residue was purified by SiO$_2$ chromatography eluting with 5% MeOH/DCM to afford 66 g (80%) of 5-(2-((4-methoxybenzyl)oxy)ethyl)-1H-pyrazol-3-amine as a yellow solid.

Step 4:

A solution 5-(2-((4-methoxy-benzyl)oxy)-ethyl)-1H-pyrazol-3-amine (66 g, 334.4 mmol) in TFA (300 mL) was heated under reflux for 16 h. After being cooled to RT, the solvent was removed in vacuo, and the residue was partitioned between DCM (400 mL) and 2 N aqueous NaHCO$_3$ (200 mL). The organic layer was separated and the aqueous layer was extracted with DCM (3×100 mL). The combined organic layers were washed with brine, dried (Na$_2$SO$_4$) and then concentrated in vacuo to afford 13 g (38%) of 2-(3-amino-1H-pyrazol-5-yl)ethanol as a yellow solid.

Step 5:

To a solution of 2-(3-amino-1H-pyrazol-5-yl)ethanol (13 g, 102.2 mmol) in DCM (200 mL) was added PBr$_3$ (83 g, 306.7 mmol). The reaction mixture was heated under reflux for 3 h and then cooled to −10° C. and carefully quenched with aq satd Na$_2$CO$_3$ (200 mL). The resulting mixture was extracted with DCM (3×200 mL), and the Na2CO3 (200 mL). The resulting mixture was extracted with DCM (3×200 mL) combined organic layers were washed with brine, dried over anhydrous Na$_2$SO$_4$, and then concentrated in vacuo to give 5-(2-bromoethyl)-1H-pyrazol-3-amine (9.3 g, 48%) as a yellow solid.

Step 6:

To a solution of 5-(2-bromoethyl)-1H-pyrazol-3-amine (9.3 g, 48.9 mmol.) in acetonitrile (100 mL) was added a solution of NaCN (2.88 g, 58.6 mmol) in water (3 mL). The reaction mixture was stirred at −70° C. for 16 h and then concentrated in vacuo to remove the solvent. The residue was partitioned between DCM and brine. The organic layer was dried (Na$_2$SO$_4$) and then concentrated in vacuo. The crude material was crystallized from MeOH-EtOAc to afford 4 g (60%) of 3-(3-amino-1H-pyrazol-5-yl)propanenitrile (87) as a yellow solid.

$^1$H NMR (400 MHz, CDCl3) δ 2.66 (2H, t, J=7.2 Hz), 2.92 (2H, t, J=7.2 Hz), 5.54 (1H, s). MS (ESI+) m/z: 137 [M+1]$^+$.

Referential Example 8

5-(Oxetan-3-yl)-1H-pyrazol-3-amine (91)

Step 1:

Into a 3 L 4-necked round-bottom flask under nitrogen was placed a solution of 3-nitro-1H-pyrazole (100 g, 884.37 mmol, 1.00 equiv.) in THF (1.5 L), followed by the addition of NaH (53 g, 1.32 mol, 1.50 equiv, 60% suspension) batchwise at 0° C. The resulting solution was stirred at 0° C. for 1 h. A solution of [2-(chloromethoxy)ethyl]trimethylsilane (117.4 g, 704.17 mmol, 1.20 equiv) in THF (500 mL) was then added dropwise with stirring at 0° C. The resulting solution was stirred at 25° C. for 1 h, quenched by the addition of EtOH (200 mL), concentrated under vacuum and diluted with 2 L of EtOAc. The resulting mixture was washed with 2×1 L of brine, dried ($Na_2SO_4$) and concentrated in vacuo. The residue was triturated with 200 mL of petroleum ether. The solids were collected by filtration and washed with petroleum ether (2×500 mL) to afford 125 g (52%) of 3-nitro-1-[[2-(trimethylsilyl)ethoxy]methyl]-1H-pyrazole as a yellow solid.

Step 2:

Into a 2 L round-bottom flask purged and maintained with an inert atmosphere of nitrogen was placed 3-nitro-1-[[2-(trimethylsilyl)ethoxy]methyl]-1H-pyrazole (125.0 g, 513.69 mmol, 1.00 equiv.), MeOH (1 L), and Pd/C (13.0 g). The suspension was the placed under an atmosphere of hydrogen. The resulting solution was stirred at 30° C. for 4 h. The solids were then filtered and the filtrate was concentrated under vacuum to afford of 1-[[2-(trimethylsilyl)ethoxy]methyl]-1H-pyrazol-3-amine (110 g 80% yield) as a light yellow solid.

Step 3:

Into a 2 L round-bottom flask under nitrogen was placed 1-[[2-(trimethylsilyl)ethoxy]methyl]-1H-pyrazol-3-amine (110 g, 515.58 mmol, 1.00 equiv.), toluene (1.2 L), hexane-2,5-dione (60.0 g, 525.66 mmol, 1.00 equiv.), and 4-methylbenzene-1-sulfonic acid (1.0 g, 5.81 mmol, 0.10 equiv.). The resulting solution was heated to reflux for 2 h, cooled and concentrated under vacuum. The residue was purified by $SiO_2$ chromatography eluting with EtOAc/petroleum ether (1:50) to afford 3-(2,5-dimethyl-1H-pyrrol-1-yl)-1-[[2-(trimethylsilyl)ethoxy]methyl]-1H-pyrazole (132 g, 83%) as a light yellow solid.

Step 4:

Into a 5 L 4-necked round-bottom flask under nitrogen was placed 3-(2,5-dimethyl-1H-pyrrol-1-yl)-1-[[2-(trimethylsilyl)ethoxy]methyl]-1H-pyrazole (132.0 g, 452.89 mmol, 1.00 equiv.) in THF (2 L), followed by the addition of butyl lithium (208 mL, 2.4 M, 1.10 equiv) dropwise with stirring at −78° C. over 15 min. The resulting solution was stirred at −50° C. for 40 min. To this was added a solution of oxetan-3-one (40.0 g, 555.07 mmol, 1.20 equiv) in THF (500 mL), dropwise with stirring at −78° C. over 30 min. The resulting solution was stirred at −78° C. for 30 min then quenched by the addition of 2 L of satd. aq. $NH_4Cl$. The mixture was concentrated in vacuo and extracted with 3×1 L of EtOAc. The combined organic layers were washed with 2×1 L of water and 1×500 mL of brine, dried ($Na_2SO_4$) and concentrated in vacuo. The residue was purified by $SiO_2$ chromatography eluting with EtOAc/petroleum ether (1:20-1:5) to afford 3-[3-(2,5-dimethyl-1H-pyrrol-1-yl)-1-[[2-(trimethylsilyl)ethoxy]methyl]-1H-pyrazol-5-yl]oxetan-3-ol (142.0 g, 82% yield) as a light yellow oil.

Step 5:

Into a 2 L 3-necked round-bottom flask under nitrogen was placed THF (800 mL), followed by the addition of NaH (10.4 g, 260 mmol, 1.50 equiv., 60% suspension) in several batches at 0° C. over 10 min. To this suspension was added a solution of 3-[3-(2,5-dimethyl-1H-pyrrol-1-yl)-1-[[2-(trimethylsilyl)ethoxy]methyl]-1H-pyrazol-5-yl]oxetan-3-ol (63.0 g, 173.3 mmol, 1.0 equiv.) in THF (300 mL), dropwise with stirring at 0° C. over 30 min. The resulting solution was stirred at 0° C. for 30 min. To the mixture was added a solution of $CS_2$ (19.7 g, 259.21 mmol, 1.50 equiv.) in THF (100 mL), dropwise with stirring at 0° C. over 20 min. The resulting solution was stirred at 0° C. for 1 h. To the mixture was added a solution of iodomethane (37.0 g, 260.7 mmol, 1.5 equiv.) in THF (100 mL), dropwise with stirring at 0° C. over 10 min. The resulting solution was stirred at 0° C. for 1 h, then quenched by the addition of 300 mL of satd. aq. $NH_4Cl$, concentrated in vacuo, diluted with 1 L of water and extracted with 3×1 L of EtOAc. The combined organic layers were washed with 2×1 L of water and 2×500 mL of brine, dried ($Na_2SO_4$) and concentrated in vacuo to afford ([3-[3-(2,5-dimethyl-1H-pyrrol-1-yl)-1-[[2-(trimethylsilyl)ethoxy]-methyl]-1H-pyrazol-5-yl]oxetan-3-yl]oxy)(methylsulfanyl)methanethione (80.0 g, 97% yield) as a yellow oil.

Step 6:

Into a 2 L round-bottom flask under nitrogen was placed a solution of ([3-[3-(2,5-dimethyl-1H-pyrrol-1-yl)-1-[[2-(trimethylsilyl)ethoxy]methyl]-1H-pyrazol-5-yl]oxetan-3-yl]oxy)(methylsulfanyl)methanethione (97.0 g, 213.8 mmol, 1.0 equiv.) in toluene (1.2 L), tributyltin hydride (74.7 g, 256.7 mmol, 1.2 equiv.), and AIBN (7.0 g, 42.6 mmol, 0.2 equiv.). The resulting solution was stirred at 120° C. for 3 h, cooled to 30° C. and concentrated in vacuo. The residue was purified by $SiO_2$ chromatography eluting with EtOAc/PE (1:100-1:5) to afford 3-(2,5-dimethyl-1H-pyrrol-1-yl)-5-(oxetan-3-yl)-1-[[2-(trimethylsilyl)ethoxy]methyl]-1H-pyrazole (30.0 g, 38% yield) as a yellow oil.

Step 7:

Into a 250-mL round-bottom flask under nitrogen was placed 3-(2,5-dimethyl-1H-pyrrol-1-yl)-5-(oxetan-3-yl)-1-[[2-(trimethylsilyl)ethoxy]methyl]-1H-pyrazole (12.0 g, 34.5 mmol, 1.0 equiv.), followed by the addition of a solution of TBAF (120 g, 5.0 equiv) in THF (120 mL). The resulting solution was stirred at 88° C. for 8 h, cooled to 30° C., concentrated in vacuo and diluted with 200 mL of EtOAc. The resulting mixture was washed with 2×300 mL of water and 2×100 mL of brine, dried ($Na_2SO_4$) and concentrated in vacuo. The residue was purified by $SiO_2$ chromatography eluting with EtOAc/PE (1:100-1:3) to afford 3-(2,5-dimethyl-1H-pyrrol-1-yl)-5-(oxetan-3-yl)-1H-pyrazole (4.0 g, 48% yield) as a white solid.

Step 8:

Into a 250-mL 3-necked round-bottom was placed 3-(2,5-dimethyl-1H-pyrrol-1-yl)-5-(oxetan-3-yl)-1H-pyrazole (4.0 g, 18.4 mmol, 1.0 equiv.), EtOH (100 mL), water (40 mL), and $NH_2OH \cdot HCl$ (10.3 g, 148.2 mmol, 8.0 equiv.), followed by the addition of $NaHCO_3$ (9.9 g, 117.8 mmol, 6.4 equiv.) portionwise. The resulting solution was stirred at 100° C. for 24 h, then cooled to 30° C. and concentrated in vacuo. The residue was diluted with 150 mL of THF. The solids were collected by filtration and dissolved in 200 mL of EtOH, filtered and the filtrate concentrated in vacuo. The residue was purified by chromatography on neutral alumina eluting with a DCM/MeOH gradient (1 to 10% MeOH) to afford 0.5 g (19%) of 5-(oxetan-3-yl)-1H-pyrazol-3-amine (91) as a white solid.

MS (ESI) m/z: 140 [M+H]+, 1H NMR (200 MHz, DMSO-d6) δ 5.39 (s, 1H), 4.82-4.77 (m, 2H), 4.59-4.56 (m, 2H), 4.13-4.02 (m, 1H).

Referential Example 9

5-(Difluoromethyl)-1H-pyrazol-3-amine (93)

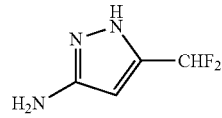

Step 1:

A flame-dried flask was charged with n-butyllithium solution (145 mL, 363 mmol, 2.5 M in hexanes) in dry THF (800 mL) under inert gas atmosphere and cooled to −78° C. MeCN (13.0 g, 318 mmol) was slowly added, and the resulting mixture was stirred for 1 h at −70° C. Ethyl difluoroacetate (25.0 g, 227 mmol) was slowly added over 10 min while maintaining the temperature below −69° C. The reaction mixture was stirred for 2 h at −45° C. and then quenched by addition of 2N HCl solution (4.8 mL) while maintaining the temperature below −20° C. The resulting clear solution was warmed to RT and then concentrated in vacuo to afford crude 4,4-difluoro-3-oxobutanenitrile, which was directly used in the next step.

Step 2:

To a solution of 4,4-difluoro-3-oxobutanenitrile in EtOH (200 mL) was added hydrazine hydrate (30 mL). The reaction was heated at reflux for 12 h before cooling to RT. After evaporation in vacuo, the residue was extracted into DCM. The organic layers were washed with water, brine, dried (MgSO4). After filtration, the solvent was evaporated in vacuo. The crude product was purified by SiO2 chromatography to afford 5-(difluoromethyl)-1H-pyrazol-3-amine (8.0 g, 27% for two steps) as an oil: MS (ESI) m/z: 134.0 [M+1]+.

Referential Example 10

(4-Ethyl-1-tetrahydropyran-2-yl-benzimidazol-5-yl)methanamine (95)

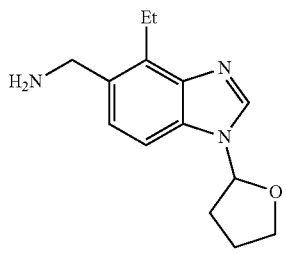 [SMILES: CCc1c(CN)ccc2c1ncn2C1CCCO1]

Step 1:

To a solution of 1H-benzo[d]imidazole-5-carboxylic acid (1.62 g, 10 mmol) in THF (20 mL), 3,4-dihydro-2H-pyran (2 mL) and CSA (100 mg) were added. The mixture was heated at reflux for 24 h under argon. Removal of solvent followed by SiO2 chromatography afforded 1-(tetrahydro-2H-pyran-2-yl)-1H-benzo[d]imidazole-5-carboxylic acid as a light red solid (1.5 g, 60% yield).

Step 2:

To a solution of 1-(tetrahydro-2H-pyran-2-yl)-1H-benzo[d]imidazole-5-carboxylic acid (170 mg, 0.69 mmol) in DCM (5 mL) was added 1-ethyl-3-(3-dimethylaminopropyl)carbodiimide hydrochloride (190 mg, 1 mmol), HOBt (160 mg, 1 mmol), TEA (0.3 mL) and N-methoxy-methanamine hydrochloride (100 mg, 1 mmol). The mixture was stirred at RT overnight. The mixture was poured into water and extracted with EtOAc. The organics were washed sequentially with water and brine, then dried (Na2SO4). Removal of solvent followed by SiO2 chromatography afforded N-methoxy-N-methyl-1-(tetrahydro-2H-pyran-2-yl)-1H-benzo[d]imidazole-5-carboxamide (140 mg, 85% yield) as a light yellow oil.

Step 3:

A solution of EtMgBr (0.72 mL, 1 mol/L) was added to N-methoxy-N-methyl-1-(tetrahydro-2H-pyran-2-yl)-1H-benzo[d]imidazole-5-carboxamide (70 mg, 0.24 mmol) in THF at 0° C. under argon. The mixture was stirred at 0° C. for 2 h. A solution of NH4Cl was added, carefully, to quench the reaction. The mixture was poured into water and extracted with EtOAc. The organics were washed sequentially with water and brine, then dried (Na2SO4). Removal of solvent followed by SiO2 chromatography afforded 1-(1-(tetrahydro-2H-pyran-2-yl)-1H-benzo[d]imidazol-5-yl)propan-1-one as a colorless oil (45 mg, 72% yield).

Step 4:

Hydroxylamine hydrochloride (54 mg, 0.78 mmol) and sodium acetate (100 mg, 1 mmol) were added to a solution of 1-(1-(tetrahydro-2H-pyran-2-yl)-1H-benzo[d]imidazol-5-yl)propan-1-one (100 mg, 0.39 mmol) in MeOH (5 mL). The mixture was refluxed overnight. The mixture was poured into water and extracted with EtOAc. The organics were washed sequentially with water and brine, then (Na2SO4). Removal of solvent followed by SiO2 chromatography afforded 1-(1-(tetrahydro-2H-pyran-2-yl)-1H-benzo[d]imidazol-5-yl)propan-1-one oxime (95 mg, 90% yield) as a light yellow oil.

Step 5:

To a solution of 1-(1-(tetrahydro-2H-pyran-2-yl)-1H-benzo[d]imidazol-5-yl)propan-1-one oxime (30 mg, 0.11 mmol) in THF (3 mL), Raney-Ni (50 mg) was added. The mixture was stirred at RT overnight. Removal of solvent followed by reverse-phase chromatography gave (4-ethyl-1-tetrahydropyran-2-yl-benzimidazol-5-yl)methanamine (10 mg, 35% yield) as a colorless oil.

MS (ESI+) m/z: 260 [M+1]+; 1H NMR (400 MHz, CDCl3) δ 7.98 (m, 1H), 7.64 (m, 1H), 7.40 (m, 1H), 7.14-7.36 (m, 1H), 5.40-5.45 (m, 1H), 4.06 (m, 1H), 3.85 (m, 1H), 3.70 (m, 1H), 2.02-2.10 (m, 3H), 1.62-1.72 (m, 7H), 0.77-0.84 (m, 3H).

Referential Example 11

(4-Methoxy-1-(tetrahydro-2H-pyran-2-yl)-1H-benzo[d]imidazol-5-yl)methanamine (97)

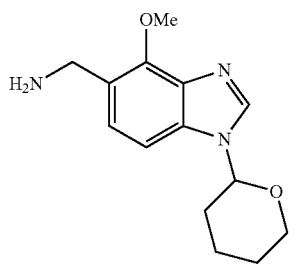 [SMILES: COc1c(CN)ccc2c1ncn2C1CCCCO1]

Step 1:

A 20 L four-necked round bottom flask fitted with an overhead stirrer was dried and cooled under a stream of nitrogen then charged with a solution of 2,4-dinitroaniline (50 g, 0.27 mol, 1.0 equiv.) and KOH pellets (45.96 g, 0.82 mol, 3.0 equiv.) in MeOH (2500 mL). The reaction mixture was heated at 50° C. To this solution was added dropwise an aqueous solution of sodium hypobromite, prepared by adding bromine (436.70 g, 2.73 mol, 10 equiv.) to a cold solution of NaOH (275.04 g, 6.826 mol, 25.0 eq) in water (4 L), at 46-48° C. for 3 h. The reaction mixture was kept at 48° C. for an additional 20 min and then cooled to RT. The yellow precipitate was collected by filtration and dried in vacuo to afford 5-bromo-4-methoxybenzofurazanoxide (15 g, crude). The crude material was taken directly to the next step.

1H NMR (300 MHz, CDCl$_3$): δ 4.46 (s, 3H), 6.92-6.94 (d, 1H), 7.27-7.29 (d, 1H). GCMS (ESI) m/z: 244 [M−1]$^+$.

Step 2:

A 2 L Parr shaker bottle was dried and cooled under a stream of nitrogen then charged with 5-bromo-4-methoxy-benzofurazanoxide (100 g, 0.44 mol, 1.0 equiv.) in EtOAc (1 L) and 10% Pd/C (10% w/w, 10.0 g) was added. The reaction was then stirred at RT overnight under hydrogen. The reaction mixture was filtered through a Celite® pad and concentrated in vacuo to afford 4-bromo-3-methoxy-benzene-1,2-diamine (61.0 g, crude) as a dark brown semi solid. The crude material was taken directly to the next step.

Step 3:

A 1 L four-necked round bottom flask fitted with a magnetic stirrer was dried and cooled under a stream of nitrogen then charged with 4-bromo-3-methoxy-benzene-1,2-diamine (61 g, 0.28 mol, 1.0 equiv.) in formic acid (200 mL). The reaction mixture was heated at 100° C. for 2 h, cooled and quenched with ice water (1 L). The reaction mixture was basified with 10% NaOH solution and extracted with ethyl acetate (2×1000 mL). The separated organic layers were combined, washed with brine solution (750 mL), dried (Na$_2$SO$_4$), filtered and concentrated in vacuo. The crude material was purified by SiO$_2$ chromatography eluting with an EtOAc/hexane gradient (30-50% EtOAc) to afford 6-bromo-7-methoxy-1H-benzoimidazole (36 g, crude) as a brown solid. 1H NMR (300 MHz, DMSO-d$_6$): δ 4.26 (br, 3H), 7.16 (s, 1H), 7.29-7.32 (d, 1H), 8.19 (s, 1H), 12.67 (br, 1H).

Step 4:

A 500 ml tube was charged with 6-bromo-7-methoxy-1H-benzoimidazole (36 g, 0.16 mol, 1.0 equiv.), dihydropyran (40.01 g, 0.48 mol, 3.0 equiv.) and pyridinium-p-toluenesulfonate (7.96 g, 0.032 mol, 0.2 equiv.) in EtOAc (400 mL), sealed and the reaction mixture was heated at 90° C. overnight. The reaction mixture was concentrated in vacuo and the crude product was purified by SiO$_2$ chromatography eluting with an EtOAc/hexane gradient (30-40% EtOAc) to afford 5-bromo-4-methoxy-1-(tetrahydro-pyran-2-yl)-1H-benzoimidazole (30 g, 60% yield) as a brown solid.

1H NMR (300 MHz, DMSO-d$_6$): δ 1.54-1.77 (m, 3H), 1.92-1.96 (m, 2H), 1.98-2.00 (m, 1H), 3.66-3.75 (m, 1H), 3.90-3.97 (m, 1H), 4.29 (s, 3H), 5.60-5.64 (d, 1H), 7.24-7.27 (d, 1H), 7.37-7.40 (d, 1H), 8.37 (s, 1H).

Step 5:

A 1 L three-necked round bottom flask fitted with an overhead stirrer was dried and cooled under a stream of nitrogen then charged with 5-bromo-4-methoxy-1-(tetrahydro-pyran-2-yl)-1H-benzoimidazole (30 g, 0.096 mol, 1.0 equiv.) in 1,4-dioxane (300 mL) and water (60 mL). The mixture was degassed with nitrogen. To the degassed solution at RT was added sequentially trans-β-styrene boronic acid (14.26 g, 0.096 mol, 1.0 equiv.), Cs$_2$CO$_3$ (62.82 g, 0.19 mol, 2.0 equiv.), Pd(II)Cl$_2$(PPh$_3$)$_2$ (3.38 g, 0.004 mol, 0.05 equiv.) then the reaction was heated with stirring at 100° C. for 6 h. The reaction mixture was quenched with ice cold water (1 L) and extracted with EtOAc (2×1 L). The organic layers were combined, washed with brine solution (500 mL), dried (Na$_2$SO$_4$), filtered and concentrated in vacuo. The crude material was purified by SiO$_2$ chromatography eluting with an EtOAc/hexane gradient (40-50% EtOAc) to afford 4-methoxy-5-styryl-1-(tetrahydro-pyran-2-yl)-1H-benzoimidazole (25 g, 77%) as a brown solid.

1H NMR (300 MHz, DMSO-d$_6$): δ 1.57-1.67 (m, 2H), 1.70-1.75 (m, 1H), 1.97-2.00 (m, 2H), 2.10-2.22 (m, 1H), 3.69-3.77 (m, 1H), 3.87-3.99 (m, 1H), 4.31 (s, 3H), 5.62-5.64 (d, 1H), 7.12-7.43 (m, 6H), 7.51-7.62 (m, 4H), 8.33 (s, 1H). MS (ESI) m/z: 335 [M+1]+.

Step 6:

A 1 L three-necked round bottom flask fitted with an overhead stirrer was dried and cooled under a stream of nitrogen then charged with 4-methoxy-5-styryl-1-(tetrahydro-pyran-2-yl)-1H-benzoimidazole (25 g, 0.074 mol, 1.0 equiv.) in dioxane (250 mL) and water (80 mL). To this solution was added sodium periodate (36.77 g, 0.17 mol, 2.3 equiv.) and osmium tetroxide (15 mL, 4% aq. soln.) at 0° C., and the reaction mixture was stirred at RT overnight. The reaction mixture was quenched with ice cold water (1 L) and extracted with EtOAc (2×750 mL). The organic layers were combined, washed with brine (500 mL), dried (Na$_2$SO$_4$), filtered and concentrated in vacuo. The crude material was purified by SiO$_2$ chromatography eluting with an EtOAc/hexane gradient (40-50% EtOAc) to afford 4-methoxy-1-(tetrahydro-pyran-2-yl)-1H-benzoimidazole-5-carbaldehyde (15 g, 77%) as a pale yellow solid.

MS (ESI) m/z: 261 [M+1]$^+$; 1H NMR (300 MHz, CDCl$_3$): δ 1.71-1.84 (m, 3H), 2.04-2.32 (m, 3H), 3.72-3.81 (m, 1H), 4.13-4.18 (m, 1H), 4.58 (s, 3H), 5.47-5.51 (d, 1H), 7.16-7.14 (d, 1H), 7.79-7.82 (d, 1H), 8.11 (s, 1H), 10.52 (s, 1H).

Step 7:

A 1 L three-necked round bottom flask equipped with a magnetic stirrer was dried and cooled under a stream of nitrogen then charged with 4-methoxy-1-(tetrahydro-pyran-2-yl)-1H-benzoimidazole-5-carbaldehyde (15 g, 0.057 mol, 1.0 equiv.), NaOAc (15.67 g, 0.12 mol, 2.0 equiv.), hydroxyamine hydrochloride (8.01 g, 0.12 mol, 2.0 equiv.) and MeOH (300 mL) and the reaction mixture was stirred at RT for 1 h. The reaction mixture was then concentrated and the residue was dissolved in EtOAc (1000 mL). The organic layer was washed with water (2×300 mL) and brine, dried (Na$_2$SO$_4$), filtered and concentrated in vacuo to afford 4-methoxy-1-(tetrahydro-pyran-2-yl)-1H-benzoimidazole-5-carbaldehyde oxime (14.5 g, 93% yield).

1H NMR (400 MHz, DMSO-d$_6$): δ 1.58-1.64 (m, 2H), 1.71-1.75 (m, 1H), 2.01-2.02 (m, 2H), 2.13-2.22 (m, 1H), 3.70-3.77 (m, 1H), 3.97-4.00 (d, 1H), 4.31 (s, 3H), 5.63-5.66 (d, 1H), 7.31-7.33 (d, 1H), 7.59-7.61 (d, 1H), 8.37-8.38 (d, 1H), 11.00 (s, 1H); LC-MS: 276 (M+1).

Step 8:

A 1 L autoclave was cooled under a stream of nitrogen and charged with 4-methoxy-1-(tetrahydro-pyran-2-yl)-1H-benzoimidazole-5-carbaldehyde oxime (14.50 g, 0.052 mol, 1.0 equiv.) and aqueous ammonia (30 mL) in MeOH (300 mL). To this was added Raney Nickel (15.0 g, w/w) and the reaction was stirred at RT under hydrogen (pressure ~60 psi) overnight. The reaction mixture was then filtered through a Celite® pad and the filtrate was concentrated in vacuo. The crude material was purified by neutral alumina column chromatography using a MeOH/DCM gradient (5 to 10% MeOH to afford (4-methoxy-1-(tetrahydro-2H-pyran-2-yl)-1H-benzo[d]imidazol-5-yl)methanamine (97, 8.0 g, 57%) as a brown viscous oily liquid.

MS (ESI) m/z: 262 [M+1]+; 1H NMR (400 MHz, DMSO-d$_6$): δ 1.58-1.64 (m, 2H), 1.68-1.75 (m, 1H), 1.95-1.98 (m, 2H), 2.13-2.25 (m, 1H), 3.68-3.80 (m, 3H), 3.92-3.98 (d, 1H), 4.31 (s, 3H), 5.58-5.61 (d, 1H), 7.10-7.24 (m, 2H), 8.29 (s, 1H); $^1$H-NMR (400 MHz, CDCl$_3$): δ 1.68-1.75 (m, 3H), 2.07-2.10 (m, 3H), 2.85 (br, 2H), 3.73-3.74 (m, 1H), 3.94 (br, 2H), 4.10-4.13 (d, 1H), 4.40 (s, 3H), 5.42-5.44 (d, 1H), 7.08-7.10 (d, 1H), 7.17-7.19 (d, 1H), 7.98 (s, 1H).

Referential Example 12

(4-Ethyl-1-(tetrahydro-2H-pyran-2-yl)-1H-benzo[d]imidazol-5-yl) methanamine (99)

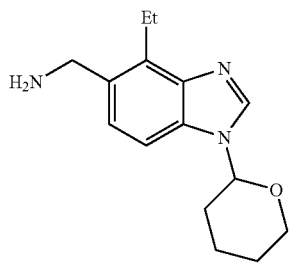 [SMILES: CCc1c(CN)ccc2c1ncn2C1CCCCO1]

Step 1:

To a solution of 5-nitro-1H-benzo[d]imidazole 1 (100 g, 0.613 mol) in THF (750 mL) was added TEA (171.71 mL, 1.23 mol, 2 equiv.) and di-tert-butyl dicarbonate (133.65 g, 0.61 mol, 1.5 equiv.) at RT, and the reaction mixture was stirred for 16 h. The reaction mixture was quenched with water and extracted with EtOAc. The combined organic layers were washed with brine and then dried (MgSO$_4$), filtered, and concentrated to afford tert-butyl 5-nitro-1H-benzo[d]imidazole-1-carboxylate (150 g, 94% yield) as an off white solid. The crude material was used for the next step without further purification.

Step 2:

To a solution of tert-butyl 5-nitro-1H-benzo[d]imidazole-1-carboxylate (150 g, 0.56 mol) in dry THF (1500 mL) was added EtMgBr (3.0 M in THF, 1.12 mol, 2 equiv.) dropwise at −15° C. The reaction mixture was stirred at −15° C. for 2 h. A solution of DDQ (129 g, 1.12 mol, 2 equiv.) in THF (120 mL) was added at −15° C., then the reaction mixture was warmed to RT and the stirring was continued for 2 h. The reaction mixture was quenched with water and extracted with EtOAc. The combined organic layers were washed with brine and then (Na$_2$SO$_4$), filtered, and concentrated. The crude material was purified by SiO$_2$ chromatography eluting with 10% EtOAc/hexane to afford tert-butyl 4-ethyl-5-nitro-1H-benzo[d]imidazole-1-carboxylate (20 g, 12% yield) as a yellow solid.

Step 3:

To a solution of tert-butyl 4-ethyl-5-nitro-1H-benzo[d]imidazole-1-carboxylate (20.0 g, 0.07 mol) in dry MeOH (500 mL) was added Pd/C (1.5 g). The suspension was then stirred under hydrogen (3 kg pressure) for 6 h. After completion, the reaction mixture was filtered through a celite pad and concentrated to give tert-butyl 5-amino-4-ethyl-1H-benzo[d]imidazole-1-carboxylate (13.6 g, 76% yield). The crude product was used for the next step without further purification.

Step 4:

To a solution of tert-butyl 4-ethyl-5-nitro-1H-benzo[d]imidazole-1-carboxylate (13.6 g, 0.052 mol) in dry DCM (140 mL) was added TFA (20 mL, 0.26 mol, 5.0 equiv.), and the reaction mixture was heated at 40° C. for 16 h. The reaction mixture was concentrated and the crude solid re-dissolved in an acetone and water mixture (1:1, 40 mL). Concentrated HCl (14 mL) and sodium nitrite (3.95 g, 0.057 mol, 1.1 eq.) were then added at 0° C., and the reaction mixture was stirred at the same temperature for 30 min. The resulting solution was added dropwise to a solution of sodium cyanide (10.21 g, 0.21 mol, 4 equiv.) and CuCN (10.5 g, 0.084 mol, 1.6 equiv.) in an EtOAc and water mixture (1:1, 40 ml) at 0° C. The reaction mixture was then warmed to RT and stirred for a further 2 h. The reaction mixture was quenched with water and extracted with EtOAc. The combined organic layers were washed with brine then dried (Na$_2$SO$_4$), filtered and concentrated. The crude product was purified by SiO$_2$ chromatography eluting with 25% EtOAc/hexane to afford 4-ethyl-1H-benzo[d]imidazole-5-carbonitrile (6.8 g, 76% yield) as a yellow solid.

Step 5:

To a solution of 4-ethyl-1H-benzo[d]imidazole-5-carbonitrile (6.8 g, 0.04 mol) in dry toluene (70 mL) was added tetrahydro-2H-pyran (10.53 g, 0.12 mol, 3 equiv.) and pyridinium-p-toluenesulfonate (4 g, 0.02 mol, 0.5 equiv.) and the reaction mixture was heated at reflux for 16 h. The reaction mixture was concentrated, quenched with water and extracted with EtOAc. The combined organic layers were washed with brine and then dried (Na$_2$SO$_4$), filtered, and concentrated. The crude product was purified by SiO$_2$ chromatography eluting with 50% EtOAc/hexane to afford 4-ethyl-1-(tetrahydro-2H-pyran-2-yl)-1H-benzo[d]imidazole-5-carbonitrile (7 g, 69% yield) as a yellow oil.

Step 6:

To a solution of 4-ethyl-1-(tetrahydro-2H-pyran-2-yl)-1H-benzo[d]imidazole-5-carbonitrile 6 (7.0 g, 0.027 mol) in dry MeOH (70 mL) at 0° C. was added CoCl$_2$ (5.69 g, 0.043 mol, 1.6 equiv.) and NaBH$_4$ (12.44 g, 0.33 mol, 12 equiv.). The reaction mixture was warmed to RT and stirred for 16 h, then filtered through a Celite® pad and concentrated in vacuo. The crude product was purified by SiO$_2$ chromatography eluting with 5% MeOH/CHCl$_3$ to afford (4-ethyl-1-(tetrahydro-2H-pyran-2-yl)-1H-benzo[d]imidazol-5-yl) methanamine (5.2 g, 73%) as off white solid.

MS (ESI) m/z: 259.2 [M+H]$^+$; 1H-NMR (400 MHz, DMSO-d6); δ 1.19-1.23 (m, 3H), 1.60-1.63 (m, 2H), 1.72-1.76 (m, 1H), 1.96-1.99 (m, 2H), 2.15-2.20 (m, 1H), 3.01-3.07 (m, 2H), 3.70-3.76 (m, 1H), 3.96-3.99 (m, 3H), 5.61-5.64 (d, 1H), 7.29-7.31 (d, 1H), 7.45-7.47 (d, 1H), 8.32 (s, 1H).

Referential Example 13

1-(6-Methyl-1-(tetrahydro-2H-pyran-2-yl)-1H-benzo[d]imidazol-5-yl)ethanamine (101)

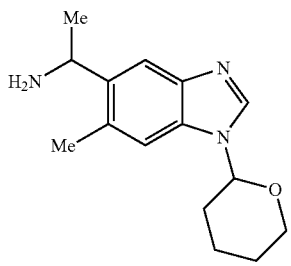 [SMILES: Cc1cc2c(cc1C(C)N)ncn2C1CCCCO1]

Step 1:

A mixture of 5-bromo-6-methyl-1H-benzo[d]imidazole (2.0 g, 9.6 mmol), p-TsOH (17 mg, 0.1 mmol), and dihydropyran (8.1 g, 96 mmol) in THF (30 mL) was heated to reflux overnight. The solvent was concentrated in vacuo and EtOAc (50 mL) and water (50 mL) were added to the residue. The pH was adjusted to about 8 with $K_2CO_3$. The aqueous phase was extracted with EtOAc (50 mL×2). The combined organic layers were washed with water and brine, dried ($Na_2SO_4$), filtered, and concentrated in vacuo. The residue was purified by $SiO_2$ chromatography eluting with petroleum ether/EtOAc (2:1) to afford 5-bromo-6-methyl-1-(tetrahydro-2H-pyran-2-yl)-1H-benzo[d]imidazole as a yellow solid (2.1 g, 71%). MS (ESI): m/z=295.2 [M+1]$^+$.

Step 2:

A mixture of 5-bromo-6-methyl-1-(tetrahydro-2H-pyran-2-yl)-1H-benzo[d]imidazolee (2.1 g, 7.1 mmol), $Zn(CN)_2$ (1.7 g, 14.2 mmol), Pd(dppf)$_2$Cl$_2$ (579 mg, 0.71 mmol) in NMP (10 mL) was stirred at 80° C. overnight. EtOAc (50 mL) and water (50 mL) were added to the reaction mixture. The aqueous phase was extracted with EtOAc (50 mL×2). The combined organic layers were washed with water and brine, dried ($Na_2SO_4$), filtered, and concentrated in vacuo. The residue was purified by $SiO_2$ chromatography eluting with petroleum ether/EtOAc (2:1) to afford 6-methyl-1-(tetrahydro-2H-pyran-2-yl)-1H-benzo[d]imidazole-5-carbonitrile as a solid (1.1 g, 62%). MS (ESI): m/z=242.3 [M+1]$^+$.

Step 3:

To a solution of 6-methyl-1-(tetrahydro-2H-pyran-2-yl)-1H-benzo[d]imidazole-5-carbonitrile (1.1 g, 4.6 mmol) in anhydrous THF (20 mL) under nitrogen at 0° C. was dropped a solution of $CH_3MgBr$ in THF (8 mL, 24 mmol) at a rate that the internal reaction temperature remained below 10° C. After the addition, the reaction mixture was stirred at RT overnight. The mixture was slowly poured into ice-water (20 mL) and stirred at RT for 0.5 h. The solution's pH was adjusted to 5.0~6.0 by using citric acid, and mixture was extracted with EtOAc (20 mL×3). The combined organic layers were washed with brine, dried ($Na_2SO_4$), and concentrated in vacuo. The crude product was purified by $SiO_2$ chromatography eluting with petroleum ether/EtOAc (1:1) to afford 1-(6-methyl-1-(tetrahydro-2H-pyran-2-yl)-1H-benzo[d]imidazol-5-yl)ethanone as a yellow solid (1.1 g, 90.1%). MS (ESI): m/z=259.2 [M+1]$^+$.

Step 4:

To a mixture of 1-(6-methyl-1-(tetrahydro-2H-pyran-2-yl)-1H-benzo[d]imidazol-5-yl)ethanone (1.1 g, 4.3 mmol) and NaOAc (3.5 g, 43 mmol) in MeOH (20 mL) at RT was added hydroxylamine hydrochloride (896 mg, 12.9 mmol). The reaction mixture was stirred at 80° C. for 0.5 h then concentrated in vacuo. Water (200 mL) was added, and the mixture was extracted with EtOAc (50 mL×3), dried ($MgSO_4$), and concentrated in vacuo to afford 1-(6-methyl-1-(tetrahydro-2H-pyran-2-yl)-1H-benzo[d]imidazol-5-yl) ethanone oxime as a yellow solid (1.1 g, 90.2%). MS (ESI): m/z=194.3 [M+1]$^+$.

Step 5:

A mixture of 1-(6-methyl-1-(tetrahydro-2H-pyran-2-yl)-1H-benzo[d]imidazol-5-yl)ethanone oxime (1.1 g, 4.0 mmol), zinc (2.6 g, 40.0 mmol) and $NH_4Cl$ (2.2 g, 40.0 mmol) in MeOH (20 mL) and HOAc (4 mL) was stirred at 80° C. for 4 h. The reaction mixture was filtered and the filtrate concentrated in vacuo. Aqueous ammonia solution (50 mL) was added to the residue, and the mixture was extracted with DCM (50 mL×3), dried ($MgSO_4$), filtered, and concentrated in vacuo. The crude product was purified by $SiO_2$ chromatography eluting with DCM/MeOH/TEA (10:1:0.2) to afford 1-(6-methyl-1-(tetrahydro-2H-pyran-2-yl)-1H-benzo[d]imidazol-5-yl)ethanamine (101) as a yellow solid (840 mg, 80%). MS (ESI): m/z=260.2 [M+1]$^+$.

Referential Example 14

1-(1-(Tetrahydro-2H-pyran-2-yl)-1H-benzo[d]imidazol-4-yl)ethanamine (103)

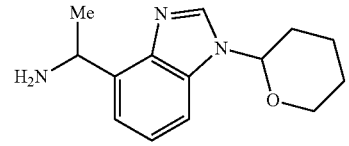 [SMILES: CC(N)c1cccc2c1ncn2C1CCCCO1]

Step 1:

A suspension of 2-bromo-6-nitrobenzenamine (2.0 g, 9 mmol) and $SnCl_2$ (10.2 g, 54 mmol) in EtOH (20 mL) was heated at reflux for 2 h, then cooled to RT and concentrated in vacuo. The residue was diluted with EtOAc (100 mL) and washed with saturated $NaHCO_3$ solution (200 mL). The resulting slurry was filtered through a pad of Celite® and washed with EtOAc (50 ml, ×3). The filtrate was washed with saturated $NaHCO_3$, water, and brine, dried ($MgSO_4$), filtered and concentrated in vacuo to afford 3-bromobenzene-1,2-diamine as a brown oil (1.5 g, 90%). MS (ESI): m/z=186.9 [M+1]$^+$.

Step 2:

A mixture of 3-bromobenzene-1,2-diamine (1.5 g, 8 mmol) in formic acid (10 mL) was heated at reflux for 2 h. The reaction mixture was concentrated in vacuo. To the residue was added a satd. aq. solution of $NaHCO_3$ and mixture was extracted with EtOAc. The combined extracts was dried ($MgSO_4$), filtered, and evaporated in vacuo to afford 4-bromo-1H-benzo[d]imidazole as a gray solid (1.5 g, 95%). MS (ESI): m/z=197 [M+1]$^+$.

Step 3:

A mixture of 4-bromo-1H-benzo[d]imidazole (1.5 g, 7 mmol), TsOH.H$_2$O (0.1 g, 0.7 mmol), and 3,4-dihydro-2H-pyran (2.9 g, 35 mmol) in THF (10 mL) was heated at reflux overnight. The reaction mixture was concentrated in vacuo. To the residue was added water and the mixture was extracted with EtOAc. The combined extracts were dried ($MgSO_4$), filtered, and concentrated in vacuo. The residue was purified by $SiO_2$ chromatography using a petroleum ether/EtOAc gradient (10:1 to 3:1) to afford 4-bromo-1-(tetrahydro-2H-pyran-2-yl)-1H-benzo[d]imidazole as a gray solid (1.6 g, 75%). MS (ESI): m/z=281 [M+1]$^+$.

Step 4.

A mixture of 4-bromo-1-(tetrahydro-2H-pyran-2-yl)-1H-benzo[d]imidazole (1.6 g, 6 mmol), tributyl(1-ethoxyvinyl)stannane (2.4 g, 6 mmol), Pd(PPh$_3$)$_4$ (0.7 g, 0.6 mmol), K$_3$PO$_4$ (2.5 g, 12 mmol) in NMP (10 mL) was heated at 80° C. for 6 h. The mixture was cooled to RT, water was added and the mixture was extracted with EtOAc (50 mL×3). HCl (1.0 eq) was added to the combined extract and the resulting mixture was stirred for 30 min. The pH of the mixture was adjusted to ~8 by addition of aqueous NH$_4$OH solution (35%). The aqueous phase was extracted with EtOAc (50 mL×3). The combined extracts were dried (MgSO$_4$), filtered, and concentrated in vacuo. The residue was purified by SiO$_2$ chromatography eluting with petroleum ether:EtOAc (10:1) to afford 1-(1-(tetrahydro-2H-pyran-2-yl)-1H-benzo[d]imidazol-4-yl)ethanone as a gray solid (0.8 g, 59%). MS (ESI): m/z=245.1 [M+1]$^+$.

Step 5.

To a mixture of 1-(1-(tetrahydro-2H-pyran-2-yl)-1H-benzo[d]imidazol-4-yl)ethanone (800 mg, 3 mmol) and NaOAc (2.5 g, 30 mmol) in MeOH (15 mL) at RT was added hydroxylamine hydrochloride (325 mg, 4.7 mmol). The reaction mixture was stirred at 80° C. for 1 h and then concentrated in vacuo. Water was added (100 mL), and the mixture was extracted with EtOAc (50 mL×3), dried (MgSO$_4$), filtered and concentrated in vacuo to afford 141-(tetrahydro-2H-pyran-2-yl)-1H-benzo[d]imidazol-4-yl)ethanone oxime as a yellow solid (538 mg, 85.0%). MS (ESI): m/z=260.3 [M+1]$^+$.

Step 6:

A mixture of 1-(1-(tetrahydro-2H-pyran-2-yl)-1H-benzo[d]imidazol-4-yl)ethanone oxime (538 mg, 1.02 mmol), Zn (651 mg, 10.2 mmol), and NH$_4$Cl (541 mg, 10.2 mmol) in MeOH (20 mL) and HOAc (5 mL) was stirred at 80° C. for 16 h. The reaction mixture was filtered and the filtrate was concentrated in vacuo. To the residue was added an aqueous NH$_4$OH (50 mL) and the resulting mixture extracted with DCM (50 mL×3). The combined extracts were dried (MgSO$_4$), filtered, and concentrated in vacuo. The crude product was purified by SiO$_2$ chromatography eluting with DCM/MeOH/TEA (10:1:0.2) to afford 1-(1-(tetrahydro-2H-pyran-2-yl)-1H-benzo[d]imidazol-4-yl)ethanamine (103) as a yellow solid (458 mg, yield, 90.1%). MS (ESI): m/z=246.1 [M+1]$^+$.

Referential Example 15

(2-Methyl-1H-indol-4-yl)methanamine (105)

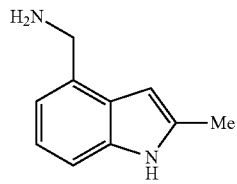

Step 1:

To a mixture of 1-(2-bromophenyl)propan-2-one (1.5 g, 7.04 mmol) and NaOAc (693 mg, 8.45 mmol) in MeOH (50 mL) at RT was added hydroxylamine hydrochloride (539 mg, 7.8 mmol). After the reaction mixture was stirred at RT for 18 h, it was concentrated in vacuo. Water was added (100 mL), and the mixture was extracted with EtOAc (50 mL×3), dried (MgSO$_4$) and concentrated in vacuo to afford 1-(2-bromophenyl)propan-2-one oxime as a yellow solid (1.51 g, 94%). MS (ESI): m/z=228.1 [M+1]$^+$.

Step 2:

To a solution of 1-(2-bromophenyl)propan-2-one oxime (1.36 g, 5.96 mmol) and TEA (722 mg, 7.15 mmol) in anhydrous THF (50 mL) at RT was added dropwise a solution of methanesulfonyl chloride (819 mg, 7.15 mmol) in anhydrous THF (5 mL). After stirring at RT for 1 h, 1,8-diazabicyclo[5.4.0]undec-7-ene (2.26 g, 14.9 mmol) was added and stirring continued at RT for 1 h. The reaction mixture was passed through a pad of SiO$_2$, concentrated in vacuo, and purified by SiO$_2$ chromatography eluting with petroleum ether/EtOAc (10:1) to afford 2-(2-bromophenyl)-3-methyl-2H-azirine as yellow oil (758 mg, yield, 60.5%). MS (ESI): m/z=242.1 [M+33]$^+$.

Step 3:

The solution of 2-(2-bromophenyl)-3-methyl-2H-azirine (758 mg, 3.61 mmol) in xylene (20 mL) was stirred at 160° C. for 7 d. The reaction mixture was concentrated in vacuo. The residue was purified by SiO$_2$ chromatography eluting with petroleum ether/EtOAc (10:1) to afford 4-bromo-2-methyl-1H-indole as yellow oil (572 mg, 75.5%). MS (ESI): m/z=210.1 [M+1]$^+$.

Step 4:

A mixture of 4-bromo-2-methyl-1H-indole (572 mg, 2.72 mmol), Zn(CN)$_2$ (351 mg, 3.0 mmol), Zn (35 mg, 0.54 mmol), dppf (606 mg, 1.09 mmol), and Pd$_2$(dba)$_3$ (498 mg, 0.54 mmol) in NMP (10 mL) under argon atmosphere was heated at 120° C. for 18 h. After cooling to RT, the reaction mixture was partitioned between EtOAc (300 mL) and water (50 mL). The organic layer was washed with brine, dried (MgSO$_4$), filtered and concentrated in vacuo. The residue was purified by SiO$_2$ chromatography eluting with petroleum ether/EtOAc (3:1) to afford 2-methyl-1H-indole-4-carbonitrile as a yellow oil (408 mg, 96%). MS (ESI): m/z=157.2 [M+1]$^+$.

Step 5:

To a solution of 2-methyl-1H-indole-4-carbonitrile (408 mg, 2.61 mmol) in NH$_3$/MeOH (7 M, 20 mL) was added Raney nickel (100 mg). The mixture was stirred under hydrogen at 1 atmosphere at RT for 3 h. The mixture was filtered with Celite® and the filtrate was concentrated in vacuo to afford (2-methyl-1H-indol-4-yl)methanamine (105) as a yellow solid (398 mg, 95.1%). MS (ESI): m/z=144.3 [M−16]$^+$.

Referential Example 16

(5-Fluoro-1H-indol-4-yl)methanamine (107)

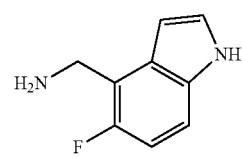 [SMILES: NCc1c(F)ccc2[nH]ccc12]

Step 1:

To a mixture of 5-fluoro-1H-indole (2.5 g, 18.52 mmol) and chlorotriisopropyl-silane (3.92 g, 20.4 mmol) in anhydrous THF (75 mL) at −78° C. was added dropwise a solution of n-BuLi in THF (1.6 mol/L, 12.7 mL, 20.37 mmol) at a rate to maintain the internal reaction temperature below −70° C.

After the addition was completed, the mixture was stirred at −78° C. for 1 h and then poured into water (250 mL), extracted with DCM (100 mL×3), and concentrated in vacuo to afford 5-fluoro-1-(triisopropylsilyl)-1H-indole as a yellow oil (5.27 g, 97.6%). MS (ESI): m/z=292.3 [M+1]$^+$.

Step 2:

To a solution of 5-fluoro-1-(triisopropylsilyl)-1H-indole (2.5 g, 8.58 mmol), 2,2,6,6-tetramethylpiperidine (2.42 g, 17.15 mmol), potassium 2-methylpropan-2-olate (1.92 g, 17.15 mmol) in anhydrous THF (75 mL) under nitrogen at −78° C. was added dropwise a solution of n-BuLi in THF (1.6 M, 10.7 mL, 17.15 mmol) at a rate to maintain the internal reaction temperature below −70° C. The mixture was then stirred at −78° C. for 2 h. The reaction mixture was poured into a slurry of ice (100 g), water (200 mL), and DCM (100 mL). The pH of aqueous phase was adjusted to 4.0 with HCl (2 M). A precipitate was formed, which was filtered, washed with water (10 mL) and ethoxyethane (10 mL) to afford 5-fluoro-1-(triisopropylsilyl)-1H-indole-4-carboxylic acid as a white solid (580 mg, 20.2%). MS (ESI): m/z=336.2 [M+1]$^+$.

Step 3:

A mixture of 5-fluoro-1-(tripropylsilyl)-1H-indole-4-carboxylic acid (500 mg, 1.49 mmol), O-(7-azabenzotriazol-1-yl)-N,N,N',N'-tetramethyluronium hexafluorophosphate (851 mg, 2.24 mmol), and TEA (452 mg, 4.48 mmol) in DMF (5 mL) was stirred at RT for 1 hour. To the mixture was added ammonia water (1 mL), followed by stirring at RT overnight. The reaction mixture was poured into water (100 mL) and extracted with EtOAc (50 mL×3). The combined organic layers were washed with water and brine, dried (Na$_2$SO$_4$), filtered, and concentrated in vacuo. The residue was purified by SiO$_2$ chromatography using petroleum ether/EtOAc (2:1) as eluting solvents to afford 5-fluoro-1H-indole-4-carboxamide as a white solid (260 mg, 52.2%). MS (ESI): m/z=179.2 [M+1]$^+$.

Step 4.

A mixture of 5-fluoro-1H-indole-4-carboxamide (240 mg, 1.35 mmol) and a solution of BH$_3$ in THF (1.0 M, 16 mL, 16 mmol) was stirred at RT for 18 hours. The reaction was quenched with a solution of HCl (1.0 M, 20 mL) followed by stirring at RT for 1.5 h. The pH of the reaction mixture was adjusted to about ca. 10 by adding a satd. aq. Na$_2$CO$_3$. The mixture was extracted with EtOAc (50 mL×3). The combined organic layers were washed with water and brine, dried (Na$_2$SO$_4$), filtered and concentrated in vacuo. The residue was purified by SiO$_2$ chromatography eluting with DCM/MeOH/TEA (10:1:0.1) to afford (5-fluoro-1H-indol-4-yl)methanamine (107) as a yellow solid (190 mg, 86.4%). MS (ESI): m/z=148.1 [M−16]$^+$.

Referential Example 17

N-Methyl-1-(3-methyl-1H-indazol-4-yl)methanamine (109)

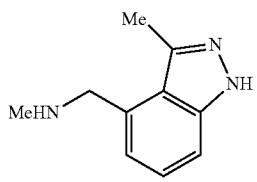

Step 1:

A mixture of 4-bromo-1H-indole (10 g, 50.7 mmol), Pd(PPh$_3$)$_4$ (8.78 g, 7.6 mmol), Zn(CN)$_2$ (9.22 g 101.4 mmol) in NMP (150 mL) under nitrogen was heated at 110° C. for 16 h. The reaction mixture was cooled, filtered and the filtrate diluted with water and extracted with EtOAc (100 mL×5). The combined extracts were washed with brine (300 mL), dried (MgSO$_4$), filtered, and concentrated in vacuo to afford 1H-indazole-4-carbonitrile (3.76 g, 52.5%) as white solid, which went to next step without further purification.

Step 2:

A mixture of 1H-indazole-4-carbonitrile (1.65 g, 11.1 mmol), KOH (1.86 g, 33.3 mmol), and I$_2$ (5.6 g, 22.2 mmol) in DMF (30 mL) was stirred at RT overnight. The reaction mixture was filtered. The filtrate was diluted with water (100 mL) and extracted with EtOAc (200 mL). The organic layer was concentrated in vacuo to afford 3-iodo-1H-indazole-4-carbonitrile as white solid (2.01 g, 64.7%). MS (ESI): m/z=270 [M+1]$^+$.

Step 3:

A mixture of 3-iodo-1H-indazole-4-carbonitrile (3.0 g, 11.1 mmol), dihydropyran (1.84 g, 22.2 mmol), and TsOH (212 mg, 1.1 mmol) under nitrogen in THF (40 mL) was heated at 85° C. overnight. Water (40 mL) was added and the mixture was extracted with EtOAc (50 mL×3). The combined extracts were washed with brine, dried (MgSO$_4$), filtered, and concentrated in vacuo. The residue was purified by SiO$_2$ chromatography eluting with petroleum ether/EtOAc (5:1) to afford 3-iodo-1-(tetrahydro-2H-pyran-2-yl)-1H-indazole-4-carbonitrile as white solid (3.31 g, 84.0%). MS (ESI): m/z=354 [M+1]$^+$.

Step 4:

A mixture of 3-iodo-1-(tetrahydro-2H-pyran-2-yl)-1H-indazole-4-carbonitrile (50 mg, 0.142 mmol), K$_3$PO$_4$ (61.34 mg, 0.284 mmol), Pd(dppf)Cl$_2$ (10.3 mg, 0.0142 mmol), 2,4,6-trimethyl-1,3,5,2,4,6-trioxatriborinane (18 mg, 0.142 mmol) in DMF (0.5 mL) under nitrogen in a sealed vial was heated at 120° C. in a microwave oven for 100 minutes. The reaction mixture was filtered and the filtrate diluted with H$_2$O and extracted with EtOAc. The combined extracts extracts were dried (MgSO$_4$), filtered, and concentrated in vacuo to afford 3-methyl-1-(tetrahydro-2H-pyran-2-yl)-1H-indazole-4-carbonitrile as white solid (12 mg, 35.5%). MS (ESI): m/z=242 [M+1]$^+$.

Step 5:

To a solution of 3-methyl-1-(tetrahydro-2H-pyran-2-yl)-1H-indazole-4-carbonitrile (130 mg, 0.54 mmol) in NH$_3$/MeOH (7N, 10 mL) was added Raney nickel (20 mg). The mixture was stirred under hydrogen overnight. The reaction mixture was filtered, and the filtrate was concentrated to afford (3-methyl-1-(tetrahydro-2H-pyran-2-yl)-1H-indazol-4-yl)methanamine (120 mg, 91.5%). MS (ESI): m/z=246 [M+1]$^+$.

Step 6:

To a mixture of (3-methyl-1-(tetrahydro-2H-pyran-2-yl)-1H-indazol-4-yl)methanamine (120 mg, 0.5 mmol) in DCM (8 mL) was added (Boc)$_2$O (109 mg, 0.5 mmol) and TEA (3 drops). The mixture was stirred at RT for 5 h. The reaction mixture was concentrated in vacuo. The residue was purified by SiO$_2$ chromatography eluting with petroleum ether/EtOAc (3:1) to afford tert-butyl (3-methyl-1-(tetrahydro-2H-pyran-2-yl)-1H-indazol-4-yl)methylcarbamate as white solid (100 mg, 59.2%). MS (ESI): m/z=346 [M+1]$^+$.

Step 7:

To a mixture of tert-butyl (3-methyl-1-(tetrahydro-2H-pyran-2-yl)-1H-indazol-4-yl)methyl carbamate (100 mg, 0.29 mmol) in THF (2 mL) was added NaH (21.6 mg, 0.9 mmol). After stirring for 30 minutes, CH$_3$I (127 mg, 0.9 mmol) was added to the reaction mixture which was stirred at RT overnight. The mixture was filtered and evaporated in vacuo. The residue was purified by SiO$_2$ chromatography using petroleum ether/EtOAc (3:1) as eluting solvents to afford tert-butyl methyl((3-methyl-1-(tetrahydro-2H-pyran-2-yl)-1H-indazol-4-yl)methyl)carbamate as white solid (85 mg, 81.6%). MS (ESI): m/z=360 [M+1]$^+$.

Step 8:

A mixture of tert-butyl methyl((3-methyl-1-(tetrahydro-2H-pyran-2-yl)-1H-indazol-4-yl)methyl)carbamate (85 mg, 0.23 mmol) in DCM (8 mL) and TFA (1 mL) was stirred at RT overnight. The reaction mixture was concentrated in vacuo. The residue was purified SiO$_2$ chromatography eluting with petroleum ether:EtOAc to afford N-methyl-1-(3-methyl-1H-indazol-4-yl)methanamine (109) as white solid (30 mg, 72.4%). MS (ESI): m/z=176 [M+1]$^+$.

Referential Example 18

(6-Chloro-2-methyl-1-(tetrahydro-2H-pyran-2-yl)-1H-benzo[d]imidazol-4-yl)methanamine (111)

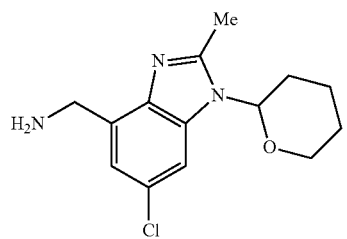 [SMILES: Cc1nc2c(CN)cc(Cl)cc2n1C1CCCCO1]

Step 1:

A mixture of 4-chloro-2-nitrobenzenamine (2.0 g, 11.59 mmol) and 1-bromopyrrolidine-2,5-dione (2.3 g, 12.75 mmol) in MeCN (30 mL) was stirred at 70° C. for 14 h. The reaction mixture was poured into water (100 mL) and stirred at RT for 1 h. The precipitate was filtered and washed with water. The solid was dried under vacuum to afford 3-bromobenzene-1,2-diamine as a yellow solid (2.6 g, 86.7%).

Step 2:

A suspension of 3-bromobenzene-1,2-diamine (4.0 g, 15.90 mmol) and SnCl$_2$ (17.9 g, 79.50 mmol) in EtOH (40 mL) was heated at reflux for 4 h. After cooling to RT, 1,1,1-trimethoxyethane (12.9 g, 79.50 mmol) was added. The reaction mixture was stirred at 120° C. for 14 h, cooled to RT and concentrated in vacuo. The residue was diluted with EtOAc (100 mL), treated with saturated NaHCO$_3$ solution (200 mL), filtered through Celite®, and washed with EtOAc (50 mL×3). The filtrate was washed with saturated NaHCO$_3$, water, and brine, dried (MgSO$_4$), filtered, and concentrated in vacuo to afford 4-bromo-6-chloro-2-methyl-1H-benzo[d]imidazole as a yellow solid (3.5 g, 89.7%). MS (ESI): m/z=244.9 [M+1]$^+$.

Step 3:

A mixture of 4-bromo-6-chloro-2-methyl-1H-benzo[d]imidazole (3.5 g, 14.26 mmol), p-TsOH.H$_2$O (272 mg, 1.43 mmol), and 3,4-dihydro-2H-pyran (5.9 g, 71.30 mmol) in THF (20 mL) was stirred at 75° C. for 4 h. The reaction mixture was concentrated in vacuo and water was added. The mixture was extracted with EtOAc and the combined extracts dried (MgSO$_4$), filtered, and concentrated in vacuo. The residue was purified by SiO$_2$ chromatography eluting with a DCM:MeOH gradient (0 to 9% MeOH) to afford 4-bromo-6-chloro-2-methyl-1-(tetrahydro-2H-pyran-2-yl)-1H-benzo[d]imidazole as a white solid (3.2 g, 69.6%). MS (ESI): m/z=329.0 [M+1]$^+$.

Step 4:

A mixture of 4-bromo-6-chloro-2-methyl-1-(tetrahydro-2H-pyran-2-yl)-1H-benzo[d]imidazole (3.2 g, 9.70 mmol), Zn(CN)$_2$ (2.3 g, 19.40 mmol), and Pd(PPh$_3$)$_4$ (1.1 g, 0.97 mmol) in NMP (20 mL) was stirred at 90° C. for 3 h. The reaction mixture was filtered and the filtrate diluted with EtOAc (50 mL). The organic layer was washed with water (50 mL×3), dried (MgSO$_4$) and concentrated in vacuo. The residue was purified by SiO$_2$ chromatography eluting with a DCM/MeOH gradient (0 to 6% MeOH) to afford 6-chloro-2-methyl-1-(tetrahydro-2H-pyran-2-yl)-1H-benzo[d]imidazole-4-carbonitrile as a white solid (1.0 g, 37.2%). MS (ESI): m/z=276.2 [M+1]$^+$.

Step 5:

A mixture of 6-chloro-2-methyl-1-(tetrahydro-2H-pyran-2-yl)-1H-benzo[d]imidazole-4-carbonitrile (1.0 g, 3.16 mmol) and Raney nickel (100 mg) in NH$_3$/MeOH (7 N, 10 mL) was stirred under hydrogen for 2 h. The reaction mixture was filtered with Celite® and the filtrate concentrated in vacuo to afford crude (6-chloro-2-methyl-1-(tetrahydro-2H-pyran-2-yl)-1H-benzo[d]imidazol-4-yl)methanamine (111, 600 mg, 59.0%) as a yellow solid. MS (ESI): m/z=280.3 [M+1]$^+$.

Referential Example 19

(6-Methyl-1-(tetrahydro-2H-pyran-2-yl)-1H-indazol-4-yl)methanamine (113)

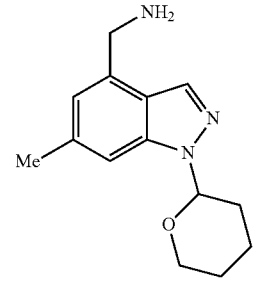 [SMILES: Cc1cc(CN)c2cnn(C3CCCCO3)c2c1]

Step 1:

A mixture of 4-bromo-6-methyl-1H-indazole (1.05 g, 5 mmol), DHP (2.1 g, 25 mmol), and TsOH.H$_2$O (96 mg, 0.5 mmol) in THF (50 ml) under nitrogen was heated at reflux overnight. The reaction mixture was concentrated in vacuo and to the residue was added DCM (300 mL) and water (50 mL). The organic layer was dried over MgSO$_4$, filtered, and concentrated in vacuo. The residue was purified by silica gel chromatography by using petroleum ether:EtOAc (100:1) as eluting solvents to afford 4-bromo-6-methyl-1-(tetrahydro-2H-pyran-2-yl)-1H-indazole as light yellow oil (1.1 g, 90%) MS (ESI): m/z=295.1 [M+1]$^+$.

Step 2:

A mixture of 4-bromo-6-methyl-1-(tetrahydro-2H-pyran-2-yl)-1H-indazole (1.1 g, 3.74 mmol), Zn(CN)$_2$ (873 mg, 7.46 mmol), and Pd(PPh$_3$)$_4$ (646 mg, 0.56 mmol) in NMP (25 mL) under nitrogen was heated at 100° C. overnight. After it was cooled to RT, the reaction mixture was partitioned between EtOAc (300 mL) and water (50 mL). The organic layer was washed with brine, dried over MgSO$_4$, and concentrated in vacuo. The residue was purified by silica gel chromatography using petroleum ether:EtOAc (10:1) as eluting solvents to afford 6-methyl-1-(tetrahydro-2H-pyran-2-yl)-1H-indazole-4-carbonitrile as white solid (400 mg, 50%). MS (ESI): m/z=242.3 [M+1]$^+$.

Step 3:

To a solution of 6-methyl-1-(tetrahydro-2H-pyran-2-yl)-1H-indazole-4-carbonitrile (120 mg, 0.5 mmol) in a solution of NH$_3$/MeOH (7 N, 10 mL) was added Raney nickel (50 mg). The mixture was stirred under hydrogen at RT for 2 hours. It was filtered with Celite, and the filtrate was concentrated in vacuo to afford (6-methyl-1-(tetrahydro-2H-pyran-2-yl)-1H-indazol-4-yl)methanamine (113) as brown solid (120 mg, ~100%). MS (ESI): m/z=246.3 [M+1]$^+$.

Referential Example 20

(6-Chloro-2-methyl-1-(tetrahydro-2H-pyran-2-yl)-1H-benzo[d]imidazol-4-yl)methanamine (115)

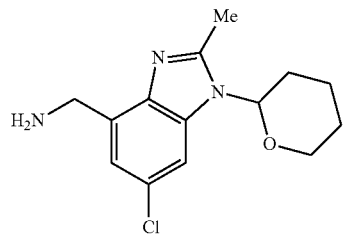 [SMILES: Cc1nc2c(CN)cc(Cl)cc2n1C1CCCCO1]

Step 1:

A mixture of 4-chloro-2-nitrobenzenamine (2.0 g, 11.59 mmol) and 1-bromopyrrolidine-2,5-dione (2.3 g, 12.75 mmol) in MeCN (30 mL) was stirred at 70° C. for 14 h. The reaction mixture was poured into water (100 mL) and stirred at RT for 1 h. The precipitate was filtered and washed with water. The solid was dried under vacuum to afford 3-bromobenzene-1,2-diamine as a yellow solid (2.6 g, 86.7%).

Step 2:

A suspension of 3-bromobenzene-1,2-diamine (4.0 g, 15.90 mmol) and SnCl$_2$ (17.9 g, 79.50 mmol) in EtOH (40 mL) was heated at reflux for 4 h. After cooling to RT, 1,1,1-trimethoxyethane (12.9 g, 79.50 mmol) was added to the mixture. The reaction mixture was stirred at 120° C. for 14 h, then cooled to RT and concentrated in vacuo. The residue was diluted with EtOAc (100 mL), treated with satd. aq. NaHCO$_3$ (200 mL), filtered with Celite®, and washed with EtOAc (50 mL×3). The filtrate was washed with satd. aq. NaHCO$_3$, water, and brine, dried (MgSO$_4$), filtered, and concentrated in vacuo to afford 4-bromo-6-chloro-2-methyl-1H-benzo[d]imidazole as a yellow solid (3.5 g, 89.7%). MS (ESI): m/z=244.9 [M+1]$^+$.

Step 3:

A mixture of 4-bromo-6-chloro-2-methyl-1H-benzo[d]imidazole (3.5 g, 14.26 mmol), p-TsOH.H$_2$O (272 mg, 1.43 mmol), and 3,4-dihydro-2H-pyran (5.9 g, 71.30 mmol) in THF (20 mL) was stirred at 75° C. for 4 h. The reaction mixture was concentrated in vacuo. The residue was diluted with water and extracted with EtOAc. The combined extracts were dried (MgSO$_4$), filtered and concentrated in vacuo. The residue was purified by SiO$_2$ chromatography eluting with a DCM/MeOH gradient (0 to 9% MeOH) to afford 4-bromo-6-chloro-2-methyl-1-(tetrahydro-2H-pyran-2-yl)-1H-benzo[d]imidazole as a white solid (3.2 g, 69.6%). MS (ESI): m/z=329.0 [M+1]$^+$.

Step 4:

A mixture of 4-bromo-6-chloro-2-methyl-1-(tetrahydro-2H-pyran-2-yl)-1H-benzo[d]imidazole (3.2 g, 9.70 mmol), Zn(CN)$_2$ (2.3 g, 19.40 mmol), and Pd(PPh$_3$)$_4$ (1.1 g, 0.97 mmol) in NMP (20 mL) was stirred at 90° C. for 3 h. The reaction mixture was filtered and the filtrate diluted with EtOAc (50 mL). The organic layer was washed with water (50 mL×3), dried (MgSO$_4$), filtered and concentrated in vacuo. The residue was purified by SiO$_2$ chromatography eluting with a DCM:MeOH gradient (0 to 6% MeOH) to afford 6-chloro-2-methyl-1-(tetrahydro-2H-pyran-2-yl)-1H-benzo[d]imidazole-4-carbonitrile as a white solid (1.0 g, 37.2%). MS (ESI): m/z=276.2 [M+1]$^+$.

Step 5:

A mixture of 6-chloro-2-methyl-1-(tetrahydro-2H-pyran-2-yl)-1H-benzo[d]imidazole-4-carbonitrile (1.0 g, 3.16 mmol) and Raney nickel (100 mg) in NH$_3$/MeOH (7 N, 10 mL) was stirred under hydrogen for 2 h. The reaction mixture was filtered through Celite® and the filtrate concentrated in vacuo to afford crude (6-chloro-2-methyl-1-(tetrahydro-2H-pyran-2-yl)-1H-benzo[d]imidazol-4-yl)methanamine (115, 600 mg, 59.0%) as a yellow solid. MS (ESI): m/z=280.3 [M+1]$^+$.

Referential Example 21

1-(6-Chloro-1-(tetrahydro-2H-pyran-2-yl)-1H-benzo[d]imidazol-4-yl)-N-methylmethanamine (117)

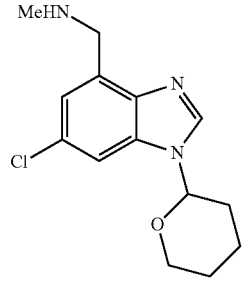 [SMILES: CNCc1cc(Cl)cc2c1ncn2C1CCCCO1]

Step 1:

To a solution of (6-chloro-1-(tetrahydro-2H-pyran-2-yl)-1H-benzo[d]imidazol-4-yl)methanamine (700 mg, 2.63 mmol) in DCM (10 mL) was added (Boc)$_2$O (632 mg, 2.90 mmol) and TEA (800 mg, 7.90 mmol). The mixture was stirred at RT for 2 h. The reaction mixture was concentrated in vacuo. The residue was purified by silica gel chromatography using with petroleum ether:EtOAc (1:1) as eluting solvents to afford tert-butyl (6-chloro-1-(tetrahydro-2H-pyran-2-yl)-1H-benzo[d]imidazol-4-yl)methylcarbamate as white solid (900 mg, 93%). MS (ESI): m/z=366.2 [M+1]$^+$.

Step 2:

To a solution of tert-butyl (6-chloro-1-(tetrahydro-2H-pyran-2-yl)-1H-benzo[d]imidazol-4-yl)methylcarbamate (300 mg, 0.82 mmol) in DMF (10 mL) at 0° C. was added NaH (60% in mineral oil, 98.4 mg, 2.46 mmol). After stirring at RT for 30 min, CH$_3$I (349 mg, 2.46 mmol) was added and the reaction mixture was stirred at RT overnight and then quenched with H$_2$O at 0° C. The mixture was extracted with EtOAc (100 mL) and the extract washed with H$_2$O (50 mL×3), dried (MgSO$_4$), filtered and concentrated in vacuo. The residue was purified by SiO$_2$ chromatography eluting with petroleum ether/EtOAc (1:1) to afford tert-butyl (6-chloro-1-(tetrahydro-2H-pyran-2-yl)-1H-benzo[d]imidazol-4-yl)methyl(methyl)carbamate as yellow oil (310 mg, 99%). MS (ESI): m/z=380.3 [M+1]⁺.

Step 3:

To a solution of tert-butyl (6-chloro-1-(tetrahydro-2H-pyran-2-yl)-1H-benzo[d]imidazol-4-yl)methylmethyl)carbamate (310 mg, 0.82 mmol) in DCM (5 mL) was added TFA (1 mL), and the reaction mixture was stirred at RT for 2 h. The mixture was quenched with NH₄OH at 0° C. and extracted with EtOAc (100 mL). The extract was washed with H₂O (50 mL×3), dried (MgSO₄), filtered, and concentrated in vacuo. The residue was purified by SiO₂ chromatography eluting with MeOH/DCM (1:30) to afford 1-(6-chloro-1-(tetrahydro-2H-pyran-2-yl)-1H-benzo[d]imidazol-4-yl)-N-methyl-methanamine (117) as yellow oil (200 mg, 88%). MS (ESI): m/z=280.1 [M+1]⁺.

Referential Example 22

(3-Methoxy-1-(tetrahydro-2H-pyran-2-yl)-1H-indazol-4-yl)methanamine (119)

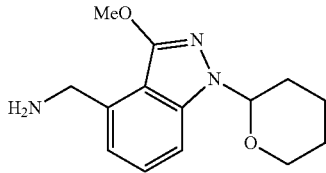 [SMILES: COc1nn(C2CCCCO2)c2cccc(CN)c12]

Step 1:

A mixture of 4-bromo-1H-indole (10 g, 50.7 mmol), Pd(PPh₃)₄ (8.78 g, 7.6 mmol), Zn(CN)₂ (9.22 g, 101.4 mmol) in NMP (150 mL) under nitrogen was heated at 110° C. for 16 h. The reaction mixture was quenched with water and extracted with EtOAc (100 mL×5). The combined extracts were washed with brine (300 mL), dried (MgSO₄), filtered, and concentrated in vacuo to afford 1H-indazole-4-carbonitrile as white solid (3.76 g, 52.5%).

Step 2:

To a mixture of 1H-indazole-4-carbonitrile (1.65 g, 11.1 mmol) in DMF (30 mL) was added KOH (1.86 g 33.3 mmol) and I₂ (5.6 g 22.2 mmol). The mixture was stirred at RT for 5 h. The reaction mixture was quenched with water (100 mL) and extracted with EtOAc (200 mL). The extract was concentrated in vacuo to afford 3-iodo-1H-indazole-4-carbonitrile as white solid (2.01 g, 64.7%). MS (ESI): m/z=270 [M+1]⁺.

Step 3:

A mixture of 3-iodo-1H-indazole-4-carbonitrile (3.0 g, 11.1 mmol), DHP (1.84 g, 22.2 mmol), and TsOH (212 mg, 1.1 mmol) in THF (40 mL) under nitrogen was heated at 85° C. overnight. The reaction mixture was quenched with water (40 mL) and extracted with EtOAc (50 mL×3). The combined extracts were washed with brine, dried (MgSO₄), filtered, and concentrated in vacuo. The residue was purified by SiO₂ chromatography using petroleum ether/EtOAc (5:1) to afford 3-iodo-1-(tetrahydro-2H-pyran-2-yl)-1H-indazole-4-carbonitrile as white solid (3.31 g, 84.0%). MS (ESI): m/z=354 [M+1]⁺.

Step 4:

A mixture of 3-iodo-1-(tetrahydro-2H-pyran-2-yl)-1H-indazole-4-carbonitrile (50 mg, 0.142 mmol), CuI (13.5 g 0.071 mmol), CsCO₃ (2.7 mg, 0.0142 mmol), and 3,4,7,8-tetramethyl-1,10-phenanthroline (0.0142 mg, 3.5 mmol) in EtOH (0.5 mL) under nitrogen in a sealed vial was heated to 90° C. in a microwave oven for 100 min. The reaction mixture was quenched with water and extracted with EtOAc. The extract was dried (MgSO₄), filtered, and concentrated in vacuo. The residue was purified by SiO₂ chromatography eluting with petroleum ether:EtOAc to afford 3-methoxy-1-(tetrahydro-2H-pyran-2-yl)-1H-indazole-4-carbonitrile as white solid (13 mg, 35.7%). MS (ESI): m/z=258 [M+1]⁺.

Step 5:

A mixture of 3-methoxy-1-(tetrahydro-2H-pyran-2-yl)-1H-indazole-4-carbonitrile (140 mg, 0.544 mmol) and Raney nickel (20 mg) in NH₃/MeOH (7N, 10 mL) was stirred under hydrogen overnight. The reaction mixture was filtered with Celite® and the filtrate concentrated in vacuo to afford (3-methoxy-1-(tetrahydro-2H-pyran-2-yl)-1H-indazol-4-yl) methanamine as an oil (119) 130 mg, 91.4%). MS (ESI): m/z=262 [M+1]⁺.

Referential Example 23

1-(6-Fluoro-1H-benzo[d]imidazol-4-yl)ethanamine (121)

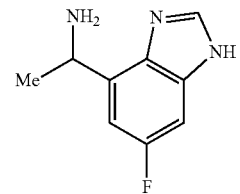

Step 1:

To a mixture of 4-fluoro-2-nitroaniline (10.0 g, 42.55 mmol) in DCM (150 mL) and HOAc (75 mL) at 0° C. was added dropwise Br₂ (9.9 ml, 130 mmol) at a rate to maintain the internal reaction temperature below 10° C. The reaction mixture was stirred at RT overnight and then poured into water (500 mL), followed by separation of the organic phase. The pH of the aqueous phase was adjusted to about 7 by adding NH₄OH, and the mixture was extracted with DCM (100 mL×3). The combined extracts were dried (MgSO₄), filtered, and concentrated in vacuo to afford 2-bromo-4-fluoro-6-nitroaniline as a yellow solid (14 g, 93%). MS (ESI): m/z=233 [M−1]⁻.

Step 2:

A suspension of 2-bromo-4-fluoro-6-nitroaniline (14 g, 59 mmol) and SnCl₂ (66 g, 295 mmol) in EtOH (50 mL) was heated at reflux for 5 h. The reaction mixture was concentrated in vacuo. To the residue was added EtOAc (100 mL) and satd. aq. NaHCO₃ (200 mL). The mixture was filtered over Celite® and washed with EtOAc (100 mL×3). The combined organic layers were washed with satd. aq. NaHCO₃, water, and brine, dried (MgSO₄), filtered, and concentrated in vacuo to afford 3-bromo-5-fluorobenzene-1,2-diamine as a gray solid (10.1 g, 100%). MS (ESI): m/z=205 [M+1]⁺.

Step 3:

A mixture of 3-bromo-5-fluorobenzene-1,2-diamine (10.1 g, 49 mmol) in formic acid (20 mL) was heated at 110° C. overnight. The reaction mixture was concentrated, and to the residue was added MeOH (5 mL) to form a precipitate. The precipitate was filtered and washed with MeOH (2 mL) to afford 4-bromo-6-fluoro-1H-benzo[d]imidazole as a yellow solid (10 g, yield, 73%). MS (ESI): m/z=215 [M+1]⁺.

Step 4:

A mixture of 4-bromo-6-fluoro-1H-benzo[d]imidazole (3 g, 14 mmol), p-toluenesulfonic acid (240 mg, 1.4 mmol), and dihydropyran (11.7 g, 140 mmol) in THF (30 mL) under nitrogen was heated at reflux for 3 h. The reaction mixture was concentrated in vacuo. The residue was partitioned between EtOAc (50 mL) and water (50 mL) and the pH was adjusted to about 8 by adding $K_2CO_3$. The mixture was extracted with EtOAc (50 mL×2). The combined organic layers were washed with water and brine, dried ($Na_2SO_4$), filtered and concentrated in vacuo. The residue was purified by $SiO_2$ chromatography eluting with petroleum ether/EtOAc (2:1) to afford 4-bromo-6-fluoro-1H-benzo[d]imidazole as white solid (2.3 g, 64%). MS (ESI): m/z=300 [M+1]$^+$.

Step 5:
A mixture of 4-bromo-6-fluoro-1H-benzo[d]imidazole (1.4 g, 4.6 mmol), $Zn(CN)_2$ (1.1 g, 9.2 mmol), and $Pd(PPh_3)_4$ (535 mg, 0.46 mmol) in NMP (10 mL) under nitrogen was stirred at 100° C. overnight. To the reaction mixture was added EtOAc (50 mL) and water (50 mL). The aqueous phase was extracted with EtOAc (50 mL×2). The combined organic layers were washed with water and brine, dried ($Na_2SO_4$), filtered, and concentrated in vacuo. The residue was purified by $SiO_2$ chromatography eluting with petroleum ether:EtOAc (2:1) to afford 6-fluoro-1-(tetrahydro-2H-pyran-2-yl)-1H-benzo[d]imidazole-4-carbonitrile as a yellow solid (1.04 g, 85%). MS (ESI): m/z=246 [M+1]$^+$.

Step 6:
To a solution of 6-fluoro-1-(tetrahydro-2H-pyran-2-yl)-1H-benzo[d]imidazole-4-carbonitrile (1 g, 4 mmol) in anhydrous THF (50 mL) under nitrogen at −78° C. was slowly added dropwise a solution of MeMgBr in THF (3.0 M, 7 mL, 21 mmol). After stirring at RT overnight, the mixture was poured into water (200 mL) and the pH was adjusted to about 5-6 by adding HCl solution (1.0 M). The mixture was extracted with EtOAc (50 mL×3). The combined organic layers were washed with brine, dried ($Na_2SO_4$), filtered, and concentrated in vacuo. The residue was purified by $SiO_2$ chromatography eluting with petroleum ether:EtOAc (1:1) to afford 1-(6-fluoro-1-(tetrahydro-2H-pyran-2-yl)-1H-benzo[d]imidazol-4-yl)ethanone as yellow solid (1.0 g, 93.5%). MS (ESI): m/z=263 [M+1]$^+$.

Step 7:
A mixture of 1-(6-fluoro-1-(tetrahydro-2H-pyran-2-yl)-1H-benzo[d]imidazol-4-yl)ethanone (1.0 g, 3.82 mmol) and TsOH (1.97 g, 11.45 mmol) in water (10 mL) and MeOH (50 mL) was heated at 80° C. for 3 h. The reaction mixture was quenched with EtOAc (50 mL) and water (50 mL). The aqueous phase was extracted with EtOAc (50 mL×2). The combined organic layers were washed with water and brine, dried ($Na_2SO_4$), filtered, and concentrated in vacuo to afford 1-(6-fluoro-1H-benzo[d]imidazol-4-yl)ethanone as a yellow solid (678 mg, 99.8%). MS (ESI): m/z=179.3 [M+1].

Step 8:
A mixture of 1-(6-fluoro-1-(tetrahydro-2H-pyran-2-yl)-1H-benzo[d]imidazol-4-yl)ethanone (676 mg, 3.8 mmol), NaOAc (3.12 g, 38 mmol), and hydroxylamine hydrochloride (792 mg, 11.4 mmol) in MeOH (60 mL) was heated at 80° C. for 1 h. The reaction mixture was concentrated in vacuo. To the residue was added water (200 mL) and the resulting mixture was extracted with EOAc (50 mL×3). The combined extracts were concentrated in vacuo to afford 1-(6-fluoro-1H-benzo[d]imidazol-4-yl)ethanone oxime as a yellow solid (658 mg, 89.8%). MS (ESI): m/z=194.3 [M+1]$^+$.

Step 9:
A mixture of 1-(6-fluoro-1H-benzo[d]imidazol-4-yl)ethanone oxime (351 mg, 1.82 mmol), Zn powder (1.18 g, 18.2 mmol), and $NH_4Cl$ (973 mg, 18.2 mmol) in MeOH (50 mL) and HOAc (10 mL) was heated at 80° C. for 4 h. The reaction mixture was filtered and the filtrate concentrated in vacuo. To the residue was added $NH_4OH$ (50 mL), and the mixture was extracted with DCM (50 mL×3). The combined extracts were dried ($MgSO_4$), filtered, and concentrated in vacuo. The crude mixture was purified by $SiO_2$ chromatography eluting with DCM/MeOH/TEA (10:1:0.2) to afford 1-(6-fluoro-1H-benzo[d]imidazol-4-yl)ethanamine (121) as a yellow solid (318 mg, 97.7%). MS (ESI): m/z=180.1 [M+1]$^+$.

Referential Example 24

(6-Chloro-3-methyl-1-(tetrahydro-2H-pyran-2-yl)-1H-indazol-4-yl)methanamine (123)

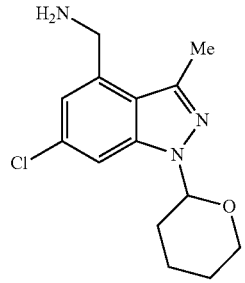 [SMILES: Cc1nn(C2CCCCO2)c2cc(Cl)cc(CN)c12]

Step 1:
A mixture of 4-bromo-6-chloro-1H-indazole (3.0 g, 12.9 mmol), $Pd(PPh_3)_4$ (2.24 g, 1.94 mmol), and $Zn(CN)_2$ (9.22 g, 25.8 mmol) in DMF (50 mL) under nitrogen was heated at 120° C. for 16 h. The reaction mixture was quenched with water and extracted with EtOAc (50 mL×5). The combined extracts were washed with brine (100 mL), dried ($MgSO_4$), filtered, and concentrated in vacuo to afford 6-chloro-1H-indazole-4-carbonitrile as white solid (2.0 g, 86.9%).

Step 2:
To a solution of 6-chloro-1H-indazole-4-carbonitrile (2.0 g, 11.26 mmol) in DMF (30 mL) was added KOH (1.89 g, 33.78 mmol) and $I_2$ (5.72 g, 22.52 mmol). The mixture was heated at 50° C. overnight. The reaction mixture was quenched with EtOAc (200 mL) and water (100 mL). The organic layer was concentrated in vacuo to afford 6-chloro-3-iodo-1H-indazole-4-carbonitrile as white solid (2.01 g, 58.8%). MS (ESI): m/z=304 [M+1]$^+$.

Step 3:
A mixture of 6-chloro-3-iodo-1H-indazole-4-carbonitrile (2.0 g, 6.59 mmol), dihydropyran (1.09 g, 13.18 mmol), and TsOH monohydrate (127 mg, 0.659 mmol) in THF (40 mL) under nitrogen was heated at 80° C. overnight. The reaction mixture was quenched with water (40 mL) and extracted with EtOAc (50 mL×3). The combined extracts were washed with brine, dried ($MgSO_4$), filtered, and concentrated in vacuo. The residue was purified by $SiO_2$ chromatography eluting with petroleum ether/EtOAc (5:1) to afford 6-chloro-3-methyl-1-(tetrahydro-2H-pyran-2-yl)-1H-indazole-4-carbonitrile as white solid (2 g, 78.4%). MS (ESI): m/z=388 [M+1]$^+$.

Step 4:
A mixture of 6-chloro-3-iodo-1-(tetrahydro-2H-pyran-2-yl)-1H-indazole-4-carbonitrile (600 mg, 1.550 mmol), $K_3PO_4$ (644 mg, 3.037 mmol), $PdCl_2$(dppf) (186 mg, 0.228 mmol), and 2,4,6-trimethyl-1,3,5,2,4,6-trioxatriborinane (290 mg, 1.52 mmol) in dioxane (2 mL) under nitrogen in a sealed vial was heated at 100° C. in a microwave oven for 18 h. The reaction mixture was quenched with EtOAc and water. The organic layer was concentrated in vacuo to afford 6-chloro-3-methyl-1-(tetrahydro-2H-pyran-2-yl)-1H-indazole-4-carbonitrile as white solid (230 mg, 53.9%). MS (ESI): m/z=276 [M+1]$^+$.

Step 5:

A mixture of 6-chloro-3-methyl-1-(tetrahydro-2H-pyran-2-yl)-1H-indazole-4-carbonitrile (150 mg, 0.545 mmol) and Raney nickel (20 mg) in NH$_3$/MeOH (7 N, 10 mL) was stirred under hydrogen at RT overnight. The reaction mixture was filtered through Celite® and the filtrate concentrated to afford (6-chloro-3-methyl-1-(tetrahydro-2H-pyran-2-yl)-1H-indazol-4-yl)methanamine (123) as an oil (130 mg, 72.3%). MS (ESI): m/z=280 [M+1]$^+$.

Referential Example 24

1-(6-Fluoro-1-(tetrahydro-2H-pyran-2-yl)-1H-benzo[d]imidazol-5-yl)-N-methylmethanamine (125)

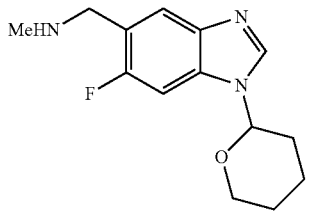 [SMILES: CNCc1cc2ncn(C3CCCCO3)c2cc1F]

Step 1:

A mixture of 6-bromo-5-fluoro-1H-benzo[d]imidazole (10.0 g, 46.5 mmol), Pd(PPh$_3$)$_4$ (7.97 g, 6.9 mmol), and Zn(CN)$_2$ (8.46 g, 93 mmol) in NMP (150 mL) under nitrogen was heated at 110° C. for 16 h. The reaction mixture was quenched with water and extracted with EtOAc (100 mL×5). The combined extracts were washed with brine (300 mL), dried (MgSO$_4$), filtered, and concentrated in vacuo to afford 6-fluoro-3H-benzo[d]imidazole-5-carbonitrile as white solid (7.0 g, 93.5%).

Step 2:

A mixture of 6-fluoro-3H-benzo[d]imidazole-5-carbonitrile (1.78 g, 11.1 mmol), DHP (1.84 g, 22.2 mmol), and TsOH (212 mg, 1.1 mmol) in THF (20 mL) under nitrogen was heated at 85° C. overnight. The reaction mixture was quenched with water (40 mL) and extracted with EtOAc (50 ml×2). The combined extracts were washed with brine, dried (MgSO$_4$), filtered, and concentrated in vacuo. The residue was purified by SiO$_2$ chromatography eluting petroleum ether:EtOAc (5:1) to afford 5-fluoro-1-(tetrahydro-2H-pyran-2-yl)-1H-benzo[d]imidazole-6-carbonitrile as white solid (2.0 g, 73.8%).

Step 3:

A mixture of 5-fluoro-1-(tetrahydro-2H-pyran-2-yl)-1H-benzo[d]imidazole-6-carbonitrile (1.2 g, 4.9 mmol) and Raney nickel (40 mg) in NH$_3$/MeOH solution (7 N, 20 mL) was stirred under hydrogen at RT overnight. The reaction mixture was filtered through Celite® and the filtrate concentrated in vacuo to afford (5-fluoro-1-(tetrahydro-2H-pyran-2-yl)-1H-benzo[d]imidazol-6-yl)methanamine as an oil (350 mg, 28.7%). MS (ESI): m/z=250 [M+1]$^+$.

Step 4:

To a mixture of (5-fluoro-1-(tetrahydro-2H-pyran-2-yl)-1H-benzo[d]imidazol-6-yl)methanamine (2.5 g, 10 mmol) in DCM (16 mL) was added (Boc)$_2$O (1.18 g, 10 mmol) and TEA (6 drops). The mixture was stirred at RT for 5 h. The reaction mixture was concentrated in vacuo. The residue was purified by SiO$_2$ chromatography eluting with petroleum ether/EtOAc (3:1) to afford tert-butyl (5-fluoro-1-(tetrahydro-2H-pyran-2-yl)-1H-benzo[d]imidazol-6-yl)methylcarbamate as white solid (2.2 g, 60.3%). MS (ESI): m/z=350 [M+1]$^+$.

Step 5:

To a mixture of tert-butyl (5-fluoro-1-(tetrahydro-2H-pyran-2-yl)-1H-benzo[d]imidazol-6-yl)methylcarbamate (200 mg, 0.57 mmol) in anhydrous THF (2 mL) cooled to −60° C. was added NaH (60% in mineral oil, 21.6 mg, 0.9 mmol). After stirring at −60° C. for 30 min, CH$_3$I (127 mg, 0.9 mmol) was added, followed by stirring at RT overnight. The reaction mixture was filtered and concentrated in vacuo. The residue was purified by SiO$_2$ chromatography eluting with petroleum ether/EtOAc (3:1) to afford tert-butyl (5-fluoro-1-(tetrahydro-2H-pyran-2-yl)-1H-benzo[d]imidazol-6-yl)methyl(methyl)carbamate as white solid (170 mg, 97%). MS (ESI): m/z=364 [M+1]$^+$.

Step 6:

A solution of tert-butyl (5-fluoro-1-(tetrahydro-2H-pyran-2-yl)-1H-benzo[d]imidazol-6-yl)methyl(methyl)carbamate (200 mg, 0.56 mmol) and TFA (1 mL) in DCM (8 mL) was stirred at 0° C. for 2 h. The reaction mixture was concentrated in vacuo. The residue was purified by SiO$_2$ chromatography eluting with petroleum ether/EtOAc (3:1) to afford 1-(6-fluoro-1-(tetrahydro-2H-pyran-2-yl)-1H-benzo[d]imidazol-5-yl)-N-methylmethanamine (125, 120 mg, 83.3%) as white solid. MS (ESI): m/z=264 [M+1]$^+$.

Referential Example 25

(1-(Tetrahydro-2H-pyran-2-yl)-6-(trifluoromethyl)-1H-indazol-4-yl)methanamine (127)

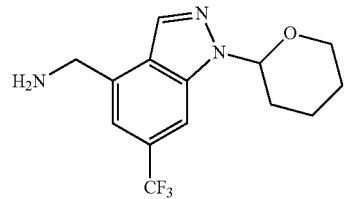 [SMILES: NCc1cc(C(F)(F)F)cc2c1cnn2C1CCCCO1]

Step 1:

A round-bottom flask was charged with 4-bromo-6-(trifluoromethyl)-1H-indazole (1.00 g, 3.8 mmol), TsOH monohydrate (27 mg, 0.15 mmol), 3,4-dihydro-2H-pyran (1.59 g, 18.9 mmol), and THF (25 mL). The reaction mixture was degassed with nitrogen and heated under reflux for 18 h, and then the solvent was removed in vacuo. The residue was purified by SiO$_2$ chromatography to afford 4-bromo-1-(tetrahydro-2H-pyran-2-yl)-6-(trifluoromethyl)-1H-indazole (1.03 g, 78%) as a yellow oil. MS (ESI) m/z: 265.2 [(M−THP group)+1]$^+$.

Step 2:

A sealed-cap vial was charged with 4-bromo-1-(tetrahydro-2H-pyran-2-yl)-6-(trifluoromethyl)-1H-indazole (1.03 g, 2.95 mmol), Zn(CN)$_2$ (0.38 g, 3.24 mmol), Pd(PPh$_3$)$_4$ (0.24 g, 0.21 mmol), and NMP (8 mL). The mixture was degassed for 5 min under nitrogen and the mixture then stirred under nitrogen at 85° C. for 16 h. The mixture was filtered and the filtrate concentrated in vacuo. The crude mixture was purified by SiO$_2$ chromatography to afford 1-(tetrahydro-2H-pyran-2-yl)-6-(trifluoromethyl)-1H-indazole-4-carbonitrile as a solid (0.69 g, 79%). MS (ESI) m/z: 296.3 [M+1]$^+$.

Step 3:

To a solution of 1-(tetrahydro-2H-pyran-2-yl)-6-(trifluoromethyl)-1H-indazole-4-carbonitrile (440 mg, 1.49 mmol) in ammonia (2M solution in methanol, 10 mL) was added Raney-Ni (1.27 g, suspension in water). The mixture was stirred under a hydrogen atmosphere (1 atm.) at RT for 16 h and then filtered. The filtrate was concentrated in vacuo to afford crude (1-(tetrahydro-2H-pyran-2-yl)-6-(trifluoromethyl)-1H-indazol-4-yl)methanamine (127, 267 mg, yield: 60%). MS (ESI) m/z: 300.2 $[M+1]^+$.

Referential Example 26

(6-Methoxy-1-(tetrahydro-2H-pyran-2-yl)-1H-indazol-4-yl)methanamine (129)

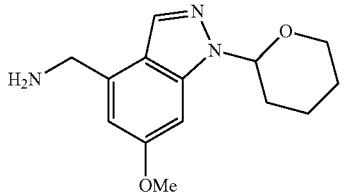 [SMILES: COc1cc(CN)c2cnn(C3CCCCO3)c2c1]

Step 1:

A round-bottom flask was charged with 4-bromo-6-methoxy-1H-indazole (1.00 g, 4.40 mmol), TsOH monohydrate (39 mg, 0.22 mmol), 3,4-dihydro-2H-pyran (1.48 g, 17.6 mmol), and THF (40 mL). The reaction mixture was degassed with nitrogen and refluxed for 18 h, and the solvent was then removed in vacuo. The residue was purified by $SiO_2$ chromatography to afford 4-bromo-6-methoxy-1-(tetrahydro-2H-pyran-2-yl)-1H-indazole (1.53 g, quantitative) as a yellow solid. MS (ESI) m/z: 311.2 $[M+1]^+$.

Step 2:

A sealed microwave vial was charged with 4-bromo-6-methoxy-1-(tetrahydro-2H-pyran-2-yl)-1H-indazole (1.50 g, 4.82 mmol), $Zn(CN)_2$ (0.62 g, 5.30 mmol), $Pd(PPh_3)_4$ (0.22 g, 0.19 mmol), and DMF (13 mL). The mixture was degassed for 5 min under nitrogen and then heated in a microwave reactor at 145° C. for 25 min. The mixture was diluted with EtOAc and filtered. The filtrate was partitioned between water and EtOAc, and the layers were separated. The organic layer was washed with water (3×), dried ($Na_2SO_4$), filtered, and concentrated in vacuo. The crude mixture was purified by $SiO_2$ chromatography to afford 6-methoxy-1-(tetrahydro-2H-pyran-2-yl)-1H-indazole-4-carbonitrile as a solid (1.06 g, 86%). MS (ESI) m/z: 258.2 $[M+1]^+$.

Step 3:

To a solution of 6-methoxy-1-(tetrahydro-2H-pyran-2-yl)-1H-indazole-4-carbonitrile (350 mg, 1.36 mmol) in ammonia (2M solution in methanol, 15 mL) was added Raney-Ni (1.17 g, suspension in water). The mixture was stirred under a hydrogen atmosphere (1 atm.) at RT for 16 h and then filtered. The filtrate was concentrated in vacuo to afford crude (6-methoxy-1-(tetrahydro-2H-pyran-2-yl)-1H-indazol-4-yl)methanamine (129, 270 mg, yield: 76%). MS (ESI) m/z: 262.4 $[M+1]^+$.

Referential Example 27

1-(6-Fluoro-1-methyl-1H-indazol-4-yl)ethanamine (131)

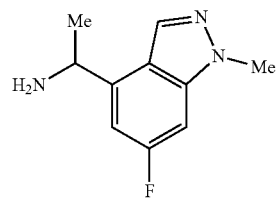 [SMILES: CC(N)c1cc(F)cc2c1cnn2C]

Step 1:

To a solution of 4-bromo-6-fluoro-1H-indazole (2.3 g, 10.7 mmol) in anhydrous DMF (36 mL) was added sodium hydride (60% dispersion in mineral oil, 0.51 g, 12.8 mmol, 1.2 eq.). After stirring at RT for 5 min, iodomethane (2.2 mL) was added, and the resulting mixture was stirred at RT overnight. The reaction mixture was poured into water (200 mL) and extracted with EtOAc (2×100 mL). The combined extracts were washed with water (200 mL) and brine (50 mL), dried ($MgSO_4$), filtered, and evaporated in vacuo. The residue was purified by $SiO_2$ chromatography eluting with hexane:EtOAc (3:1) to afford 4-bromo-6-fluoro-1-methyl-1H-indazole as a tan solid (1.42 g, 58%) and 4-bromo-6-fluoro-2-methyl-2H-indazole (0.29 g, 12%) as a tan solid. MS (ESI): m/z=229.1 $[M+1]^+$.

Step 2:

To a mixture of 4-bromo-6-fluoro-1-methyl-1H-indazole (1.42 g, 6.25 mmol) and tributyl(1-ethoxyvinyl)stannane (2.74 mL, 8.13 mmol, 1.3 eq.) in NMP (24 mL) under an argon atmosphere was added $Pd(0)(PPh_3)_4$ (1.08 g, 0.94 mmol, 0.2 eq.). After the mixture was heated at 110° C. overnight, it was cooled and partitioned between EtOAc and water. The organic layer was washed with brine, dried ($MgSO_4$), and evaporated in vacuo. The crude was purified by $SiO_2$ chromatography eluting with hexane:ethyl acetate (3:1) to afford 4-(1-ethoxyvinyl)-6-fluoro-1-methyl-1H-indazole as a yellow oil (1.24 g, 90%). MS (ESI): m/z=221.3 $[M+1]^+$.

Step 3:

A solution of 4-(1-ethoxyvinyl)-6-fluoro-1-methyl-1H-indazole (1.24 g, 5.62 mmol) in THF (10 mL) and aqueous HCl (2.0 N, 10 mL) was stirred at RT for 2 h then poured into water (200 mL) and extracted with EtOAc (2×50 mL). The combined extracts were washed with an aqueous $NH_4OH$ (30 mL) and brine (50 mL), dried ($MgSO_4$), filtered, and evaporated in vacuo to afford 1-(6-fluoro-1-methyl-1H-indazol-4-yl)ethanone as a white solid (600 mg, 55%). MS (ESI): m/z=193.2 $[M+1]^+$.

Step 4:

To the solution of 1-(6-fluoro-1-methyl-1H-indazol-4-yl)ethanone (900 mg, 4.68 mmol) in EtOH (20 mL) was added hydroxylamine hydrochloride (1.64 g, 23.4 mmol, 5.0 eq.) and NaOAc (3.84 g, 46.8 mmol, 10 eq.). The mixture was stirred at 40° C. overnight, and the solvent was concentrated in vacuo to afford 1-(6-fluoro-1-methyl-1H-indazol-4-yl)ethanone oxime as a white solid (848 mg, 87%). MS (ESI): m/z=208.2 $[M+1]^+$.

Step 5:

To the solution of 1-(6-fluoro-1-methyl-1H-indazol-4-yl)ethanone oxime (848 mg, 4.10 mmol) in MeOH (60 mL) was added powdered Zn (13.6 g, 212.5 mmol, 50.0 eq.) and $NH_4Cl$ (13.6 g, 251 mmol, 60.0 eq.). The mixture was heated at reflux overnight, filtered, and concentrated in vacuo. To the residue was added DCM, and the mixture was washed with water, dried (MgSO$_4$) and concentrated in vacuo to afford 1-(6-fluoro-1-methyl-1H-indazol-4-yl)ethanamine (131) as syrup (785 mg, 87%). MS (ESI): m/z=177.2 [M–NH$_2$]$^+$.

Referential Example 28

(3-Chloro-1H-indol-4-yl)methanamine (133)

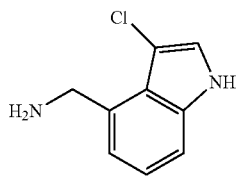 [SMILES: NCc1cccc2[nH]cc(Cl)c12]

Step 1:
To 1H-indole-4-carbonitrile (514.0 mg, 3.61 mmol) in anhydrous DMF (2.8 mL) at 0° C. was added dropwise NCS (517.3 mg, 3.80 mmol) dissolved in DMF (8.5 mL). The reaction mixture was slowly warmed to RT. After stirring for 20 h, the mixture was diluted with EtOAc. The organic layer was washed with satd. aq. NaHCO$_3$ solution, water and brine, dried (Na$_2$SO$_4$), filtered and concentrated in vacuo. The crude residue was purified by SiO$_2$ chromatography eluting with heptane:EtOAc to afford 3-chloro-1H-indole-4-carbonitrile as a white solid (630 mg, 98.7%). MS (ESI) m/z: 177.1 [M+1]$^+$. $^1$H NMR (400 MHz, DMSO) 11.99 (br s, 1H), 7.80 (d, J=2.8 Hz, 1H), 7.78 (d, J=8.2 Hz, 1H), 7.61 (d, J=7.2 Hz, 1H), 7.37-7.26 (m, 1H).

Step 2:
To a solution of 3-chloro-1H-indole-4-carbonitrile (630.0 mg, 3.57 mmol) in ammonia in MeOH (2M, 45 mL) was added Raney Ni (3.05 g) in water (2 mL). The reaction mixture was then hydrogenated under H$_2$ balloon at 1 atm for 20 h. The reaction mixture was filtered through a pad of Celite®, and the pad was washed alternatively with MeOH (10 mL×3) and water (10 mL×3). Volatile solvents were removed from the filtrate. The remaining crude was extracted with EtOAc (3×75 mL). The combined organic layers were dried (Na$_2$SO$_4$), filtered, and concentrated in vacuo. Crystallization from ether/heptane afforded (3-chloro-1H-indol-4-yl)methanamine (133) as a white solid (633 mg, 98.2%). $^1$H NMR (400 MHz, DMSO) δ 11.33 (br s, 1H), 7.44 (s, 1H), 7.27 (d, J=8.0 Hz, 1H), 7.11-7.01 (m, 2H), 4.18 (s, 2H), 1.73 (br s, 2H).

Example 1

N$^2$-((1H-Benzo[d]imidazol-5-yl)methyl)-N$^4$-(5-cyclopropyl-1H-pyrazol-3-yl)pyrimidine-2,4-diamine (I-13)

Step 1:
Thionyl chloride (10 mL) was added dropwise to a solution of 1H-benzo[d]imidazole-5-carboxylic acid (4.8 g, 30 mmol) in MeOH (150 mL) cooled to 0° C. The reaction mixture was heated at reflux for 18 h, and then solvent (about 2/3) was concentrated under reduced pressure. After cooling, a yellow solid was precipitated from the solution and was filtered to afford 4 g (90%) of methyl 1H-benzo[d]imidazole-5-carboxylate (20): MS (ESI) m/z=177 [M+1]+.

Step 2:
A round-bottom flask was charged with 20 (1.76 g, 10 mmol), p-TsOH.H$_2$O (38 mg, 0.2 mmol), 3,4-dihydro-2H-pyran (1.26 g, 15 mmol) and THF (20 mL). The reaction mixture was degassed with nitrogen and heated at reflux for 18 h, and then the solvent was removed under reduced pressure. The residue was diluted with DCM (250 mL) and water (50 mL). The organic layer was dried (MgSO$_4$), filtered and concentrated in vacuo. The residue was purified by SiO$_2$ chromatography eluting with a DCM/MeOH gradient (0.5 to 1.0% MeOH) to afford 2.5 g (90%) of methyl 1-(tetrahydro-2H-pyran-2-yl)-1H-benzo[d]imidazole-5-carboxylate (22) as a grey oil: MS (ESI) m/z=261.2 [M+1]+.

Step 3:
A solution of 22 (2.5 g, 9.61 mmol) in anhydrous THF (10 mL) was added dropwise to a mixture of LiAlH$_4$ (0.55 g, 14.42 mmol) in anhydrous THF (20 mL) at 0° C. under nitrogen. The reaction mixture was stirred for 30 min at 0° C. then treated sequentially with water (2 mL) and 10% NaOH (1.8 mL). The resulting mixture was extracted with ether (2×100 mL). The combined organic layers were dried (Na$_2$SO$_4$), filtered and concentrated in vacuo to afford 2.24 g (95%) of (1-(tetrahydro-2H-pyran-2-yl)-1H-benzo[d]imidazol-5-yl)methanol (24) as yellow oil: MS (ESI) m/z=233.2 [M+1]+.

Step 4:
To a stirred solution of 24 (2.2 g, 9.6 mmol) in THF (20 mL) under nitrogen at RT was added diphenylphosphoryl azide (3.96 g, 14.4 mmol) and DIPEA (5 mL). The reaction was stirred for 18 h then diluted with DCM (200 mL) and water (50 mL). The organic layer was dried (MgSO$_4$), filtered and concentrated in vacuo. The residue was purified by SiO$_2$ chromatography eluting with petroleum ether/EtOAc (2:1) to afford 1.2 g (48%) of 5-(azidomethyl)-1-(tetrahydro-2H-pyran-2-yl)-1H-benzo[d]imidazole (26) as yellow oil: MS (ESI) m/z=258.2 [M+1]+.

Step 5:
To a solution of 26 (1.0 g, 3.9 mmol) in MeOH (20 mL) was added 20% Pd—C (200 mg), and the mixture was stirred vigorously under H2 (1 atm.) atmosphere at RT for 18 h. The reaction mixture was filtered through a pad of Celite® and concentrated in vacuo to afford 740 mg (82%) (1-(tetrahydro-2H-pyran-2-yl)-1H-benzo[d]imidazol-5-yl)methanamine (28) as yellow oil, which was used into the next step without further purification: MS (ESI) m/z=232.2 [M+1]+.

Step 6:
A microwave vial was charged with 53 (750 mg, 3.20 mmol), 28 (740 mg, 3.20 mmol), DIPEA (2.0 mL) and EtOH (10.0 mL), sealed and heated at 120° C. for 18 h. The reaction mixture was concentrated in vacuo and purified by SiO$_2$ chromatography eluting with DCM:MeOH (8:1) to afford 1.12 g (81%) of N$^4$-(5-cyclopropyl-1H-pyrazol-3-yl)-N$^2$-((1-(tetrahydro-2H-pyran-2-yl)-1H-benzo[d]imidazol-5-yl)methyl)pyrimidine-2,4-diamine (32) as white solid: MS (ESI) m/z=431.2 [M+1]+.

Step 7:
To a solution of 32 (406 mg, 0.94 mmol) in MeOH (5 mL) and water (1 mL) was added p-TsOH.H$_2$O (178 mg, 0.94 mmol). The reaction mixture was heated at reflux for 18 h. The solvent was evaporated under reduced pressure and the residue was purified by preparative HPLC to afford 180 mg (55%) of N$^2$-41H-benzo[d]imidazol-5-yl)-methyl)-N$^4$-(5-cyclopropyl-1H-pyrazol-3-yl)pyrimidine-2,4-diamine (I-13) as white solid.

Example 2

N$^2$-((1H-Indol-6-yl)methyl)-N$^4$-(5-cyclopropyl-1H-pyrazol-3-yl)pyrimidine-2,4-diamine (I-35)

Step 1:
To a solution of 1H-indole-6-carbonitrile (70 mg, 0.5 mmol, CASRN 15861-36-6) in THF (5 mL) cooled to 0° C. was added with vigorous stirring NaH (25 mg, 60% in oil, 0.65 mmol). After stirring for 30 min, TsCl (140 mg, 0.75 mmol) was added to the mixture. The reaction mixture was stirred at RT for 18 h then partitioned between DCM (300 mL) and water (50 mL). The organic layer was separated, dried (MgSO$_4$), filtered and concentrated in vacuo. The resulting residue was purified by SiO$_2$ chromatography eluting with a petroleum ether/EtOAc gradient (5 to 10% EtOAc) to afford 100 mg (67%) of 1-tosyl-1H-indole-6-carbonitrile (34) as a white solid: MS (ESI) m/z=297.1 [M+1]+.

Step 2:

To a solution of 34 (100 mg, 0.34 mmol) and 7 M ammonia solution in MeOH (5 mL) was added Raney Ni (10 mg) and the mixture was stirred vigorously under H2 (1 atm.) atmosphere at RT for 18 h. The catalyst was filtered was and the filtrate concentrated in vacuo to afford 80 mg (78%) of (1-tosyl-1H-indol-6-yl)methanamine (36) as syrup: MS (ESI) m/z=301.2 [M+1]+.

Step 3:

A microwave vial was charged with 53 (80 mg, 0.34 mmol), 36 (80 mg, 0.27 mmol), DIPEA (0.2 mL) and n-BuOH (2.0 mL), sealed and irradiated in a microwave reactor at 180° C. for 80 min. The reaction mixture was concentrated and purified with a CombiFlash® to afford 130 mg (95%) of N$^4$-(5-cyclopropyl-1H-pyrazol-3-yl)-N$^2$-((1-tosyl-1H-indol-6-yl)methyl)pyrimidine-2,4-diamine (38) as yellow solid; MS (ESI) m/z=500.1 [M+1]+.

Step 4:

To a solution of 38 (130 mg, 0.25 mmol) in MeOH (2 mL) was added a 2.0 N solution of KOH in water (2 mL). The mixture was stirred at 100° C. for 18 h. The solvent was evaporated under reduced pressure and the residue was purified by preparative HPLC to afford 20 mg (22%) of I-35 as white solid.

Example 3

N$^2$-((1H-Indol-5-yl)methyl)-N$^4$-(5-cyclopropyl-1H-pyrazol-3-yl)pyrimidine-2,4-diamine (I-15)

N$^2$-((1H-Indol-5-yl)methyl)-N$^4$-(5-cyclopropyl-1H-pyrazol-3-yl)pyrimidine-2,4-di amine was prepared in accord with Example 2 except in step 1, 1H-indole-6-carbonitrile was replaced by 1H-indole-5-carbonitrile which afforded 100 mg (30%) of I-15 as white solid.

Example 4

N$^2$-((1H-Indol-4-yl)methyl)-N$^4$-(5-cyclopropyl-1H-pyrazol-3-yl)pyrimidine-2,4-diamine (I-38)

Step 1:

To a solution of 1H-indole-4-carbaldehyde (2.9 g, 20 mmol) in THF (50 mL) cooled in an ice bath was added NaH (0.96 g, 60% in oil, 24 mmol) with vigorous stirring. After stirring for 30 min, 4-toluenesulfonyl chloride (5.73 g, 30 mmol) was added. The mixture was stirred at RT overnight and the solvent was removed in vacuo. The residue was diluted with DCM (500 mL) and water (50 mL). The organic layer was separated, dried (MgSO$_4$), filtered and concentrated. The crude product was purified by SiO$_2$ chromatography eluting with a petroleum ether/EtOAc gradient (5 to 10% EtOAc) to afford 900 mg (15%) of 1-tosyl-1H-indole-4-carbaldehyde (42) as white solid: MS (ESI) m/z=300.1 [M+1]+.

Step 2:

To a solution of 42 (900 mg, 3 mmol) in EtOH (10 mL) was added hydroxylamine hydrochloride (1.0 g, 15 mmol) and pyridine (1.0 mL). After the reaction mixture was stirred at 70° C. overnight, the solvent was removed in vacuo to afford 800 mg (85%) of 1-tosyl-1H-indole-4-carbaldehyde oxime (44) as white solid: MS (ESI) m/z=315 [M+1]+.

Step 3:

To a solution of 44 (620 mg, 2 mmol) in EtOH (15 mL) was added zinc powder (320 mg, 5.0 mmol) and NH$_4$Cl (0.53 g, 10 mmol). The reaction mixture was heated at reflux overnight and the filtrate was concentrated to dryness. The residue was diluted with DCM (100 mL) and water (20 mL). The organic layer was separated, dried (MgSO$_4$), filtered and concentrated to afford 600 mg (100%) of (1-tosyl-1H-indol-4-yl)methanamine (46) as yellow syrup: MS (ESI) m/z=284.1 [M−15]+.

Step 4:

A tube was charged with 53 (415 mg, 1.38 mmol), 46 (486 mg, 2.07 mmol), DIPEA (1.0 ml) and IPA (3 mL), degassed, sealed and heated at 120° C. overnight. The mixture was concentrated in vacuo. The residue was purified by SiO$_2$ chromatography eluting with a DCM/MeOH gradient (3.3 to 5% MeOH) to afford 330 mg (48%) of N$^4$-(5-cyclopropyl-1H-pyrazol-3-yl)-N$^2$-((1-tosyl-1H-indol-4-yl)methyl)pyrimidine-2,4-diamine (50) as yellow solid: MS (ESI) m/z=500.3 [M+1]+.

Step 5:

To a solution of 50 (330 mg, 0.73 mmol) in MeOH (5.0 mL) was added a solution of KOH (2.0 N, 5 mL). The mixture was heated in a sealed tube at 100° C. overnight then concentrated in vacuo. The residue was purified by preparative HPLC to afford 145 mg (57%) of I-38 as white solid.

Example 5

N$^2$-((1H-benzo[d]imidazol-4-yl)methyl)-N$^4$-(5-cyclopropyl-1H-pyrazol-3-yl)pyrimidine-2,4-diamine (I-39)

Step 1:

To a mixture of 3-bromo-2-nitrobenzenamine (4.7 g, 21.66 mmol) in formic acid (98%, 50 mL) was added 10% Pd/C and ammonium formate (13.6 g, 216.6 mmol) and the reaction mixture was stirred under nitrogen at 120° C. for 24 h. The catalyst was filtered, the filtrate was concentrated, the residue was dissolved in water (100 mL) and extracted with EtOAc (2×150 mL). The combined organic extracts were washed with water and brine, dried (Na$_2$SO$_4$), filtered and concentrated in vacuo to afford 1.3 g (30%) of crude 4-bromo-1H-benzo[d]imidazole (52) as dark brown solid: MS (ESI) m/z=197.1 [M+1]+.

Step 2:

To a mixture of 52 (1.30 g, 6.6 mmol) and 3,4-dihydro-2H-pyran (2.78 g, 33.0 mmol) in THF (15 mL) was added p-TsOH.H$_2$O (0.11 g, 0.66 mmol). The mixture was stirred at 80° C. for 14 h, then the solvent was removed in vacuo. The residue was purified by SiO$_2$ chromatography eluting with 10% petroleum ether/EtOAc to afford 1.3 g (70%) 4-bromo-1-(tetrahydro-2H-pyran-2-yl)-1H-benzo[d]imidazole (54) as brown oil: MS (ESI) m/z=281.0 [M+1]+.

Step 3:

A mixture of 54 (1.30 g, 4.62 mmol), Zn(CN)$_2$ (1.08 g, 9.24 mmol), Pd(PPh$_3$)$_4$ (0.53 g, 0.46 mmol) and NMP (15 mL) was stirred under nitrogen at 85° C. for 14 h. The mixture was filtered and the filtrate was purified by reverse phase chromatography eluting with 35% MeCN/H$_2$O (containing 0.5% ammonia) to afford 0.75 g (70%) 1-(tetrahydro-2H-pyran-2- yl)-1H-benzo[d]imidazole-4-carbonitrile (56) as brown solid: MS (ESI) m/z=228.3 [M+1]+.

Step 4:

Reduction of 56 was carried out in accord with step 2 of example 2 to afford 0.7 g (92%) of crude (1-(tetrahydro-2H-pyran-2-yl)-1H-benzo[d]imidazol-4-yl)methanamine 58 as yellow oil: MS (ESI) m/z=232.3 [M+1]+.

Step 5:

A mixture of 58 (200 mg, 0.87 mmol), DIPEA (335 mg, 2.61 mmol) and 53 (203 mg, 0.87 mmol) in IPA (3 mL) was irradiated in a microwave reactor at 120° C. for 2 h. The solvent was removed under reduced pressure to afford 110 mg (30%) of crude $N^4$-(5-cyclopropyl-1H-pyrazol-3-yl)-$N^2$-((1-(tetrahydro-2H-pyran-2-yl)-1H-benzo[d]imidazol-4-yl)methyl)pyrimidine-2,4-diamine (60) as brown solid, which was used in the step without further purification: MS (ESI) m/z=431.7 [M+1]+.

Step 6:

A mixture of 60 (110 mg, 0.26 mmol) and p-TsOH.H$_2$O (44 mg, 0.26 mmol) in MeOH (5 mL) and water (1 mL) was heated at 80° C. for 14 h. The solvent was removed in vacuo. The crude product was purified by preparative HPLC to afford 45 mg (51%) I-39 as white solid.

Example 6

$N^2$-((1H-Benzo[d]imidazol-5-yl)methyl)-$N^4$-(5-cyclopropyl-1H-pyrazol-3-yl)-$N^2$-methylpyrimidine-2, 4-diamine (I-12)

Step 1:

To a solution of oxalyl chloride (1.17 g, 9.23 mol) in DCM (10 mL) at −70° C. was added dropwise DMSO (1.41 g, 18.09 mmol). The reaction mixture was stirred at −70° C. for 30 min. To the resulting solution was added dropwise over 30 min a solution of 24 (1.4 g, 6.03 mmol) in DCM (20 mL). After the addition the reaction temperature was raised to −55° C. The reaction was stirred for 1 h while the temperature was maintained between −55° C. and −45° C., then DIPEA (6.0 mL) was added dropwise over 5 min. The reaction mixture was warmed to 0° C. over 10 min then quenched with 1 M HCl (50 mL). The organic layer was separated, dried (MgSO$_4$), filtered and concentrated in vacuo to afford 1.0 g (72%) of 1-(tetrahydro-2H-pyran-2-yl)-1H-benzo[d]imidazole-5-carbaldehyde (64) as red oil: MS (ESI) m/z=231.1 [M+1]+.

Step 2:

To a solution of 64 (1.0 g, 4.34 mmol) in MeOH (10 mL) at 0° C. was added a solution of MeNH$_2$ in EtOH (33%, 2 mL). After stirring at RT for 2 h, the mixture was concentrated under reduced pressure to afford 1.0 g (94%) of N-((1-(tetrahydro-2H-pyran-2-yl)-1H-benzo[d]imidazol-5-yl)methylene)-methanamine (66) as yellow oil: MS (ESI) m/z=244.2 [M+1]+.

Step 3:

To a solution of 66 (1.0 g, 4.11 mmol) in MeOH (10 mL) cooled to 0° C. was added NaBH$_4$ (300 mg, 8.23 mmol). After stirring at RT overnight, the mixture was quenched with water (3 mL) and extracted with DCM (3×50 mL). The organic layers were separated, washed with brine, dried (MgSO$_4$), filtered and concentrated in vacuo to afford 880 mg (66%) of N-methyl-1-(1-(tetrahydro-2H-pyran-2-yl)-1H-benzo[d]imidazol-5-yl)methanamine (68) as yellow oil: MS (ESI) m/z=246.2 [M+1]+.

Step 4:

A tube was charged with 53 (846 mg, 3.6 mmol), 68 (880 mg, 3.6 mmol), DIPEA (5 mL) and IPA (10 mL), degassed, sealed and then heated at 120° C. overnight. The solvent was evaporated in vacuo to afford 444 mg (27%) $N^4$-(5-cyclopropyl-1H-pyrazol-3-yl)-$N^2$-methyl-$N^2$-((1-(tetrahydro-2H-pyran-2-yl)-1H-benzo[d]imidazol-5-yl)methyl)-pyrimidine-2, 4-diamine (70) as a yellow solid; MS (ESI) m/z=445.2 [M+1]+.

Step 5:

A tube was charged with a solution of 70 (444 mg, 1.0 mmol) in MeOH (5 mL) and water (1 mL) then TsOH.H$_2$O (190 mg, 1.0 mmol) was added. The tube was sealed and heated at 80° C. overnight. The solvent was evaporated in vacuo and the residue was purified by preparative HPLC to afford 240 mg (66%) of I-12 as a white solid.

Example 7

$N^4$-(5-Cyclopropyl-1H-pyrazol-3-yl)-$N^2$-((7-methyl-1H-benzo[d]imidazol-5-yl)methyl)-pyrimidine-2,4-diamine (I-26)

Step 1:

To a suspension of 4-bromo-2-methyl-6-nitroaniline (2.0 g, 8.7 mmol) in EtOH (20 mL) was added SnCl$_2$ (5.0 g, 26.1 mmol). The reaction mixture was heated at reflux for 14 h, cooled to RT and concentrated in vacuo. The residue was diluted with EtOAc (100 mL) and partitioned between satd. aq. NaHCO$_3$ solution (200 mL). The resulting slurry was filtered through a pad of Celite® and the wet cake was washed with EtOAc (3×50 mL). The filtrate was washed sequentially with satd. aq. NaHCO$_3$, water, and brine, dried (MgSO$_4$), filtered and concentrated in vacuo to afford 1.27 g (72%) of 5-bromo-3-methylbenzene-1,2-diamine (72) as yellow oil: MS (ESI) m/z=201.1 [M+1]+.

Step 2:

A mixture of 72 (1.27 g, 6.32 mmol) in formic acid (10 mL) was heated at reflux overnight. The reaction mixture was concentrated in vacuo to afford brown oil, which was treated with a satd. aq. NaHCO3. The aqueous solution was extracted with EtOAc (3×300 mL). The extracts were dried MgSO$_4$), filtered and concentrated to afford 1.09 g (82%) of 5-bromo-7-methyl-1H-benzo[d]imidazole (74) as yellow solid; MS (ESI) m/z 211.1 [M+1]+.

Step 3:

A mixture of 74 (1.09 g, 5.19 mmol), TsOH.H$_2$O (98 mg, 0.51 mmol), 3,4-dihydro-2H-pyran (2.4 mL, 26 mmol) in THF (15 mL) was degassed and then heated to reflux overnight. The solvent was removed in vacuo. The residue was partitioned between with DCM (300 mL) and water (50 mL). The organic layer was separated, dried (MgSO$_4$), filtered and concentrated. The crude product was purified by SiO$_2$ chromatography eluting with a MeOH/DCM gradient (0.5% to 1% MeOH) to afford 1.45 g (95%) of 5-bromo-7-methyl-1-(tetrahydro-2H-pyran-2-yl)-1H-benzo[d]imidazole (76) as yellow solid: MS (ESI) m/z=295.1 [M+1]$^+$.

5-Bromo-7-methyl-1-(tetrahydro-2H-pyran-2-yl)-1H-benzo[d]imidazole (76) was converted to I-26 in accord with the procedures described in steps 3 to 6 of example 5. The crude product was purified by preparative HPLC to afford 71 mg (25%) of I-26.

Example 8

(S)—N²-(1-(1H-benzo[d]imidazol-5-yl)ethyl)-N⁴-(5-cyclopropyl-1H-pyrazol-3-yl)-N²-methylpyrimidine-2,4-diamine (I-9) and (R)—N²-(1-(1H-benzo[d]imidazol-5-yl)ethyl)-N⁴-(5-cyclopropyl-1H-pyrazol-3-yl)-N²-methylpyrimidine-2,4-diamine (I-55)

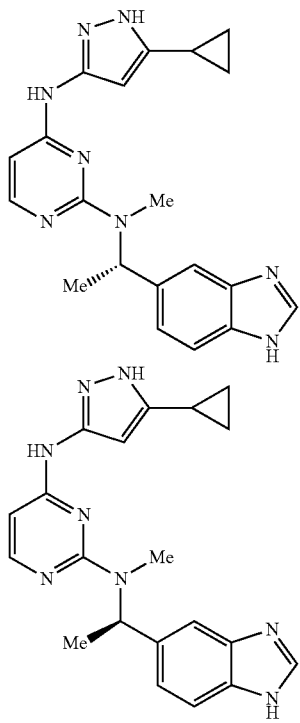

Step 1:
A mixture of 4-bromobenzene-1,2-diamine (4.0 g, 21.5 mmol) and formic acid (95%, 100 mL) was stirred at 100° C. overnight. The reaction mixture was cooled to RT and concentrated in vacuo to afford a dark oil. The crude oil was partitioned between EtOAc (500 mL) and NH₃/H₂O (50 mL). The EtOAc layer was separated and concentrated in vacuo to afford 4.5 g (100%) of 5-bromo-1H-benzo[d]imidazole (78) as brown solid: MS (ESI) m/z=197.0 (M+1).

Step 2:
A mixture of 78 (4.5 g, 23 mmol), 3,4-dihydro-2H-pyran (9 mL, 0.1 mol), p-TsOH.H₂O (1.0 g, 3.4 mmol) in THF (200 mL) was stirred under nitrogen at 80° C. for 18 h. The reaction mixture was concentrated in vacuo. The crude product was purified by SiO₂ chromatography eluting with DCM/MeOH (100:1) to afford 6.0 g (100%) of 5-bromo-1-(tetrahydro-2H-pyran-2-yl)-1H-benzo[d]imidazole (80) as yellow oil: MS (ESI) m/z=281.0 (M+1).

Step 3:
A mixture of 80 (2.81 g, 0.01 mol), butyl vinyl ether (1.5 g, 0.015 mol), PdCl₂ (26 mg, 0.14 mmol), (o-tolyl)₃P (88 mg, 0.29 mmol), K₃PO₄ (1.5 g, 0.02 mol), and IPA (20 ml) was heated at reflux under nitrogen overnight. The mixture was cooled to RT and the solvent was removed in vacuo. To the residue was added 6M HCl (60 mL) and the resulting solution stirred for 15 min. The mixture was adjusted to pH 8 with aqueous NH₄OH (35%) and was extracted with EtOAc (300 mL). The organic layer was washed with brine (50 mL), dried (Na₂SO₄), filtered and concentrated in vacuo. The residue was purified by SiO₂ chromatography eluting with a DCM/MeOH gradient (5 to 10% MeOH) to afford 1.2 g (86%) of 1-(1-(tetrahydro-2H-pyran-2-yl)-1H-benzo[d]imidazol-5-yl)ethanone (82) as yellow oil: MS (ESI) m/z=245.3 (M+1).

Step 4:
A solution of 82 (1.2 g, 4.9 mmol) in 30% methanamine in MeOH (50 mL) was stirred at RT for 15 h. To the reaction mixture was added NaBH₄ (186 mg, 4.9 mmol) at RT in several portions and stirred overnight. The reaction mixture was concentrated in vacuo. The crude product was purified by SiO₂ chromatography eluting with DCM/MeOH (100:1) followed by reverse phase chromatography on CombiFlash® eluting with 0.01% NH₄OH ammonia in water (solvent A) and MeCN (solvent B) to afford 200 mg (15%) of (±)-N-methyl-1-(1-(tetrahydro-2H-pyran-2-yl)-1H-benzo[d]imidazol-5-yl)ethanamine (84) as yellow oil: MS (ESI) m/z=260.3 (M+1).

Step 5:
A tube was charged with mixture of 84 (200 mg, 0.77 mmol), 53 (181 mg, 0.77 mmol) and DIPEA (200 mg, 1.5 mmol) in IPA (5 mL), sealed and stirred at 120° C. overnight. The reaction mixture was cooled to RT and concentrated under reduced pressure. The crude residue was purified by SiO₂ chromatography eluting with a MeOH/DCM gradient (5% to 15% MeOH) to afford 68 mg (19%) of (±)-N⁴-(5-cyclopropyl-1H-pyrazol-3-yl)-N²-methyl-N²-(1-(1-(tetrahydro-2H-pyran-2-yl)-1H-benzo[d]imidazol-5-yl)ethyl)pyrimidine-2,4-diamine (86) as white solid: MS (ESI) m/z=459.2 (M+1).

Step 6:
To a solution of 86 (68 mg, 0.148 mmol) in MeOH (50 mL) and water (10 mL) was added TsOH.H₂O (44 mg, 0.148 mmol). The reaction mixture was heated at 50° C. for 18 h. The solvent was evaporated in vacuo and the residue was purified by preparative HPLC to afford 25 mg (45%) of (±)-N²-(1-(1H-benzo[d]imidazol-5-yl)ethyl)-N4-(5-cyclopropyl-1H-pyrazol-3-yl)-N²-methylpyrimidine-2,4-diamine (88) as white solid: MS (ESI) m/z=375.3 (M+1).

Step 7:
Chiral resolution of 88 was carried out using a CHIRALPAK AS-H column (5 μm, 30×250 mm) at a column temperature of 40° C. with 10 mM diethanolamine (DEA) buffer in MeOH/CO₂ (82:18 v/v) as mobile phase and a flow rate of 60 mL/min. The load amount per injection was 10 mg. Analytical chiral purity checks were carried out by using a CHIRALPAK AS-H column (5 μm, 4.6×150 mm) at a column temperature of 40° C. with 10 mM DEA buffer/MeOH (70:30 v/v) as mobile phase with a flow rate of 2.1 mL/min. The injection volume was 3 μL. Removal of the solvent from one fraction afforded 4.5 mg of I-9 as white solid (4.5 mg, 8.18%). Removal of the solvent from the second fraction afforded 6.0 mg (10.8%) of I-55 as yellow solid.

Example 9

N²-(2-(1H-Benzo[d]imidazol-5-yl)propan-2-yl)-N⁴-(5-cyclopropyl-1H-pyrazol-3-yl)pyrimidine-2,4-diamine (I-17)

Step 1:
A mixture of 3,4-diaminobenzonitrile (2.0 g, 15.04 mmol) in 98% formic acid (35 mL) was stirred at 110° C. for 18 h. The reaction mixture was cooled to RT and concentrated in vacuo. The crude residue was washed with NH₃/H₂O (3×20 mL) and water (20 mL) to afford 1.63 g (75.8%) of 1H-benzo[d]imidazole-5-carbonitrile (90) as yellow solid: MS (ESI) m/z=144.2 [M+1]+.

Step 2:

A mixture of 90 (1.63 g, 11.4 mmol), 3,4-dihydro-2H-pyran (2.87 g, 34.2 mmol), and p-TsOH.H$_2$O (196 mg, 1.14 mmol) in THF (60 mL) was stirred under nitrogen at 80° C. for 18 h. The reaction mixture was concentrated in vacuo. The crude product was purified by SiO$_2$ chromatography with eluting with petroleum ether/EtOAc (1:1) to afford 2.48 g (95.9%) of 1-(tetrahydro-2H-pyran-2-yl)-1H-benzo[d]imidazole-5-carbonitrile (92) as yellow oil: MS (ESI) m/z=228.1 [M+1]+.

Step 3:

A solution of methyl magnesium bromide (1.4 M in toluene and THF, 21.4 mL, 29.96 mmol) was added dropwise to a stirred mixture of 92 (1.70 g, 7.49 mmol) in anhydrous toluene (50 mL) at RT maintained under nitrogen. After the addition, the mixture was stirred under nitrogen at RT for 40 min, followed by addition of tetraisopropoxytitanium (IV) (259 mg, 0.912 mmol). The mixture was stirred under nitrogen at 40° C. for 18 h then cooled to RT and poured into 1N aq. NaOH (100 mL). The solution was filtered and the wet cake was washed with DCM (3×20 mL). The aqueous layer was extracted with DCM (3×80 mL). The combined organic extracts were concentrated in vacuo. The crude product was purified by preparative HPLC to afford 1.08 g (55.7%) of 2-(1-(tetrahydro-2H-pyran-2-yl)-1H-benzo[d]imidazol-5-yl)propan-2-amine (94) as a yellow oil: MS (ESI) m/z=260.2 [M+1]+.

Step 4:

A neat mixture of 94 (691 mg, 2.67 mmol) and 53 (210 mg, 0.89 mmol) was stirred under nitrogen at 140° C. for 18 h. The dark brown mixture was cooled to RT and was purified by preparative HPLC to afford 25 mg (7.5%) of I-17 as white solid.

Example 10

N$^4$-(5-Cyclopropyl-1H-pyrazol-3-yl)-N$^2$-((6-fluoro-1H-benzo[d]imidazol-5-yl)methyl)pyrimidine-2,4-diamine (I-28)

Step 1:

A solution of 5-fluoro-2-nitroaniline (1.5 g, 9.61 mmol) and NBS (1.7 g, 9.55 mmol) in HOAc (75 mL) was heated at reflux for 90 min. The reaction mixture was then poured into ice water (300 mL) and stirred for 10 min. A bright yellow precipitate was collected by filtration and dried in vacuo overnight to afford 1.57 g (76%) of 4-bromo-5-fluoro-2-nitroaniline (96): MS (ESI) m/z=235 [M+1]+.

Step 2:

To a suspension of 96 (1.57 g, 6.74 mmol) in EtOH (16 mL) was added SnCl$_2$ (3.82 g, 20.2 mmol). The reaction mixture was heated at reflux for 14 h, cooled to RT and concentrated in vacuo. The residue was partitioned between EtOAc (100 mL) and sat'd. aq. NaHCO$_3$ (200 mL). The resulting slurry was filtered through a pad of Celite® and the wet cake was washed with EtOAc (3×50 mL). The organic layer was washed sequentially with saturated NaHCO$_3$, water, and brine, dried (MgSO$_4$), filtered and concentrated in vacuo to afford 600 mg (43%) of 4-bromo-5-fluorobenzene-1,2-diamine (98) as yellow solid: MS (ESI) m/z=205 [M+1]+.

Step 3:

A mixture of 98 (600 mg, 2.93 mmol) in formic acid (5.0 mL) was heated to reflux overnight. The reaction mixture was concentrated in vacuo to afford a brown oil that was partitioned between EtOAc (300 mL) and a sat'd. aq. NaHCO$_3$ (100 mL). The organic layer was separated, dried (MgSO$_4$), filtered and evaporated in vacuo to afford 550 mg (87%) of 5-bromo-6-fluoro-1H-benzo[d]imidazole (100) as white solid (550 mg, 87%): MS (ESI) m/z=215 [M+1]+.

Step 4:

A mixture of 100 (550 mg, 2.57 mmol), TsOH.H$_2$O (50 mg, 0.26 mmol), and 3,4-dihydro-2H-pyran (1.08 g, 12.85 mmol) in THF (10 mL) was heated at reflux overnight. After the solvent was removed in vacuo, the residue was partitioned between DCM (300 mL) and water (100 mL). The organic layer was separated, dried (MgSO$_4$), filtered and concentrated in vacuo. The residue was purified by SiO$_2$ chromatography eluting with a MeOH/DCM gradient (0.5 to 1% MeOH) to afford 817 mg (100%) of 5-bromo-6-fluoro-1-(tetrahydro-2H-pyran-2-yl)-1H-benzo[d]imidazole (102) as yellow oil: MS (ESI) m/z=299 [M+1]+.

Step 5:

The conversion of 102 to 6-fluoro-1-(tetrahydro-2H-pyran-2-yl)-1H-benzo[d]imidazole-5-carbonitrile (104) was carried out in accord with step 3 of example 5. The crude product was purified by SiO$_2$ chromatography eluting with MeOH/DCM (1:150) to afford 500 mg (79%) of 104 as yellow oil: MS (ESI) m/z=246 [M+1]+.

Step 6:

To a solution of 104 (245 mg, 1.0 mmol) in 7N NH$_3$ in MeOH (20 mL) was added Ra—Ni (50 mg), and then it was stirred under hydrogen (1 atm) at RT overnight. The dark mixture was filtered and the filtrate was concentrated in vacuo to afford 230 mg (96%) of (6-fluoro-1-(tetrahydro-2H-pyran-2-yl)-1H-benzo[d]imidazol-5-yl)methanamine (106) as yellow oil: MS (ESI): m/z=250 [M+1]+.

Step 7:

A tube was charged with 53 (235 mg, 1.0 mmol), 106 (237 mg, 0.95 mmol), DIPEA (1.0 mL) and IPA (3 mL), degassed, sealed and heated at 120° C. overnight. The solvent was evaporated in vacuo to afford 170 mg (39%) of N$^4$-(5-cyclopropyl-1H-pyrazol-3-yl)-N$^2$-((6-fluoro-1-(tetrahydro-2H-pyran-2-yl)-1H-benzo[d]imidazol-5-yl)methyl)pyrimidine-2,4-diamine (108) as white solid: MS (ESI) m/z=449.2 [M+1]+.

Step 8:

A mixture of 108 (170 mg, 0.38 mmol) and TsOH.H$_2$O (72 mg, 0.38 mmol) in MeOH (5 mL) and water (1 mL) was heated at reflux for 2 h. After solvent was removed in vacuo, the residue was purified by preparative HPLC to give 60 mg (43%) of I-28 as white solid.

Example 11

N$^4$-(5-cyclopropyl-1H-pyrazol-3-yl)-N$^2$-((7-fluoro-1H-indol-4-yl)methyl)pyrimidine-2,4-diamine (I-47)

Step 1:

To a solution of 4-bromo-1-fluoro-2-nitrobenzene (1.1 g, 5.0 mmol) in THF (20 mL) at −40° C. under nitrogen atmosphere was added slowly vinylmagnesium bromide (1 M in THF, 15.5 mL, 15.5 mmol). The reaction mixture was stirred for 1.5 h then quenched with saturated NH$_4$Cl aqueous solution (10 mL). The mixture was partitioned between EtOAc (300 mL) and water (50 mL). The organic layer was separated, washed with brine, dried (MgSO$_4$), filtered and evaporated in vacuo. The residue was purified by SiO$_2$ chromatography eluting with 2.5% EtOAc/petroleum ether to afford 0.125 g (12%) of 4-bromo-7-fluoro-1H-indole (110) as brown oil: MS (ESI) m/z=214 [M−1]+.

Step 2:

Conversion of 110 to 7-fluoro-1H-indole-4-carbonitrile as white solid (112) was carried out in accord with the procedure in step 3 of example 5. The crude product was purified by $SiO_2$ chromatography eluting with MeOH/DCM (1:180) to afford 43 mg (56%) of 112: MS (ESI) m/z=161.1 [M+1]+.

Step 3:

To a solution of 112 (43 mg, 0.27 mmol) in 7N $NH_3$ in MeOH (10 mL) was added Ra—Ni (10 mg), and the mixture was stirred under hydrogen (1 atm) at RT overnight. The dark mixture was filtered and the filtrate was concentrated in vacuo to afford 44 mg (100%) of (7-fluoro-1H-indol-4-yl)methanamine (114) as yellow oil: MS (ESI) m/z=148.1 [M−16]+.

Step 4:

A tube was charged with 53 (63 mg, 0.27 mmol), 114 (44 mg, 0.27 mmol), DIPEA (2 mL) in IPA (5 mL), degassed, sealed and heated at 120° C. overnight. The solvent was evaporated in vacuo and the residue was purified by preparative HPLC to afford 56 mg (57%) of I-47 as white solid.

Example 12

$N^2$-[(1S)-1-(1H-Benzimidazol-5-yl)ethyl]-$N^4$-(5-cyclopropyl-1H-pyrazol-3-yl)pyrimidine-2,4-diamine (I-5)

Step 1:

To a solution of (R)-2-methylpropane-2-sulfinamide (6.9 g, 57.31 mmol) and $Ti(OEt)_4$ (26.1 g, 114.62 mmol) in THF (200 mL) at RT was added 82 (14 g, 57.31 mmol). The reaction mixture was heated to 75° C. overnight. After MS analysis indicated complete conversion of 122, the mixture was cooled to RT and then to −48.0° C. L-Selectride (172 mL, 1M solution in THF) was added dropwise. The reaction mixture was warmed. When the reduction was complete the reaction mixture was cooled to 0° C. and MeOH was added dropwise until gas evolution was no longer observed. The crude reaction mixture was poured into an equal volume of rapidly stirred brine. The resulting suspension was filtered through a plug of Celite® and the filter cake was washed with EtOAc. The filtrate was washed with brine, and the brine layer was extracted with EtOAc, dried ($Na_2SO_4$) and evaporated under reduced pressure. The residue was purified by $SiO_2$ chromatography eluting with DCM/MeOH (20:1) to afford 10 g (50%) of (S)-2-methyl-N-((1S)-1-(1-(tetrahydro-2H-pyran-2-yl)-1H-benzo[d]imidazol-5-yl)ethyl)propane-2-sulfinamide (124) as yellow oil.

Step 2:

To a solution of 124 (3 g, 8.58 mmol) in EtOAc (10 mL) was added HCl/EtOAc (25 mL, 2 M in EtOAc) dropwise and stirred at RT. When the reaction was complete the reaction mixture was filtered, the solid was collected and washed with EtOAc to afford 2 g (83%) of (1S)-1-(1-(tetrahydro-2H-pyran-2-yl)-1H-benzo[d]imidazol-5-yl)ethanamine hydrochloride (126) as a white solid.

Step 3:

A 5 mL microwave tube was charged with 126 (208.2 mg, 0.85 mmol), 53 (100 mg, 0.42 mmol) and n-BuOH (1.2 mL) then DIPEA (0.371 mL) was added, the tube sealed and heated to 140° C. for 18 h in an oil bath. The reaction cooled and diluted with EtOAc (50 mL). Water (25 mL) and some MeOH (1 mL) were added and the phases were separated. The organic layer was washed with brine (25 mL), dried ($Na_2SO_4$), filtered and concentrated. The residue was purified by HPLC and SFC to afford 34.4 mg (22%) of I-5 as a white solid: SFC RT=0.72 min.

Example 13

$N^2$-[(4-Chloro-1H-benzimidazol-5-yl)methyl]-$N^4$-(5-cyclopropyl-1H-pyrazol-3-yl)pyrimidine-2,4-diamine (I-3)

Step 1:

A mixture of 4-bromo-3-chloro-benzene-1,2-diamine (CASRN 1008361-80-5, 27 g, 0.1221 mol) and formic acid (80 mL) was heated to reflux for 1.5 h. After the completion of the reaction, 10% NaOH was added until the solution basic. The resulting solid was filtered and washed well with water then dried over night over suction to afford 22 g (78%) of 5-bromo-4-chloro-1H-benzoimidazole (128) as pale yellow solid which was used without additional purification.

Step 2:

To a solution of 128 (22 g, 0.095 mol) in dry THF (660 mL) was added 3,4-dihydro-2H-pyran (24 g, 0.286 mol) and camphorsulfonic acid (2.2 g, 0.00948 mol) and the solution was heated to reflux for 16 h. The resulting mixture was concentrated, and the residue obtained was purified by $SiO_2$ chromatography eluting with 20% EtOAc/petroleum ether to afford 27 g (90%) of 5-bromo-4-chloro-1-(tetrahydro-pyran-2-yl)-1H-benzoimidazole (130) as pale yellow solid.

Step 3:

A solution of 130 (26 g, 0.082 mol) in dry DMF (550 mL) was degassed for 10 min. To the solution was added sequentially $Pd_2(dba)_3$ (1.5 g, 0.00164 mol), dppf (1.8 g, 0.00328 mol) and $Zn(CN)_2$ (9.19 g, 0.0657 mol). After degassing for 15 min the resulting solution was heated to 110° C. for 6 h. After the reaction was complete, the reaction mixture was filtered through a Celite® pad. The pad was washed well with EtOAc. The filtrate was washed with water and saturated brine solution. The organic phase was dried ($Na_2SO_4$), filtered and concentrated in vacuo to afford 15 g (70%) of 4-chloro-1-(tetrahydro-pyran-2-yl)-1H-benzoimidazole-5-carbonitrile (132) as a pale yellow solid.

Step 4:

To a solution of 132 (15 g, 0.057 mol) in MeOH saturated with ammonia gas (500 mL) was added Raney nickel (75 g). The resulting mixture was stirred under 5 kg/cm2 hydrogen pressure for 16 h. The mixture was filtered through a Celite® pad to remove the catalyst. The filtrate obtained was concentrated and the crude product was purified by $SiO_2$ chromatography eluting with 5% MeOH/$CHCl_3$ to afford 6.8 g (46%) of 0-chloro-1-tetrahydropyran-2-yl-benzimidazol-5-yl)methanamine (134) as yellow solid: 1H-NMR at RT—(400 MHz, DMSO-$d_6$) δ 1.6-1.75 (m, 3H), 1.96-2.02 (m, 2H), 2.16-2.24 (m, 1H), 3.72-3.77 (m, 1H), 3.97-4.00 (m, 1H), 4.1-4.2 (br, 2H), 5.7-5.73 (dd, 1H), 7.0 (br, 2H), 7.47 (br, 1H), 7.74 (br, 1H) and 8.53 (s, 1H).

Step 5:

A 5 mL microwave tube was charged with 134 (169.1 mg, 0.63648 mmol, 1.5 equiv), 53 (100 mg, 0.42432 mmol) and n-BuOH (1.2 mL). DIPEA (5 equiv., 0.371 mL 276, 2.1216 mmol) was added, the tube sealed and heated to 140° C. overnight. The reaction was cooled to RT, filtered and concentrated in vacuo to afford ca. 200 mg. of a crude oil which was used in the next step without further purification.

Step 6:

The material from the step 5 was taken up in MeOH (4.32 mL) and p-TsOH.$H_2O$ (73.8 mg; 0.42432 mmol) was added. The mixture was heated to 100° C. in a sealed vial overnight. The solvent was evaporated under reduced pressure and the residue purified by preparative HPLC to afford 45.4 g (28.1%) of I-3 as a yellow solid.

5-chloro-N²-((4-chloro-1H-benzo[d]imidazol-5-yl)methyl)-N⁴-(5-cyclopropyl-1H-pyrazol-3-yl)pyrimidine-2,4-diamine (I-106) was prepared analogously except 57 replaced 53, TEA replaced DIPEA in step 5 and removal of the THP was carried out in 1:1 MeOH/DCM. The crude mixture was purified by reverse phase HPLC to afford 3.3 mg (1.6%) of I-106.

N²-((4-chloro-1H-benzo[d]imidazol-5-yl)methyl)-N⁴-(5-cyclopentyl-1H-pyrazol-3-yl)pyrimidine-2,4-diamine (I-107) was prepared using procedures analogous to those used in the preparation of I-106 except 67 replaced 57.

N²-((4-chloro-1H-benzo[d]imidazol-5-yl)methyl)-N⁴-(5-cyclobutyl-1H-pyrazol-3-yl)pyrimidine-2,4-diamine (I-108) was prepared using procedures analogous to those used in the preparation of I-106 except 65 replaced 57.

N²-((4-chloro-1H-benzo[d]imidazol-5-yl)methyl)-N⁴-(5-(tetrahydrofuran-2-yl)-1H-pyrazol-3-yl)pyrimidine-2,4-diamine (I-109) was prepared using procedures analogous to those used in the preparation of I-106 except 83 replaced 57.

N²-((4-chloro-1H-benzo[d]imidazol-5-yl)methyl)-N⁴-(5-cyclopropyl-1H-pyrazol-3-yl)-5-fluoropyrimidine-2,4-diamine (I-117) was prepared using procedures analogous to those used in the preparation of I-106 except 55 replaced 57.

Example 14

N²-[(1S)-1-(1H-Benzimidazol-5-yl)ethyl]-N⁴-(5-benzyloxy-1H-pyrazol-3-yl)pyrimidine-2,4-diamine (I-21)

Step 1:
A 2 mL microwave vial was charged with 69 (155 mg, 0.41 mmol), 136 (151.2 mg, 0.62 mmol), DIPEA (0.358 mL) and n-BuOH (1 mL), sealed and heated to 140° C. overnight in an oil bath. The reaction was cooled and then partitioned between EtOAc (50 mL) and water (25 mL). The organic layer was washed with water (2×25 mL). The aqueous layers were back extracted with EtOAc (2×20 mL) and the combined organics washed with brine (50 mL), dried ($Na_2SO_4$), filtered and concentrated to yield a crude oil which was used in the next step without further purification: MS (ESI) m/z=427.2 [(M−THP)+1]+.

Step 2:
A vial was charged with the material from step 1, MeOH (4 mL) and p-TsOH.$H_2O$ (35.7 mg, 0.206 mmol), sealed and heated to 100° C. After 2 d, the reaction mixture was concentrated and taken up in EtOAc (50 mL) and washed with water. The organic layers were back extracted with EtOAc and the combined extracts, dried ($Na_2SO_4$), filtered and concentrated. The residue was purified by HPLC to yield 7.5 mg (4.3%) of I-21 as an off-white solid.

Example 15

N⁴-(5-Cyclopropyl-1H-pyrazol-3-yl)-N²-[(4-fluoro-1H-benzimidazol-5-yl)methyl]pyrimidine-2,4-diamine (I-29)

Step 1:
To a solution of 1,3-difluoro-2-nitro-benzene (30 g, 0.188 moles) in EtOH (300 mL) was added 25% aq. ammonia solution (300 mL) and the resulting mixture was heated to 75° C. for 16 h then cooled and concentrated in vacuo. The residue was dissolved in EtOAc, washed with water and brine solution, dried ($Na_2SO_4$), filtered and concentrated to afford 25 g (85%) of 3-fluoro-2-nitro-phenylamine (138) as a brown solid which was used without any further purification.

Step 2:
To a solution of 138 (25 g, 0.160 mol) in DMF (250 mL) at 0° C. was added dropwise a solution of NBS (28.5 g, 0.160 mol) in DMF (100 mL). The resulting mixture was stirred at 0° C. for 1 h and then at RT for another hour. After the completion of the reaction, the mixture was poured into water (4 L) and extracted with EtOAc. The combined organic layers were washed with water and brine solution, dried ($Na_2SO_4$), filtered and concentrated in vacuo to afford 34 g (90%) of 4-bromo-3-fluoro-2-nitro-phenylamine (140) as a yellow solid which was used without further purification.

Step 3:
To a solution of 140 (34 g, 0.144 mol) and EtOH (510 mL) was added $SnCl_2.2H_2O$ (130.1 g, 0.576 mol) and the resulting mixture was heated to reflux for 4 h. After the completion of the reaction, the solvent was removed in vacuo. The residue was taken up in water and made slightly basic with 10% NaHCO3. The resulting solid was filtered and washed well with EtOAc. The aqueous layer was separated and extracted with EtOAc. The combined organic layers were dried ($Na_2SO_4$), filtered and concentrated in vacuo to afford 25 g (84%) of 4-bromo-3-fluoro-benzene-1,2-diamine (142) as yellow solid which was used without further purification.

Step 4:
A mixture of 142 (25 g, 0.121 mol) and formic acid (75 mL) was heated to reflux for 1.5 h. After the completion of the reaction the reaction was cooled and made basic with 10% NaOH. The resulting solid was filtered and washed with water. Drying overnight under suction afforded 24 g (92%) of 5-bromo-4-fluoro-1H-benzoimidazole (144) as pale yellow solid which was used without further purification.

Step 5:
To a solution of 144 (24 g, 0.111 mol) in dry THF (720 mL) was added 3,4-dihydro-2H-pyran (28.1 g, 0.334 mol) and camphorsulfonic acid (2.6 g, 0.011 mol) then heated to reflux for 16 h. The resulting mixture was concentrated and the residue purified by $SiO_2$ chromatography eluting with 20% EtOAc/petroleum ether to afford 26 g (78%) of 5-bromo-4-fluoro-1-(tetrahydro-pyran-2-yl)-1H-benzoimidazole (146) as pale yellow oil: 1H-NMR (400 MHz, RT, DMSO-d6): δ 1.57-1.63 (m, 2H), 1.70-1.74 (m, 1H), 1.91-2.04 (m, 2H), 2.15-2.19 (m, 1H), 3.73-3.77 (m, 1H), 3.96-4.03 (m, 1H), 5.68-5.71 (dd, 1H), 7.50-7.53 (d, 2H), and 8.51 (s, 1H); MS (ESI): m/z=301.0 [M+1]+.

Step 6:
To a solution of 146 (10 g, 0.034 mol) in dry THF (100 mL) at −78° C. was added dropwise 1.6 M N-butyl lithium solution in hexane (23 mL, 0.0374 mol). After stirring for 45 min at −78° C., a solution of DMF (5 g, 0.068 mol) in THF (20 mL) was added dropwise. After 1 h at −78° C. the reaction mixture was quenched slowly by adding water. The aqueous phase separated was extracted with EtOAc and the combined organic extracts washed with water and brine, dried ($Na_2SO_4$), filtered and concentrated in vacuo. The crude product was purified by $SiO_2$ chromatography eluting with 15% EtOAc/petroleum ether to afford 7.7 g (93%) of 4-fluoro-1-(tetrahydro-pyran-2-yl)-1H-benzoimidazole-5-carbaldehyde (148) as a yellow solid.

Step 7:
To a solution of 148 (7.7 g, 0.031 mol) in dry MeOH (120 mL) was added NaOAc (3.31 g, 0.0372 moles) and hydroxylamine hydrochloride (2.57 g, 0.0372 mol). The reaction mixture was stirred at RT for 16 h. The solution was concentrated in vacuo, the residue taken up in water and extracted with DCM. The combined organic extracts were washed sequentially with water and brine, dried ($Na_2SO_4$), filtered and concentrated in vacuo to afford 5.8 g (71%) of 4-fluoro-1-(tetrahydro-pyran-2-yl)-1H-benzoimidazole-5-carbaldehyde oxime (150) as a white solid which was used without further purification.

Step 8:

To a solution of 150 (5.8 g, 0.022 mol) in MeOH (100 mL) was added zinc dust (2.9 g, 0.044 mol) and ammonium formate (2.8 g, 0.044 mol). The resulting mixture was heated to 75° C. for 2 h. The mixture was filtered through a Celite® pad. The filtrate was concentrated and the crude product was purified by $SiO_2$ chromatography eluting with 5% MeOH/DCM to afford 2.6 g (47%) of (4-fluoro-1-tetrahydropyran-2-yl-benzimidazol-5-yl)methanamine (152) as a yellow solid: 1H-NMR (400 MHz, RT, CDCl3): δ 1.66-1.80 (m, 3H), 1.92-1.96 (m, 1H), 2.06-2.14 (m, 2H), 3.68-3.74 (m, 1H), 4.23-4.26 (m, 1H), 4.40 (br, 2H), 5.49-5.52 (dd, 1H), 6.94-6.99 (dd, 1H), 7.18-7.23 (t, 1H), and 7.37-7.39 (d, 1H); MS (ESI) m/z=250.2 [M+1]+.

Step 9:

A 5 mL microwave tube was charged with 152 (1.5 equiv., 158.7 mg, 0.65 mmol), 53 (100 mg, 0.42 mmol) and n-butyl alcohol (1.2 mL). To the solution was added DIPEA (0.371 mL), the tube sealed and the reaction mixture heated to 140° C. overnight. The reaction was cooled to RT, filtered and concentrated in vacuo. The crude oil was used in the next step without further purification.

Step 10:

The crude oil from step 9 was taken up in MeOH (4.32 mL) and p-TsOH.$H_2O$ (73.8 mg) was added. The mixture was heated to 100° C. overnight. The solvent was evaporated in vacuo and the residue was purified by preparative HPLC to afford 25.6 mg (16.6%) of I-29 as a white solid.

Example 16

$N^4$-(5-Cyclopropyl-1H-pyrazol-3-yl)-$N^2$-[(6-methyl-1H-benzimidazol-5-yl)methyl]pyrimidine-2,4-diamine (I-30)

Step 1:

To a stirred solution of 6-methyl-1H-benzo[d]imidazole-5-carbonitrile (7.9 g, 50 mmol, CASRN 952511-47-6) and THF (85 mL) at RT under nitrogen was added 3,4-dihydro-2H-pyran (34 g, 0.4 mol) and p-TsOH.$H_2O$ (0.9 g, 5 mmol) and the resulting mixture was heated at 75° C. for 3 h. The reaction mixture was cooled to RT, diluted with EtOAc (200 mL), and washed sequentially with sat'd. aq. $Na_2CO_3$ (300 mL) and brine (300 mL). The organic phase was dried ($Na_2SO_4$), filtered and concentrated in vacuo. The residue was purified by $SiO_2$ chromatography eluting with a MeOH/DCM gradient (0 to 5% MeOH) to afford 7.2 g (60%) of 6-methyl-1-(tetrahydro-2H-pyran-2-yl)-1H-benzo[d]imidazole-5-carbonitrile (176) as a yellow oil: MS (ESI) m/z=242 [M+1]+.

Step 2:

A suspension of 176 (4.6 g, 19 mmol) Raney-Ni (>15 eq) in 7N $NH_3$ solution in MeOH (10 mL) was stirred under hydrogen at 25° C. for 2 h. The mixture was filtered and concentrated in vacuo. The crude product was purified by $SiO_2$ chromatography eluting with a MeOH/DCM gradient (3 to 5% MeOH) to afford 3.2 g (69%) of (6-methyl-1-tetrahydro-pyran-2-yl-benzimidazol-5-yl)methanamine (178) as a yellow oil: MS (ESI) m/z=246 [M+1]+.

Step 3:

A 5 mL microwave tube was charged with 178 (208.2 mg, 0.85 mmol), 53 (100 mg, 0.42 mmol) and n-BuOH (1.2 mL). DIPEA (0.37 mL) was added, the tube was sealed and heated to 140° C. for 18 h in an oil bath. The reaction mixture was cooled then partitioned between water (10 mL) and EtOAc (50 mL). The layers were separated and the organic phase washed with brine (25 mL), dried ($Na_2SO_4$), filtered, and concentrated to afford a crude orange solid which was used without further purification.

Step 4:

The crude material from step 3 was taken up in MeOH (8.62 mL) in a microwave tube, p-TsOH.$H_2O$ (30 mg) was added, and the vial was sealed and heated to 100° C. for 16 h with stirring. Additional p-TsOH.$H_2O$ (30 mg) was added, and the reaction mixture was stirred at 110° C. for 3 d. The MeOH was removed and the crude residue taken up in EtOAc (100 mL) and filtered. $NaHCO_3$ (50 mL) was added to the filtrate and the layers were separated, washed with brine, dried ($Na_2SO_4$), filtered and concentrated in vacuo. The filter and from the reaction was suspended in MeOH, sonicated, then filtered and the resultant filtrate combined with the other organics and concentrated to afford a crude orange solid. The residue was purified by preparative HPLC to afford 72.2 mg (47%) of I-30 as a white solid; MS (ESI) m/z=361.3 [M+1]+.

Example 17

$N^2$-[(1S)-1-(1H-benzimidazol-5-yl)propyl]-$N^4$-(5-cyclopropyl-1H-pyrazol-3-yl)pyrimidine-2,4-diamine (I-6)

Step 1:

To the solution of 1H-benzoimidazole-5-carboxylic acid (1.62 g, 10 mmol) in THF (20 mL) was added 3,4-dihydro-2H-pyran (2 mL) and camphorsulfonic acid (100 mg, 0.42 mmol, 0.04 equiv). The mixture was refluxed for 24 h under argon. Concentration and chromatography afforded 1.5 g (60%) of 1-(tetrahydro-pyran-2-yl)-1H-benzoimidazole-5-carboxylic acid (166) as a light red solid.

Step 2:

To the solution of 166 (170 mg, 0.69 mmol) in DCM (5 mL) was added EDC.HCl (190 mg, 1 mmol), HOBt (160 mg, 1 mmol), TEA (0.3 mL) and N-methoxymethanamine hydrochloride (100 mg, 1 mmol). The mixture was stirred at RT overnight. The mixture was poured into water, extracted with EtOAc, washed sequentially with $H_2O$ and brine, dried ($Na_2SO_4$), filtered and concentrated in vacuo. The crude product was purified by $SiO_2$ chromatography affording 140 mg (85%) of 1-(tetrahydro-pyran-2-yl)-1H-benzoimidazole-5-carboxylic acid methoxy-methyl-amide (168) as a light yellow oil.

Step 3:

To the solution of 168 (70 mg, 0.24 mmol) and THF cooled to 0° C. under Ar was added EtMgBr (0.72 mL, 1M solution). The mixture was stirred at 0° C. for 2 h then NH4Cl solution was added carefully. The mixture was extracted with EtOAc, washed sequentially with $H_2O$ and brine and dried ($Na_2SO_4$), filtered and concentrated in vacuo. The crude product was purified by $SiO_2$ chromatography to afford 45 mg (72%) of 1-[1-(tetrahydro-pyran-2-yl)-1H-benzoimidazol-5-yl]-propan-1-one (170) as a colorless oil.

Step 4:

To a solution of 170 (100 mg, 0.39 mmol) in MeOH (5 mL) was added hydroxylamine hydrochloride (54 mg, 0.78 mmol) and NaOAc (100 mg, 1 mmol). The mixture was refluxed overnight. The mixture was extracted with EtOAc, washed sequentially with $H_2O$ and brine and dried ($Na_2SO_4$), filtered and concentrated in vacuo to afford 95 mg (90%) of 1-[1-(tetrahydro-pyran-2-yl)-1H-benzoimidazol-5-yl]-propan-1-one oxime (172) as a light yellow oil.

Step 5:
To a solution of 172 (30 mg, 0.11 mmol) in THF (3 mL) was added Raney-Ni (50 mg) and the mixture was stirred at RT overnight, filtered and concentrated in vacuo. Purification by HPLC afforded 10 mg (35%) of 1-(1-tetrahydropyran-2-ylbenzimidazol-5-yl)propan-1-amine (174) as a colourless oil: 1H NMR (400 MHz, CDCl3): δ 7.98 (m, 1H), 7.64 (m, 1H), 7.40 (m, 1H), 7.14-7.36 (m, 1H), 5.40-5.45 (m, 1H), 4.06 (m, 1H), 3.85 (m, 1H), 3.70 (m, 1H), 2.02-2.10 (m, 3H), 1.62-1.72 (m, 8H), 0.77-0.84 (m, 3H); MS (ESI+) m/z=260 [M+1]+.

Step 6:
A microwave tube was charged with 174 (165.1 mg), 53 (100 mg, 0.42432 mmol) and n-BuOH (1.2 mL) then DIPEA (0.37 mL) was added, the tube sealed and the reaction mixture heated to 140° C. for 18 h in an oil bath. The reaction was cooled to RT, filtered and concentrated in vacuo to afford a crude oil which was used in the next step without further purification.

Step 7:
The crude material from step 6 was taken up in MeOH (3 mL) and p-TsOH.H$_2$O (73.8 mg) was added, the vial was sealed and heated to 100° C. overnight. The solvent was evaporated under reduced pressure and the residue purified by preparative HPLC and subsequently SFC chromatography to separate the enantiomers and afford 7.9 mg (5%) of I-6 as a white solid: SFC retention time: 0.84 min. The SFC purification was carried out using Chiralcel OJ (21.2×250 mm, 5 micron) at 35% MeOH w/0.1% NH$_4$OH at 70 mL/min and a pressure of 100 bars at 40° C.

$N^2$-[(1R)-1-(1H-benzimidazol-5-yl)propyl]-$N^4$-(5-cyclopropyl-1H-pyrazol-3-yl)pyrimidine-2,4-diamine (I-43) was isolated as a white solid (8.7 mg) in the final SFC separation step: SFC retention time: 1.06 min.

Example 18

$N^4$-(5-Cyclopropyl-1H-pyrazol-3-yl)-$N^2$-((4-methyl-1H-benzo[d]imidazol-5-yl)methyl)pyrimidine-2,4-diamine (I-16)

Step 1:
To a cold (0° C.) solution of 2-bromo-6-nitrotoluene (43.2 g, 0.2 mol) in con H$_2$SO$_4$ (600 mL) was added HNO$_3$ (37 g, 0.24 mol) in small portions with efficient agitation while maintaining the temperature at 0-10° C. The reaction mixture was allowed to slowly warm to RT with stirring overnight then poured into crushed ice (1600 g). The solid was collected by filtration, thoroughly washed with water and dried in air. The crude material was recrystallised from EtOAc/hexanes to afford 40 g (77%) of 1-bromo-2-methyl-3,4-dinitrobenzene (154) as a pale white solid: MS (ESI) m/z=262 [M+1]+.

Step 2:
A mixture of 154 (40 g, 154 mmol), SnCl$_2$.2H$_2$O (208 g, 920 mmol), EtOAc (300 mL) and EtOH (150 mL) was heated to 80° C. for 12 h, cooled to RT, poured into crushed ice (2 Kg) and the pH adjusted to pH 7-8 with solid NaHCO$_3$. The solid was filtered and washed with EtOAc. The filtrate was thrice extracted with EtOAc. The combined extracts were washed with brine, dried (Na$_2$SO$_4$), filtered and concentrated in vacuo. The crude product was purified by SiO$_2$ chromatography eluting with an EtOAc/hexane gradient (10 to 50% EtOAc) to afford 28 g (91%) of 4-bromo-3-methyl-1,2-benzenediamine (156) as a brown oil: MS (ESI) m/z=202 [M+1]+.

Step 3:
A mixture of 156 (28 g, 140 mmol), formic acid (240 mL) and 37% concentrated HCl (400 mL) was heated to 60° C. for 12 h, cooled in an ice-water bath, and the pH slowly adjusted to 8-9 with 28% concentrated NH$_4$OH. The solid was collected by filtration, washed with water and dried in air to afford 25 g (98%) of 5-bromo-4-methyl-1H-benzo[d]imidazole (158) as a yellow solid: MS (ESI) m/z=213 [M+1]+.

Step 4:
A mixture of 158 (21 g; 99 mmol), Zn(CN)$_2$ (23.2 g; 198 mmol), Pd(dppf)Cl$_2$ (6.4 g; 9.9 mmol) and zinc (258 mg; 4 mmol) in dry DMF (150 mL) under inert atmosphere was heated at 120° C. for 2 h. The reaction mixture was filtered through a pad of Celite® that was washed with EtOAc. The organics were washed with water, dried (MgSO$_4$), filtered and evaporated in vacuo. The crude product was purified by SiO$_2$ chromatography eluted with a DCM/MeOH gradient (0 to 10% MeOH) to afford 8.3 g (53%) of 4-methyl-1H-benzo[d]imidazole-5-carbonitrile (160) as a brown solid: MS (ESI) m/z=158 [M+1]+.

Step 5:
To a stirred solution of 160 (8.3 g, 52.5 mmol) and THF (100 mL) at RT under nitrogen was added, 3,4-dihydro-2H-pyran (35 g, 420 mmol) and p-TsOH.H$_2$O (0.9 g, 5.3 mmol) and the reaction mixture was heated at 75° C. for 4 h. The mixture was cooled to RT, diluted with EtOAc and sequentially washed with sat'd. aq. NaHCO$_3$, and brine. The organic extract was dried (Na$_2$SO$_4$), filtered and concentrated in vacuo. The crude product was purified by SiO$_2$ chromatography eluting with a MeOH/DCM gradient (0 to 5% MeOH) to afford 9.8 g (77%) of 4-methyl-1-(tetrahydro-2H-pyran-2-yl)-1H-benzo[d]imidazole-5-carbonitrile (162) as a light yellow solid: MS (ESI) m/z=242 [M+1]+.

Step 6:
A mixture of 162 (9.8 g, 52.5 mmol), MeOH(NH$_3$ in MeOH) and Raney-Ni (>15 eq) was stirred under hydrogen at 25° C. for 2 h. The mixture was filtered and concentrated in vacuo. The crude product was purified by SiO$_2$ chromatography eluting with a MeOH/DCM gradient (0% to 10% MeOH) to afford 7.0 g (70%) of (4-methyl-1-tetrahydropyran-2-yl-benzimidazol-5-yl)methanamine (164) as yellowish oil: LC/MS: m/z=246 [M+1]+.

Step 7:
A microwave tube was charged with 164 (156.1 mg, 0.64 mmol), 53 (100 mg, 0.42 mmol), n-BuOH (1.2 mL), DIPEA (0.371 mL) was added, the tube was sealed and heated to 140° C. for 17 h. The reaction was diluted with water (2 mL) and EtOAc (5 mL). Water (25 mL) and additional EtOAc (50 mL) were added, and the phases were separated. The organic layers were filtered through a Na$_2$SO$_4$ drying cartridge, filtered, and concentrated. The crude oil obtained was used in the next step without further purification.

Step 8:
The crude material from step 7 was taken up in MeOH (4.32 mL) and p-TsOH.H$_2$O (36.9 mg) was added. The reaction mixture was heated in a sealed vial overnight at 100° C., cooled and concentrating in vacuo. The residue was purified by preparative HPLC to afford 58 mg (38%) of I-16 as a white solid.

Example 19

(S)—$N^2$-(1-(1H-indol-5-yl)ethyl)-$N^4$-(5-cyclopropyl-1H-pyrazol-3-yl)pyrimidine-2,4-diamine (I-8)

Step 1:
A vessel was charged with 53 (665 mg, 2.82 mmol), 1-(1H-indol-5-yl)ethanamine adipic acid salt (1.45 g mg, 6.20 mmol, CASRN 1282097-87-3), DIPEA (7.4 mL) and n-BuOH (57 mL), sealed and heated at 120° C. for 12 d. The reaction mixture was cooled and diluted with EtOAc. The organic layer was washed sequentially with water and brine, dried (Na$_2$SO$_4$), filtered and concentrated in vacuo. The crude was purified by reverse-phase HPLC purification to afford 250.0 mg (24.7%) of racemic N$^2$-(1-(1H-indol-5-yl)ethyl)-N$^4$-(5-cyclopropyl-1H-pyrazol-3-yl)pyrimidine-2,4-diamine (180) as a white solid.

Racemic I-8 was resolved by chiral HPLC using SFC purification. The first eluant peak was collected to afford 104.9 mg (41.9%) of I-8 (S)—N$^2$-(1-(1H-indol-5-yl)ethyl)-N$^4$-(5-cyclopropyl-1H-pyrazol-3-yl)pyrimidine-2,4-diamine (104.9 mg, 41.9%) as a white solid: SFC LC-MS, RT=1.06 min.

The second eluant peak afforded 105.0 mg (42.0%) of (R)—N$^2$-(1-(1H-indol-5-yl)ethyl)-N$^4$-(5-cyclopropyl-1H-pyrazol-3-yl)pyrimidine-2,4-diamine (I-60, 105.0 mg, 42.0%) as a white solid: SFC LC-MS, RT=1.69 min.

SFC chiral chromatography was carried out using Chiralcel OJ (21.2×250 mm, 5 micron) eluting with 35% MeOH containing 0.1% NH$_4$OH at 70 mL/min at a pressure of 100 bars and a temperature of 40° C.

Example 20

(S)—N$^2$-(1-(1H-indol-5-yl)ethyl)-N$^4$-(5-cyclopropyl-1H-pyrazol-3-yl)-6-methylpyrimidine-2,4-diamine (I-7)

Step 1:

A mixture of 53 (1.98 g, 16.07 mmol, CASRN 175137-46-9), 2,4-dichloro-6-methyl-pyrimidine (2.62 g, 16.07 mmol, CASRN 5424-21-5), DIPEA (5.7 mL, 32.15 mmol), and anhydrous EtOH (50 mL) was stirred at 70° C. under N$_2$ for 3 d. The reaction mixture was cooled, poured into water (ca. 700 mL) and stirred at RT overnight which afforded a precipitate. The solid was filtered, washed with additional water, and pumped dry on high-vacuum to afford 2.037 g (59%) of solid 2-chloro-N-(5-cyclopropyl-1H-pyrazol-3-yl)-6-methyl-pyrimidin-4-amine (185): 1H NMR (400 MHz, DMSO-d6): δ 12.12 (s, 1H), 10.08 (s, 1H), 7.04 (br s, 1H), 5.93 (br s, 1H), 2.27 (s, 3H), 1.93 to 1.84 (m, 1H), 0.96-0.88 (m, 2H), 0.70-0.64 (m, 2H).

Step 2:

I-7 was prepared in accord with the procedure in example 19 except 185 (CASRN 5424-21-5) was used in place of 53: SFC LC-MS, RT=1.09 min.

N$^2$-((4-chloro-1H-indol-5-yl)methyl)-N$^4$-(5-cyclopropyl-1H-pyrazol-3-yl)-6-methylpyrimidine-2,4-diamine (I-19) was prepared in accord with the procedure in example 19 except in step 1, 185 and tert-butyl 5-(aminomethyl)-4-chloro-1H-indole-1-carboxylate were used in place of 2-chloro-N-(5-cyclopropyl-1H-pyrazol-3-yl)pyrimidin-4-amine and 1-(1H-indol-5-yl)ethanamine adipic acid salt to afford I-19.

N$^2$-((1H-benzo[d]imidazol-5-yl)methyl)-N$^4$-(5-cyclopropyl-1H-pyrazol-3-yl)-6-methylpyrimidine-2,4-diamine (I-10) was prepared analogously except 28 replaced tert-butyl 5-(aminomethyl)-4-chloro-1H-indole-1-carboxylate as starting material which afforded N$^4$-(5-cyclopropyl-1H-pyrazol-3-yl)-6-methyl-N$^2$-[(1-tetrahydropyran-2-ylbenzimidazol-5-yl)methyl]pyrimidine-2,4-diamine (182): 1H NMR (400 MHz, DMSO-d6): δ 8.03 (s, 1H), 7.80-7.70 (m, 1H), 7.55-7.43 (m, 1H), 7.30 (dd, J=13.7, 8.4 Hz, 1H), 6.05 (br s, 1H), 5.83 (br s, 1H), 5.58-5.37 (m, 2H), 4.71 (t, J=6.1 Hz, 2H), 4.11-4.06 (m, 1H), 3.73 (t, J=10.8 Hz, 1H), 2.63 (br s, 2H), 2.23 (d, J=4.4 Hz, 3H), 2.18-2.04 (m, 4H), 1.84-1.60 (m, 5H), 1.09 (s, 2H); MS (ESI) m/z=445.3 [M+1]$^+$.

A mixture of 182 (230.0 mg, 0.52 mmol) and p-TsOH.H$_2$O (36.0 mg, 0.20 mmol) in anhydrous MeOH (9.4 mL) was stirred at 100° C. for 6 d. The reaction mixture was cooled and concentrated in vacuo. The crude was diluted with EtOAc. The organic layer was washed sequentially with sat'd. aq. NaHCO$_3$ solution, water and brine, dried (Na$_2$SO$_4$), filtered, and concentrated in vacuo. The crude product was purified by reverse-phase HPLC which afforded 94.9 mg (50.9%) of I-10 as a white solid.

(S)—N$^2$-(1-(1H-benzo[d]imidazol-5-yl)ethyl)-N$^4$-(5-cyclopropyl-1H-pyrazol-3-yl)-6-methylpyrimidine-2,4-diamine (I-4) was prepared in accord with the procedures used to prepare I-10 except 126 replaced 28 as starting material. Removal of the pyran protecting group afforded I-4.

N$^2$-((1H-indol-4-yl)methyl)-N$^4$-(5-cyclopropyl-1H-pyrazol-3-yl)-6-methylpyrimidine-2,4-diamine (I-54) was prepared in accord with the procedure used for I-10 except 1H-indol-4-ylmethanamine replaced tert-butyl 5-(aminomethyl)-4-chloro-1H-indole-1-carboxylate. Reverse-phase HPLC purification gave the formate salt of I-54.

Example 21

(S)—N$^2$-(1-(1H-indol-5-yl)ethyl)-N$^4$-(5-cyclopropyl-1H-pyrazol-3-yl)-5-methylpyrimidine-2,4-diamine (I-31)

Step 1: 2-Chloro-N-(5-cyclopropyl-1H-pyrazol-3-yl)-5-methyl-pyrimidin-4-amine (184) was prepared using the procedure as described in Example 20, except in step 1 2,4-dichloro-5-methyl-pyrimidine replaced 2,4-dichloro-6-methyl-pyrimidine: 1H NMR (400 MHz, DMSO-d6): δ 12.17 (s, 1H), 9.23 (s, 1H), 7.97 (s, 1H), 6.28 (s, 1H), 2.12 (s, 3H), 1.97-1.85 (m, 1H), 0.93 (d, J=7.4 Hz, 2H), 0.69 (d, J=4.6 Hz, 2H); MS (ESI) m/z=250.0.2 [M+1]+.

Step 2:

I-31 was prepared using the procedures as described in Example 19 except 184 replaced with 89: SFC LC-MS, RT=0.73 min.

N$^2$-(1H-Benzoimidazol-5-ylmethyl)-N$^4$-(5-cyclopropyl-1H-pyrazol-3-yl)-5-methyl-pyrimidine-2,4-diamine (I-32) was prepared in accord with the procedures used to prepare I-10 in Example 20, using 2-chloro-N-(5-cyclopropyl-1H-pyrazol-3-yl)-5-methyl-pyrimidin-4-amine in place of 2-chloro-N-(5-cyclopropyl-1H-pyrazol-3-yl)-4-methyl-pyrimidin-4-amine.

Example 22

(S)—N$^2$-(1-(1H-indol-5-yl)ethyl)-N$^4$-(5-cyclopropyl-1H-pyrazol-3-yl)-6-(trifluoromethyl) pyrimidine-2,4-diamine (I-18)

Step 1:

A mixture of 5-cyclopropyl-1H-pyrazol-3-amine (1.42 g, 11.5 mmol), 2,4-dichloro-6-(trifluoromethyl)pyrimidine (2.50 g, 11.5 mmol), DIPEA (4.05 mL, 23.0 mmol), and anhydrous EtOH (35 mL) was stirred at 70° C. under N$_2$ for 22 h. The reaction mixture was concentrated in vacuo. The residue was diluted with EtOAc and the organic layer was washed sequentially with water and brine, dried (Na$_2$SO$_4$), filtered and concentrated in vacuo. Trituration with DCM afforded 1.80 g (51.5%) of 2-chloro-N-(5-cyclopropyl-1H-pyrazol-3-yl)-6-(trifluoromethyl)pyrimidin-4-amine (186) as a white solid: 1H NMR (400 MHz, DMSO-d6): δ 12.35 (br d, J=30.2 Hz, 1H), 10.97 (s, 1H), 8.14 (s, 0.50H, rotamer), 7.13 (s, 0.50H, rotamer), 6.38 (s, 0.50H, rotamer), 5.73 (s, 0.50H, rotamer), 1.91 (s, 1H), 0.98-0.90 (m, 2H), 0.70 (q, J=5.5 Hz, 2H); MS (ESI) m/z=304.2/306.2 [M+1]+.

Step 2:

Racemic $N^2$-(1-(1H-indol-5-yl)ethyl)-$N^4$-(5-cyclopropyl-1H-pyrazol-3-yl)-6-(trifluoromethyl)pyrimidine-2,4-diamine (188) was prepared in accord with the procedure in Example 19 except 186 replaced 53: MS (ESI) m/z=428.2 [M+1]+.

Step 3:

Racemic 188 (400.0 mg, 0.936 mmol) was resolved by chiral chromatographic separation using SFC purification. The second eluant peak was collected to afford 143.3 mg (35.8%) of I-18 as a white solid: SFC LC-MS, RT=1.96 min.

$N^2$-((1H-benzo[d]imidazol-5-yl)methyl)-$N^4$-(5-cyclopropyl-1H-pyrazol-3-yl)-6-(trifluoromethyl)pyrimidine-2,4-diamine (I-11) as prepared in accord with the procedures used to prepare I-10 using the procedures as described in Example 20, except 186 was used in place of in place of 53 as starting material.

$N^2$-((1H-indol-4-yl)methyl)-$N^4$-(5-cyclopropyl-1H-pyrazol-3-yl)-6-(trifluoromethyl)pyrimidine-2,4-diamine (I-41) was prepared in accord with the procedure used for I-54 in example 20 except 1H-indol-4-ylmethanamine replaced tert-butyl 5-(aminomethyl)-4-chloro-1H-indole-1-carboxylate: MS (ESI) m/z=414.2 [M+1]+.

Example 23

$N^2$—((S)-1-(1H-benzo[d]imidazol-5-yl)ethyl)-$N^4$-(5-((trans)-2-phenylcyclopropyl)-1H-pyrazol-3-yl)pyrimidine-2,4-diamine (I-24)

Step 1:

To a tube containing a solution of 77 (156 mg, 0.5 mmol) in n-BuOH (5 mL) was added 126 (184 mg, 0.75 mmol). DIPEA (0.26 mL, 1.5 mmol) was added dropwise and the tube was capped and placed in a shaker block and heated to 120° C. for 20 h. The solvent was concentrated in vacuo. The crude residue was partitioned between EtOAc (5 mL) and water (3 mL). The organic layer was removed and concentrated in vacuo. Crude $N^4$-(5-((trans)-2-phenylcyclopropyl)-1H-pyrazol-3-yl)-$N^2$-((1S)-1-(1-(tetrahydro-2H-pyran-2-yl)-1H-benzo[d]imidazol-5-yl)ethyl)pyrimidine-2,4-diamine (190) was used in the next step without further purification: MS (ESI) m/z=521.4 [M+1]+.

Step 2:

To a solution of 190 in MeOH (5 mL) was added p-TsOH.H$_2$O (258 mg, 1.5 mmol). The reaction mixture was heated in a shaker block at 60° C. for 18 h. The solvent was concentrated in vacuo. The crude residue was diluted in DMF (2 mL) and filtered to remove undissolved solids. The remaining liquid was concentrated in vacuo. The residue was purified by reverse phase HPLC to afford 9.6 mg (4%) of I-24.

The following products were prepared using the procedure described in Example 23 using the materials detailed in the table below.

$N^2$—((S)-1-(1H-benzo[d]imidazol-5-yl)ethyl)-$N^4$-(5-((trans)-2-(2-fluorophenyl)cyclopropyl)-1H-pyrazol-3-yl)pyrimidine-2,4-diamine (I-23), (S)—$N^2$-(1-(1H-benzo[d]imidazol-5-yl)ethyl)-$N^4$-(5-cyclobutyl-1H-pyrazol-3-yl)pyrimidine-2,4-diamine (I-1), (S)—$N^2$-(1-(1H-benzo[d]imidazol-5-yl)ethyl)-$N^4$-(5-cyclopentyl-1H-pyrazol-3-yl)pyrimidine-2,4-diamine (I-2), $N^2$—((S)-1-(1H-benzo[d]imidazol-5-yl)ethyl)-$N^4$-(5-(tetrahydro-furan-2-yl)-1H-pyrazol-3-yl)pyrimidine-2,4-diamine (I-44) and (S)—$N^2$-(1-(1H-benzo[d]imidazol-5-yl)ethyl)-$N^4$-(5-(cyclopropylmethyl)-1H-pyrazol-3-yl)pyrimidine-2,4-diamine (I-45) were prepared analogously starting from 5-(trans-2-(2-fluorophenyl)cyclopropyl)-1H-pyrazol-3-amine, 5-cyclobutyl-1H-pyrazol-3-amine (CASRN 326827-21-8), 5-cyclopentyl-1H-pyrazol-3-amine (CASRN 264209-16-7), 5-(tetrahydrofuran-2-yl)-1H-pyrazol-3-amine (CASRN 1028843-21-1) and 5-(cyclopropylmethyl)-1H-pyrazol-3-amine CASRN 852443-64-2) respectively as the pyrazole moiety.

$N^2$-(1H-Benzimidazol-5-ylmethyl)-$N^4$-[5-[(trans)-2-phenylcyclopropyl]-1H-pyrazol-3-yl]pyrimidine-2,4-diamine (I-27) prepared analogously starting from 91 and condensing with (1-(tetrahydro-2H-pyran-2-yl)-1H-benzo[d]imidazol-5-yl)methanamine (28) and subsequently removing the pyran in accord with the procedure in steps 6 and 7 of example 1.

Example 24

$N^2$-((1H-indol-4-yl)methyl)-$N^4$-(5-((trans)-2-phenylcyclopropyl)-1H-pyrazol-3-yl)pyrimidine-2,4-diamine (I-57)

To a solution of 77 (156 mg, 0.5 mmol) in n-BuOH (5 mL) was added (1H-indol-4-yl)methanamine (110 mg, 0.75 mmol, CASRN 3468-18-6) then DIPEA (0.26 mL, 1.5 mmol) was added dropwise. The reaction mixture was placed in a shaker block and heated to 130° C. for 20 h. The solvent was concentrated in vacuo then the crude residue was diluted in DCM (5 mL) and MeOH (5 mL) then the solvent was again concentrated in vacuo. The crude residue was diluted in DMF (2 mL) and filtered to remove undissolved solids. The resultant liquid was concentrated in vacuo. The residue was purified by reverse phase HPLC to afford 121.4 mg (82%) of I-57.

$N^2$-((1H-indol-4-yl)methyl)-$N^4$(5-(cyclopropylmethoxy)-1H-pyrazol-3-yl)pyrimidine-2,4-diamine (I-42) was prepared analogously except 77 was replaced with (2-chloropyrimidin-4-yl)-(5-cyclopropylmethoxy-1H-pyrazol-3-yl)-amine and (1H-indol-4-yl)methanamine was replaced with 116.

$N^2$-((1H-indol-4-yl)methyl)-$N^4$-(5-cyclobutyl-1H-pyrazol-3-yl)pyrimidine-2,4-diamine (I-36) was prepared analogously except 77 was replaced with 65.

$N^2$-((1H-indol-4-yl)methyl)-$N^4$-(5-cyclopentyl-1H-pyrazol-3-yl)pyrimidine-2,4-diamine (I-50) was prepared analogously except 77 was replaced with 67.

$N^2$-((1H-indol-4-yl)methyl)-$N^4$-(5-(tetrahydrofuran-3-yl)-1H-pyrazol-3-yl)pyrimidine-2,4-diamine (I-51) was prepared analogously except 77 was replaced with 89.

$N^2$-((1H-indol-4-yl)methyl)-$N^4$-(5-(cyclopropylmethyl)-1H-pyrazol-3-yl)pyrimidine-2,4-diamine (I-48) was prepared analogously except 77 was replaced with 61.

$N^2$-((1H-indol-4-yl)methyl)-$N^4$-(5-methyl-1H-pyrazol-3-yl)pyrimidine-2,4-diamine (I-56) was prepared analogously except 77 was replaced with 2-chloro-N-(5-methylpyrazol-3-yl)-4-pyrimidinamine (CASRN 543712-91-0).

$N^2$-((1H-indol-4-yl)methyl)-$N^4$-(5-isopropyl-1H-pyrazol-3-yl)pyrimidine-2,4-diamine (I-58) was prepared analogously except 77 was replaced with 59.

$N^2$-((1H-indol-4-yl)methyl)-5-chloro-$N^4$-(5-cyclopropyl-1H-pyrazol-3-yl)pyrimidine-2,4-diamine (I-49) was prepared analogously except 77 was replaced with 57.

Example 25

$N^2$—((S)-1-(1H-benzo[d]imidazol-5-yl)ethyl)-$N^4$-(5-(tetrahydrofuran-3-yl)-1H-pyrazol-3-yl)pyrimidine-2,4-diamine (I-14)

Step 1:

To a solution of 89 (133 mg, 0.5 mmol) in n-BuOH (5 mL) was added 126 (184 mg, 0.75 mmol), then DIPEA (0.26 mL, 1.5 mmol) was added dropwise. The reaction mixture was placed in a shaker block and heated to 120° C. for 60 h. The solvent was concentrated in vacuo. The crude residue was diluted with EtOAc (5 mL) and water (3 mL). The organic layer was removed and concentrated in vacuo. The crude reaction mixture was carried on to the next step without further purification: MS (ESI) m/z=475.4 [M+1]+

Step 2:
To a solution of the crude product from step 1 dissolved in MeOH (5 mL) was added p-TsOH.H$_2$O (258 mg, 1.5 mmol). The reaction mixture was placed in a shaker block at 60° C. for 18 h. The solvent was concentrated in vacuo. The crude residue was diluted in DMF (2 mL) and filtered to remove undissolved solids. The filtrate was concentrated in vacuo and the residue was purified by reverse phase HPLC to afford 3.3 mg (2%) of I-14:

Example 26

(S)—N$^2$-(1-(1H-benzo[d]imidazol-5-yl)ethyl)-5-chloro-N$^4$-(5-cyclopropyl-1H-pyrazol-3-yl)pyrimidine-2,4-diamine (I-46)

Step 1:
To a solution of 57 (135 mg, 0.5 mmol) in n-BuOH (3 mL) in a microwave vial was added 126 (184 mg, 0.75 mmol), then DIPEA (0.26 mL, 1.5 mmol) was added dropwise. The vial was sealed with a rubber septa and heated in the microwave for 90 min at 160° C. The solvent was evaporated under reduced pressure and the crude residue was taken up in DCM (5 mL) and MeOH (5 mL) and the solvent was again concentrated in vacuo. The residue was diluted in DMF (2 mL) and filtered to remove any undissolved solids. The filtrate was concentrated in vacuo. The residue was purified by reverse phase HPLC to afford 13 mg (6%) of I-46.

Example 27

1-(4-((4-(5-cyclopropyl-1H-pyrazol-3-ylamino)pyrimidin-2-ylamino)methyl)-1H-indol-3-yl)-2,2,2-trifluoroethanone (I-37)

Step 1:
A vial was charged with 53 (300 mg, 1.27 mmol), (1H-indol-4-yl)methanamine (279 mg, 1.903.20 mmol, CASRN 3468-18-6), DIPEA (0.67 mL) and n-BuOH (3 mL), sealed and heated at 140 C for 72 h. The reaction mixture was concentrated in vacuo, and the residue was partitioned between EtOAc and H$_2$O. The aqueous layer was extracted once with EtOAc. The combined organic extracts were dried (Na$_2$SO$_4$), filtered and concentrated in vacuo. The crude produce was directly dissolved in TFA (3 mL), and the mixture was heated at 70° C. for 2 h. The reaction mixture was concentrated under reduced pressure and the residue purified by preparative HPLC to afford 38.3 mg (7%) of I-37.

Example 28

(S)—N$^2$-(1-(1H-indol-6-yl)ethyl)-N$^4$-(5-cyclopropyl-1H-pyrazol-3-yl)pyrimidine-2,4-diamine (I-34)

The title compound was prepared in accord with the procedure in example 19 except (1S)-1-(1H-indol-6-yl)ethanamine (CASRN 3468-17-5) instead of 1-(1H-indol-5-yl) ethanamine adipic acid salt as the starting material.

Example 29

N$^4$-(5-cyclopropyl-1H-pyrazol-3-yl)-N$^2$-((3-methyl-1H-indol-5-yl)methyl)pyrimidine-2,4-diamine (I-25)

Step 1:
A vessel was charged with 5-bromo-3-methyl-1H-indole (1.06 g, 5.05 mmol), copper (I) cyanide (542.83 mg, 6.0608 mmol), and degassed NMP (10 mL), sealed and heated to 200° C. with stirring for 5 h, then at 110° C. for 16 h. The cooled reaction was diluted with EtOAc and the organic layer was washed sequentially with water and brine, dried (Na$_2$SO$_4$), filtered and concentrated in vacuo. The crude product was purified by SiO$_2$ chromatography eluting with an EtOAc/heptane gradient (0 to 100% EtOAc) to afford 640 mg (81.1%) of 3-methyl-1H-indole-5-carbonitrile (192): 1H NMR (400 MHz, CDCl3): δ 8.22 (br s, 1H), 7.91 (s, 1H), 7.42-7.35 (m, 2H), 7.07 (s, 1H), 2.32 (s, 3H).

Step 2:
Raney Nickel (wet, 1.0 g) was added to a stirred solution of 192 (220.0 mg, 1.41 mmol) in 2.0 M ammonia in MeOH (10 mL). The reaction mixture was hydrogenated under an H$_2$ balloon at 1 atmosphere pressure at RT for 3 d. The reaction mixture was filtered through a pad of Celite® and the pad was rinsed well with MeOH and water. Volatile solvent from the filtrate was removed in vacuo. The aqueous phase from filtrate was thrice extracted with EtOAc. The combined organic extracts were dried (Na$_2$SO$_4$), filtered and concentrated in vacuo. Crystallization from DCM/heptane afforded 219.1 mg (97%) of (3-methyl-1H-indol-5-yl)methanamine (194) as a white solid: 1H NMR (400 MHz, CDCl$_3$): δ 7.87 (br s, 1H), 7.49 (s, 1H), 7.29 (d, J=8.3 Hz, 1H), 7.12 (d, J=8.3 Hz, 1H), 6.95 (s, 1H), 3.95 (s, 2H), 2.31 (s, 3H), 1.59 (br s, 2H).

Step 3:
The title compound I-25 was prepared using the procedure as described in step 1 of example 19 except 194 replaced 1-(1H-indol-5-yl)ethanamine adipic acid salt as starting material.

Example 30

N$^2$-((1H-Indazol-4-yl)methyl)-N$^4$-(5-cyclopropyl-1H-pyrazol-3-yl)pyrimidine-2,4-diamine (I-59)

Step 1:
A mixture of 4-bromo-1H-indazole (0.5 g, 2.53 mmol), p-TsOH.H$_2$O (50 mg, 0.25 mmol), and 3,4-dihydro-2H-pyran (0.64 g, 7.61 mmol) in THF (20 mL) was degassed then heated to reflux overnight. After the solvent was removed, the residue was partitioned between DCM (300 mL) and water (50 mL). The organic layer was separated, dried (MgSO$_4$), filtered and concentrated. The crude residue was purified by SiO$_2$ chromatography eluting with a DCM/MeOH gradient (0.5 to 1% MeOH) to afford 570 mg (81%) of 4-bromo-1-(tetrahydro-2H-pyran-2-yl)-1H-indazole (196) as yellow solid: MS (ESI) m/z=282.2 [M+1]+.

Step 2:
To a mixture of 196 (0.57 g, 2.05 mmol), Zn(CN)$_2$ (264 mg, 2.25 mmol) in NMP (6 mL) under an argon atmosphere was added (Ph$_3$P)$_4$Pd(0) (356 mg, 0.31 mmol). The mixture was heated at 85° C. overnight, cooled, and partitioned between EtOAc (300 mL) and H$_2$O (50 mL). The organic layer was separated and washed with brine, dried (MgSO$_4$) and concentrated in vacuo. The residue was purified by SiO$_2$ chromatography eluting with 1% MeOH/DCM to afford 430 mg (75%) of 1-(tetrahydro-2H-pyran-2-yl)-1H-indazole-4-carbonitrile (198) as yellow solid: MS (ESI) m/z=228 [M+1]+.

Step 3:

To a solution of 198 (430 mg, 1.89 mmol) in a 7N solution of NH$_3$ in MeOH (20 mL) was added Raney nickel (50 mg), and the mixture was stirred under hydrogen (1 atm) at RT overnight. The Raney nickel was removed by filtration. The filtrate was concentrated to afford 340 mg (79%) of (1-(tetrahydro-2H-pyran-2-yl)-1H-indazol-4-yl) methanamine (199) as yellow syrup: MS (ESI) m/z=232.2 [M+1]$^+$.

Step 4:

A tube was charged with 53 (350 mg, 1.47 mmol), 199 (340 mg, 1.47 mmol), and DIPEA (5 mL) in IPA (10 mL), degassed, sealed and heated at 120° C. for 48 h. The solvent was evaporated in vacuo. The crude product was purified by SiO$_2$ chromatography to afford 600 mg (94%) of N$^4$-(5-cyclopropyl-1H-pyrazol-3-yl)-N$^2$-((1-(tetrahydro-2H-pyran-2-yl)-1H-indazol-4-yl)methyl)pyrimidine-2,4-diamine (200) as yellow solid: MS (ESI) m/z=431.2 [M+1]+.

Step 5:

To a solution of 200 (215 mg, 0.5 mmol) in MeOH (5 mL) and water (1 mL) was added p-TsOH.H$_2$O (95 mg, 0.5 mmol) and the mixture was heated in a sealed tube at 80° C. overnight. The solvent was evaporated in vacuo. The residue was purified by preparative HPLC to afford 110 mg (63%) of I-59 as white solid.

Example 31

N$^2$—((S)-1-(1H-benzo[d]imidazol-5-yl)ethyl)-N$^4$-(5-((S)-2,2-difluorocyclopropyl)-1H-pyrazol-3-yl)pyrimidine-2,4-diamine (I-61) and N$^2$—((S)-1-(1H-benzo[d]imidazol-5-yl)ethyl)-N$^4$-(5-((R)-2,2-difluorocyclopropyl)-1H-pyrazol-3-yl)pyrimidine-2,4-diamine (I-62)

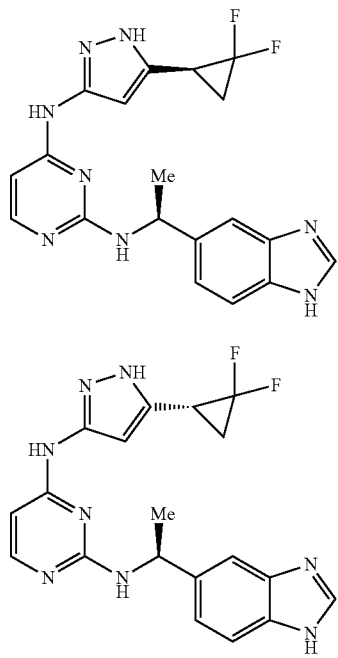

Step 1:

A vial was charged with racemic 81 (125 mg, 0.46 mmol), 126 (169 mg, 0.69 mmol), DIPEA (0.28 mL) and n-BuOH (1.5 mL), sealed and heated at 125° C. for 96 h. The reaction mixture was concentrated under reduced pressure. The crude mixture was purified by preparative HPLC, followed by chiral SFC chromatography to afford the corresponding 2 diastereomers: N$^2$—((S)-1-(1H-benzo[d]imidazol-5-yl)ethyl)-N$^4$-(5-((S)-2,2-difluorocyclopropyl)-1H-pyrazol-3-yl)pyrimidine-2,4-diamine (I-61, 20.4 mg, 11%) and N$^2$—((S)-1-(1H-benzo[d]imidazol-5-yl)ethyl)-N$^4$-(5-((R)-2,2-difluorocyclopropyl)-1H-pyrazol-3-yl)pyrimidine-2,4-diamine (I-62, 13.9 mg, 8%).

Example 32

2-(((1H-benzo[d]imidazol-5-yl)methyl)(4-(5-cyclopropyl-1H-pyrazol-3-ylamino)pyrimidin-2-yl)amino) ethanol (I-63)

Step 1:

To a solution of 126 (1.7 g, 7.3 mmol) in THF (35 mL) was added 1M aq. NaOH (37 mL) and the reaction was cooled to 0° C. and di-tert-butyl dicarbonate (1.7 g, 7.6 mmol) was added. The reaction was warmed to RT and stirred for 16 h at which time additional di-tert-butyl dicarbonate (477 mg, 2.19 mmol) was added. The reaction was stirred for an additional 4 h then the THF was removed in vacuo and aqueous residue was thrice extracted with EtOAc. The combined extracts were dried (Na2SO4), filtered and concentrated in vacuo to afford 2.0 g (82%) of crude tert-butyl (1-(tetrahydro-2H-pyran-2-yl)-1H-benzo[d]imidazol-5-yl)methylcarbamate (202): MS (ESI) m/z=332.4 [M+1]+.

Step 2:

To a solution of 202 (0.75 g, 2.26 mmol) in DMF (7 mL) was added NaH (118 mg, 2.94 mmol, 60% in oil) at 0° C. The reaction was a warmed to RT and stirred for 25 min, then re-cooled to 0° C. and 2-bromoethoxy-tert-butyl-dimethyl-silane (812 mg, 3.40 mmol) and tetrabutyl ammonium iodide (42.7 mg, 0.11 mmol) were added sequentially. The reaction was warmed to RT and stirred for 72 h. Since conversion to desired product was low, the reaction mixture was cooled back to 0° C. and additional NaH (91 mg, 2.26 mmol, 60% in oil) was added. The reaction was warmed at RT and stirred for 20 min then re-cooled to 0° C. and additional 2-bromoethoxy-tert-butyl-dimethyl-silane (541 mg, 2.26 mmol) and TBAI (42.7 mg, 0.11 mmol) were added sequentially. The reaction was warmed to RT and stirred for 3 h. The reaction mixture was partitioned between EtOAc and water. The organic layer was thrice washed with water, dried (Na$_2$SO$_4$), filtered and concentrated in vacuo. The crude residue was purified by SiO$_2$ chromatography to afford 434 mg (39%) of tert-butyl 2-(tert-butyldimethylsilyloxy)ethyl((1-(tetrahydro-2H-pyran-2-yl)-1H-benzo[d]imidazol-5-yl)methyl)carbamate (204): MS (ESI) m/z=490.4 [M+1]+.

Step 3:

To a solution of 204 (434 mg, 0.89 mmol) in MeOH (6 mL) was added 4N HCl/dioxane (2.66 mL, 10.6 mmol). The reaction was stirred at RT for 16 h, then concentrated in vacuo to afford 306 mg (99%) of crude 2-((1-(tetrahydro-2H-pyran-2-yl)-M-benzo[d]imidazol-5-yl)methylamino)ethanol (206) as the bis-HCl salt: MS (ESI) m/z=276.4 [M+1]+.

Step 4:

A vial was charged with 53 (90 mg, 0.38 mmol), bis-HCl salt of 206 (160 mg, 0.46 mmol), DIPEA (0.33 mL) and n-BuOH (0.8 mL), sealed and heated at 120° C. for 60 h. The reaction mixture was concentrated in vacuo. The crude mixture was purified by preparative HPLC to afford 58.6 mg (39%) of I-63.

Example 33

N²—((S)-1-(1H-indol-5-yl)ethyl)-N⁴-(5-((1S,2S)-2-fluorocyclopropyl)-1H-pyrazol-3-yl)pyrimidine-2,4-diamine (I-64) and N²—((S)-1-(1H-indol-5-yl)ethyl)-N⁴-(5-((1R,2R)-2-fluorocyclopropyl)-1H-pyrazol-3-yl)pyrimidine-2,4-diamine (I-65)

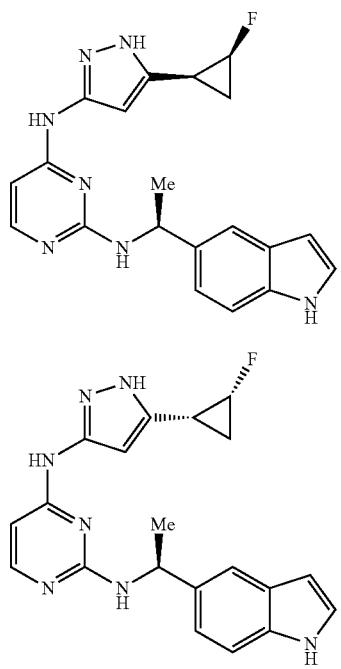

Step 1:

A vial was charged with racemic 49 (75 mg, 0.30 mmol), (S)-1-(1H-indol-5-yl)ethanamine (177, 72 mg, 0.45 mmol, CASRN 1213145-32-3), DIPEA (0.18 mL) and n-BuOH (1 mL), sealed and heated at 115° C. for 48 h. The reaction mixture was concentrated in vacuo. The crude mixture was purified by preparative HPLC, followed by chiral SFC chromatography to afford 13.2 mg, (12%) of N²—((S)-1H-indol-5-yl)ethyl)-N⁴-(5-((1S,2S)-2-fluorocyclopropyl)-1H-pyrazol-3-yl)pyrimidine-2,4-diamine (I-64) and 16.0 mg, (14%) N²—((S)-1-(1H-indol-5-yl)ethyl)-N⁴-(5-((1R,2R)-2-fluorocyclopropyl)-1H-pyrazol-3-yl)pyrimidine-2,4-diamine (I-65).

Example 34

N²—((S)-1-(1H-indol-5-yl)ethyl)-N⁴-(5-(2,2-difluorocyclopropyl)-1H-pyrazol-3-yl)pyrimidine-2,4-diamine (I-66)

A vial was charged with racemic 81 (125 mg, 0.46 mmol), 177 (147 mg, 0.92 mmol), DIPEA (0.32 mL) and n-BuOH (1.5 mL), sealed and heated at 115° C. for 60 h. The reaction mixture was concentrated in vacuo. The crude mixture was purified by preparative HPLC to afford 51.8 mg (29%) of I-66 as a mixture of two diastereomers. MS (ESI) m/z=396.2 [M+1]+.

N₂—((1H-indol-4-yl)methyl)-N4-(5-(2,2-difluorocyclopropyl)-1H-pyrazol-3-yl)pyrimidine-2,4-diamine (I-82) was prepared analogously except (1H-indol-4-yl)methanamine replaced 177. The crude mixture was purified by preparative HPLC to afford 84.4 mg (48%) of I-82.

Example 35

N²—((S)-1-(1H-benzo[d]imidazol-5-yl)ethyl)-N⁴-(5-((1S,2S)-2-fluorocyclopropyl)-1H-pyrazol-3-yl)pyrimidine-2,4-diamine (I-67) and N²—((S)-1-(1H-benzo[d]imidazol-5-yl)ethyl)-N⁴-(5-((1R,2R)-2-fluorocyclopropyl)-1H-pyrazol-3-yl)pyrimidine-2,4-diamine (I-68)

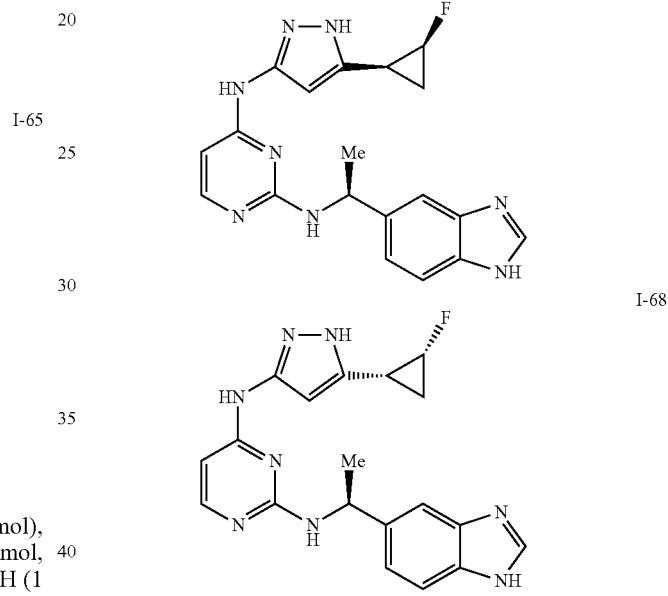

A vial was charged with racemic 73 (80 mg, 0.32 mmol), 126 (139 mg, 0.57 mmol), DIPEA (0.19 mL) and n-BuOH (0.8 mL), sealed and heated at 120° C. for 48 h. The reaction mixture was concentrated in vacuo. The crude product was purified by preparative HPLC, followed by chiral SFC chromatography to afford 9.1 mg (8%) of I-67 and 9.4 mg (8%) of I-68. Stereochemical assignments are tentative.

N²-((4-chloro-1H-benzo[d]imidazol-5-yl)methyl)-N⁴-(5-((1S,2S)-2-fluorocyclopropyl)-1H-pyrazol-3-yl)pyrimidine-2,4-diamine (I-76) and N²-((4-chloro-1H-benzo[d]imidazol-5-yl)methyl)-N⁴-(5-((1R,2R)-2-fluorocyclopropyl)-1H-pyrazol-3-yl)pyrimidine-2,4-diamine (I-77) were prepared analogously except (4-chloro-1-(tetrahydro-2H-pyran-2-yl)-1H-benzo[d]imidazol-5-yl)methanamine (134) replaced 177. The crude mixture was purified by preparative HPLC, followed by chiral SFC chromatography to afford the corresponding 2 enantiomers.

Cis-N²-((1H-indol-4-yl)methyl)-N⁴-(5-2-fluorocyclopropyl)-1H-pyrazol-3-yl)pyrimidine-2,4-diamine (I-81) was prepared analogously except (1H-indol-4-yl)methanamine replaced 126 and the deprotection step was unnecessary. The crude mixture was purified by preparative HPLC to afford 77.3 mg (72%) of I-81.

Examples 36

N²—((S)-1-(1H-benzo[d]imidazol-5-yl)ethyl)-N⁴-(5-((1S,2R)-2-fluorocyclopropyl)-1H-pyrazol-3-yl)pyrimidine-2,4-diamine (I-69) and N²—((S)-1-(1H-benzo[d]imidazol-5-yl)ethyl)-N⁴-(5-((1R,2S)-2-fluorocyclopropyl)-1H-pyrazol-3-yl)pyrimidine-2,4-diamine (I-70)

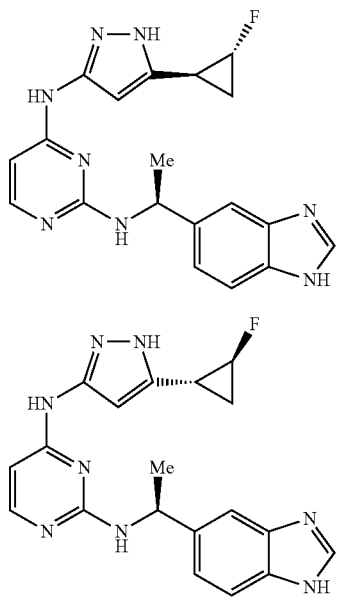

I-69

I-70

A vial was charged with racemic 71 (80 mg, 0.32 mmol), 126 (139 mg, 0.57 mmol), DIPEA (0.19 mL) and n-BuOH (0.8 mL), sealed and heated at 120° C. for 48 h. The reaction mixture was concentrated in vacuo. The crude mixture was purified by preparative HPLC, followed by chiral SFC chromatography to afford 4.2 mg (4%). of I-69 and 4.6 mg (4%) of I-70.

N²—((S)-1-(1H-indol-5-yl)ethyl)-N⁴-(5-((1S,2R)-2-fluorocyclopropyl)-1H-pyrazol-3-yl)pyrimidine-2,4-diamine (I-72) and N²—((S)-1-(1H-indol-5-yl)ethyl)-N⁴-(5-((1R,2S)-2-fluorocyclopropyl)-1H-pyrazol-3-yl)pyrimidine-2,4-diamine (I-73) were prepared analogously except (S)-1-(1H-indol-5-yl)ethanamine (177) replaced 126 and the deprotection step was unnecessary to afford 17.0 mg, (15%) of I-72 and 17.2 mg (15%) of I-73.

N²-((4-chloro-1H-benzo[d]imidazol-5-yl)methyl)-N⁴-(5-((1S,2R)-2-fluorocyclopropyl)-1H-pyrazol-3-yl)pyrimidine-2,4-diamine (I-78) and N²-((4-chloro-1H-benzo[d]imidazol-5-yl)methyl)-N⁴-(5-((1R,2S)-2-fluorocyclopropyl)-1H-pyrazol-3-yl)pyrimidine-2,4-diamine (I-79) were prepared analogously except 126 was replaced by 134. The crude mixture was purified by preparative HPLC, followed by chiral SFC chromatography to resolve the two enantiomers.

trans-N²-((1H-indol-4-yl)methyl)-N⁴-(5-(2-fluorocyclopropyl)-1H-pyrazol-3-yl)pyrimidine-2,4-diamine (I-80) was prepared analogously except 4-aminomethyl-indole replaced 126. The crude mixture was purified by preparative HPLC to afford I-80 as a racemic mixture.

Example 37

N²-((1H-benzo[d]imidazol-5-yl)methyl)-N⁴-(5-cyclopropyl-1H-pyrazol-3-yl)-N²-ethylpyrimidine-2,4-diamine (I-71)

Step 1:

To a solution of 202 (600 mg, 1.81 mmol) in DMF (4.5 mL) at 0° C. was added NaH (101 mg, 2.54 mmol, 60% in oil). The reaction was warmed to RT and stirred for 25 min, then re-cooled to 0° C. and iodoethane (0.27 mL, 3.26 mmol) was added. The reaction was warmed to RT and stirred for 5 h. The reaction mixture was partitioned between EtOAc and H₂O. The EtOAc extract was washed thrice with water, dried (Na₂SO₄), filtered and concentrated in vacuo. The crude residue was purified by SiO₂ chromatography to afford 360 mg (55%) of tert-butyl ethyl((1-(tetrahydro-2H-pyran-2-yl)-1H-benzo[d]imidazol-5-yl)methyl)carbamate (208): MS (ESI) m/z=360.3 [M+1]+

Step 2:

To a solution of 208 (360 mg, 1.00 mmol) in MeOH (5 mL) was added 4N HCl/dioxane (1.00 mL, 4.01 mmol) and the reaction was stirred at RT for 4 h after which additional 4N HCl/dioxane (0.75 mL, 3.00 mmol) was added. The reaction was maintained at RT for 2 h, then concentrated in vacuo to afford 318 mg (100%) of N-(0-(tetrahydro-2H-pyran-2-yl)-1H-benzo[d]imidazol-5-yl)methyl)ethanamine (210)—as the bis-HCl salt: MS (ESI) m/z=260.4 [M+1]+.

Step 3:

A vial was charged with 53 (100 mg, 0.42 mmol), the bis-HCl salt of 210 (169 mg, 0.51 mmol), DIPEA (0.37 mL) and n-BuOH (1.2 mL), sealed and heated at 125° C. for 96 h. The reaction mixture was concentrated in vacuo. The crude mixture was purified by preparative HPLC to afford 8.5 mg (5%) of I-71.

Example 38

(S)—N²-((4-chloro-1H-benzo[d]imidazol-5-yl)methyl)-N⁴-(5-(2,2-difluorocyclopropyl)-1H-pyrazol-3-yl)pyrimidine-2,4-diamine (I-74) and (R)—N²-((4-chloro-1H-benzo[d]imidazol-5-yl)methyl)-N⁴-(5-(2,2-difluorocyclopropyl)-1H-pyrazol-3-yl)pyrimidine-2,4-diamine (I-75)

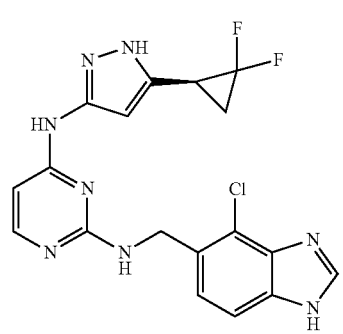

I-74

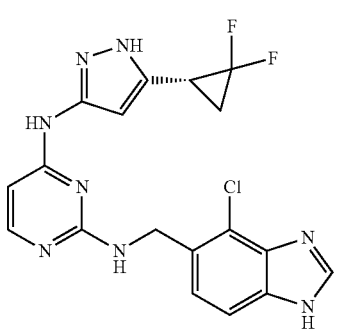

I-74 and I-75 were prepared in accord with the procedure in example 34 except (4-chloro-1-(tetrahydro-2H-pyran-2-yl)-1H-benzo[d]imidazol-5-yl)methanamine (134) replaced 177. The crude mixture was purified by preparative HPLC, followed by chiral SFC chromatography to afford 20.7 mg (11%) of I-74 and 19.3 mg (10%) of I-75.

Example 39

(S)-2-(2-(1-(1H-indol-5-yl)ethylamino)-6-(5-cyclopropyl-1H-pyrazol-3-ylamino)pyrimidin-4-yl)propan-2-ol (I-83)

Step 1:
A round-bottom flask was charged with methyl 2,6-dichloropyrimidine-4-carboxylate (6.9 g, 33.2 mmol), 5-cyclopropyl-1H-pyrazol-3-amine (4.13 g, 33.6 mmol), DIPEA (11.6 mL) and DMSO (40 mL). The reaction was stirred at RT for 4 h then $H_2O$ (150 mL) was added. The mixture was vigorously stirred for 20 min, the resulting precipitate was filtered and washed with water, then dried under high vacuum to afford 10.87 g (>100%) of methyl 2-chloro-6-(5-cyclopropyl-1H-pyrazol-3-ylamino)pyrimidine-4-carboxylate (212): MS (ESI) m/z=294.2 [M+1]+.

Step 2:
To a solution of 212 (3.0 g, 10.2 mmol) in THF (50 mL) at 0° C. was added methylmagnesium chloride (24 mL, 71.5 mmol, 3M ether solution). The reaction was warmed at RT and stirred for 4 h. The THF was removed in vacuo and the residue partitioned between EtOAc and a sat'd. aq. NH4Cl. The aqueous layer was extracted with EtOAc and dried ($Na_2SO_4$), filtered and concentrated in vacuo. The crude residue was purified by $SiO_2$ chromatography to afford 1.11 g (27%) of 2-(2-chloro-6-(5-cyclopropyl-1H-pyrazol-3-ylamino)pyrimidin-4-yl)propan-2-ol (214)

Step 3:
A vial was charged with 214 (115 mg, 0.39 mmol), 177 (113 mg, 0.70 mmol), DIPEA (0.24 mL) and n-BuOH (1.0 mL), sealed and heated at 115° C. for 48 h. The reaction mixture was concentrated in vacuo. The crude product was purified by preparative HPLC to afford 40.4 mg (25%) of I-83.

2-(2-((4-chloro-1H-benzo[d]imidazol-5-yl)methylamino)-6-(5-cyclopropyl-1H-pyrazol-3-ylamino)pyrimidin-4-yl)propan-2-ol (I-84) was prepared analogously from 214 and 134 in accord with the procedures in steps 5 and 6 of example 13. The crude mixture was purified by preparative HPLC to afford 33.4 g (19%) of I-84.

2-(2-((1H-indol-4-yl)methylamino)-6-(5-cyclopropyl-1H-pyrazol-3-ylamino)pyrimidin-4-yl)propan-2-ol (I-85) was prepared analogously from 214 and (1H-indol-4-yl)methanamine in accord with the procedures in step 5 of example 13. The crude mixture was purified by preparative HPLC to afford 93.9 g (60%) of I-85.

Example 40

$N^2$-((4-chloro-1H-benzo[d]imidazol-5-yl)methyl)-$N^4$-(5-cyclopropyl-1H-pyrazol-3-yl)-5-fluoro-$N^2$-methylpyrimidine-2,4-diamine (I-86)

Step 1:
To a solution of 134 (550 mg, 2.1 mmol) in THF (10 mL) was added 1M aq. NaOH (8.3 mL, 8.3 mmol). The reaction was cooled at 0° C. and di-tert-butyl dicarbonate (593 mg, 2.7 mmol) was added. The reaction was warmed to RT, stirred for 16 h then the THF was removed in vacuo. The resulting aqueous residue was twice extracted with EtOAc. The combined extracts were dried ($Na_2SO_4$), filtered and concentrated in vacuo to afford 659 mg (70%) of crude tert-butyl (4-chloro-1-(tetrahydro-2H-pyran-2-yl)-1H-benzo[d]imidazol-5-yl)methylcarbamate (216) which was used without additional purification: MS (ESI) m/z=366.2 [M+1]+.

Step 2:
To a solution of 216 (620 mg, 1.7 mmol) in DMF (8 mL) at 0° C. was added NaH (102 mg, 2.54 mmol, 60% in oil). The reaction was warmed to RT and stirred for 25 min then re-cooled to 0° C. and iodomethane (0.19 mL, 3.05 mmol) was added. The reaction was warmed to RT and stirred for 3 h. The conversion was low so the reaction mixture was cooled back to 0° C. and additional NaH (67 mg, 1.69 mmol, 60% in oil) was added. The reaction was warmed to RT and stirred for 20 min, re-cooled to 0° C. and iodomethane (0.11 mL, 1.69 mmol) was added. The reaction was warmed to RT and stirred for 3 h then partitioned between EtOAc and $H_2O$. The combined organic extracts were thrice washed with $H_2O$, dried ($Na_2SO_4$), filtered and concentrated in vacuo. The crude residue was purified by $SiO_2$ chromatography to afford 363 mg (56%) of tert-butyl (4-chloro-1-(tetrahydro-2H-pyran-2-yl)-1H-benzo[d]imidazol-5-yl)methyl(methyl)carbamate (218): MS (ESI) m/z=380.2 [M+1]+.

Step 3:
To a solution of 218 (363 mg, 0.96 mmol) in MeOH (6 mL) was added 4N HCl/dioxane (2.87 ml, 11.5 mmol) and the reaction was stirred at RT for 2 h then concentrated in vacuo to afford 394 g (100%) of 1-(4-chloro-1-(tetrahydro-2H-pyran-2-yl)-1H-benzo[d]imidazol-5-yl)-N-methylmethanamine (220) as its bis-HCl salt: MS (ESI) m/z=280.1 [M+1]+.

Step 4:
A vial was charged with 2-chloro-N-(5-cyclopropyl-1H-pyrazol-3-yl)-5-fluoropyrimidin-4-amine (55, 95 mg, 0.37 mmol, CASRN 854434-98-5), the bis-HCl salt of 220 (185 mg, 0.52 mmol), DIPEA (0.33 mL) and n-BuOH (0.8 mL), sealed and heated at 120° C. for 96 h. The reaction mixture was concentrated in vacuo. The crude mixture was purified by preparative HPLC to afford 93.2 mg (60%) of I-86: MS (ESI) m/z=413.1 [M+1]+.

$N^2$-((4-chloro-1H-benzo[d]imidazol-5-yl)methyl)-$N^4$-(5-cyclopropyl-1H-pyrazol-3-yl)-$N^2$-methylpyrimidine-2,4-diamine (I-87) was prepared analogously except in step 4, 53 replaced 55 and the crude product was purified by preparative HPLC to afford 78.7 mg (52%) of I-87.

Example 41

$N^4$-(5-Cyclobutyl-1H-pyrazol-3-yl)-$N^2$-((6-fluoro-1H-indol-4-yl)methyl)pyrimidine-2,4-diamine Formate (I-88)

Step 1:
To a solution of 1-bromo-5-fluoro-2-methyl-3-nitrobenzene (4.69 g, 20 mmol) in 1,4-dioxane (25 mL) at RT was slowly added DMF dimethylacetal (13.3 mL) and pyrrolidine (1.7 mL). The solution was heated at 100° C. for 18 h, then concentrated in vacuo to give a dark residue. To the residue was added HOAc (30 mL) and iron powder (11 g, 200 mmol) then the mixture was heated to reflux for 1 h, cooled to RT, neutralized by addition of 50% aq. NaOH and extracted with EtOAc (2×200 mL). The combined organic extracts were dried (MgSO$_4$), filtered and concentrated in vacuo. The residue was purified by SiO$_2$ chromatography eluting with an EtOAc/petroleum ether gradient (5 to 30% EtOAc) to afford 1.16 g (27%) of 4-bromo-6-fluoro-1H-indole (224)—as brown solid: MS (ESI) m/z=213.9 [M+1]+.

Step 2:
To a solution of 224 (1.16 g, 5.42 mmol) in NMP (8.5 mL) under argon atmosphere was added Zn(CN)$_2$ (634 mg, 5.42 mmol), zinc powder (70 mg, 1.1 mmol), Pd$_2$(dba)$_3$ (743 mg, 0.81 mmol) and dppf (900 mg, 1.62 mmol). The reaction was stirred at 140° C. for 18 h, cooled and partitioned between EtOAc (200 mL) and H$_2$O (50 mL). The organic layer was separated, washed with brine, dried (MgSO$_4$), filtered and concentrated to dryness in vacuo. The residue was purified by SiO$_2$ chromatography eluting with 15% EtOAc/petroleum ether to afford 588 mg (68%) of 6-fluoro-1H-indole-4-carbonitrile (226) as yellow solid (588 mg, 68%): MS (ESI) m/z=161.1 [M+1]+.

Step 3:
To a solution of 226 (588 mg, 3.68 mmol) in 7N NH$_3$ in MeOH (20 mL) was added Raney nickel (20 mg), and then the reaction was stirred under hydrogen (1 atm.) at RT overnight. The dark mixture was filtered and the filtrate was concentrated in vacuo to afford 500 mg (85%) of (6-fluoro-1H-indol-4-yl)methanamine (228) as white solid: MS (ESI) m/z=148.1 [M−16]+.

Step 4:
A sealed tube was charged with 65 (114 mg, 0.46 mmol), 228 (114 mg, 0.69 mmol), DIPEA (0.1 mL) in hexan-3-ol (1 mL), degassed, sealed and heated at 140° C. overnight. The solvent was concentrated to dryness in vacuo. The residue was purified by preparative HPLC to afford 35 mg (20%) of I-88 as white solid.

Example 42

N$^4$-(5-Cyclopropyl-1H-pyrazol-3-yl)-N$^2$-((6-fluoro-1H-indol-4-yl)methyl)-6-methylpyrimidine-2,4-diamine Formate (I-89)

The title compound (I-89) was prepared in accord with the procedure in step 4 of example 41 except 65 was replaced with 185. The residue was purified by preparative HPLC to afford 40 mg (21%) of I-89 as white solid.

N$^4$-(5-Cyclobutyl-1H-pyrazol-3-yl)-5-fluoro-N$^2$-((6-fluoro-1H-indol-4-yl)methyl)pyrimidine-2,4-diamine formate (I-90) was prepared in accord with the procedure in step 4 of example 41 except 65 was replaced with 2-chloro-N-(5-cyclobutyl-1H-pyrazol-3-yl)-5-fluoropyrimidin-4-amine (prepared in accord with the preparation of 55 except 5-cyclobutyl-1H-pyrazol-3-amine (CASRN 326827-21-8) was used). The residue was purified by preparative HPLC to afford 30 mg (23%) of I-90 as white solid (30 mg, 23%).

N$^4$-(5-Cyclopropyl-1H-pyrazol-3-yl)-5-fluoro-N$^2$-((6-fluoro-1H-indol-4-yl)methyl)pyrimidine-2,4-diamine diformate (I-91) was prepared in accord with the procedure in step 4 of example 41 except 65 replaced with 55. The residue was purified by preparative HPLC to afford 31 mg (24%) of I-91

N$^4$-(5-cyclopropyl-1H-pyrazol-3-yl)-N$^2$-((6-fluoro-1H-indol-4-yl)methyl)pyrimidine-2,4-diamine (I-53) was prepared in accord with the procedure in step 4 of example 41 except 65 replaced with 53.

Example 43

N$^4$-(5-Cyclopropyl-1H-pyrazol-3-yl)-N$^2$-((3-methyl-1H-indol-4-yl)methyl)pyrimidine-2,4-diamine (I-92)

Step 1:
To a refluxing solution of 4-bromo-1H-indole-3-carbaldehyde (644 mg, 2.87 mmol) in dry THF (20 mL) was added LiAlH$_4$ (218 mg, 5.75 mmol) in several small portions. Heating at reflux was continued for 1 h, the reaction cooled to RT and quenched with water (220 µL), 15% aq. NaOH (w/w, 220 µL), and water (650 µL). The resulting precipitate was filtered and the filtrate was concentrated under reduced pressure to dryness. To the residue was added aq. NaOH (10 mL) and the solution twice extracted with DCM (2×10 mL). The combined extracts were dried (MgSO$_4$), filtered and concentrated in vacuo to afford 454 mg (75%) of 4-bromo-3-methyl-1H-indole (230) as light brown oil: MS (ESI) m/z=210.1 [M+1]+

Step 2:
To a solution of 230 (454 mg, 2.16 mmol) in NMP (4.5 mL) under argon atmosphere was added Zn(CN)$_2$ (252 mg, 2.16 mmol), zinc powder (27 mg, 0.43 mmol), Pd$_2$(dba)$_3$ (0) (293 mg, 0.32 mmol), and dppf (358 mg, 0.65 mmol). The solution was heated at 140° C. for 18 h, the mixture was cooled and partitioned between EtOAc (100 mL) and H$_2$O (30 mL). The organic layer was separated, washed with brine, dried (MgSO$_4$), filtered and concentrated to dryness in vacuo. The residue was purified by SiO$_2$ chromatography eluting with 10% EtOAc/petroleum ether to afford 200 mg (59%) of 3-methyl-1H-indole-4-carbonitrile (232) as white solid: MS (ESI) m/z=157.1 [M+1]+.

Step 3:
To a solution of 232 (200 mg, 1.28 mmol) in 7 N NH$_3$ in MeOH (10 mL) was added Raney nickel (20 mg) and the solution was stirred under hydrogen (1 atm.) at RT overnight. The dark mixture was filtered and the filtrate was concentrated under reduced pressure to afford 200 mg (91%) (3-methyl-1H-indol-4-yl)methanamine (234) as white solid: MS (ESI) m/z=144.3 [M−16]+.

Step 4:
A tube was charged with 53 (200 mg, 0.85 mmol), 234 (181 mg, 1.13 mmol), DIPEA (0.2 mL) and IPA (2 mL), degassed, sealed and heated at 120° C. overnight. The solvent was concentrated to dryness in vacuo. The residue was purified by preparative HPLC to afford 80 mg (26%) of I-92 as white solid.

Example 44

N$^2$-((6-Chloro-1H-indol-5-yl)methyl)-N$^4$ (5-cyclopropyl-1H-pyrazol-3-yl)pyrimidine-2,4-diamine (I-93)

Step 1:
A mixture of 4-amino-2-chlorobenzonitrile (5.0 g, 0.033 mol) and N-iodosuccinimide (8.28 g, 0.036 mol) in HOAc (35 mL) was stirred at RT overnight. A brown solid formed, which was collected by filtration, washed with hexanes, and dried in vacuo to afford 3.6 g (39%) of 4-amino-2-chloro-5-iodobenzonitrile (236) as a pale brown solid: MS (ESI) m/z=278.8 [M+1]+.

Step 2:

A round bottom bottle was charged with 236 (2.78 g, 0.01 mol), CuI (95 mg, 0.5 mmol), Pd(PPh$_3$)Cl$_2$ (200 mg, 0.5 mmol), DIPEA (3.87 g, 0.03 mol) and ethynyltrimethylsilane (2.94 g, 0.03 mol). The mixture was heated under nitrogen atmosphere at 70° C. overnight then cooled and partitioned between EtOAc (500 mL) and H$_2$O (100 mL). The organic layer was concentrated to dryness in vacuo. The crude was purified by SiO$_2$ chromatography eluting with 10% EtOAc/petroleum ether to afford 1.2 g (48%) of 4-amino-2-chloro-5-((trimethylsilyl)ethynyl)benzonitrile (238) as brown solid: MS (ESI) m/z=249.1 [M+1]+

Step 3:

To a solution of 238 (1.0 g, 4 mmol) in THF (100 mL) was added tetrabutylammonium fluoride (2.0 g, 7.6 mmol). The mixture was heated at 75° C. overnight then concentrated and the residue partitioned between EtOAc (500 mL) and H$_2$O (50 mL). The organic layer was separated, washed with brine, concentrated to dryness in vacuo. The crude was purified by CombiFlash chromatography eluting with an EtOAc/petroleum ether gradient (10% to 45% EtOAc) to afford 700 mg (48%) 4-amino-2-chloro-5-ethynylbenzonitrile (240) as yellow solid: MS (ESI) m/z=177.0 [M+1]+.

Step 4:

To a solution of 240 (50 mg, 0.284 mmol) in THF (100 mL) was added t-BuOK (160 mg, 1.42 mmol). The mixture was heated at 75° C. for 3 h during which the color of the reaction mixture changed from yellow to brown. After the mixture was cooled, it was partitioned between EtOAc (200 mL) and H$_2$O (50 mL). The organic layer was separated, washed with brine, dried and concentrated in vacuo to afford 43 mg (86%) of 6-chloro-1H-indole-5-carbonitrile (242) as white solid: 1H NMR (500 MHz, DMSO-d6) (511.80 (s, 1H), 8.21 (s, 1H), 7.70 (s, 1H), 7.60 (d, 1H), 6.61 (d, 1H); MS (ESI) m/z=177.0 [M+1]+.

Step 5:

To a solution of 242 (43 mg, 0.24 mmol) in MeOH (10 mL) and 7M NH$_3$ in MeOH (5 mL) was added Raney nickel and the reaction mixture was stirred vigorously under hydrogen (1 atm.) at RT for 3 h. The reaction mixture was filtered through a pad of Celite® and concentrated under reduced pressure to afford (6-chloro-1H-indol-5-yl)methanamine (244) as pale oil: MS (ESI)=164.1 [M−NH2]+.

Step 6:

A sealed vial was charged with 53 (80 mg, 0.34 mmol), 244 (45 mg, 0.25 mmol), DIPEA (100 mg, 0.75 mmol), and IPA (3.0 mL). The reaction mixture was heated at 120° C. for 18 h. The solution was concentrated and purified by preparative HPLC to afford 40 mg (42%) of I-93 as white solid.

Example 45

N$^2$-((6-chloro-1H-benzo[d]imidazol-5-yl)methyl)-N$^4$-(5-cyclopropyl-1H-pyrazol-3-yl)-pyrimidine-2,4-diamine (I-94)

Step 1:

A mixture of 5-chloro-2-nitrobenzenamine (6.0 g, 34.9 mmol) and NBS (6.06 g, 34.0 mmol) in HOAc (240 mL) was heated at 110° C. for 1 h. The solution was cooled to RT and the reaction mixture was poured into an ice-water (800 mL). The resulting solid was filtered, washed with water (50 mL×3), and dry under vacuum to afford 4.0 g (44%) of 4-bromo-5-chloro-2-nitrobenzenamine (246) as yellow solid: MS (ESI) m/z=250.9 (M−1).

Step 2:

A mixture of 246 (500 mg, 2.0 mmol) and SnCl$_2$ (2.26 g, 10.0 mmol) in EtOH (10 mL) was heated at 80° C. for 3 h. After cooling to RT, the reaction mixture was filtered, and the filtrate concentrated in vacuo. Water (100 mL) was added to the residue, followed by addition of solid NaHCO$_3$. The mixture was then extracted with EtOAc (3×50 mL), washed with brine (50 mL), and concentrated in vacuo to afford 440 mg of a yellow solid. Formic acid (10 mL) was added to the solid and the mixture stirred at 100° C. for 2 h then concentrated in vacuo. Water (100 mL) was added to the residue followed by addition of solid NaHCO$_3$. The mixture was extracted with EtOAc (3×50 mL), and the combined extracts were dried (Na$_2$SO$_4$), filtered and concentrated to afford 400 mg (86%) of 5-bromo-6-chloro-1H-benzo[d]imidazole (248) as yellow solid: MS (ESI) m/z=231.1 (M+1).

Step 3:

A mixture of 248 (550 mg, 2.38 mmol), Pd(PPh$_3$)$_4$ (275 mg, 0.238 mmol), and Zn(CN)$_2$ (279 mg, 2.38 mmol) in NMP (10 mL) was stirred under nitrogen atmosphere at 120° C. for 18 h. The reaction mixture was poured into water (50 mL), extracted with EtOAc (3×20 mL), and concentrated to dryness in vacuo. The crude was purified by SiO$_2$ chromatography eluting with DCM:MeOH (12:1) to afford 217 mg (51.5%) of 6-chloro-1H-benzo[d]imidazole-5-carbonitrile (250) as yellow solid (217 mg, 51.5%): MS (ESI) m/z=178.2 (M+1).

Step 4:

Reduction of 250 to afford (6-chloro-1H-benzo[d]imidazol-5-yl)methanamine (252) was carried out using the procedure in step 4 of example 5 which afforded 120 mg (54.1%) of 252: MS (ESI) m/z=182.2 (M+1).

Step 5:

A tube was charged with 252 (110 mg, 0.608 mmol), 53 (143 mg, 0.608 mmol), and DIPEA (235 mg, 1.823 mmol) in IPA (3 mL), sealed and heated 120° C. for 18 h with stirring. The reaction was cooled to RT and concentrated in vacuo. The crude product was purified by preparative HPLC to afford 72 mg (31.3%) of I-94 as white solid.

Example 46

N$^4$-(5-Cyclopropyl-1H-pyrazol-3-yl)-N$^2$-methyl-N$^2$-((4-methyl-1H-benzo[d]imidazol-5-yl)methyl)pyrimidine-2,4-diamine (I-95)

Step 1:

To a solution of 5-bromo-4-methyl-1H-benzo[d]imidazole (1.0 g, 4.74 mmol, CASRN 952511-48-7) and 3,4-dihydro-2H-pyran (2.0 g, 23.70 mmol) in THF (10 mL) was added p-TsOH.H$_2$O (90 mg, 0.47 mmol). The mixture was heated at 80° C. overnight, cooled and the solvent was removed in vacuo. The residue was diluted with DCM (100 mL) and water (50 mL). The organic layer was separated, dried (MgSO$_4$), filtered and concentrated to dryness in vacuo. The crude product was purified by SiO$_2$ chromatography eluting with a petroleum ether/EtOAc gradient (10 to 50% EtOAc) to afford 800 mg (57%) of 5-bromo-4-methyl-1-(tetrahydro-2H-pyran-2-yl)-1H-benzo[d]imidazole (254) as light yellow solid: MS (ESI) m/z=295.1 [M+1]+.

Step 2:

4-Methyl-1-(tetrahydro-2H-pyran-2-yl)-1H-benzo[d]imidazole-5-carbonitrile was prepared from 254 utilizing the procedure in step 3 of example 45. The residue was purified by SiO$_2$ chromatography eluting with 3% MeOH/DCM to afford 450 mg (92%) 4-methyl-1-(tetrahydro-2H-pyran-2- yl)-1H-benzo[d]-imidazole-5-carbonitrile (256) as yellow solid: MS (ESI) m/z=242.3 [M+1]+.

Step 3:
Reduction of 256 to afford (4-methyl-1-(tetrahydro-2H-pyran-2-yl)-1H-benzo[d]-imidazol-5-yl)methanamine (258) was carried out using the procedure in step 2 of example 2 which afforded 430 mg (94%) of 258 as yellow syrup: MS (ESI) m/z=246.1 [M+1]+.

Step 4:
tert-Butyl (4-methyl-1-(tetrahydro-2H-pyran-2-yl)-1H-benzo[d]-imidazol-5-yl)methylcarbamate (260) was prepared from 258 using the procedure described in step 1 of example 40. The crude product was purified by $SiO_2$ chromatography eluting with a petroleum ether/EtOAc gradient (10 to 50% EtOAc) to afford 400 mg (71%) of 260 as yellow solid: MS (ESI) m/z=346.3 [M+1]+.

Step 5:
tert-Butyl methyl((4-methyl-1-(tetrahydro-2H-pyran-2-yl)-1H-benzo[d]imidazol-5-yl)methyl)carbamate (262) was prepared from 260 using the procedure described in step 2 of example 40 which afforded 100 mg (48%) of 262 as brown solid (100 mg, 48%): MS (ESI) m/z=361.3 [M+1]+.

Step 6:
A solution of 262 (100 mg, 0.28 mmol) in DCM (2 mL) and TFA (2 mL) was stirred at RT for 30 min. The solvent was removed and the residue was dissolved in EtOAc and neutralized with ammonia. The organic layers were separated, washed with brine, dried ($MgSO_4$), filtered and concentrated in vacuo to afford 40 mg (82%) of N-methyl(4-methyl-1H-benzo[d]imidazol-5-yl)methanamine (264): MS (ESI) m/z=176.3 [M+l]+.

Step 7:
A tube was charged with 264 (40 mg, 0.23 mmol), 53 (100 mg, 0.57 mmol), and DIPEA (0.3 ml) in IPA (3 mL), degassed, sealed and heated at 120° C. overnight. After removal of the solvent in vacuo, the crude was purified by preparative HPLC to afford 25 mg (29%) of I-95 as white solid.

Example 47

$N^4$-(5-cyclopropyl-1H-pyrazol-3-yl)-$N^2$-((7-fluoro-1H-benzo[d]imidazol-5-yl)methyl)pyrimidine-2,4-diamine (I-96)

Step 1:
To a solution of 5-bromo-7-fluoro-1H-benzo[d]imidazole (650 mg, 3.02 mmol, CASRN 1197944-33-2) and 3,4-dihydro-2H-pyran (1.27 g, 15.12 mmol) in THF (10 mL) was added p-TsOH.$H_2O$ (58 mg, 0.30 mmol). The reaction was stirred at 80° C. overnight, cooled and the solvent removed in vacuo. The residue was diluted with DCM (100 mL) and water (50 mL). The organic layer was separated, dried ($MgSO_4$), filtered and concentrated in vacuo. The crude product was purified by $SiO_2$ chromatography eluting with a petroleum ether/EtOAc gradient (10 to 50% EtOAc)) to afford 580 mg (64%) of 5-bromo-7-fluoro-1-(tetrahydro-2H-pyran-2-yl)-1H-benzo[d]imidazole (266) as yellow solid: MS (ESI) m/z=299.1 [M+1]+.

Step 2:
7-Fluoro-1-(tetrahydro-2H-pyran-2-yl)-1H-benzo[d]imidazole-5-carbonitrile (268) was prepared from 266 utilizing the procedure in step 3 of example 45. The crude product was purified by $SiO_2$ chromatography eluting with 3% MeOH/DCM to afford 280 mg (89%) of 268 as yellow solid (280 mg, 89%). MS (ESI) m/z=246.3 [M+1]+.

Step 3:
Reduction of 268 to afford (7-fluoro-1-(tetrahydro-2H-pyran-2-yl)-1H-benzo[d]-imidazol-5-yl)methanamine (270) was carried out using the procedure in step 2 of example 2 which afforded 260 mg (92%) of 270 as brown syrup: MS (ESI) m/z=182.2 (M+1).

Step 4:
A tube was charged with 270 (260 mg, 1.04 mmol), 53 (100 mg, 0.57 mmol), DIPEA (0.5 ml) in IPA (3 mL), degassed, sealed and heated at 120° C. overnight. The solvent was evaporated under reduced pressure to afford 160 mg (34%) $N^4$-(5-cyclopropyl-1H-pyrazol-3-yl)-$N^2$-((7-fluoro-1-(tetrahydro-2H-pyran-2-yl)-1H-benzo[d]imidazol-5-yl)methyl)pyrimidine-2,4-diamine (272) as yellow solid: MS (ESI) m/z=449.2 [M+1]+.

Step 5:
A mixture of 272 (140 mg, 0.31 mmol) and p-TsOH.$H_2O$ (59 mg, 0.31 mmol) in MeOH (5 mL) and $H_2O$ (1 mL) was heated at reflux for 2 h. The mixture was cooled and concentrated in vacuo. The crude product was purified by preparative HPLC to afford 50 mg (44%) of I-96 as white solid.

Example 48

$N^2$-((3H-benzo[d]imidazol-4-yl)methyl)-$N^4$-(3-cyclopropyl-1H-pyrazol-5-yl)-5-fluoropyrimidine-2,4-diamine (I-97)

Step 1:
A tube was charged with 58 (273 mg, 1.18 mmol), 55 (150 mg, 0.59 mmol), DIPEA (0.5 ml) and IPA (4 mL), degassed, sealed and heated at 120° C. for 72 h. The solvent was evaporated in vacuo to afford 150 mg (57%) of $N^4$-(3-cyclopropyl-1H-pyrazol-5-yl)-5-fluoro-$N^2$-((1-(tetrahydro-2H-pyran-2-yl)-1H-benzo[d]imidazol-4-yl)methyl)pyrimidine-2,4-diamine (280)—as yellow solid: MS (ESI) m/z=449.7 [M+1]+.

Step 2:
A mixture of 280 (150 mg, 0.33 mmol) and p-TsOH.$H_2O$ (62 mg, 0.33 mmol) in MeOH (5 mL) and $H_2O$ (1 mL) was heated to reflux for 2 h. The solution was concentrated in vacuo and the residue purified by preparative HPLC to afford 40 mg (33%) of I-97.

Example 49

$N^4$-(5-cyclopropyl-1H-pyrazol-3-yl)-$N^2$-[(1S)-1-(1H-indol-4-yl)ethyl]pyrimidine-2,4-diamine (I-98)

Step 1:
To a stirred solution of 1-(1-tosyl-1H-indol-4-yl)ethanone (500 mg, 1.4 mmol, CASRN 112970-73-7) in dry MeOH (5 mL) at 0° C. was added $NaBH_4$ (80 mg, 2.1 mmol) and the mixture was stirred at RT overnight. The mixture was concentrated in vacuo and the residue was diluted with EtOAc, washed sequentially with water and brine. The organics were dried ($Na_2SO_4$), filtered and concentrated in vacuo. The crude product was purified by $SiO_2$ chromatography to afford 420 mg (95%) of 1-(1-tosyl-1H-indol-4-yl)ethanol (282) as white semi-solid: 1H NMR (400 MHz, DMSO-d6) δ 7.85 (d, J=8.4 Hz, 2H), 7.81-7.76 (m, 2H), 7.37 (d, J=8.0 Hz, 2H), 7.31-7.23 (m, 2H), 6.98 (d, J=3.6 Hz, 1H), 5.23 (d, J=4 Hz, 1H), 5.04-5.01 (m, 1H), 2.30 (s, 3H), 1.33 (d, J=6.4 Hz, 3H).

Step 2:
To a solution of 282 (400 mg, 1.27 mmol) in dry DCM (2 mL) and dry $Et_2O$ (2 mL) at 0° C. under Argon was added $PBr_3$ (515 mg, 1.91 mmol) and the mixture was stirred at RT overnight. The mixture was poured into cold NaHCO₃ (aq.) and extracted with EtOAc. The combined extracts were washed sequentially with water and brine, dried (Na₂SO₄), filtered and concentrated in vacuo to afford 450 mg (92%) of 4-(1-bromoethyl)-1-tosyl-1H-indole (284) give as a yellow oil, which was used in the next step without further purification: 1H NMR (400 MHz, CDCl₃) δ 7.94 (d, J=8.0 Hz, 1H), 7.78 (d, J=8.0 Hz, 2H), 7.65 (d, J=2.8 Hz, 1H), 7.35-7.23 (m, 4H), 6.89 (d, J=2.8 Hz, 1H), 5.53-5.50 (m, 1H), 2.36 (s, 3H), 2.13 (d, J=6.8 Hz, 3H).

Step 3:

To a solution of isoindoline-1,3-dione (3.83 g, 20.0 mmol), in dry DMF (70 mL) at 0° C. under argon was added NaH (1.04 g, 26 mmol). The resultant mixture was stirred at RT for 30 min. A solution of 284 (9.8 g, 26 mmol) in dry DMF (30 mL) was added and the mixture was stirred at RT for 4 h. The mixture was concentrated in vacuo and purified by SiO₂ chromatography to afford 10 g (86%) of 2-(1-(1-tosyl-1H-indol-4-yl)ethyl)isoindoline-1,3-dione (286) as a white solid: 1H NMR (400 MHz, DMSO-d⁶) δ 7.87-7.81 (m, 8H), 7.48 (d, J=7.6 Hz, 1H), 7.38-7.33 (m, 3H), 6.82 (d, J=3.6 Hz, 1H), 5.77-5.74 (m, 1H), 2.29 (s, 3H), 1.84 (d, J=6.8 Hz, 3H).

Step 4:

To a solution of 286 (200 mg, 0.45 mmol) in EtOH (3 mL) was added N₂H₄.H₂O (0.06 mL, 1.35 mmol) and the mixture was heated at reflux for 2 h. The mixture was filtered and the filtrate concentrated in vacuo then purified by SiO₂ chromatography to afford 120 mg (85%) of 3-(1-tosyl-1H-indol-4-yl)ethanamine (288) as a pale-yellow semi-solid: 1H NMR (400 MHz, DMSO-d6) δ 7.85 (d, J=8.4 Hz, 1H), 7.78-7.75 (m, 2H), 7.36 (d, J=8.0 Hz, 1H), 7.34-7.25 (m, 2H), 7.01 (d, J=3.6 Hz, 1H), 4.33 (q, J=6.4 Hz, 1H), 2.30 (s, 3H), 1.25 (d, J=6.4 Hz, 3H).

Step 5:

To a solution of 288 (500 mg, 1.59 mmol) in MeOH (5 mL) was added KOH (446 mg, 7.95 mmol) and the mixture was heated at reflux for 4 h. The mixture was concentrated in vacuo and purified by SiO₂ chromatography to afford 200 mg (79%) of 1-(1H-indol-4-yl)ethanamine (290) as a pale-yellow solid: 1H NMR (400 MHz, DMSO-d⁶) 511.02 (br, s, 1H), 7.30-7.23 (m, 1H), 7.22 (d, J=7.6 Hz, 1H), 7.06-6.99 (m, 2H), 6.53 (br, s, 1H), 4.37 (, J=6.4 Hz, 1H), 1.33 (d, J=6.4 Hz, 3H).

Step 6:

To a solution of 53 (200 mg; 0.85 mmol) and 290 (204 mg; 1.5 equiv, 1.27 mmol) in n-BuOH (2.4 mL) was added DIPEA (554 mg; 4.24 mmol) and the reaction was heated to 140° C. for 2 d. The reaction was cooled and the solvents were removed in vacuo. The crude product was purified by HPLC. Subsequent SFC chromatography was employed to separate the enantiomers and afford 64.1 mg (21%) of I-98 (formate salt) as off-white solid: SFC retention time: 0.90 min.

N⁴-(5-cyclopropyl-1H-pyrazol-3-yl)-N²-[(1R)-1-(1H-indol-4-yl)ethyl]pyrimidine-2,4-diamine (292) was isolated from the SFC chromatography to afford 57.3 mg of 292 as an off-white solid: 1H NMR (400 MHz, DMSO) δ 12.18-11.51 (m, 1H), 11.02 (s, 1H), 9.39-8.93 (m, 1H), 7.75 (d, J=5.6 Hz, 1H), 7.39-7.12 (m, 2H), 7.10-6.83 (m, 3H), 6.60 (s, 1H), 6.06 (s, 2H), 5.63-5.38 (m, 1H), 1.92-1.68 (m, 1H), 1.53 (d, J=7.0 Hz, 3H), 0.98-0.52 (m, 4H); MS (ESI) m/z=360.2 [M+1]⁺; SFC retention time: 1.36 min.

N⁴-(5-cyclopropyl-1H-pyrazol-3-yl)-5-fluoro-N²-[(1S)-1-(1H-indol-4-yl)ethyl]pyrimidine-2,4-diamine (I-99) was prepared analogously except in step 6, 221 replaced 53 to afford 14.1 mg (9%) of I-99 as an off-white solid. The peak eluted from SFC on a chiral column at 0.58 min.

N⁴-(5-cyclopropyl-1H-pyrazol-3-yl)-5-fluoro-N²-[(1R)-1-(1H-indol-4-yl)ethyl]pyrimidine-2,4-diamine (I-100) was recovered from a peak eluting at 0.95 min which afforded 16 mg (11%) as an off-white solid.

Example 50

N⁴-(5-cyclopropyl-1H-pyrazol-3-yl)-N²-(1H-indazol-5-ylmethyl)pyrimidine-2,4-diamine (I-102)

A 5 mL microwave tube was charged with 1H-indazol-5-ylmethanamine (312.3 mg; 2.12 mmol, CASRN 267413-25-2), 53 (100 mg; 0.42 mmol) and n-BuOH (1.2 mL). DIPEA (277 mg; 2.12 mmol) was added, the tube sealed and heated to 140° C. for 17 h. The crude reaction mixture was partitioned between EtOAc (50 mL) and water (25 mL) and the organic phase washed with brine (25 mL) and dried (Na₂SO₄), filtered and concentrated in vacuo. The crude product was purified by HPLC to afford 82.2 mg (56%) of I-102 as an off-white solid.

Example 51

N⁴-(5-cyclopropyl-1H-pyrazol-3-yl)-N²-(1H-indazol-6-ylmethyl)pyrimidine-2,4-diamine (I-103)

A microwave tube was charged with 1H-indazol-6-ylmethanamine (187.4 mg; 1.27 mmol), 53 (100 mg; 0.42 mmol) and n-BuOH. DIPEA (277.0 mg; 2.12 mmol), was added, the tube capped and irradiated in a microwave at 170° C. for 5 h. The crude reaction mixture was partitioned between EtOAc (50 mL) and water (25 mL), filtered through a drying cartridge (Na₂SO₄), which was washed with EtOAc (50 mL). The crude organic phase was reduced and purified by HPLC to afford 99.7 mg (68%) of I-103 as a light yellow solid.

N²-[(1S)-1-(1H-benzimidazol-5-yl)propyl]-N⁴-(5-cyclopropyl-1H-pyrazol-3-yl)-5-fluoro-pyrimidine-2,4-diamine (I-101) was prepared analogously except 55 replaced 53. The crude product was purified by HPLC and the enantiomers subsequently resolved by chiral SFC. The peak eluting at 1.21 min afforded 4.6 mg (6%) of I-101 as a white solid.

Example 52

(S)—N²-(1-(1H-indol-5-yl)ethyl)-5-chloro-N⁴-(5-cyclopropyl-1H-pyrazol-3-yl)pyrimidine-2,4-diamine (I-110)

To a solution of 57 (135 mg, 0.5 mmol) in n-BuOH (2 mL) was added 177 (120 mg, 0.75 mmol) then TEA (0.21 mL, 1.5 mmol) was added dropwise. The reaction mixture was irradiated in a microwave synthesizer at 110° C. for 1 h. The reaction was then heated in an oil bath at 100° C. for 24 h. The solvent was removed in vacuo and the crude residue was taken up in DCM (5 mL) and MeOH (5 mL) and then concentrated in vacuo. The residue was diluted in DMF (1 mL) and filtered. The crude product was purified by reverse phase HPLC to afford 83 mg (42%) of I-110.

(S)—N²-(1-(1H-indol-5-yl)ethyl)-N⁴-(5-(3,3-difluorocyclobutyl)-1H-pyrazol-3-yl)pyrimidine-2,4-diamine (I-111) was prepared analogously except 63 replaced 57.

(S)—N²-(1-(1H-indol-5-yl)ethyl)-N⁴-(5-methyl-1H-pyrazol-3-yl)pyrimidine-2,4-diamine (I-112) was prepared analogously except 2-chloro-N-(5-methyl-1H-pyrazol-3-yl)-pyrimidin-4-amine (CASRN 543712-91-0) replaced 57.

(S)—N²-(1-(1H-indol-5-yl)ethyl)-N⁴-(5-cyclopentyl-1H-pyrazol-3-yl)pyrimidine-2,4-diamine (I-113) was prepared analogously except 67 replaced 57.

(S)—N²-(1-(1H-indol-5-yl)ethyl)-N⁴-(5-cyclobutyl-1H-pyrazol-3-yl)pyrimidine-2,4-diamine (I-114) was prepared analogously except 65 replaced 57.

N²—((S)-1-(1H-indol-5-yl)ethyl)-N⁴-(5-(tetrahydrofuran-3-yl)-1H-pyrazol-3-yl)pyrimidine-2,4-diamine (I-115) was prepared analogously except 753 replaced 57.

N²—((S)-1-(1H-indol-5-yl)ethyl)-N⁴-(5-(tetrahydrofuran-2-yl)-1H-pyrazol-3-yl)pyrimidine-2,4-diamine (I-116) was prepared analogously except 83 replaced 57.

Example 53

N²-((1H-indol-4-yl)methyl)-N⁴-(5-(trans-2-(2-fluorophenyl)cyclopropyl)-1H-pyrazol-3-yl)pyrimidine-2,4-diamine (I-118)

To a solution of 2-chloro-N-(5-(trans-2-(2-fluorophenyl)cyclopropyl)-1H-pyrazol-3-yl)pyrimidin-4-amine (79, 165 mg, 0.5 mmol) in n-BuOH (5 mL) was added (1H-indol-4-yl)methanamine (110 mg, 0.75 mmol). DIPEA (0.26 mL, 1.5 mmol) was added dropwise then the reaction mixture was placed in a shaker block and heated to 130° C. for 20 h. The reaction mixture was cooled and evaporated in vacuo. The crude residue was diluted in DCM (5 mL) and MeOH (5 mL) and then the solvent was evaporated in vacuo. The crude residue was diluted in DMF (2 mL) and filtered. The remaining liquid was removed in vacuo. The residue was purified by reverse phase HPLC to afford 114 mg (52%) of I-118.

N²-((1H-indol-4-yl)methyl)-N⁴-(5-(tetrahydrofuran-2-yl)-1H-pyrazol-3-yl)pyrimidine-2,4-diamine (I-119) and N²-(1H-indol-4-yl)methyl)-N⁴-(5-cyclopropyl-1H-pyrazol-3-yl)-5-fluoropyrimidine-2,4-diamine (I-120) were prepared analogously except 2-chloro-N-(5-(trans-2-(2-fluorophenyl)cyclopropyl)-1H-pyrazol-3-yl)pyrimidin-4-amine was replaced with 83 and 55, respectively Example 54

(S)—N²-(1-(1H-benzo[d]imidazol-5-yl)ethyl)-N⁴-(5-methyl-1H-pyrazol-3-yl)pyrimidine-2,4-diamine (I-121)

To a solution of 2-chloro-N-(5-methyl-1H-pyrazol-3-yl)pyrimidin-4-amine (105 mg, 0.5 mmol) in n-BuOH (2 mL) in a microwave vial was added 126 (184 mg, 0.75 mmol). To the solution was added dropwise TEA (0.21 mL, 1.5 mmol) and the vial sealed and irradiated in a in the microwave synthesizer at 110° C. for 6 h. The solvent was evaporated under reduced pressure and the crude residue was taken up in DCM (5 mL) and MeOH (5 mL) and the solvent was again concentrated in vacuo. The residue was diluted in DMF (1 mL) and filtered. The crude mixture was purified by reverse phase HPLC to afford 9 mg (5%) of I-121.

Example 55

N²-((1H-Indol-4-yl)methyl)-N⁴-(5-cyclopropyl-1H-pyrazol-3-yl)-N²-methylpyrimidine-2,4-diamine (I-40)

Step 1:
To a solution of methanamine (536 mg, 17.24 mmol) in MeOH (10 mL) was added 1H-indole-4-carbaldehyde (500 mg, 3.45 mmol). The reaction mixture was stirred at RT for 14 h. The reaction was cooled in an ice bath and NaBH₄ (130 mg, 3.45 mmol) was added in several portions. The reaction was stirred at 0° C. for 5 min then stirred at RT for 4 h. The solvent was removed under reduced pressure to afford 300 mg (54.5%) of (1H-indol-4-yl)-N-methylmethanamine (116) which was used in the next step without further purification: MS (ESI) m/z=161.3 [M+1]+.

Step 2:
A tube was charged with 116 (280 mg, 1.75 mmol), 53 (412 mg, 1.75 mmol), DIPEA (678 mg, 5.25 mmol) and IPA (5 mL), sealed and heated at 120° C. for 14 h. The mixture was concentrated in vacuo and the residue was purified by preparative HPLC to afford 260 mg (41.4%) of I-40.

Example 56

N²-((1H-indol-4-yl)methyl)-N⁴-(5-(3,3-difluorocyclobutyl)-1H-pyrazol-3-yl)pyrimidine-2,4-diamine (I-104)

To a solution of 63 (143 mg, 0.5 mmol) in n-BuOH (2 mL) was added (1H-indol-4-yl)methanamine (110 mg, 0.75 mmol). TEA (0.21 mL, 1.5 mmol) was then added dropwise and the reaction mixture irradiated in the microwave synthesizer at 150° C. for 150 min. The reaction mixture was then placed in an oil bath at 100° C. for 30 h. The crude residue was diluted in DCM (5 mL) and MeOH (5 mL) and the solvent was removed in vacuo. The crude residue was diluted in DMF (2 mL) and filtered to remove undissolved solids. The remaining liquid was removed in vacuo. The crude product was purified by reverse phase HPLC to afford 42 mg (21%) of I-104.

N²-((4-chloro-1H-benzo[d]imidazol-5-yl)methyl)-N⁴-(5-(3,3-difluorocyclobutyl)-1H-pyrazol-3-yl)pyrimidine-2,4-diamine (I-105) was prepared in two steps. Step 1 was carried out analogously except 134 replaced (1H-indol-4-yl)methanamine. The THP protecting group was removed in accord with the procedure in step 6 of example 13. The crude mixture was purified by reverse phase HPLC to afford 3 mg (1%) of I-105.

Example 57

N⁴-(5-Cyclopropyl-1H-pyrazol-3-yl)-N²-((1-methyl-1H-indol-5-yl)methyl)pyrimidine-2,4-diamine (I-33)

Step 1:
To a solution of 1H-indole-5-carbonitrile (600 mg, 4.2 mmol) in DMF (5 mL) at 0° C. was added NaH (201 mg, 60% in oil, 8.4 mmol) with vigorous stirring. The solution was stirred 30 min, then iodomethane (1.8 g, 12.6 mmol) was added. The reaction mixture was stirred at RT for 4 h. The reaction was quenched with water (50 mL) and extracted with EtOAc (3×100 mL). The organic layers were combined, dried (MgSO₄), filtered, and concentrated under reduced pressure to afford 800 mg of 1-methyl-1H-indole-5-carbonitrile (294) as white solid: MS (ESI) m/z=157.3 [M+1]+.

Step 2:
To a solution of 294 (800 mg, 5.12 mmol) in 7M ammonia in MeOH (50 mL) was added Raney Ni (2.0 g) and the reaction mixture was stirred vigorously under H₂ (1 atm.) atmosphere at RT for 18 h. The reaction mixture was filtered through a pad of Celite® and concentrated in vacuo to afford 800 mg of (1-methyl-1H-indol-5-yl)methanamine (296) as yellow oil: MS (ESI) m/z=144.3 [M-NH₂]+.

Step 3:
A microwave vial was charged with 2-chloro-N-(5-cyclopropyl-1H-pyrazol-3-yl)pyrimidin-4-amine (160 mg, 0.68 mmol), 296 (800 mg, 5.59 mmol), DIPEA (1 ml), and IPA (5.0 mL), sealed and heated at 120° C. for 18 h. It was concentrated and purified by SiO$_2$ chromatography, and then preparative HPLC to afford 30 mg (12%) of I-33 as white solid.

Example 58

N$^4$-(5-Cyclopropyl-1H-pyrazol-3-yl)-N$^2$-((5-methyl-1H-indol-4-yl)methyl)pyrimidine-2,4-diamine (I-122)

Step 1:
To a mixture of 2-bromo-1,3-dimethylbenzene (5.0 g, 27.03 mmol) in sulfuric acid (98%, 40 mL) at −10° C. was added dropwise a solution of nitric acid (68%, 2.74 g, 27.03 mmol) in sulfuric acid (98%, 10 mL). After the reaction was complete the mixture was stirred at −10° C. for 1 h. The reaction mixture was poured onto ice (200 g) the resulting solid filtered, washed with water, and dried in vacuo. The crude was purified by SiO$_2$ chromatography eluting with petroleum ether/EtOAc (100:1) as eluting solvent to afford 2.3 g (37%) of 2-bromo-1,3-dimethyl-4-nitrobenzene as yellow solid (298): $^1$H NMR (500 MHz, DMSO-d$_6$): δ 7.79 (d, J=8.5, 1H), 7.43 (d, J=8.5, 1H), 2.47 (s, 3H), 2.44 (s, 3H).

Step 2:
A mixture of 298 (3.0 g, 13.04 mmol), pyrrolidine (926 mg, 13.04 mmol), and DMF-DMA (7.76 g, 65.22 mmol) in 1,4-dioxane (20 mL) under nitrogen atmosphere was heated at 100° C. for 18 h. The reaction was concentrated under to dryness in vacuo and to the residue was added iron (3.65 g, 65.22 mmol) and HOAc (40 mL). The resulting mixture was heated at 110° C. for 4 h, cooled to RT and filtered. The filtrate was concentrated in vacuo. The crude was purified by SiO$_2$ chromatography eluting with petroleum ether/EtOAc (10:1) to afford 150 mg (5.5%) of 4-bromo-5-methyl-1H-indole (300) as a yellow solid: MS (ESI) m/z=210.1 (M+1).

Step 3:
A mixture of 300 (150 mg, 0.714 mmol), Pd$_2$(dba)$_3$ (131 mg, 0.143 mmol), dppf (159 mg, 0.286 mmol), Zn(CN)$_2$ (84 mg, 0.714 mmol), and zinc (4.6 mg, 0.0714 mmol) in NMP (10 mL) under nitrogen atmosphere was heated at 145° C. for 18 h. The reaction mixture was poured into water (50 mL) and extracted with EtOAc (20 mL×3). The combined extracts were dried (MgSO$_4$), filtered, and concentrated to dryness. The crude was purified by SiO$_2$ chromatography eluting with petroleum ether/EtOAc (3:1) to afford 54 mg (48.5%) 5-methyl-1H-indole-4-carbonitrile (302) as yellow solid: MS (ESI) m/z=157.1 (M+1).

Step 4:
A mixture of 302 (54 mg, 0.346 mmol) and Raney Ni (100 mg) in 7M ammonia in MeOH (20 mL) was stirred under hydrogen at RT for 3 h. It was filtered through Celite®, and the filtrate was concentrated under reduced pressure to afford 53 mg (95.7%) of (5-methyl-1H-indol-4-yl)methanamine (304) as yellow solid: MS (ESI) m/z=144.3 (M−16).

Step 5:
A mixture of 304 (53 mg, 0.331 mmol) 53 (94 mg, 0.397 mmol), and DIPEA (128 mg, 0.993 mmol) in WA (2 mL) under nitrogen atmosphere was heated in a sealed tube at 120° C. for 18 h. The crude was purified by preparative HPLC to afford 38 mg (32%) of I-122.

Example 59

N$^4$-(5-Cyclopropyl-1H-pyrazol-3-yl)-N$^2$-((7-methyl-1H-indol-4-yl)methyl)pyrimidine-2,4-diamine (I-52)

Step 1:
To a solution of 4-bromo-1-methyl-2-nitrobenzene (10 g) in THF (130 mL) was slowly added vinylmagnesium bromide (1 M in THF, 162 mL) at −40° C. under nitrogen atmosphere. The reaction mixture was stirred for 1.5 h and then quenched with sat'd. aq. NH$_4$Cl (50 mL). The mixture was partitioned between EtOAc (500 mL) and water (150 mL). The organic layer was separated, washed with brine, dried (MgSO$_4$), filtered, and evaporated in vacuo. The residue was purified by SiO$_2$ chromatography eluting with 2.5% EtOAc/petroleum ether to afford 1.54 g (16%) of 4-bromo-7-methyl-1H-indole (306) as brown solid: MS (ESI) m/z=209.9 [M+1]$^+$.

Step 2:
To a solution of 306 (300 mg, 1.43 mmol) in NMP (3 mL) under argon atmosphere were added Zn(CN)$_2$ (167 mg, 1.43 mmol), zinc powder (18 mg, 0.28 mmol), Pd$_2$(dba)$_3$ (198 mg, 0.21 mmol), and dppf (237 mg, 0.42 mmol). After stirring at 140° C. for 18 h, the mixture was cooled and partitioned between ethyl EtOAc (200 mL) and water (50 mL). The organic layer was separated, washed with brine, dried (MgSO$_4$), filtered, and evaporated in vacuo. The residue was purified by SiO$_2$ chromatography eluting with 15% EtOAc/petroleum ether to afford 222 mg (85%) of 7-methyl-1H-indole-4-carbonitrile (308) as yellow solid.

Step 3:
To a solution of 308 (222 mg, 1.42 mmol) in 7M ammonia in MeOH (15 mL) was added Raney Ni (20 mg), and then it was stirred under hydrogen (1 atm.) at RT overnight. The dark mixture was filtered, and the filtrate was concentrated in vacuo to afford (137 mg (62%) of 7-methyl-1H-indol-4-yl)methanamine (310) as yellow solid: MS (ESI) m/z=144.1 [M−16]$^+$.

Step 4:
A mixture of 53 (116 mg, 0.50 mmol), 310 (137 mg, 0.86 mmol), DIPEA (2 ml) in IPA (5 mL) was degassed, and then heated in a sealed tube at 120° C. overnight. The solvent was evaporated under reduced pressure and the residue was purified by preparative HPLC to afford 109 mg (35%) of I-52 as white solid.

Example 60

N$^2$-((4-chloro-1H-indol-5-yl)methyl)-N$^4$-(5-cyclopropyl-1H-pyrazol-3-yl)pyrimidine-2,4-diamine (I-20)

Step 1:
To a stirred solution of 2-chloro-1,3-dimethylbenzene (100.0 g, 0.71 mol) in glacial HOAc (500 mL) was added dropwise fuming HNO$_3$ (200 mL). The reaction mixture was stirred at 80° C. for 3 h. The cooled reaction was poured into ice-water and thrice extracted with EtOAc. The combined organic layers were washed with brine, dried (Na$_2$SO$_4$), filtered, and concentrated in vacuo. The crude product was purified by SiO$_2$ chromatography eluting with hexane to afford 101.0 g (77%) of 4:1 mixture of 2-chloro-1,3-dimethyl-4-nitrobenzene and 2-chloro-1,3-dimethyl-5-nitrobenzene, respectively. $^1$H NMR (400 MHz, CDCl$_3$) δ 7.61 (d, J=8.4 Hz, 1H), 7.19 (d, J=8.4 Hz, 1H), 2.54 (s, 3H), 2.44 (s, 3H).

Step 2:
To a stirred solution of 4:1 mixture from step 1 (100.0 g, 0.539 mol), in anhydrous DMF (500 mL) was added DMF-DMA (77.5 g, 0.650 mol) followed by DABCO (72.9 g, 0.650 mol). The reaction mixture was stirred at 110° C. overnight and then cooled to RT. Raney-Ni (wet, 20 g) was added, and the resulting mixture was hydrogenated under 30 psi at 50° C. overnight. The catalyst was filtered through a pad of Celite®. The filtrate was diluted with EtOAc, and the organic layer was washed with water and brine, dried (Na$_2$SO$_4$), filtered, and concentrated in vacuo. The crude product was purified by SiO$_2$ chromatography eluting with an EtOAc/hexane gradient (5 to 10% EtOAc) to afford 20.1 g (23%) of 4-chloro-5-methyl-1H-indole (312) as a solid: $^1$H NMR (400 MHz, CDCl$_3$) δ 8.17 (br s, 1H), 7.22-7.19 (m, 2H), 7.05 (d, J=8.2 Hz, 1H), 6.64-6.62 (m, 1H), 2.48 (s, 3H).

Step 3:

A mixture of 312 (27.0 g, 0.163 mol), di-tert-butyl dicarbonate (53.0 g, 0.243 mol), and DMAP (2.0 g, 0.0164 mol) in anhydrous MeCN (200 mL) was stirred at RT for 4 h. The reaction mixture was diluted with EtOAc, and the organic layer was washed with water and brine, dried (Na$_2$SO$_4$), filtered, and concentrated in vacuo. The crude product was purified by SiO$_2$ chromatography eluting with an EtOAc/hexane gradient (2 to 10% EtOAc) to afford 38.0 g (88%) of tert-butyl-4-chloro-5-methyl-1H-indole-1-carboxylate (314) as colorless oil: $^1$H NMR (400 MHz, CDCl$_3$) δ 7.92 (br s, 1H), 7.57 (s, 1H), 7.15 (d, J=8.4 Hz, 1H), 6.66 (d, J=3.7 Hz, 1H), 2.46 (s, 3H), 1.67 (s, 9H).

Step 4:

To a stirred solution of 314 (38.1 g, 0.143 mol) in CCl$_4$ (300 mL) at 80° C. was added NBS (30.6 g, 0.172 mol) followed by AIBN (1.2 g, 7.31 mmol), and the reaction mixture was stirred at 80° C. overnight. The cooled reaction mixture was diluted with EtOAc, and the organic layer was washed with water and brine, dried (Na$_2$SO$_4$), filtered, and concentrated in vacuo. The crude product was purified by SiO$_2$ chromatography eluting with an EtOAc/hexane gradient (2 to 20% EtOAc) to afford 16.1 g (33%) of tert-butyl-5-(bromomethyl)-4-chloro-1H-indole-1-carboxylate (316) as a white solid: NMR (400 MHz, CDCl$_3$) δ 8.03 (d, J=8.4 Hz, 1H), 7.63 (s, 1H), 7.36 (d, J=8.4 Hz, 1H), 6.71 (d, J=3.8 Hz, 1H), 4.75 (s, 2H), 1.67 (s, 9H).

Step 5:

A mixture of 316 (16.1 g, 0.0467 mol) and potassium phthalimide (26.1 g, 0.141 mol) in anhydrous DMF (150 mL) was stirred at 80° C. overnight. The cooled reaction mixture was diluted with EtOAc and the organic layer was washed with water and brine, dried (Na$_2$SO$_4$), filtered, and concentrated in vacuo. The crude product was purified by SiO$_2$ chromatography eluting with an EtOAc/hexane gradient (5 to 20% EtOAc) to afford 10.8 g (56%) of tert-butyl-4-chloro-5-((1,3-dioxoisoindolin-2-yl)methyl)-1H-indole-1-carboxylate (318) as a white solid: $^1$H NMR (400 MHz, CDCl$_3$) δ 7.96 (d, J=8.2 Hz, 1H), 7.88-7.86 (m, 2H), 7.74-7.72 (m, 2H), 7.62 (d, J=3.7 Hz, 1H), 7.27-7.25 (m, 2H), 5.12 (s, 2H), 1.65 (s, 9H).

Step 6:

To a stirred suspension of 318 (10.75 g, 0.026 mol) in EtOH (200 mL) was added hydrazine hydrate (2.52 mL, 0.052 mol), and the resulting reaction mixture was heated at 100° C. for 1 h. The cooled reaction mixture was diluted with water and thrice extracted with DCM. The combined organic layers were washed with water and brine, dried (Na$_2$SO$_4$), filtered, and concentrated in vacuo. The solid was suspended in hexane (100 mL) and ethyl acetate (5 mL) and filtered. The filtrate was concentrated under reduced pressure to afford 5.34 g (73%) of tert-butyl-5-(aminomethyl)-4-chloro-1H-indol-1-carboxylate (320) as a white solid: 1H NMR (400 MHz, DMSO-d6) δ 7.97 (d, J=8.5 Hz, 1H), 7.73 (s, 1H), 7.50 (d, J=8.5 Hz, 1H), 6.71 (d, J=3.7 Hz, 1H), 2.09 (s, 2H), 1.63 (s, 9H); 2H not seen; MS (ESI) m/z=281.5 [M+1]+.

Step 7:

The title compounds (I-20) was prepared using prepared using procedure analogous to the preparation of I-8, Step 1, using tert-butyl 5-(aminomethyl)-4-chloro-1H-indole-1-carboxylate in place of 1-(1H-indol-5-yl)ethanamine adipic acid salt as starting material.

N$^2$-((4-chloro-1H-indol-5-yl)methyl)-N$^4$-(5-cyclopropyl-1H-pyrazol-3-yl)-6-methylpyrimidine-2,4-diamine (I-19) was prepared using procedure analogous to the preparation of I-8, step 1, except 2-chloro-N-(5-cyclopropyl-1H-pyrazol-3-yl)-6-methyl-pyrimidin-4-amine 185 and tert-butyl 5-(aminomethyl)-4-chloro-1H-indole-1-carboxylate were used in place of 53 and 1-(1H-indol-5-yl)ethanamine adipic acid salt, respectively, to afford I-19; MS (ESI) m/z=394.1 [M+1]$^+$.

Example 61

(S)—N$^2$-(1-(4-chloro-1H-indol-5-yl)ethyl)-N$^4$-(5-cyclopropyl-1H-pyrazol-3-yl)pyrimidine-2,4-diamine (I-22)

Step 1:

A mixture of tert-butyl 5-(aminomethyl)-4-chloro-1H-indole-1-carboxylate (1.147 g, 4.087 mmol) and benzophenone imine (0.75 mL, 4.496 mmol) in anhydrous DCM (39.3 mL) was stirred at 40° C. under N$_2$ for 4 d. The reaction mixture was diluted with EtOAc, and the organic layer was washed with water and brine, dried (Na$_2$SO$_4$), filtered, and concentrated in vacuo. The crude product was purified by SiO$_2$ chromatography eluting with and EtOAc/heptane gradient (0 to 70% EtOAc) to afford 1.22 g (67%) of tert-butyl 5-[(benzhydrylideneamino)methyl]-4-chloro-1H-indole-1-carboxylate (322) as an oil: $^1$H NMR (400 MHz, CDCl$_3$) δ 8.01 (d, J=8.5 Hz, 1H), 7.82-7.77 (m, 1H), 7.69 (d, J=7.2 Hz, 2H), 7.60-7.56 (m, 1H), 7.48 (d, J=8.2 Hz, 1H), 7.43 (d, J=8.9 Hz, 2H), 7.37 (d, J=7.0 Hz, 1H), 7.33 (t, J=7.3 Hz, 2H), 7.25-7.20 (m, 2H), 6.66 (d, J=3.7 Hz, 1H), 4.75 (s, 2H), 1.66 (s, 9H); MS (ESI) m/z=445.2 [M+1]$^+$.

Step 2:

To a stirred solution of 322 (1.22 g, 2.74 mmol) and iodomethane (0.17 mL, 2.74 mmol) in anhydrous THF (22.3 mL) at 0° C. was added dropwise a solution of potassium tert-butoxide (358.4 mg, 3.098 mmol) dissolved in THF (~0.50 mL) over 5 min. The reaction mixture was stirred at RT under N$_2$ for 3 h. The reaction mixture was diluted with EtOAc, and the organic layer was washed with water and brine, dried (Na$_2$SO$_4$), filtered, and concentrated in vacuo to afford 1.19 g (94.6%) of tert-butyl 5-[1-(benzhydrylideneamino)ethyl]-4-chloro-1H-indole-1-carboxylate (324) as a foam: MS (ESI) m/z=459.1 [M+1]$^+$.

Step 3:

To a stirred solution of 324 (880.0 mg, 1.92 mmol) in anhydrous MeOH (20 mL) was added hydroxylamine hydrochloride (532.9 mg, 7.70 mmol), and the reaction mixture was stirred at 40° C. under N$_2$ for 16 h. Volatile solvents were removed in vacuo, and the residue was diluted with EtOAc. The organic layer was washed with sat'd. aq. NaHCO$_3$, water and brine, dried (Na$_2$SO$_4$), filtered, and concentrated in vacuo. The crude product was purified by SiO$_2$ chromatography eluting with an EtOAc/heptane gradient (20 to 100% EtOAc), followed a MeOH/EtOAc (+1% TEA) gradient (0 to 80% MeOH) to afford 290 mg (51.3%) of tert-butyl 5-(1-aminoethyl)-4-chloro-1H-indole-1-carboxylate (326) as a white solid. $^1$H NMR (400 MHz, DMSO-d$_6$) δ 7.99 (d, J=8.7 Hz, 1H), 7.73 (d, J=3.7 Hz, 1H), 7.64 (d, J=8.7 Hz, 1H), 6.71 (d, J=3.7 Hz, 1H), 4.49 (d, J=6.6 Hz, 1H), 2.36-1.90 (m, 2H), 1.63 (s, 9H), 1.26 (d, J=6.6 Hz, 3H).

Step 4:

Racemic N$^2$-(1-(4-chloro-1H-indol-5-yl)ethyl)-N$^4$-(5-cyclopropyl-1H-pyrazol-3-yl)pyrimidine-2,4-diamine was prepared using the procedure as described in Example 19, Step 1, using tert-butyl 5-(1-aminoethyl)-4-chloro-1H-indole-1-carboxylate in place of 1-(1H-indol-5-yl)ethanamine adipic acid salt as starting material. MS (ESI) m/z=394.2 [M+1]$^+$.

Step 5:

Racemic $N^2$-(1-(4-chloro-1H-indol-5-yl)ethyl)-$N^4$-(5-cyclopropyl-1H-pyrazol-3-yl)pyrimidine-2,4-diamine (182.7 mg, 0.46 mmol) was subjected to chiral separation using SFC purification. The first eluant peak was collected to afford 20.2 mg (7.5%) of (S)—$N^2$-(1-(4-chloro-1H-indol-5-yl)ethyl)-$N^4$-(5-cyclopropyl-1H-pyrazol-3-yl)pyrimidine-2,4-diamine as a white solid. Enantiomeric assignment was based on SAR from known stereochemistry; SFC LC-MS, RT=1.02 min.

Example 62

$N^4$-(5-Cyclopropyl-1H-pyrazol-3-yl)-$N^2$-(1H-indol-4-ylmethyl)-$N^2$-(3-pyridylmethyl)pyrimidine-2,4-diamine (II-10)

A 5 mL microwave tube was charged with N-(1H-indol-4-ylmethyl)-1-(3-pyridyl)methanamine (200 mg, 0.843 mmol, 2 equiv.), 2-chloro-N-(5-cyclopropyl-1H-pyrazol-3-yl)pyrimidin-4-amine (100 mg, 0.424 mmol) and n-butanol (1.2 mL). DIPEA (5 equiv., 276.98 mg, 2.1216 mmol, 0.371 mL) was added, and the reaction mixture was heated to 140° C. for 17 h in an oil bath. The reaction was filtered and the solvent was evaporated in vacuo. The residue was purified by preparative HPLC to afford 5836 mg (32%) of $N^4$-(5-cyclopropyl-1H-pyrazol-3-yl)-$N^2$-(1H-indol-4-ylmethyl)-$N^2$-(3-pyridylmethyl)pyrimidine-2,4-diamine (II-10) as a light brown solid.

Example 63

$N^2$-((4-chloro-1H-benzo[d]imidazol-5-yl)methyl)-$N^4$-(5-(difluoromethyl)-1H-pyrazol-3-yl)-$N^2$-methylpyrimidine-2,4-diamine (II-81)

Step 1:

To a solution of 5-(difluoromethyl)-1H-pyrazol-3-amine (8.0 g, 60.1 mmol) in EtOH (350 mL) was added 2,4-dichloropyrimidine (10.7 g, 72.1 mmol) and DIPEA (10.9 g, 84.1 mmol). The reaction was stirred at 70° C. for 30 h. The reaction mixture was concentrated in vacuo. The crude product was purified by SiO$_2$ chromatography to afford 2-chloro-N-(5-(difluoromethyl)-1H-pyrazol-3-yl)pyrimidin-4-amine (1.00 g, 7%). $^1$H NMR (400 MHz, DMSO) δ 13.23 (d, J. 68.6 Hz, 1H), 10.57 (s, 1H), 8.22 (d, J=4.9 Hz, 1H), 7.08 (m, 3H). MS (ESI) m/z: 246.0 [M+1]$^+$.

Step 2:

A vial was charged with 2-chloro-N-(5-(difluoromethyl)-1H-pyrazol-3-yl)pyrimidin-4-amine (80 mg, 0.33 mmol), the bis HCl salt of 1-(4-chloro-1-(tetrahydro-2H-pyran-2-yl)-1H-benzo[d]imidazol-5-yl)-N-methylmethanamine (138 mg, 0.39 mmol), DIPEA (0.29 mL, 1.63 mmol) and n-BuOH (1.5 mL), sealed and heated at 90° C. for 8 h. The reaction mixture was then cooled to RT, and 4N HCl/dioxane (0.81 mL, 3.26 mmol) was added. The mixture was stirred at 40° C. for 3 h and then concentrated in vacuo. The crude mixture was purified by preparative HPLC to afford 15.1 Mg9 12%) of $N^2$-((4-chloro-1H-benzo[d]imidazol-5-yl)methyl)-$N^4$-(5-(difluoromethyl)-1H-pyrazol-3-yl)-$N^2$-methylpyrimidine-2,4-diamine (II-81).

Example 64

$N^4$-(5-cyclopropyl-1H-pyrazol-3-yl)-$N^2$-((6-fluoro-1H-indazol-4-yl)methyl)-$N^2$-(2-(methylamino)ethyl)pyrimidine-2,4-diamine (II-47)

Step 1:

To a solution of n-butyllithium (13 mL, 21.4 mmol, 1.6 M in hexanes) in THF (60 mL) at −78° C. was added dropwise over 30 min a solution of 4-bromo-6-fluoro-1-tetrahydropyran-2-yl-indazole (4.00 g, 13.4 mmol) in THF (20 mL). The reaction was warmed to −40° C. for 5 min, re-cooled to −78° C., and DMF (4.2 mL, 53.5 mmol) was added. The reaction mixture was allowed to warm to RT and stirred for 2 h. The reaction was then quenched with a satd. aq. NH$_4$Cl at 0° C. EtOAc was added and the layers were separated, and the aqueous layer was extracted once with EtOAc. The combined extracts were dried (Na$_2$SO$_4$), filtered and concentrated in vacuo. The crude mixture was purified by SiO$_2$ chromatography to afford 6-fluoro-1-(tetrahydro-2H-pyran-2-yl)-1H-indazole-4-carbaldehyde (2.18 g, 66%), as a white solid. MS (ESI) m/z: 249.3 [M+1]$^+$.

Step 2:

To a solution of 6-fluoro-1-tetrahydropyran-2-yl-indazole-4-carbaldehyde (175 mg, 0.71 mmol) in MeOH (7 mL) was added tert-butyl N-(2-aminoethyl)-N-methyl-carbamate (184 mg, 1.06 mmol). The reaction was stirred at RT for 4 h, and then NaBH$_4$ (35.4 mg, 0.92 mmol) was added. The reaction mixture was stirred at RT for 4 h and water was added. MeOH was removed under reduced pressure and the residue was diluted with 1N NaOH solution. The aqueous solution extracted with twice with EtOAc. The combined organic layers were dried (Na$_2$SO$_4$), filtered, and concentrated in vacuo to obtain crude tert-butyl (2-(((6-fluoro-1-(tetrahydro-2H-pyran-2-yl)-1H-indazol-4-yl)methyl)amino)ethyl)(methyl)carbamate (300 mg, quantitative yield). MS (ESI) m/z: 407.2 [M+1]$^+$.

Step 3:

A vial was charged with 2-chloro-N-(5-cyclopropyl-1H-pyrazol-3-yl)pyrimidin-4-amine (100 mg, 0.42 mmol), tert-butyl (2-(((6-fluoro-1-(tetrahydro-2H-pyran-2-yl)-1H-indazol-4-yl)methyl)amino)ethyl)(methyl)carbamate (207 mg, 0.51 mmol), DIPEA (0.22 mL, 1.27 mmol) and n-BuOH (0.9 mL), sealed and heated at 115° C. for 4 d. The reaction mixture was then cooled to RT and 4N HCl/dioxane (1.06 mL, 4.24 mmol) was added. The reaction mixture was stirred at RT for 16 h then concentrated nvacuo. The crude mixture was purified by preparative HPLC to afford 22.4 mg (13%) of $N^4$-(5-cyclopropyl-1H-pyrazol-3-yl)-$N^2$-((6-fluoro-1H-indazol-4-yl)methyl)-$N^2$-(2-(methylamino)ethyl)pyrimidine-2,4-diamine (II-47).

Example 65

GST-PAK1-KD (Kinase Domain) IC$_{50}$ Biochemical Assay Protocol

Activity of human recombinant GST-PAK1-KD protein was assessed in vitro assay by observing the phosphorylation of a fluorogenic peptide substrate. Catalytically active GST-tagged human recombinant PAK1-KD protein (residues #249-545 of human PAK1, UniProtKP/Swiss Q13153 with His6-GST fusion protein on the N-terminus) was cloned into a pAcGP67 baculovirus expression vector (EMD Biosciences) and infected into Sf9 cells.

The activity/inhibition of GST-PAK1-KD was estimated by measuring the phosphorylation of a fluorogenic peptide substrate (5FAM-RRRLSFAEPG) using a microfluidic mobility shift assay. The peptide substrate is a consensus sequence based on various PAK1 substrates reported in the scientific literature. The 20 µL assay mixtures contained 25 mM Tris-HCl (pH 7.5), 1 mM DTT, 0.01% Triton X-100, 10 mM MgCl$_2$, 5 mM β-glycerophosphate, 0.1 mM Na$_3$VO$_4$, 0.1% BGG (bovine gamma globulin), 1 µM peptide substrate (5FAM-RRRLSFAEPG), and 250 pM GST-PAK1-KD. Incubations were carried out at 22° C. in MatriCal MP101 384-well Metriplates™. Prior to the assay, GST-PAK1-KD and test compounds were preincubated together in assay buffer at 2× concentration (5 µL of 500 pM enzyme and 5 µL of serially diluted compound) for 10 min, and the assay was initiated by the addition of 10 µL assay buffer containing 2 µM peptide substrate (2×) and 80 µM ATP (2×). Following the 30-minute incubation, the assay mixtures were quenched by the addition of 3 µL of 250 mM EDTA, and the substrate and phosphorylated product were separated by capillary electrophoresis and detected using LabChip® Caliper 3000 (Caliper Life Sciences).

TABLE III

| Cpd. No. | PAK1[1] inhibition K$_i$ (µM) | MEK1(S298)[2] phosphorylation IC$_{50}$ (µM) | Cpd. No. | PAK1[1] inhibition K$_i$ (µM) | MEK1(S298)[2] phosphorylation IC$_{50}$ (µM) |
|---|---|---|---|---|---|
| I-62 | 0.00513 | 0.244 | I-59 | 0.037 | 0.104 |
| I-114 | 0.00675 | 0.133 | I-109 | 0.0275 | 0.786 |
| I-7 | 0.0135 | 0.212 | I-11 | 0.033 | 0.917 |
| I-8 | 0.0151 | 0.133 | I-106 | 0.0148 | 1.3 |
| I-39 | 0.0747 | 0.205 | I-45 | 0.041 | 1.2 |
| II-2 | 0.0071 | 0.475 | II-11 | 0.0016 | 0.043 |
| II-23 | 0.036 | 0.188 | II-24 | 0.0413 | 0.339 |
| II-33 | 0.0979 | 0.648 | II-43 | 0.284 | — |
| II-45 | 0.165 | 1.9 | II-51 | 0.0025 | 0.0661 |
| II-56 | 0.0042 | 0.0708 | II-59 | 0.0060 | 0.257 |
| II-73 | 0.013 | 0.419 | II-74 | 0.0136 | 0.189 |
| II-81 | 0.0197 | 0.235 | II-94 | 0.0368 | 0.0641 |
| II-97 | 0.0417 | 1.7 | II-102 | 0.0633 | 1.5 |

[1]GST-PAK1-KD Inhibition Assay - Example 65
[2]MEK1(S298)[2] Phosphorylation Assay - Example 66

Example 66

Cellular PAK IC$_{50}$ Assay Protocol

Group I PAKs (PAK1-3) are activated upon binding to the Rho GTPases, Rac1 and Cdc42. Activated group I PAKs phosphorylate MEK1 at Serine 298 (S298), one of the two sites in the catalytic domain that is important for stable association between Raf and MEK1 and subsequent MAPK activation. The inhibition of group I PAKs in EBC1 cells is assessed by detecting changes in the level of MEK1 phosphorylation at S298 using homogenous time-resolved fluorescence (HTRF). Inhibitory activity was estimated by treating 2×10$^4$ EBC1 cells for 2 h with PAK inhibitors in media containing 0.1% FBS. Following inhibitor treatment, cells were lysed with 25 µL of 1× cellular kinase lysis buffer (Cisbio) containing 1× cellular kinase blocking reagent (Cisbio). Cellular lysis was carried out at 4° C. for 2 h with constant shaking before lysate (16 µL) was transferred to white 384-well ProxiPlates™ (Perkin Elmer). Anti-total MEK1 antibody labeled with Europium cryptate donor (1 ng/well) (Cell Signaling Technologies catalog number 2352) and anti-phospho MEK1 (S298) antibody labeled with d2 acceptor (Cell Signaling Technologies catalog number 9128) (10 ng/well) were prepared in 1× detection buffer (CisBio) and added to each well of the assay plate and allowed to incubate at RT overnight. The following day the fluorescence emission from each well was measured in EnVision® (Perkin Elmer) at an excitation of 330 nm and dual emission wavelengths of 615 nm and 665 nm. The signal in each well at 665 nm was multiplied by 10,000 and divided by the signal in the same well at 615 nm to obtain a ratio. Ratio values ([665·10,000]÷615) were plotted as a function of the concentration of compound to determine IC50 values.

Example 67

Pharmaceutical compositions of the subject Compounds for administration via several routes can be prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

219

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula I

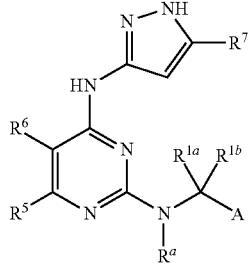

(I)

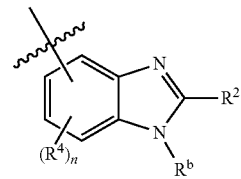

A1

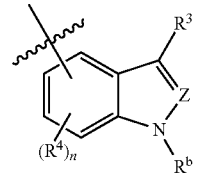

A2 wherein:
A is A-1 or A-2;
Z is N or $CR^2$;
$R^{1a}$ and $R^{1b}$ are (i) each independently hydrogen, $C_{1-6}$ alkyl, $C_{1-6}$ haloalkyl, $C_{1-6}$ hydroxyalkyl or $C_{1-3}$ alkoxy-$C_{1-6}$ alkyl, or, (ii) $R^{1a}$ and $R^{1b}$ together are $(CH_2)_{2-5}$;
$R^2$ is hydrogen, $C_{1-6}$ alkyl, $C_{1-6}$ alkoxy or $C_{3-6}$ cycloalkyl;
$R^a$ is hydrogen, $C_{1-6}$ alkyl, $C_{1-6}$ haloalkyl, $C_{1-6}$ hydroxyalkyl, $C_{1-3}$ alkoxy-$C_{1-6}$ alkyl, $C_{4-7}$ cycloalkyl, pyrrolidinyl, piperidinyl or $R^cR^dN[C(R^{10})_2]_{2-6}$;
$R^b$ is hydrogen, $C_{1-6}$ alkyl or $C_{3-6}$ cycloalkyl;
$R^c$ and $R^d$ are independently (i) hydrogen or $C_{1-6}$ alkyl or (ii) $R^c$ and $R^d$ together with the nitrogen to which they are attached are a pyrrolidine and piperidine ring;
$R^3$ is hydrogen, $C_{1-6}$ alkyl, $C_{1-6}$ haloalkyl, $C_{1-6}$ alkoxy, halogen, $C_{1-6}$ acyl or $C_{1-3}$ haloalkanoyl;
$R^4$ is independently in each occurrence hydroxy, thiol, cyano, $C_{1-6}$ alkyl, $C_{1-6}$ alkoxy, $C_{1-6}$ haloalkyl, $C_{1-6}$ haloalkoxy, halogen, $C_{1-6}$ alkoxycarbonyl, carboxyl, $C_{1-6}$ alkylthio, $C_{1-6}$ hydroxyalkyl, nitro, amino, $C_{1-3}$ alkylamino, $C_{1-3}$ dialkylamino, amino-$C_{1-3}$ alkyl, $C_{1-3}$ alkylamino-$C_{1-3}$ alkyl, $C_{1-3}$ dialkylamino $C_{1-3}$ alkyl, $C_{1-6}$ alkylsulfonyl, arylsulfonyl, $C_{1-6}$ alkylaminosulfonyl, arylaminosulfonyl, $C_{1-6}$ alkylsulfonylamido, arylsulfonylamido, carbamoyl, $C_{1-3}$ alkylcarbamoyl and $C_{1-3}$ dialkylcarbamoyl, arylcarbamoyl, $C_{1-6}$ alkylcarbonylamino, arylcarbonylamino;

n is zero, one, two or three;

$R^5$ is hydrogen, $C_{1-6}$ alkyl, $C_{1-6}$ haloalkyl, $C_{1-6}$ hydroxyalkyl, $C_{1-3}$ alkoxy-$C_{1-6}$ alkyl, cyano or $OR^9$;

$R^6$ is hydrogen, halogen, $C_{1-6}$ alkyl, $C_{1-6}$ haloalkyl, cyano, $C_{1-6}$ hydroxyalkyl or $C_{1-3}$ alkoxy-$C_{1-6}$ alkyl;

$R^7$ is selected from the group consisting of (i) $C_{1-10}$ alkyl, (ii) $C_{1-10}$ haloalkyl, (iii) optionally substituted $C_{3-7}$ cycloalkyl (iv) $C_{3-7}$ cycloalkyl-$C_{1-6}$ alkyl, (v))$R^9O[C(R^{10})_2]_{0-6}$, (vi) $C_{3-7}$ heterocyclyl and (vii) $C_{3-7}$ heterocyclyl-$C_{1-6}$ alkyl (viii) $C_{1-6}$ cyanoalkyl;

$R^9$ is independently in each occurrence $C_{1-10}$ alkyl, $C_{1-6}$ haloalkyl, $C_{3-7}$ cycloalkyl, $C_{3-7}$ cycloalkyl-$C_{1-6}$ alkyl, phenyl-$C_{1-6}$ alkyl, pyridinyl-$C_{1-6}$ alkyl, pyridinyl or phenyl;

$R^{10}$ is independently in each occurrence hydrogen or $C_{1-6}$ alkyl;

said cycloalkyl in each occurrence is independently optionally substituted with $C_{1-6}$ alkyl, halogen or optionally substituted phenyl;

said phenyl in each occurrence is independently optionally substituted with $C_{1-6}$ alkyl, halogen or $C_{1-6}$ alkoxy;

said heterocyclyl is independently substituted with halogen or $C_{1-6}$ alkyl; or, a pharmaceutically acceptable salt thereof.

2. The compound according to claim 1 wherein A is A2, Z is $CR^2$ and, $R^2$ and $R^b$ are hydrogen.

3. The compound according to claim 2 wherein A is optionally substituted indol-5-yl (A2a):

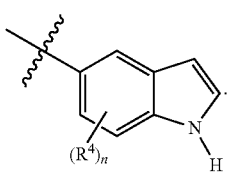

(A2a)

4. The compound according to claim 3 wherein:

$R^a$ is independently hydrogen, $C_{1-6}$ alkyl or $R^cR^dN[C(R^{10})_2]_{2-6}$;

$R^{1a}$ is hydrogen or $C_{1-6}$ alkyl;

$R^{1b}$ is hydrogen;

$R^5$ is hydrogen, $C_{1-6}$ alkyl or $C_{1-6}$ haloalkyl;

$R^6$ is hydrogen or halogen;

$R^7$ is optionally substituted $C_{3-7}$ cycloalkyl, $C_{3-7}$ heterocyclyl or $C_{1-6}$ haloalkyl.

5. The compound according to claim 4 wherein $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl.

6. The compound according to claim 5 wherein $R^{1a}$ is $C_{1-6}$ alkyl, $R^{1b}$ is hydrogen and the configuration of the carbon atom to which they both are attached is (S).

7. The compound according to claim 2 wherein A is optionally substituted indol-4-yl (A2b):

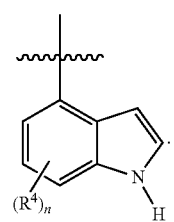

(A2b)

8. The compound according to claim 7 wherein:

$R^a$ is independently hydrogen, $C_{1-6}$ alkyl or $R^cR^dN[C(R^{10})_2]_{2-6}$;

$R^{1a}$ is hydrogen or $C_{1-6}$ alkyl;

$R^{1b}$ is hydrogen;

$R^5$ is hydrogen, $C_{1-6}$ alkyl or $C_{1-6}$ haloalkyl;

$R^6$ is hydrogen or halogen;

$R^7$ is optionally substituted $C_{3-7}$ cycloalkyl, $C_{3-7}$ heterocyclyl or $C_{1-6}$ haloalkyl.

9. The compound according to claim 8 wherein $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl.

10. The compound according to claim 8 wherein $R^{1a}$ is $C_{1-6}$ alkyl, $R^{1b}$ is hydrogen and the configuration of the carbon atom to which they both are attached is (S).

11. The compound according to claim 1 wherein A is A-1 and $R^2$ is hydrogen.

12. The compound according to claim 11 wherein A is optionally substituted benzimidazol-5-yl (A1a):

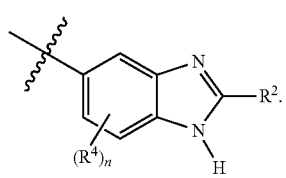

(A1a)

13. The compound according to claim 12 wherein:

$R^a$ is independently hydrogen, $C_{1-6}$ alkyl or $R^cR^dN[C(R^{10})_2]_{2-6}$;

$R^{1a}$ is hydrogen or $C_{1-6}$ alkyl; $R^2$ is hydrogen or $C_{1-6}$ alkyl;

$R^{1b}$ is hydrogen;

$R^5$ is hydrogen, $C_{1-6}$ alkyl or $C_{1-6}$ haloalkyl;

$R^6$ is hydrogen or halogen;

$R^7$ is optionally substituted $C_{3-7}$ cycloalkyl, $C_{3-7}$ heterocyclyl or $C_{1-6}$ haloalkyl.

14. The compound according to claim 13 wherein $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl.

15. The compound according to claim 14 wherein $R^{1a}$ is $C_{1-6}$ alkyl, $R^{1b}$ is hydrogen and the configuration of the carbon atom to which they both are attached is (S).

16. The compound according to claim 11 wherein A is optionally substituted benzimidazol-4-yl (A1b):

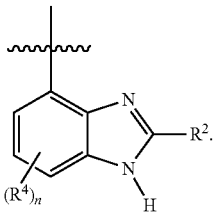

(A1b)

17. The compound according to claim 16 wherein:
$R^a$ is independently hydrogen, $C_{1-6}$ alkyl or $R^cR^dN[C(R^{10})_2]_{2-6}$;
$R^{1a}$ is hydrogen or $C_{1-6}$ alkyl;
$R^{1b}$ is hydrogen;
$R^5$ is hydrogen, $C_{1-6}$ alkyl or $C_{1-6}$ haloalkyl;
$R^6$ is hydrogen or halogen;
$R^7$ is optionally substituted $C_{3-7}$ cycloalkyl, $C_{3-7}$ heterocyclyl or $C_{1-6}$ haloalkyl.

18. The compound according to claim 17 wherein $R^7$ is optionally substituted $C_{3-7}$ cycloalkyl, $C_{1-6}$ haloalkyl, oxetan-2-yl, oxetan-3-yl, tetrahydrofuran-2-yl, tetrahydrofuran-3-yl or tetrahydropyranyl.

19. The compound according to claim 18 wherein $R^{1a}$ is $C_{1-6}$ alkyl, $R^{1b}$ is hydrogen and the configuration of the carbon atom to which they both are attached is (S).

20. The compound according to claim 1 wherein A is A2, Z is N, $R^b$ is hydrogen and $R^3$ is hydrogen, $C_{1-6}$ alkyl or $C_{1-6}$ alkoxy.

21. The compound according to claim 20 wherein:
$R^a$ is independently hydrogen, $C_{1-6}$ alkyl or $R^cR^dN[C(R^{10})_2]_{2-6}$;
$R^{1a}$ is hydrogen or $C_{1-6}$ alkyl;
$R^{1b}$ is hydrogen;
$R^5$ is hydrogen, $C_{1-6}$ alkyl or $C_{1-6}$ haloalkyl;
$R^6$ is hydrogen or halogen;
$R^7$ is optionally substituted $C_{3-7}$ cycloalkyl, $C_{3-7}$ heterocyclyl or $C_{1-6}$ haloalkyl.

22. The compound according to claim 1 which compound is any one or more compounds selected from the group consisting of compounds I-1 to I-117 of TABLE I or compounds II-1 to II-113 of TABLE II.

23. A composition comprising a compound according to any of claim 1 and at least one pharmaceutically acceptable carrier, excipient or diluent.

* * * * *